US007947459B2

(12) United States Patent
Hubert et al.

(10) Patent No.: US 7,947,459 B2
(45) Date of Patent: *May 24, 2011

(54) SERPENTINE TRANSMEMBRANE ANTIGENS EXPRESSED IN HUMAN CANCERS AND USES THEREOF

(75) Inventors: Rene S. Hubert, Los Angeles, CA (US); Arthur B. Raitano, Los Angeles, CA (US); Douglas Saffran, Encinitas, CA (US); Daniel E. H. Afar, Brisbane, CA (US); Steven Chappell Mitchell, Gurnee, IL (US); Mary Faris, Los Angeles, CA (US); Aya Jakobovits, Beverly Hills, CA (US)

(73) Assignee: Agensys, Inc., Santa Monica, CA (US)

( * ) Notice: Subject to any disclaimer, the term of this patent is extended or adjusted under 35 U.S.C. 154(b) by 1883 days.

This patent is subject to a terminal disclaimer.

(21) Appl. No.: 10/753,195

(22) Filed: Jan. 6, 2004

(65) Prior Publication Data

US 2005/0004349 A1 Jan. 6, 2005
US 2006/0020113 A9 Jan. 26, 2006

Related U.S. Application Data

(63) Continuation of application No. 10/165,044, filed on Jun. 6, 2002, now abandoned, which is a continuation-in-part of application No. 09/455,486, filed on Dec. 6, 1999, now Pat. No. 6,833,438, which is a continuation-in-part of application No. 09/323,873, filed on Jun. 1, 1999, now Pat. No. 6,329,503.

(60) Provisional application No. 60/296,656, filed on Jun. 6, 2001, provisional application No. 60/091,183, filed on Jun. 30, 1998, provisional application No. 60/087,520, filed on Jun. 1, 1998.

(51) Int. Cl.
*G01N 33/53* (2006.01)
*G01N 33/567* (2006.01)
*C07K 16/00* (2006.01)
*C12P 21/08* (2006.01)
*G01N 33/574* (2006.01)

(52) U.S. Cl. ..... 435/7.1; 435/7.21; 435/7.23; 530/387.1; 530/387.7; 530/387.9; 530/388.1; 530/388.8; 530/391.1; 530/391.3

(58) Field of Classification Search .......................... None
See application file for complete search history.

(56) References Cited

U.S. PATENT DOCUMENTS

| 5,001,225 | A | * | 3/1991 | Taylor | 530/388.6 |
| 5,571,894 | A | * | 11/1996 | Wels et al. | 530/387.3 |
| 6,329,503 | B1 | | 12/2001 | Afar et al. | 530/350 |
| 6,833,438 | B1 | * | 12/2004 | Afar et al. | 530/350 |
| 7,319,006 | B2 | * | 1/2008 | Afar et al. | 435/6 |
| 2002/0022248 | A1 | | 2/2002 | Xu et al. | 435/69.1 |
| 2002/0146692 | A1 | | 10/2002 | Yamazaki et al. | 435/6 |
| 2002/0192763 | A1 | | 12/2002 | Xu et al. | 435/69.7 |
| 2003/0045682 | A1 | | 3/2003 | Afar et al. | |
| 2003/0060612 | A1 | | 3/2003 | Goddard et al. | 536/23.1 |
| 2003/0064397 | A1 | | 4/2003 | Spancake et al. | 435/6 |
| 2003/0100540 | A1 | | 5/2003 | Zhang et al. | 514/165 |
| 2004/0005598 | A1 | * | 1/2004 | DeVaux et al. | 435/6 |

FOREIGN PATENT DOCUMENTS

| EP | 0834563 | 4/1998 |
| EP | 1308459 | 5/2003 |
| JP | 11164691 | 9/1999 |
| JP | 2002-517184 | 9/2003 |
| WO | WO 94/09150 | 4/1994 |
| WO | WO 95/14772 | 6/1995 |
| WO | WO 98/18489 | 5/1998 |
| WO | WO 98/37093 | 8/1998 |
| WO | WO 98/37418 | 8/1998 |
| WO | WO 98/53071 | 11/1998 |
| WO | WO 99/06548 | 2/1999 |
| WO | WO 99/06550 | 2/1999 |
| WO | WO 99/61469 | 2/1999 |
| WO | WO 99/62941 | 12/1999 |
| WO | WO 00/04149 | 1/2000 |
| WO | WO 00/35937 | 6/2000 |
| WO | WO 00/77021 | 12/2000 |
| WO | WO 01/08636 A2 | 2/2001 |
| WO | WO 01/12662 | 2/2001 |
| WO | WO 01/25272 | 4/2001 |

(Continued)

OTHER PUBLICATIONS

Greenbaum et al. (Genome Biology, 2003, vol. 4, Issue 9, pp. 117.1-117.8).*
Brennan et al. (J. Autoimmunity, 1989, 2 (suppl.): 177-186).*
Zimmer (Cell Motility and the Cytoskeleton, 1991. 20:325-337).*
Hell et al. (Laboratory Investigation, 1995, 73: 492-496).*
Fu et al. (EMBO J.; 1996, 15:43982-4401).*
Vallejo et al. (Biochimie, 2000 82:1129-1133).*
Jang et al. (Clinical Exp. Metastasis, 1997, 15: 469-483).*
Bowie et al (Science, 1990: 257:1306-1310).*
Coleman et al. (Research in Immunology, 1994; 145(1): 33-36).*
Abaza et al. (Journal of Protein Chemistry, vol. 11, No. 5, 1992, pp. 433-444, see abstract in particular).*
Roitt et al (1998, Immunology, 4th ed, Mosby).*
Holmes (Exp. Opin.Invest. Drugs, 2001, 10(3): 511-519).*
Herbert et al. (The Dictionary of Immunology, Academic Press, 4th edition, 1995, p. 58).*

(Continued)

*Primary Examiner* — Peter J Reddig
(74) *Attorney, Agent, or Firm* — Mark T. Kresnak; Shane M. Popp, JD, LLM; Ginger R. Dreger

(57) ABSTRACT

Described is a novel family of cell surface serpentine transmembrane antigens. Two of the proteins in this family are exclusively or predominantly expressed in the prostate, as well as in prostate cancer, and thus members of this family have been termed "STEAP" (Six Transmembrane Epithelial Antigen of the Prostate). Four particular human STEAPs are described and characterized herein. The human STEAPs exhibit a high' degree of structural conservation among them but show no significant structural homology to any known human proteins. STEAP-2 is a 454 amino acid protein characterized by a predicted molecular topology of six transmembrane domains and intracellular N- and C-termini, suggesting that it folds in a "serpentine" manner into three extracellular and two intracellular loops.

11 Claims, 51 Drawing Sheets

FOREIGN PATENT DOCUMENTS

| | | |
|---|---|---|
| WO | WO 01/34802 | 5/2001 |
| WO | WO 01/40276 | 6/2001 |
| WO | WO 01/42270 A1 | 6/2001 |
| WO | WO 01/45728 A2 | 6/2001 |
| WO | WO 01/51633 | 7/2001 |
| WO | WO 01/57190 | 8/2001 |
| WO | WO 01/57273 | 8/2001 |
| WO | WO 01/57276 | 8/2001 |
| WO | WO 01/57277 | 8/2001 |
| WO | WO 01/60860 | 8/2001 |
| WO | WO 01/70979 | 9/2001 |
| WO | WO 01/72962 | 10/2001 |
| WO | WO 01/73032 | 10/2001 |
| WO | WO 01/75067 | 10/2001 |
| WO | WO 01/86003 | 11/2001 |
| WO | WO 01/94629 | 12/2001 |
| WO | WO 01/96388 | 12/2001 |
| WO | WO 02/10449 | 2/2002 |
| WO | WO 02/16429 | 2/2002 |
| WO | WO 02/26822 | 4/2002 |
| WO | WO 02/30268 | 4/2002 |
| WO | WO 02/057303 | 7/2002 |
| WO | WO 02/059260 | 8/2002 |
| WO | WO 02/077013 | 10/2002 |
| WO | WO 02/077186 | 10/2002 |
| WO | WO 02/089747 | 11/2002 |
| WO | WO 02/092787 | 11/2002 |
| WO | WO 02/095010 | 11/2002 |
| WO | WO 02/102993 | 12/2002 |
| WO | WO 02/102994 | 12/2002 |
| WO | WO 03/004622 | 1/2003 |
| WO | WO 03/004623 | 1/2003 |
| WO | WO 03/009814 | 2/2003 |
| WO | WO 03/022995 | 3/2003 |
| WO | WO 2005/113601 A2 | 12/2005 |
| WO | WO 2006/034488 A2 | 3/2006 |

OTHER PUBLICATIONS

Greenspan et al. (Nature Biotechnology 7:936-937, 1999).*
Harlow and Lane (Antibodies, a Laboratory Manual, Cold Spring Harbor Laboratory Press, 1988, Ch. 5, p. 76).*
Burgess et al (J of Cell Bio. 111:2129-2138, 1990).*
Lazar et al (Molecular and Cellular Biology, 1988, 8:1247-1252).*
Cruse et al. (Illustrated Dictionary of Immunology, CRC Press, New York, p. 241, 1995).*
Dorland's Illustrated Medical Dictionary 26th ed. (W. B. Saunders Co. Philadelphia, 1985, p. 1193).*
Abu-Threideh et al., Genbank, (Accession No. 095034), National Library of Medicine, Bethesda MD, May 1, 1999.
Alberts et al., Molecular Biology of the Cell, 3rd edition (1994) p. 465.
Bellone et al., Immunology Today (1999) 20(10):457-462.
Bowie et al. (1990) Science 247:1306-1310.
Burgess et al. (1990) Jnl. Cell Biol. 111:2129-2138.
Cate et al., Genbank, (Accession No. W86309), National Library of Medicine, Bethesda MD, Nov. 1998.
Database EMBL Nucleotide and Protein Sequences, Aug. 25, 1996, XP002128081, AA032221, Hinxton, GB.
Database EMBL Nucleotide and Protein Sequences, May 13, 1997, XP002128082, AC002064, Hinxton, GB.
Database EMBL Nucleotide and Protein Sequences, Jun. 15, 1998, XP002128084, AC004969 (clone DJ1121E10), Hinxton, GB.
Database EMBL, "Human BAC clone CTB-167B5 form 7q21, complete sequence," Jun. 17, 1998 XP002173859 (Accession AC 003991 (Waterstone, R.)).
Diss et al. (1998) "Expression of skeletal muscle-type voltage-gated Na+ channel in rat and human prostate cancer cell lines," FEBS Letters 427:5-10.
Dulcert et al., Genbank, (Accession No. Y11840), National Library of Medicine, Bethesda MD, Feb. 11, 1999.
Falk et al., Nature (1991) 351:390-296.
Fu et al., EMBO Journal (1996) 15:4392-4401.
Greenberg et al., PNAS (1995) 92:3439.
Greenspan et al., (Nature Biotechnology 7:936-937 (1999)).
Grimes et al. (1998) "Electrophysiological characterization of voltage-gated Na+current expressed in the highly metastatic Mat-LyLu cell line of rat prostate cancer," Journal of Cellular Physiology 175:50-58.
Gura, Science (1997) 278:1041-1042.
Gutierrez et al. (1999) "Activation of a $Ca^{2+}$; -permeable cation channel by two different inducers of appoptosis in a human prostatic cancer cell line," Journal of Physiology 517.1:95-107.
Haverstick et al. (2000) "Inhibition of human prostate cancer proliferation in vitro and in a mouse model by a compound synthesized to block $Ca^{2+}Entry^1$," Cancer Research pp. 1002-1008.
Herbert et al. (The Dictionary of Immunology, Academic Press, 4th edition, 1995).
Hubert et al. (1999) PNAS USA 96(25):14523-14528.
Hunt et al., Science (1992) 255:1261-1263.
Lal et al. (US Patent No. 6048970, May 1998, USPTO database sequence listing).
Lazar et al. (1988) Mol. Cell. Biol. 8(3):1247-1252.
Lepple-Wienhues et al. (1996) "K + Channels and the intracellular calcium signal in human melanoma cell proliferation," J. Membrane Biol. 151:149-157.
Lewin, Genes VI, Oxford University Press, Inc., NY, Chapter 29, 1997.
Marino et al. (1994) "Association between cell membrane potential and breast cancer," Tumor Biol. 15:82-89.
McClean et al., Eur. J. of Cancer (1993) 29A:2243-2248.
Muller et al., MCB (1991) 11:1785.
Nie et al. (1997) "Inhibition of proliferation of MCF-7 breast cancer cells by a blocker of $Ca^{2+}$-permeable channel," Cell Calcium 22(2):75-82.
Pancrazio et al. (1989) "Voltage-dependent ion channels in small-cell lung cancer cells[1]," Cancer Research 49:5901-5906.
Parker et al., J. Immunol. (1994) 152:163-175.
Peshwa et al., Prostate (1998) 36:129-138.
Rama et al.. Biochem. J. 318:333-341 (1996).
Rieger et al., Glossary of Genetics and Cytogenetics, Springer-Verlag (1976) p. 17.
Shantz et al., Int. J. of Biochem. and Cell Bio. (1999)31:107-122.
Skryma et al. (1997) "Potassium conductance in the androgen-sensitive prostate cancer cell line, LNCaP: involvement in cell proliferation," The Prostate 33:112-122.
Spitler, Cancer Biotherapy (1995) 10:1-3.
Stewart et al., Genome Res. (1997) 7:422.
Walter et al., Nat. Genetics (1994) 7:22.
Xue et al., Prostate (1997) 30:73-78.
Challita-Eid Pia M., et al., "Monoclonal antibodies to six-transmembrane epithelial antigen of the prostate-1 inhibit intercellular communication in vitro and growth of human tumor xenografts in vivo", vol. 67, No. 12, pp. 5798-5805, (2007).
Faris M., et al., "Validation of STEAP-1 as a cell surface cancer therapeutic target", Proceedings of the annual meeting of the American Association for Cancer Research, vol. 43, p. 947, (2002).

* cited by examiner

FIG. 1A

```
       11          20          29          38          47          56
5' GAG ACT CAC GGT CAA GCT AAG GCG AAG AGT GGG TGG CTG AAG CCA TAC TAT TTT
   --- --- --- --- --- --- --- --- --- --- --- --- --- --- --- --- --- ---

65          74          83          92         101         110
   ATA GAA TTA ATG GAA AGC AGA AAA GAC ATC ACA AAC CAA GAA GAA CTT TGG AAA
   --- --- --- --- --- --- --- --- --- --- --- --- --- --- --- --- --- ---
            M   E   S   R   K   D   I   T   N   Q   E   E   L   W   K 119         128         137         146         155         164
   ATG AAG CCT AGG AGA AAT TTA GAA GAA GAC GAT TAT TTG CAT AAG GAC ACG GGA
   --- --- --- --- --- --- --- --- --- --- --- --- --- --- --- --- --- ---
    M   K   P   R   R   N   L   E   E   D   D   Y   L   H   K   D   T   G 173         182         191         200         209         218
   GAG ACC AGC ATG CTA AAA AGA CCT GTG CTT TTG CAT TTG CAC CAA ACA GCC CAT
   --- --- --- --- --- --- --- --- --- --- --- --- --- --- --- --- --- ---
    E   T   S   M   L   K   R   P   V   L   L   H   L   H   Q   T   A   H 227         236         245         254         263         272
   GCT GAT GAA TTT GAC TGC CCT TCA GAA CTT CAG CAC ACA CAG GAA CTC TTT CCA
   --- --- --- --- --- --- --- --- --- --- --- --- --- --- --- --- --- ---
    A   D   E   F   D   C   P   S   E   L   Q   H   T   Q   E   L   F   P 281         290         299         308         317         326
   CAG TGG CAC TTG CCA ATT AAA ATA GCT GCT ATT ATA GCA TCT CTG ACT TTT CTT
   --- --- --- --- --- --- --- --- --- --- --- --- --- --- --- --- --- ---
    Q   W   H   L   P   I   K   I   A   A   I   I   A   S   L   T   F   L 335         344         353         362         371         380
   TAC ACT CTT CTG AGG GAA GTA ATT CAC CCT TTA GCA ACT TCC CAT CAA CAA TAT
   --- --- --- --- --- --- --- --- --- --- --- --- --- --- --- --- --- ---
    Y   T   L   L   R   E   V   I   H   P   L   A   T   S   H   Q   Q   Y 389         398         407         416         425         434
   TTT TAT AAA ATT CCA ATC CTG GTC ATC AAC AAA GTC TTG CCA ATG GTT TCC ATC
   --- --- --- --- --- --- --- --- --- --- --- --- --- --- --- --- --- ---
    F   Y   K   I   P   I   L   V   I   N   K   V   L   P   M   V   S   I 443         452         461         470         479         488
   ACT CTC TTG GCA TTG GTT TAC CTG CCA GGT GTG ATA GCA GCA ATT GTC CAA CTT
   --- --- --- --- --- --- --- --- --- --- --- --- --- --- --- --- --- ---
    T   L   L   A   L   V   Y   L   P   G   V   I   A   A   I   V   Q   L 497         506         515         524         533         542
   CAT AAT GGA ACC AAG TAT AAG AAG TTT CCA CAT TGG TTG GAT AAG TGG ATG TTA
   --- --- --- --- --- --- --- --- --- --- --- --- --- --- --- --- --- ---
    H   N   G   T   K   Y   K   K   F   P   H   W   L   D   K   W   M   L 451         560         569         578         587         596
   ACA AGA AAG CAG TTT GGG CTT CTC AGT TTC TTT TTT GCT GTA CTG CAT GCA ATT
   --- --- --- --- --- --- --- --- --- --- --- --- --- --- --- --- --- ---
    T   R   K   Q   F   G   L   L   S   F   F   F   A   V   L   H   A   I 605         614         623         632         641         650
   TAT AGT CTG TCT TAC CCA ATG AGG CGA TCC TAC AGA TAC AAG TTG CTA AAC TGG
   --- --- --- --- --- --- --- --- --- --- --- --- --- --- --- --- --- ---
    Y   S   L   S   Y   P   M   R   R   S   Y   R   Y   K   L   L   N   W
```

FIG. 1B

```
         659         668         677         686         695         704
GCA TAT CAA CAG GTC CAA CAA AAT AAA GAA GAT GCC TGG ATT GAG CAT GAT GTT
--- --- --- --- --- --- --- --- --- --- --- --- --- --- --- --- ---
 A   Y   Q   Q   V   Q   Q   N   K   E   D   A   W   I   E   H   D   V 713         722         731         740         749         758
TGG AGA ATG GAG ATT TAT GTG TCT CTG GGA ATT GTG GGA TTG GCA ATA CTG GCT
--- --- --- --- --- --- --- --- --- --- --- --- --- --- --- --- ---
 W   R   M   E   I   Y   V   S   L   G   I   V   G   L   A   I   L   A 767         776         785         794         803         812
CTG TTG GCT GTG ACA TCT ATT CCA TCT GTG AGT GAC TCT TTG ACA TGG AGA GAA
--- --- --- --- --- --- --- --- --- --- --- --- --- --- --- --- ---
 L   L   A   V   T   S   I   P   S   V   S   D   S   L   T   W   R   E 821         830         839         848         857         866
TTT CAC TAT ATT CAG AGC AAG CTA GGA ATT GTT TCC CTT CTA CTG GGC ACA ATA
--- --- --- --- --- --- --- --- --- --- --- --- --- --- --- --- ---
 F   H   Y   I   Q   S   K   L   G   I   V   S   L   L   L   G   T   I 875         884         893         902         911         920
CAC GCA TTG ATT TTT GCC TGG AAT AAG TGG ATA GAT ATA AAA CAA TTT GTA TGG
--- --- --- --- --- --- --- --- --- --- --- --- --- --- --- --- ---
 H   A   L   I   F   A   W   N   K   W   I   D   I   K   Q   F   V   W 929         938         947         956         965         974
TAT ACA CCT CCA ACT TTT ATG ATA GCT GTT TTC CTT CCA ATT GTT GTC CTG ATA
--- --- --- --- --- --- --- --- --- --- --- --- --- --- --- --- ---
 Y   T   P   P   T   F   M   I   A   V   F   L   P   I   V   V   L   I 983         992        1001        1010        1019        1028
TTT AAA AGC ATA CTA TTC CTG CCA TGC TTG AGG AAG AAG ATA CTG AAG ATT AGA
--- --- --- --- --- --- --- --- --- --- --- --- --- --- --- --- ---
 F   K   S   I   L   F   L   P   C   L   R   K   K   I   L   K   I   R 1037        1046        1055        1064        1073        1082
CAT GGT TGG GAA GAC GTC ACC AAA ATT AAC AAA ACT GAG ATA TGT TCC CAG TTG
--- --- --- --- --- --- --- --- --- --- --- --- --- --- --- --- ---
 H   G   W   E   D   V   T   K   I   N   K   T   E   I   C   S   Q   L 1091        1100        1109        1118        1127        1136
TAG AAT TAC TGT TTA CAC ACA TTT TTG TTC AAT ATT GAT ATA TTT TAT CAC CAA
--- --- --- --- --- --- --- --- --- --- --- --- --- --- --- --- ---
 *   K   Y   C   L   H   T   F   L   F   N   I   D   I   F   Y   H   Q 1145        1154        1163        1172        1181        1190
CAT TTC AAG TTT GTA TTT GTT AAT AAA ATG ATT ATT CAA GGA AAA AAA AAA AAA
--- --- --- --- --- --- --- --- --- --- --- --- --- --- --- --- ---
 H   F   K   F   V   F   V   N   K   M   I   I   Q   G   K   K   K   K

AAA AA 3'    SEQ ID NO:1
--- --
 K           SEQ ID NO:2
```

Extracellular

Intracellular

FIG. 1D

5' GGC GCA GGC GCA GGC GGA GGG CGA GGG GCG GGG AGC GCC GCC TGG AGC GCG

GCA GGT CAT ATT GAA CAT TCC AGA TAC CTA TCA TTA CTC GAT GCT GTT GAT

AAC AGC AAG 3'   SEQ ID NO:3

FIG. 2A
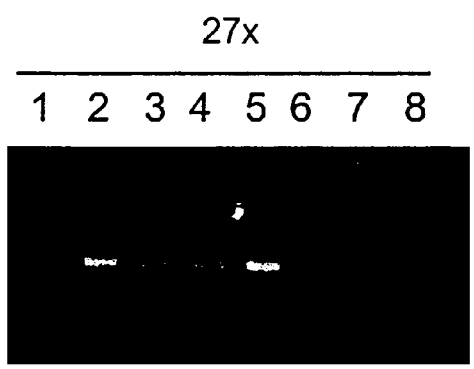
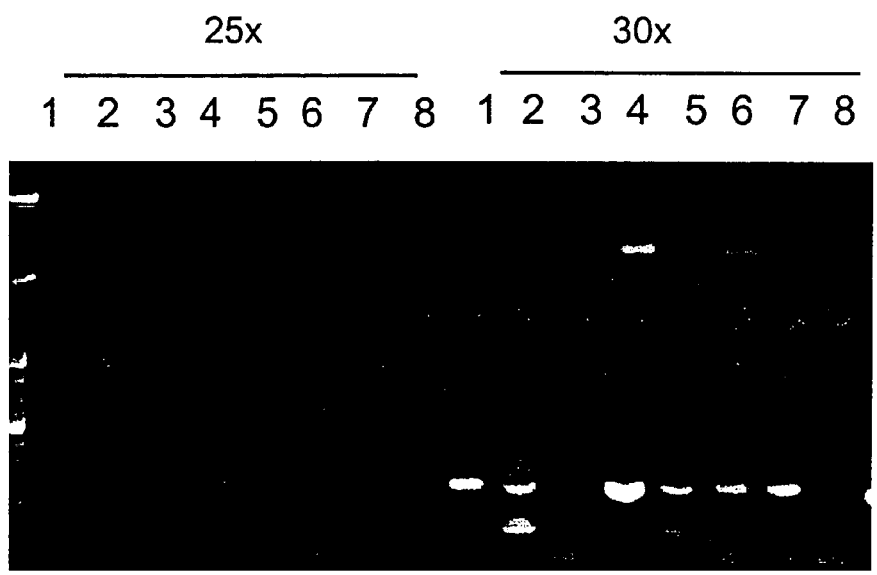
FIG. 2B
FIG. 2C

FIG. 4A

GGGGCCCGCACCTCTGGGCAGCAGCGGCAGCCGAGACTCACGGTCAAGCTAAGGCGAAGAGTGGGTGGCTGAAGCC

ATACTATTTTATAGAATTA<u>ATG</u>GAAAGCAGAAAAGACATCACAAACCAAGAAGAACTTTGGAAAATGAAGCCTAGG

AGAAATTTAGAAGAAGACGATTATTTGCATAAGGACACGGGAGAGACCAGCATGCTAAAAAGACCTGTGCTTTTGC

ATTTGCACCAAACAGCCCATGCTGATGAATTTGACTGCCCTTCAGAACTTCAGCACACACAGGAACTCTTTCCACA

GTGGCACTTGCCAATTAAAATAGCTGCTATTATAGCATCTCTGACTTTTCTTTACACTCTTCTGAGGGAAGTAATT

CACCCCTTAGCAACTTCCCATCAACAATATTTTTATAAAATTCCAATCCTGGTCATCAACAAAGTCTTGCCAATGG

TTTCCATCACTCTCTTGGCATTGGTTTACCTGCCAGGTGTGATAGCAGCAATTGTCCAACTTCATAATGGAACCAA

GTATAAGAAGTTTCCACATTGGTTGGATAAGTGGATGTTAACAAGAAAGCAGTTTGGGCTTCTCAGTTTCTTTTTT

GCTGTACTGCATGCAATTTATAGTCTGTCTTACCCAATGAGGCGATCCTACAGATACAAGTTGCTAAACTGGGCAT

ATCAACAGGTCCAACAAAATAAAGAAGATGCCTGGATTGAGCATGATGTTTGGAGAATGGAGATTTATGTGTCTCT

GGGAATTGTGGGATTGGCAATACTGGCTCTGTTGGCTGTGACATCTATTCCATCTGTGAGTGACTCTTTGACATGG

AGAGAATTTCACTATATTCAG<u>GTAAATAATA</u>TATAAAATAACCCTAAGACGTAAATCTTCTTTTTGTGTTTATGAT

ATAGAATATGTTGACTTTACCCCATAAAAAATAACAAATGTTTTTCAACAGCAAAGATCTTATACTTGTTCCAATT

AATAATGTGCTCTCCTGTTGTTTCCCTATTGCTTCTAATTAGGACAAGTCTTTCCTAGACATAAATAAAAGCCAT

TAAAATATTCTTTCTTTTTTTTTTTGTTTGTTTGTTTTTGTTTGTTTGTTTGTTTTTTGAGATGAAGTCTCG

CTCTGTTGCCCATGCTGGACTACAGTGGCACGATCTCGGCTCACTGCAACCTGCGCCTCCTGGGTTCAGGCGATTC

TCTTGCCTCAGCCTCCTGAGTAGCTGGGATTACAGGCACCCATCACCATGTCCAGCTAATTTTTGTATTTTTAGTA

GAGACAGGGTTTTCCCATGTTGGCCAGGCTGGTCTCGATCTCCTGACCTCAAATGATCCGCCCACCTCGGCCTCCC

AAAGTGCTGGGATGACAGTTGTGAGCCACCACACTCAGCCTGCTCTTTCTAATATTTGAAACTTGTTAGACAATTT

GCTACCCATCTAATGTGATATTTAGGAATCCAATATGCATGGTTTATTATTCTTAAAAAAAATATTCTTTTACC

TGTCACCTGAATTTAGTAATGCCTTTTATGTTACACAACTTAGCACTTTCCAGAAACAAAAACTCTCTCCTTGAAA

TAATAGAGTTTTTATCTACCAAAGATATGCTAGTGTCTCATTTCAAAGGCTGCTTTTTCCAGCTTACATTTTATAT

ACTTACTCACTTGAAGTTTCTAAATATTCTTGTAATTTTAAAACTATCTCAGATTTACTGAGGTTTATCTTCTGGT

GGTAGATTATCCATAAGAAGAGTGATGTGCCAGAATCACTCTGGGATCCTTGTCTGACAAGATTCAAAGGACTAAA

TTTAATTCAGTCATGAACACTGCCAATTACCGTTTATGGGTAGACATCTTTGGAAATTTCCACAAGGTCAGACATT

CGCAACTATCCTTCTACATGTCCACACGTATACTCCAACACTTTATTAGGCATCTGATTAGTTTGGAAAGTATGC

CTCCATCTGAATTAGTCCAGTCTGGCTTAGAGTTGGTACAACATTCTCACAGAATTTCCTAATTTTGTAGGTTCAG

FIG. 4B

```
CCTGATAACCACTGGAGTTCTTTGGTCCTCATTAAATAGCTTTCTTCACACATTGCTCTGCCTGTTACACATATCA
TGAACACTGCTTTTTAGACTTCATTAGGAATTTAGGACTGCATCTTGACAACTGACCCTATTCTACTATATGTACA
ATACCTAGCCCATAATAGGTATACAATACACATTTGGTAAAACTAATTTTCAACCAATGACATGTATTTTTCAACT
AGTAACCTAGAAATGTTTCACTTAAAATCTGAGAACTGGTTACACTACAAGTTACCTTGGAGATTCATATATGAAA
ACGCAAACTTAGCTATTTGATTGTATTCACTGGGACTTAAGAATCCGCCTCAATAATTGTGAGTTCGATCTGTTCT
GGCAGGCTAATGACCATTTCCAGTAAAGTGAATAGAGGTCAGAAGTCGTATAAAAGAGGTGTTGTCAGAACACCGT
TGAGATTACATAGGTGAACAACTATTTTTAAGCAACTTTATTTGTGTAGTGACAAAGCATCCCAATGCAGGCTGAA
ATGTTTCATCACATCTCTGGATCTCTCTATTTTGTGCAGACATTGAAAAAATTGTTCATATTATTTCCATGTTATC
AGAATATTTGATTTTTTAAAAACATAGGCCAAGTTCATTCACTTCATTATTCATTTATCAAAATCAGAGTGAATCA
CATTAGTCGCCTTCACAACTGATAAAGATCACTGAAGTCAAATTGATTTTGCTATAATCTTCAATCTACCTATAT
TTAATTGAGAATCTAAAATGTACAAATCATTGTGTTGATTCTGCAGTGATCCTGCTATAAGTAAGACTCAGTCCCT
GATTTTAGCTATCCTGTGAAAAGCAGAATAAGACAAATACACAAGAGACAAAGCACAAAAAATAAATATCATAAG
GGGATGAACAAAATGGTGGAGAAAGAGTAGACAAAGTTTTTGATCACCTGCCTTCAAAGAAAGGCTGTGAATTTTG
TTCACTTAGACAGCTTGGAGACAAGAAATTACCCAAAAGTAAGGTGAGGAGGATAGGCAAAAAGACCAGAAAGATG
TGAATGGACATTGTTGAGAAATGTGATAGGAAAACAATCATAGATAAAGGATTTCCAAGCAACAGAGCATATCCAG
ATGAGGTAGGATGGGATAAACTCTTATTGAACCAATCTTCACCAATTTTGTTTT<u>TCTTTTGCAG</u>**AGCAAGCTAGGA
ATTGTTTCCCTTCTACTGGGCACAATACACGCATTGATTTTTGCCTGGAATAAGTGGATAGATATAAAACAATTTG
TATGGTATACACCTCCAACTTTTATGATAGCTGTTTTCCTTCCAATTGTTGTCCTGATATTTAAAAGCATACTATT
CCTGCCATGCTTGAGGAAGAAGATACTGAAGATTAGACATGGTTGGGAAGACGTCACCAAAATTAACAAAACTGAG
ATATGTTCCCAGTTG<u>TAG</u>**AATTACTGTTTACACACATTTTTGTTCAATATTGATATATTTTATCACCAACATTTCA
AGTTTGTATTTGTTAATAAAATGATTATTCAAGGAAAAAAAAAAAAAAAAAAAA    SEQ ID NO:6
```

FIG. 9A

```
              10          19          28          37          46           55
5' GGA CGC GTG GGC GGA CGC GTG GGT TCC TCG GGC CCT CGG CGC CAC AAG CTG TCC
   --- --- --- --- --- --- --- --- --- --- --- --- --- --- --- --- --- ---
               64          73          82          91         100         109
   GGG CAC GCA GCC CCT AGC GGC GCG TCG CTG CCA AGC CGG CCT CCG CGC GCC TCC
   --- --- --- --- --- --- --- --- --- --- --- --- --- --- --- --- --- ---
              118         127         136         145         154         163
   CTC CTT CCT TCT CCC CTG GCT GTT CGC GAT CCA GCT TGG GTA GGC GGG GAA GCA
   --- --- --- --- --- --- --- --- --- --- --- --- --- --- --- --- --- ---
              172         181         190         199         208         217
   GCT GGA GTG CGA CCG CCA CGG CAG CCA CCC TGC AAC CGC CAG TCG GAG GTG CAG
   --- --- --- --- --- --- --- --- --- --- --- --- --- --- --- --- --- ---
              226         235         244         253         262         271
   TCC GTA GGC CCT GGC CCC CGG GTG GGC CCT TGG GGA GTC GGC GCC GCT CCC GAG
   --- --- --- --- --- --- --- --- --- --- --- --- --- --- --- --- --- ---
              280         289         298         307         316         325
   GAG CTG CAA GGC TCG CCC CTG CCC GGC GTG GAG GGC GCG GGG GGC GCG GAG GAT
   --- --- --- --- --- --- --- --- --- --- --- --- --- --- --- --- --- ---
              334         343         352         361         370         379
   ATT CTT GGT GAT CTT GGA AGT GTC CGT ATC ATG GAA TCA ATC TCT ATG ATG GGA
   --- --- --- --- --- --- --- --- --- --- --- --- --- --- --- --- --- ---
                                                    M   E   S   I   S   M   M   G.

388         397         406         415         424         433
   AGC CCT AAG AGC CTT AGT GAA ACT TGT TTA CCT AAT GGC ATA AAT GGT ATC AAA
   --- --- --- --- --- --- --- --- --- --- --- --- --- --- --- --- --- ---
    S   P   K   S   L   S   E   T   C   L   P   N   G   I   N   G   I   K 442         451         460         469         478         487
   GAT GCA AGG AAG GTC ACT GTA GGT GTG ATT GGA AGT GGA GAT TTT GCC AAA TCC
   --- --- --- --- --- --- --- --- --- --- --- --- --- --- --- --- --- ---
    D   A   R   K   V   T   V   G   V   I   G   S   G   D   F   A   K   S 496         505         514         523         532         541
   TTG ACC ATT CGA CTT ATT AGA TGC GGC TAT CAT GTG GTC ATA GGA AGT AGA AAT
   --- --- --- --- --- --- --- --- --- --- --- --- --- --- --- --- --- ---
    L   T   I   R   L   I   R   C   G   Y   H   V   V   I   G   S   R   N 550         559         568         577         586         595
   CCT AAG TTT GCT TCT GAA TTT TTT CCT CAT GTG GTA GAT GTC ACT CAT CAT GAA
   --- --- --- --- --- --- --- --- --- --- --- --- --- --- --- --- --- ---
    P   K   F   A   S   E   F   F   P   H   V   V   D   V   T   H   H   E 604         613         622         631         640         649
   GAT GCT CTC ACA AAA ACA AAT ATA ATA TTT GTT GCT ATA CAC AGA GAA CAT TAT
   --- --- --- --- --- --- --- --- --- --- --- --- --- --- --- --- --- ---
    D   A   L   T   K   T   N   I   I   F   V   A   I   H   R   E   H   Y 658         667         676         685         694         703
   ACC TCC CTG TGG GAC CTG AGA CAT CTG CTT GTG GGT AAA ATC CTG ATT GAT GTG
   --- --- --- --- --- --- --- --- --- --- --- --- --- --- --- --- --- ---
    T   S   L   W   D   L   R   H   L   L   V   G   K   I   L   I   D   V 712         721         730         739         748         757
   AGC AAT AAC ATG AGG ATA AAC CAG TAC CCA GAA TCC AAT GCT GAA TAT TTG GCT
   --- --- --- --- --- --- --- --- --- --- --- --- --- --- --- --- --- ---
    S   N   N   M   R   I   N   Q   Y   P   E   S   N   A   E   Y   L   A
```

FIG. 9B

```
          766              775              784              793              802              811
TCA TTA TTC CCA GAT TCT TTG ATT GTC AAA GGA TTT AAT GTT GTC TCA GCT TGG
--- --- --- --- --- --- --- --- --- --- --- --- --- --- --- --- --- ---
 S   L   F   P   D   S   L   I   V   K   G   F   N   V   V   S   A   W 820              829              838              847              856              865
GCA CTT CAG TTA GGA CCT AAG GAT GCC AGC CGG CAG GTT TAT ATA TGC AGC AAC
--- --- --- --- --- --- --- --- --- --- --- --- --- --- --- --- --- ---
 A   L   Q   L   G   P   K   D   A   S   R   Q   V   Y   I   C   S   N 874              883              892              901              910              919
AAT ATT CAA GCG CGA CAA CAG GTT ATT GAA CTT GCC CGC CAG TTG AAT TTC ATT
--- --- --- --- --- --- --- --- --- --- --- --- --- --- --- --- --- ---
 N   I   Q   A   R   Q   Q   V   I   E   L   A   R   Q   L   N   F   I 928              937              946              955              964              973
CCC ATT GAC TTG GGA TCC TTA TCA TCA GCC AGA GAG ATT GAA AAT TTA CCC CTA
--- --- --- --- --- --- --- --- --- --- --- --- --- --- --- --- --- ---
 P   I   D   L   G   S   L   S   S   A   R   E   I   E   N   L   P   L 982              991             1000             1009             1018             1027
CGA CTC TTT ACT CTC TGG AGA GGG CCA GTG GTG GTA GCT ATA AGC TTG GCC ACA
--- --- --- --- --- --- --- --- --- --- --- --- --- --- --- --- --- ---
 R   L   F   T   L   W   R   G   P   V   V   V   A   I   S   L   A   T 1036             1045             1054             1063             1072             1081
TTT TTT TTC CTT TAT TCC TTT GTC AGA GAT GTG ATT CAT CCA TAT GCT AGA AAC
--- --- --- --- --- --- --- --- --- --- --- --- --- --- --- --- --- ---
 F   F   F   L   Y   S   F   V   R   D   V   I   H   P   Y   A   R   N 1090             1099             1108             1117             1126             1135
CAA CAG AGT GAC TTT TAC AAA ATT CCT ATA GAG ATT GTG AAT AAA ACC TTA CCT
--- --- --- --- --- --- --- --- --- --- --- --- --- --- --- --- --- ---
 Q   Q   S   D   F   Y   K   I   P   I   E   I   V   N   K   T   L   P 1144             1153             1162             1171             1180             1189
ATA GTT GCC ATT ACT TTG CTC TCC CTA GTA TAC CTT GCA GGT CTT CTG GCA GCT
--- --- --- --- --- --- --- --- --- --- --- --- --- --- --- --- --- ---
 I   V   A   I   T   L   L   S   L   V   Y   L   A   G   L   L   A   A 1198             1207             1216             1225             1234             1243
GCT TAT CAA CTT TAT TAC GGC ACC AAG TAT AGG AGA TTT CCA CCT TGG TTG GAA
--- --- --- --- --- --- --- --- --- --- --- --- --- --- --- --- --- ---
 A   Y   Q   L   Y   Y   G   T   K   Y   R   R   F   P   P   W   L   E 1252             1261             1270             1279             1288             1297
ACC TGG TTA CAG TGT AGA AAA CAG CTT GGA TTA CTA AGT TTT TTC TTC GCT ATG
--- --- --- --- --- --- --- --- --- --- --- --- --- --- --- --- --- ---
 T   W   L   Q   C   R   K   Q   L   G   L   L   S   F   F   F   A   M 1306             1315             1324             1333             1342             1351
GTC CAT GTT GCC TAC AGC CTC TGC TTA CCG ATG AGA AGG TCA GAG AGA TAT TTG
--- --- --- --- --- --- --- --- --- --- --- --- --- --- --- --- --- ---
 V   H   V   A   Y   S   L   C   L   P   M   R   R   S   E   R   Y   L 1360             1369             1378             1387             1396             1405
TTT CTC AAC ATG GCT TAT CAG CAG GTT CAT GCA AAT ATT GAA AAC TCT TGG AAT
--- --- --- --- --- --- --- --- --- --- --- --- --- --- --- --- --- ---
 F   L   N   M   A   Y   Q   Q   V   H   A   N   I   E   N   S   W   N
```

FIG. 9C

```
        1414        1423        1432        1441        1450        1459
GAG GAA GAA GTT TGG AGA ATT GAA ATG TAT ATC TCC TTT GGC ATA ATG AGC CTT
--- --- --- --- --- --- --- --- --- --- --- --- --- --- --- --- --- ---
 E   E   E   V   W   R   I   E   M   Y   I   S   F   G   I   M   S   L 1468        1477        1486        1495        1504        1513
GGC TTA CTT TCC CTC CTG GCA GTC ACT TCT ATC CCT TCA GTG AGC AAT GCT TTA
--- --- --- --- --- --- --- --- --- --- --- --- --- --- --- --- --- ---
 G   L   L   S   L   L   A   V   T   S   I   P   S   V   S   N   A   L 1522        1531        1540        1549        1558        1567
AAC TGG AGA GAA TTC AGT TTT ATT CAG TCT ACA CTT GGA TAT GTC GCT CTG CTC
--- --- --- --- --- --- --- --- --- --- --- --- --- --- --- --- --- ---
 N   W   R   E   F   S   F   I   Q   S   T   L   G   Y   V   A   L   L 1576        1585        1594        1603        1612        1621
ATA AGT ACT TTC CAT GTT TTA ATT TAT GGA TGG AAA CGA GCT TTT GAG GAA GAG
--- --- --- --- --- --- --- --- --- --- --- --- --- --- --- --- --- ---
 I   S   T   F   H   V   L   I   Y   G   W   K   R   A   F   E   E   E 1630        1639        1648        1657        1666        1675
TAC TAC AGA TTT TAT ACA CCA CCA AAC TTT GTT CTT GCT CTT GTT TTG CCC TCA
--- --- --- --- --- --- --- --- --- --- --- --- --- --- --- --- --- ---
 Y   Y   R   F   Y   T   P   P   N   F   V   L   A   L   V   L   P   S 1684        1693        1702        1711        1720        1729
ATT GTA ATT CTG GAT CTT TTG CAG CTT TGC AGA TAC CCA GAC TGA GCT GGA ACT
--- --- --- --- --- --- --- --- --- --- --- --- --- --- --- --- --- ---
 I   V   I   L   D   L   L   Q   L   C   R   Y   P   D   *

1738        1747        1756        1765        1774        1783
GGA ATT TGT CTT CCT ATT GAC TCT ACT TCT TTA AAA GCG GCT GCC CAT TAC ATT
--- --- --- --- --- --- --- --- --- --- --- --- --- --- --- --- --- ---
        1792        1801        1810        1819        1828        1837
CCT CAG CTG TCC TTG CAG TTA GGT GTA CAT GTG ACT GAG TGT TGG CCA GTG AGA
--- --- --- --- --- --- --- --- --- --- --- --- --- --- --- --- --- ---
        1846        1855        1864        1873        1882        1891
TGA AGT CTC CTC AAA GGA AGG CAG CAT GTG TCC TTT TTC ATC CCT TCA TCT TGC
--- --- --- --- --- --- --- --- --- --- --- --- --- --- --- --- --- ---
        1900        1909        1918        1927        1936        1945
TGC TGG GAT TGT GGA TAT AAC AGG AGC CCT GGC AGC TGT CTC CAG AGG ATC AAA
--- --- --- --- --- --- --- --- --- --- --- --- --- --- --- --- --- ---
        1954        1963        1972        1981        1990        1999
GCC ACA CCC AAA GAG TAA GGC AGA TTA GAG ACC AGA AAG ACC TTG ACT ACT TCC
--- --- --- --- --- --- --- --- --- --- --- --- --- --- --- --- --- ---
        2008        2017        2026        2035        2044        2053
CTA CTT CCA CTG CTT TTC CTG CAT TTA AGC CAT TGT AAA TCT GGG TGT GTT ACA
--- --- --- --- --- --- --- --- --- --- --- --- --- --- --- --- --- ---
        2062        2071        2080        2089        2098        2107
TGA AGT GAA AAT TAA TTC TTT CTG CCC TTC AGT TCT TTA TCC TGA TAC CAT TTA
--- --- --- --- --- --- --- --- --- --- --- --- --- --- --- --- --- ---
        2116        2125        2134        2143        2152        2161
ACA CTG TCT GAA TTA ACT AGA CTG CAA TAA TTC TTT CTT TTG AAA GCT TTT AAA
--- --- --- --- --- --- --- --- --- --- --- --- --- --- --- --- --- ---
```

FIG. 9D

```
        2170            2179            2188            2197            2206            2215
GGA TAA TGT GCA ATT CAC ATT AAA ATT GAT TTT CCA TTG TCA ATT AGT TAT ACT
--- --- --- --- --- --- --- --- --- --- --- --- --- --- --- --- --- ---
        2224            2233            2242            2251            2260            2269
CAT TTT CCT GCC TTG ATC TTT CAT TAG ATA TTT TGT ATC TGC TTG GAA TAT ATT
--- --- --- --- --- --- --- --- --- --- --- --- --- --- --- --- --- ---
        2278            2287            2296            2305            2314            2323
ATC TTC TTT TTA ACT GTG TAA TTG GTA ATT ACT AAA ACT CTG TAA TCT CCA AAA
--- --- --- --- --- --- --- --- --- --- --- --- --- --- --- --- --- ---
        2332            2341            2350            2359            2368            2377
TAT TGC TAT CAA ATT ACA CAC CAT GTT TTC TAT CAT TCT CAT AGA TCT GCC TTA
--- --- --- --- --- --- --- --- --- --- --- --- --- --- --- --- --- ---
        2386            2395            2404            2413            2422            2431
TAA ACA TTT AAA TAA AAA GTA CTA TTT AAT GAT TTA AAA AAA AAA AAA AAA AAA
--- --- --- --- --- --- --- --- --- --- --- --- --- --- --- --- --- ---
        2440            2449
AAA AAA AAA AAA AAA AAA AAA AA 3'  SEQ ID NO:7
--- --- --- --- --- --- --- --     SEQ ID NO:8
```

FIG. 10A

```
  1  CGAAACTTCC CTCTACCCGC CCGGCCCGCG GCGCGCACCG TTGGCGCTGG ACGCTTCCTC
     GCTTTGAAGG GAGATGGGCG GGCCGGGCGC CGCGCGTGGC AACCGCGACC TGCGAAGGAG

M  E  K  T  C  I  D  A  L  P  L  T
 61  CTTGGAAGCG CCTCTCCCTC AGTTATGGAG AAAACTTGTA TAGATGCACT TCCTCTTACT
     GAACCTTCGC GGAGAGGGAG TCAATACCTC TTTTGAACAT ATCTACGTGA AGGAGAATGA

M  N  S  S  E  K  Q  E  T  V  C  I  F  G  T  G  D  F  G  R
121  ATGAATTCTT CAGAAAAGCA AGAGACTGTA TGTATTTTTG GAACTGGTGA TTTTGGAAGA
     TACTTAAGAA GTCTTTTCGT TCTCTGACAT ACATAAAAAC CTTGACCACT AAAACCTTCT

S  L  G  L  K  M  L  Q  C  G  Y  S  V  V  F  G  S  R  N  P
181  TCACTGGGAT TGAAAATGCT CCAGTGTGGT TATTCTGTTG TTTTTGGAAG TCGAAACCCC
     AGTGACCCTA ACTTTTACGA GGTCACACCA ATAAGACAAC AAAAACCTTC AGCTTTGGGG

Q  K  T  T  L  L  P  S  G  A  E  V  L  S  Y  S  E  A  A  K
241  CAGAAGACCA CCCTACTGCC CAGTGGTGCA GAAGTCTTGA GCTATTCAGA AGCAGCCAAG
     GTCTTCTGGT GGGATGACGG GTCACCACGT CTTCAGAACT CGATAAGTCT TCGTCGGTTC

K  S  G  I  I  I  A  I  H  R  E  H  Y  D  F  L  T  E  L
301  AAGTCTGGCA TCATAATCAT AGCAATCCAC AGAGAGCATT ATGATTTTCT CACAGAATTA
     TTCAGACCGT AGTATTAGTA TCGTTAGGTG TCTCTCGTAA TACTAAAAGA GTGTCTTAAT

T  E  V  L  N  G  K  I  L  V  D  I  S  N  N  L  K  I  N  Q
361  ACTGAGGTTC TCAATGGAAA AATATTGGTA GACATCAGCA ACAACCTCAA AATCAATCAA
     TGACTCCAAG AGTTACCTTT TTATAACCAT CTGTAGTCGT TGTTGGAGTT TTAGTTAGTT

Y  P  E  S  N  A  E  Y  L  A  H  L  V  P  G  A  H  V  V  K
421  TATCCAGAAT CTAATGCAGA GTACCTTGCT CATTTGGTGC CAGGAGCCCA CGTGGTAAAA
     ATAGGTCTTA GATTACGTCT CATGGAACGA GTAAACCACG GTCCTCGGGT GCACCATTTT

A  F  N  T  I  S  A  W  A  L  Q  S  G  A  L  D  A  S  R  Q
481  GCATTTAACA CCATCTCAGC CTGGGCTCTC CAGTCAGGAG CACTGGATGC AAGTCGGCAG
     CGTAAATTGT GGTAGAGTCG GACCCGAGAG GTCAGTCCTC GTGACCTACG TTCAGCCGTC

V  F  V  C  G  N  D  S  K  A  K  Q  R  V  M  D  I  V  R  N
541  GTGTTTGTGT GTGGAAATGA CAGCAAAGCC AAGCAAAGAG TGATGGATAT TGTTCGTAAT
     CACAAACACA CACCTTTACT GTCGTTTCGG TTCGTTTCTC ACTACCTATA ACAAGCATTA

L  G  L  T  P  M  D  Q  G  S  L  M  A  A  K  E  I  E  K  Y
601  CTTGGACTTA CTCCAATGGA TCAAGGATCA CTCATGGCAG CCAAAGAAAT TGAAAAGTAC
     GAACCTGAAT GAGGTTACCT AGTTCCTAGT GAGTACCGTC GGTTTCTTTA ACTTTTCATG

P  L  Q  L  F  P  M  W  R  F  P  F  Y  L  S  A  V  L  C  V
661  CCCCTGCAGC TATTTCCAAT GTGGAGGTTC CCCTTCTATT TGTCTGCTGT GCTGTGTGTC
     GGGGACGTCG ATAAAGGTTA CACCTCCAAG GGGAAGATAA ACAGACGACA CGACACACAG

F  L  F  F  Y  C  V  I  R  D  V  I  Y  P  Y  V  Y  E  K  K
721  TTCTTGTTTT TCTATTGTGT TATAAGAGAC GTAATCTACC CTTATGTTTA TGAAAAGAAA
     AAGAACAAAA AGATAACACA ATATTCTCTG CATTAGATGG GAATACAAAT ACTTTTCTTT
```

FIG. 10B

```
         D  N  T  F  R  M  A     I  S  I     P  N  R  I     F  P  I     T  A  L
 781  GATAATACAT TTCGTATGGC TATTTCCATT CCAAATCGTA TCTTTCCAAT AACAGCACTT
      CTATTATGTA AAGCATACCG ATAAAGGTAA GGTTTAGCAT AGAAAGGTTA TTGTCGTGAA

T  L  L  A  L  V  Y     L  P  G     V  I  A  A     I  L  Q     L  Y  R
 841  ACACTGCTTG CTTTGGTTTA CCTCCCTGGT GTTATTGCTG CCATTCTACA ACTGTACCGA
      TGTGACGAAC GAAACCAAAT GGAGGGACCA CAATAACGAC GGTAAGATGT TGACATGGCT

G  T  K  Y  R  R  F     P  D  W     L  D  H  W     M  L  C     R  K  Q
 901  GGCACAAAAT ACCGTCGATT CCCAGACTGG CTTGACCACT GGATGCTTTG CCGAAAGCAG
      CCGTGTTTTA TGGCAGCTAA GGGTCTGACC GAACTGGTGA CCTACGAAAC GGCTTTCGTC

L  G  L  V  A  L  G     F  A  F     L  H  V  L     Y  T  L     V  I  P
 961  CTTGGCTTGG TAGCTCTGGG ATTTGCCTTC CTTCATGTCC TCTACACACT TGTGATTCCT
      GAACCGAACC ATCGAGACCC TAAACGGAAG GAAGTACAGG AGATGTGTGA ACACTAAGGA

I  R  Y  Y  V  R  W     R  L  G     N  L  T  V     T  Q  A     I  L  K
1021  ATTCGATATT ATGTACGATG GAGATTGGGA AACTTAACCG TTACCCAGGC AATACTCAAG
      TAAGCTATAA TACATGCTAC CTCTAACCCT TTGAATTGGC AATGGGTCCG TTATGAGTTC

K  E  N  P  F  S  T     S  S  A     W  L  S  D     S  Y  V     A  L  G
1081  AAGGAGAATC CATTTAGCAC CTCCTCAGCC TGGCTCAGTG ATTCATATGT GGCTTTGGGA
      TTCCTCTTAG GTAAATCGTG GAGGAGTCGG ACCGAGTCAC TAAGTATACA CCGAAACCCT

I  L  G  F  F  L  F     V  L  L     G  I  T  S     L  P  S     V  S  N
1141  ATACTTGGGT TTTTTCTGTT TGTACTCTTG GGAATCACTT CTTTGCCATC TGTTAGCAAT
      TATGAACCCA AAAAAGACAA ACATGAGAAC CCTTAGTGAA GAAACGGTAG ACAATCGTTA

A  V  N  W  R  E  F     R  F  V     Q  S  K  L     G  Y  L     T  L  I
1201  GCAGTCAACT GGAGAGAGTT CCGATTTGTC CAGTCCAAAC TGGGTTATTT GACCCTGATC
      CGTCAGTTGA CCTCTCTCAA GGCTAAACAG GTCAGGTTTG ACCCAATAAA CTGGGACTAG

L  C  T  A  H  T  L     V  Y  G     G  K  R  F     L  S  P     S  N  L
1261  TTGTGTACAG CCCACACCCT GGTGTACGGT GGGAAGAGAT TCCTCAGCCC TTCAAATCTC
      AACACATGTC GGGTGTGGGA CCACATGCCA CCCTTCTCTA AGGAGTCGGG AAGTTTAGAG

R  W  Y  L  P  A  A     Y  V  L     G  L  I  I     P  C  T     V  L  V
1321  AGATGGTATC TTCCTGCAGC CTACGTGTTA GGGCTTATCA TTCCTTGCAC TGTGCTGGTG
      TCTACCATAG AAGGACGTCG GATGCACAAT CCCGAATAGT AAGGAACGTG ACACGACCAC

I  K  F  V  L  I  M     P  C  V     D  N  T  L     T  R  I     Q  G
1381  ATCAAGTTTG TCCTAATCAT GCCATGTGTA GACAACACCC TTACAAGGAT CCGCCAGGGC
      TAGTTCAAAC AGGATTAGTA CGGTACACAT CTGTTGTGGG AATGTTCCTA GGCGGTCCCG

W  E  R  N  S  K  H
1441  TGGGAAAGGA ACTCAAAACA CTAGAAAAAG CATTGAATGG AAAATCAATA TTTAAAACAA
      ACCCTTTCCT TGAGTTTTGT GATCTTTTTC GTAACTTACC TTTTAGTTAT AAATTTTGTT
```

FIG. 10C

```
1501  AGTTCAATTT AGCTGGATTT CTGAACTATG GTTTTGAATG TTTAAAGAAG AATGATGGGT
      TCAAGTTAAA TCGACCTAAA GACTTGATAC CAAAACTTAC AAATTTCTTC TTACTACCCA

1561  ACAGTTAGGA AAGTTTTTTT CTTACACCGT GACTGAGGGA AACATTGCTT GTCTTTGAGA
      TGTCAATCCT TTCAAAAAAA GAATGTGGCA CTGACTCCCT TTGTAACGAA CAGAAACTCT

1621  AATTGACTGA CATACTGGAA GAGAACACCA TTTTATCTCA GGTTAGTGAA GAATCAGTGC
      TTAACTGACT GTATGACCTT CTCTTGTGGT AAAATAGAGT CCAATCACTT CTTAGTCACG

1681  AGGTCCCTGA CTCTTATTTT CCCAGAGGCC ATGGAGCTGA GATTGAGACT AGCCTTGTGG
      TCCAGGGACT GAGAATAAAA GGGTCTCCGG TACCTCGACT CTAACTCTGA TCGGAACACC

1741  TTTCACACTA AAGAGTTTCC TTGTTATGGG CAACATGCAT GACCTAATGT CTTGCAAAAT
      AAAGTGTGAT TTCTCAAAGG AACAATACCC GTTGTACGTA CTGGATTACA GAACGTTTTA

1801  CCAATAGAAG TATTGCAGCT TCCTTCTCTG GCTCAAGGGC TGAGTTAAGT GAAAGGAAAA
      GGTTATCTTC ATAACGTCGA AGGAAGAGAC CGAGTTCCCG ACTCAATTCA CTTTCCTTTT

1861  ACAGCACAAT GGTGACCACT GATAAAGGCT TTATTAGGTA TATCTGAGGA AGTGGGTCAC
      TGTCGTGTTA CCACTGGTGA CTATTTCCGA AATAATCCAT ATAGACTCCT TCACCCAGTG

1921  ATGAAATGTA AAAAGGGAAT GAGGTTTTTG TTGTTTTTTG GAAGTAAAGG CAAACATAAA
      TACTTTACAT TTTTCCCTTA CTCCAAAAAC AACAAAAAAC CTTCATTTCC GTTTGTATTT

1981  TATTACCATG ATGAATTCTA GTGAAATGAC CCCTTGACTT TGCTTTTCTT AATACAGATA
      ATAATGGTAC TACTTAAGAT CACTTTACTG GGAACTGAA ACGAAAAGAA TTATGTCTAT

2041  TTTACTGAGA GGAACTATTT TTATAACACA AGAAAAATTT ACAATTGATT AAAAGTATCC
      AAATGACTCT CCTTGATAAA AATATTGTGT TCTTTTTAAA TGTTAACTAA TTTTCATAGG

2101  ATGTCTTGGA TACATACGTA TCTATAGAGC TGGCATGTAA TTCTTCCTCT ATAAAGAATA
      TACAGAACCT ATGTATGCAT AGATATCTCG ACCGTACATT AAGAAGGAGA TATTTCTTAT

2161  GGTATAGGAA AGACTGAATA AAAATGGAGG GATATCCCCT TGGATTTCAC TTGCATTGTG
      CCATATCCTT TCTGACTTAT TTTTACCTCC CTATAGGGGA ACCTAAAGTG AACGTAACAC

2221  CAATAAGCAA AGAAGGGTTG ATAAAGTTC TTGATCAAAA AGTTCAAAGA AACCAGAATT
      GTTATTCGTT TCTTCCCAAC TATTTTCAAG AACTAGTTTT TCAAGTTTCT TTGGTCTTAA

2281  TTAGACAGCA AGCTAAATAA ATATTGTAAA ATTGCACTAT ATTAGGTTAA GTATTATTTA
      AATCTGTCGT TCGATTTATT TATAACATTT AACGTGATA TAATCCAATT CATAATAAAT

2341  GGTATTATAA TATGCTTTGT AAATTTTATA TTCCAAATAT TGCTCAATAT TTTTCATCTA
      CCATAATATT ATACGAAACA TTTAAAATAT AAGGTTTATA ACGAGTTATA AAAGTAGAT

2401  TTAAATTAAT TTCTAGTGTA ATAAGTAGC TTCTATATCT GTCTTAGTCT ATTATAATTG
      AATTTAATTA AAGATCACAT TTATTCATCG AAGATATAGA CAGAATCAGA TAATATTAAC
```

FIG. 10D

```
2461  TAAGGAGTAA AATTAAATGA ATAGTCTGCA GGTATAAATT TGAACAATGC ATAGATGATC
      ATTCCTCATT TTAATTTACT TATCAGACGT CCATATTTAA ACTTGTTACG TATCTACTAG

2521  GAAAATTACG GAAAATCATA GGGCAGAGAG GTGTGAAGAT TCATCATTAT GTGAAATTTG
      CTTTTAATGC CTTTTAGTAT CCCGTCTCTC CACACTTCTA AGTAGTAATA CACTTTAAAC

2581  GATCTTTCTC AAATCCTTGC TGAAATTTAG GATGGTTCTC ACTGTTTTC TGTGCTGATA
      CTAGAAAGAG TTTAGGAACG ACTTTAAATC CTACCAAGAG TGACAAAAAG ACACGACTAT

2641  GTACCCTTTC CAAGGTGACC TTCAGGGGGA TTAACCTTCC TAGCTCAAGC AATGAGCTAA
      CATGGGAAAG GTTCCACTGG AAGTCCCCCT AATTGGAAGG ATCGAGTTCG TTACTCGATT

2701  AAGGAGCCTT ATGCATGATC TTCCCACATA TCAAAATAAC TAAAAGGCAC TGAGTTTGGC
      TTCCTCGGAA TACGTACTAG AAGGGTGTAT AGTTTTATTG ATTTTCCGTG ACTCAAACCG

2761  ATTTTTCTGC CTGCTCTGCT AAGACCTTTT TTTTTTTTTT ACTTTCATTA TAACATATTA
      TAAAAGACG GACGAGACGA TTCTGGAAAA AAAAAAAAAA TGAAAGTAAT ATTGTATAAT

2821  TACATGACAT TATACAAAAA TGATTAAAAT ATATTAAAAC AACATCAACA ATCCAGGATA
      ATGTACTGTA ATATGTTTTT ACTAATTTTA TATAATTTTG TTGTAGTTGT TAGGTCCTAT

2881  TTTTTCTATA AAACTTTTTA AAAATAATTG TATCTATATA TTCAATTTTA CATCCTTTTT
      AAAAGATAT TTTGAAAAAT TTTTATTAAC ATAGATATAT AAGTTAAAAT GTAGGAAAAA

2941  CAAAGGCTTT GTTTTTCTAA AGGCTTTGTT TTCCTTTTTA TTATTTTTTT CTTTTTTATT
      GTTTCCGAAA CAAAAAGATT TCCGAAACAA AAGGAAAAAT AATAAAAAAA GAAAAAATAA

3001  TTTTTGAGAC AGTCTTGCTC TGTCGCTCAG GCTGGAGTGC AGTGGCACGA TCTCAGCTCA
      AAAAACTCTG TCAGAACGAG ACAGCGAGTC CGACCTCACG TCACCGTGCT AGAGTCGAGT

3061  CTGCAACCTC CTCCTCCCAG GTTCAAGTGA TTCTTGTTCA TCAGCCTCCC GAGTAGCTGG
      GACGTTGGAG GAGGAGGGTC CAAGTTCACT AAGAACAAGT AGTCGGAGGG CTCATCGACC

3121  GACTACAGGC ATGTGCCACT ATGCCCAGCT AATTTTTGTA CTTTTAGTAG AGACAGGGTT
      CTGATGTCCG TACACGGTGA TACGGGTCGA TTAAAAACAT GAAAATCATC TCTGTCCCAA

3181  TCACCACATT GGTCAGGCTG GTCTTGAAAT GCTGGCGTCA AGTGATCTGC CTGCCTCCGC
      AGTGGTGTAA CCAGTCCGAC CAGAACTTTA CGACCGCAGT TCACTAGACG GACGGAGGCG

3241  CTTACGTAAT ATATTTTCTT AATGGCTGCA TAATATCACA TCAAATAGGC ATTTTTCAAA
      GAATGCATTA TATAAAGAA TTACCGACGT ATTATAGTGT AGTTTATCCG TAAAAAGTTT

3301  CCTCTTTCCT TATTAAACAT GTAGACTATA TCCATTTTTT ACTAAAATAA ATAACATTTC
      GGAGAAAGGA ATAATTTGTA CATCTGATAT AGGTAAAAAA TGATTTTATT TATTGTAAAG

3361  AGATAATATC TTTGCACTGA TAATGTTGCC AAGCCATTTC TAAAGTGACC TTATCAATTT
      TCTATTATAG AAACGTGACT ATTACAACGG TTCGGTAAAG ATTTCACTGG AATAGTTAAA
```

FIG. 10E

```
3421  AATTACCATT GGATGAGGGT GTTGCTTTCA TCGCACCATT GTAGATTGTC TTTTTTATTT
      TTAATGGTAA CCTACTCCCA CAACGAAAGT AGCGTGGTAA CATCTAACAG AAAAAATAAA

3481  CAATTTGCGT TTATTTATAA CTGGTTGCAA AGGTACACAG AACACACGCT CCTTCAACTT
      GTTAAACGCA AATAAATATT GACCAACGTT TCCATGTGTC TTGTGTGCGA GGAAGTTGAA

3541  ATCTTTGATA AACCCAAGCA AGGATACAAA AAGTTGGACG ACATTGAGTA GAGTCATGGT
      TAGAAACTAT TTGGGTTCGT TCCTATGTTT TTCAACCTGC TGTAACTCAT CTCAGTACCA

3601  ATACGGTGCT GACCCTACAG TATCAGTGGA AAAGATAAGG AAAATGTCAC TACTCACCTA
      TATGCCACGA CTGGGATGTC ATAGTCACCT TTTCTATTCC TTTTACAGTG ATGAGTGGAT

3661  TGTTATGCAA AACAGTTAGG TGTGCTGGGG CTGGATACTG CTCTTTTACT TGAGCATTGG
      ACAATACGTT TTGTCAATCC ACACGACCCC GACCTATGAC GAGAAAATGA ACTCGTAACC

3721  TTGATTAAAG TTTAGGTACC ATCCAGGCTG GTCTAGAGAA GTCTTTGGAG TTAACCATGC
      AACTAATTTC AAATCCATGG TAGGTCCGAC CAGATCTCTT CAGAAACCTC AATTGGTACG

3781  TCTTTTTGTT AAAGAAGAGA GTAATGTGTT TATCCTGGCT CATAGTCCGT CACCGAAAAT
      AGAAAAACAA TTTCTTCTCT CATTACACAA ATAGGACCGA GTATCAGGCA GTGGCTTTTA

3841  AGAAAATGCC ATCCATAGGT AAAATGCTGA CCTATAGAAA AAAATGAACT CTACTTTTAT
      TCTTTTACGG TAGGTATCCA TTTTACGACT GGATATCTTT TTTTACTTGA GATGAAAATA

3901  AGCCTAGTAA AAATGCTCTA CCTGAGTAGT TAAAAGCAAT TCATGAAGCC TGAAGCTAAA
      TCGGATCATT TTTACGAGAT GGACTCATCA ATTTTCGTTA AGTACTTCGG ACTTCGATTT

3961  GAGCACTCTG ATGGTTTTGG CATAATAGCT GCATTCCAG ACCTGACCTT TGGCCCCAAC
      CTCGTGAGAC TACCAAAACC GTATTATCGA CGTAAGGTC TGGACTGGAA ACCGGGGTTG

4021  CACAAGTGCT CCAAGCCCCA CCAGCTGACC AAAGAAAGCC CAAGTTCTCC TTCTGTCCTT
      GTGTTCACGA GGTTCGGGGT GGTCGACTGG TTTCTTTCGG GTTCAAGAGG AAGACAGGAA

4081  CCCACAACCT CCCTGCTCCC AAAACTATGA AATTAATTTG ACCATATTAA CACAGCTGAC
      GGGTGTTGGA GGGACGAGGG TTTTGATACT TTAATTAAAC TGGTATAATT GTGTCGACTG

4141  TCCTCCAGTT TACTTAAGGT AGAAAGAATG AGTTTACAAC AGATGAAAAT AAGTGCTTTG
      AGGAGGTCAA ATGAATTCCA TCTTTCTTAC TCAAATGTTG TCTACTTTTA TTCACGAAAC

4201  GGCGAACTGT ATTCCTTTTA ACAGATCCAA ACTATTTTAC ATTTAAAAAA AAAGTTAAAC
      CCGCTTGACA TAAGGAAAAT TGTCTAGGTT TGATAAAATG TAAATTTTTT TTTCAATTTG

4261  TAAACTTCTT TACTGCTGAT ATGTTTCCTG TATTCTAGAA AAATTTTTAC ACTTTCACAT
      ATTTGAAGAA ATGACGACTA TACAAGGAC ATAAGATCTT TTTAAAAATG TGAAAGTGTA

4321  TATTTTTGTA CACTTTCCCC ATGTTAAGGG ATGATGGCTT TTATAAATGT GTATTCATTA
      ATAAAAACAT GTGAAAGGGG TACAATTCCC TACTACCGAA ATATTTACA CATAAGTAAT

4381  AATGTTACTT TAAAAATAAA AAAAAAAAAA AAAAAAAAAA AAAAAAAA    SEQ ID NO:9
      TTACAATGAA ATTTTTATTT TTTTTTTTTT TTTTTTTTTT TTTTTTTT    SEQ ID NO:10
```

FIG. 10F

STEAP-1, AA50880 (NCI_CGAP Pr6)  SEQ ID NO:11
ggtcgacttttcctttattcctttgtcagagatctgattcatccatatgctagaaaccaacagagtgacttttaca
aaattcctatagagattgtgaataaaaccttacctatagttgccattactttgctctccctagtataccttgcagg
tcttctggcagctgcttatcaactttattacgcaccaagtataggagatttccaccttggttggaaacctggtta
cagtgtagaaaacagcttggattactaagttgttctttcgctatggtccatgttgcctacagcctctgcttaccga
tgagaaggtcagagagat STEAP-2, 98P4B6 SSH fragment  SEQ ID NO:12
tttgcagctttgcagataccagactgagctggaactggaatttgtcttcctattgactctacttctttaaaagcg
gctgccattacattcctcagctgtccttgcagttaggtgtacatgtgactgagtgttggccagtgagatgaagtc
tcctcaaaggaaggcagcatgtgtccttttt AI239607 (testis EST)  SEQ ID NO:13
aagaaggagaatccatttagcacctcctcagcctggctcagtgattcatatgtggctttgggaatacttgggtttt
ttctgttttgtactcttgggaatcacttctttgccatctgttagcaatgcagtcaactggagagattccgatttgt
ccagtccaaactggggtatttgaccctgatcttgtgtacagcccacacctggtgtacggtgggaagagattcctc
agccttcaaatctcagatggtatcttcctgcagcctacgtgttagggcttatcattccttgcactgtgctggtga
tcaagtttgtcctaatcatgccatgtgtagacaacaccttacaaggatccgccagggctgggaaaggaactcaaa
acactagaaaaagcattgaatggaaaatcaatatttaaaacaaagttcaatttagctggaaaaaaaaa R80991 (placental EST)  SEQ ID NO:14
ggccgcggcaaccgctacgacctggtcaacctggcagtcaagcaggtcttggccanacaagagccacctctgggtg
aaggaggaggtctggcggatggagatctacctctccctgggagtgctggccctcggcacgttgtccctgctggccg
tgacctcactgccgtccattgcaaactcgctcaactggagggagttcagcttcgttcagtcctcactgggctttgt
ggcctcgtgctgagcacactncacacgctcacctacggctggaccgcgccttcgaggagagccgctacaagttc
tacctncctcccaccttcacgntcacgctgctggtgccctgcgttcgttcatcctgggccaaagccctgttt ntac
tgccttgcattcagccgnaga

FIG. 11A

```
               1               15 16              30 31              45 46              60 61              75 76              90
2 STEAP2    MESISMMGSPKSLSE TC---LRNGINGIKD ARKVTVGVIQSDPA KSETIRLIRCEFTNV IQRRFKFASEFFPH VVDUTHHEDALTNTN      87
3 STEAP3    -------------MEK TGIDALHLTMNSSE- -KQETWVCIFTWTDG RELGLKMLQCHNSMV FHRRNFQKTT-LLPS GAEFLSYSEAAKLSG     75
4 STEAP1    --------------- ---------------- --------------- --------------- --------------- ---------------     0
5 STEAP4    --------------- ---------------- --------------- --------------- --------------- ---------------     0

91             105 106             120 121             135 136             150 151             165 166             180
2 STEAP2    FIFVNIARYTSLW DFRHLYVGETILDVQ NEMRINQYPRNAFY LASLFRDSLIVQGPN VVEAMALQLGPKDAH FQVWIGSNIQAHQ    177
3 STEAP3    MHIIAIHRENPFLT EHTEVLNRQDGHIS NFLKHINRRENPAVG LHVLGAHVIPALAL TIFAMALQSALDAE FQVFVQGDSKHQR    165
4 STEAP1    --------------- ---------------- ------MESRKDIT QEELHKMK-PRRNLE EDD-L--HKDTGETS     36
5 STEAP4    --------------- ---------------- --------------- --------------- --------------- ---------------     0

181            195 196             210 211             225 226             240 241             255 256             270
2 STEAP2    YIELAQGNF-IEIH LQEHSSARKIENLPH RINTLARGHVVVAIS BATHFLNSFVRDYE HKYYRNQQSDEAKIR HRVMAETHIHLTIM    266
3 STEAP3    VMDIVRNVGL-TPM QGELMANVKLKYIR QIATPMIFPYLSAV ICVELFYCVIRDYV YYVYEKKDNTPRMA ISHPHRIFRHTLEI    254
4 STEAP1    MLKRPVLLHHQTAH ADEFDCPSELQH-TQ BREQHLIKIELI IASLTHYTLLEYV TSHQYTSHQYFKLE LVILNVDMVSEMI    125
5 STEAP4    --------------- ---------------- --------------- --------------- --------------- ---------------     0

271            285 286             300 301             315 316             330 331             345 346             360
2 STEAP2    ESLMTIAGLLANAYQ LHYTKFREEYHLE THLQCRQQGLNSEE PAMVHVAYSLCLPMR RHEYVLFLENAXQQV HANIENSWNEEEVM    356
3 STEAP3    ENVIAIVGRGLVNR HNLRAGELVIVPMD HHLEVLHGQNEVALG LAFLMLTIVIRIIQ YVVWRFGNLIVTQA ILKRFPFSTSSAWL    344
4 STEAP1    LANYLKDGVLAVYG LSNGETFKPHLQEH QQNLEDANIEHDVE KSYEKQLALMAYQQV QQNKEDANIEHDVR    215
5 STEAP4    --------------- ---------------- --------------- ---------------A AAKATTWSTMQSSRS NPXASHLMVKEAVH     31
```

```
STEAP-1   67 LFPQWHLPIKIAAIIASLTFLYTLLREVIHPLATSHQQYFYKIPILVINKVLPMVSITLL
STEAP-2  208 LFTLWRGPVVVAISLATFFFLYSFVRDVIHPYARNQQSDFYKIPIEIVNKTLPIVAITLL
             **  *         *    *  ***  *  ****  *  ******   ** **  * ****

STEAP-1  127 ALVYLPGVIAAIVQLHNGTKYKKFPHWLDKWMLTRKQFGLLSFFFAVLHAIYSLSYPMRR
STEAP-2  268 SLVYLAGLLAAAYQLYYGTKYRRFPFWLETWLQCRKQLGLLSFFFAMVHVAYSLCLPMRR
             ****  *   **  **  ****  ** **   *     *** *******  *  ***  ****

STEAP-1  187 SYRYKLLNWAYQQVQQNKEDAWIEHDVWRMEIYVSLGIVGLAILALLAVTSIPSVSDSLT
STEAP-2  328 SERYLFLNMAYQQVHANIENSWNEEEVWRIEMYISFGIMSLGLLSLLAVTSIPSVSNALN
              * **  ******* *   *   ***  *  *  **    *   *  ***********

STEAP-1  247 WREFHYTQSKLGIVSLLLGTIHALIFAWNKWIDIKQFVWYTPPTFMIAVFLPIVVLI  portion of
                                                                        SEQ ID NO:2
STEAP-2  388 WREFSFIQSTLGYVALLISTFHVLTYGWKRAFEEEYYRFYTPPNFVLALVLPSIVIL  portion of
             ****   ***  ** *  * ***  *  **  *           ****   *   **  *    SEQ ID NO:3
```

FIG. 11D

```
STEAP-1   66  ELFPQWHLPIKIAAIIASLTFLYTLLREVIHPLATSHQQYFYKIPILVINKVLPMVSITL
STEAP-3  195  QLFPMWRFPFYLSAVLCVFLFFYCVIRDVIYPYVYEKKDNTFRMAISIPNRIFPICALTL
              ***  *   *      *     * *    *  * **  *          *   *     **

STEAP-1  126  LALVYLPGVIAAIVQLHNGTKYKKFPHWLDKWMLTRKQFGLLSFFFAVLHAIYSLSYPMR
STEAP-3  255  LALVYLPGVIAAILQLYRGTKYRRFPDWLDHWMLCRKQLGLVALGFAFLHVLYTLVIPIR
              ************ ** ****  ** *** *** ***  ** **  *  *   *    *

STEAP-1  186  RSYRYKLLNWAYQQVQQNKEDAWIEHDVWRMEIYVSLGIVGLAILALLAVTSIPSVSDSL
STEAP-3  315  YYVRWRLGNLTVTQAILKKENPFSTSSAWLSDSYVALGILGFFLFVLLGITSLPSVSNAV
               * *    *   *  **   *          *   ****  *   ** ** **  ****

STEAP-1  246  TWREFHYIQSKLGIVSLLLGTIHALIFAWNKWIDIKQFVWYTPPTFMIAVFLPIVVLIFK
STEAP-3  375  NWREFRFVQSKLGYLTLILCTAHTLVYGGKRFLSPSNLRWYLPAAYVLGLIIPCTVLVIK
               ****    *****   * *  *  *               **         *  * *

STEAP-1  306  SILFLPCLRKKILKIRHGWEDVTK   portion of SEQ ID NO:2
STEAP-3  435  FVLIMPCVDNTLTRIRQGWERNSK   portion of SEQ ID NO:10
                *  **      ** ***  *
```

FIG. 11E

```
STEAP-2   29  RKVTVGVIGSGDFAKSLTIRLIRCGYHVVIGSRNPKFASEFFPHVVDVTHREDALTKTNI
STEAP-3   16  KQETVCIFGTGDFGRSIGLKMLQCGYSVVFGSRNPQ-KTTLLPSGAEVLSYSEAAKKSCI
               *    *  **    **     ***  ** *****        *      *     *   *

STEAP-2   89  IFVAIHREHYTSLWDLRHLLVGKILIDVSNNMRINQYPESNAEYLASLFPDSLIVKGFNV
STEAP-3   77  IIIAIHREHYDFLPELTEVLNGKILVDISNNLKTNQYPESNAEYIAHLVPGAHVVKAFNT
              *  *******    * *  * ****  ** *** ************  *  *     *  *

STEAP-2  149  VSAWALQLGPKDASRQVYICSNNIQARQQVIELARQLNFIPIDLGSLSSAREIENLPLRL
STEAP-3  137  ISAWALQSGALDASRQVFVCGNDSKAKQRVMDIVRNLGLTPMDQGSLMAAKEIEKYPLQL
               ****** *  ****** *  *    * *  *  * **       ***  *** *  *

STEAP-2  209  FTLWRGPVVVAISLATFFFLYSFVRDVIHPYARNQQSDFYKIPIEIVNKTLPIVAITLLS
STEAP-3  197  FPMWRFPFYLSAVLCVFLFFYCVIRDVIYPYVYEKKDNTFRMAISIPNRIFPITALTLLA
                 **  *    *  *  * ** * ****  *           *  *  *    ***  *

STEAP-2  269  LVYLAGLLAAAYQLYYGTKYRRFPPWLETWLQCRKQLGLLSFFFAMVHVAYSLCLPMRRS
STEAP-3  257  LVYLPGVIAAILQLYRGTKYRRFPDWLDHWMLCRKQLGLVALGFAFLHVLYTLVIPIRYY
              ****    ***  ***  *********  **   ****      *    **    *    *   *

STEAP-2  329  ERYLFLNMAYQQVHANIENSWNEEEVWRIEMYISFGIMSLGLLSLLAVTSIPSVSNALNW
STEAP-3  317  VRWRLGNLTVTQAILKKENPFSTSSAWLSDSYVALGILGFFLFVLLGITSLFSVSNAVNW
                *    *       *    **       *     *    *    *  ** ***** **

STEAP-2  389  REFSFIQSTLGYVALLISTPHVLIYGWKRAFEEEYYRFYTPPNFVLALVLPSIVIL  portion of
                                                                        SEQ ID NO:8
STEAP-3  377  REFRFVQSKLGYLTLILCTAHTLVYGGKRFLSPSNLRNVLPAAYVLGLIIPCIVLV  portion of
              ***  *  ** ***  *   **  * **     **  *     **   * *      *  *   SEQ ID NO:10
```

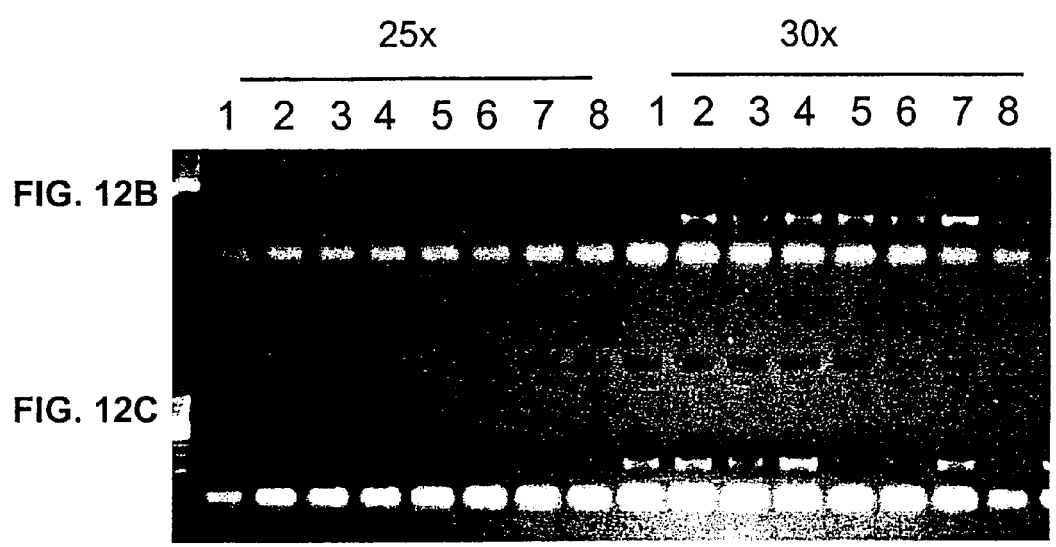

|  | 25x | 30x |
|---|---|---|
|  | 1 2 3 4 5 6 7 8 | 1 2 3 4 5 6 7 8 |

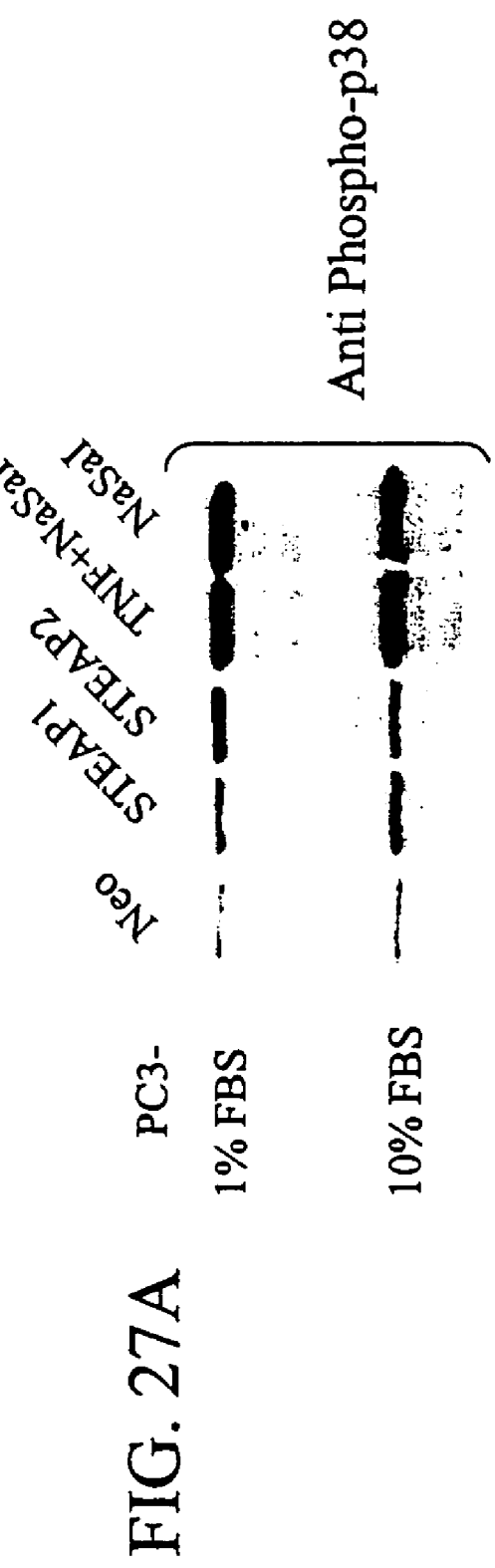
FIG. 27A
FIG. 27B

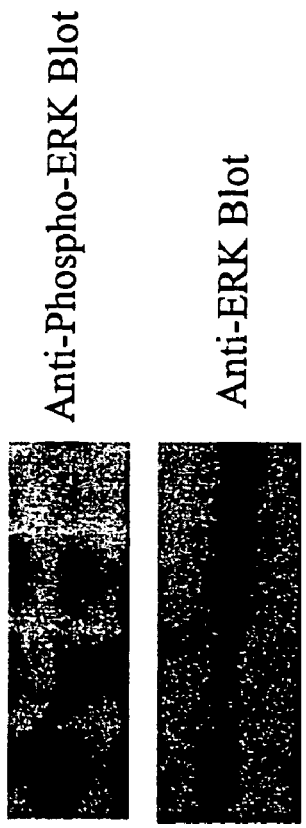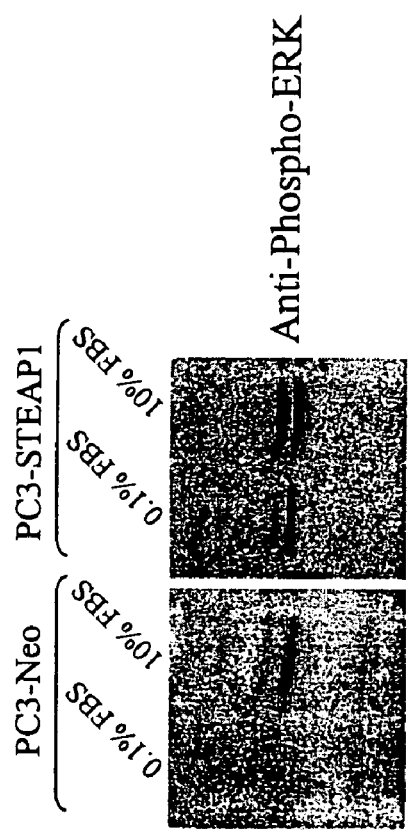
FIG. 28A
FIG. 28B

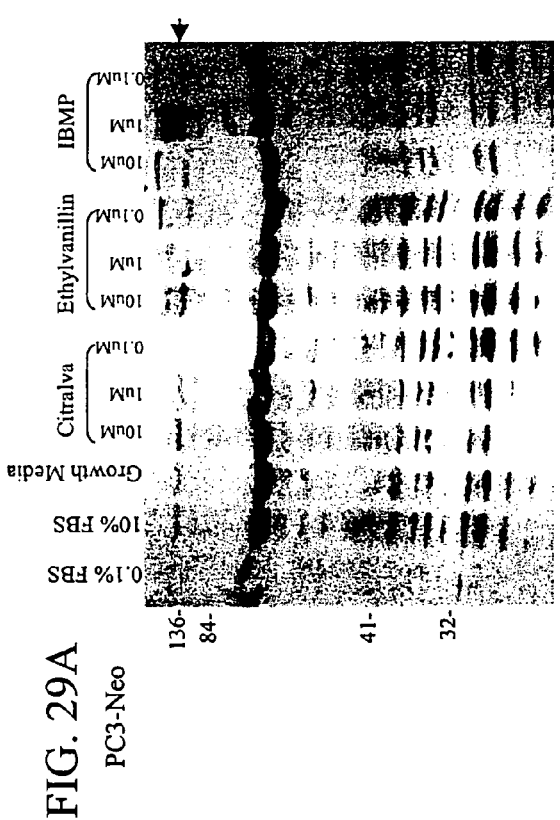
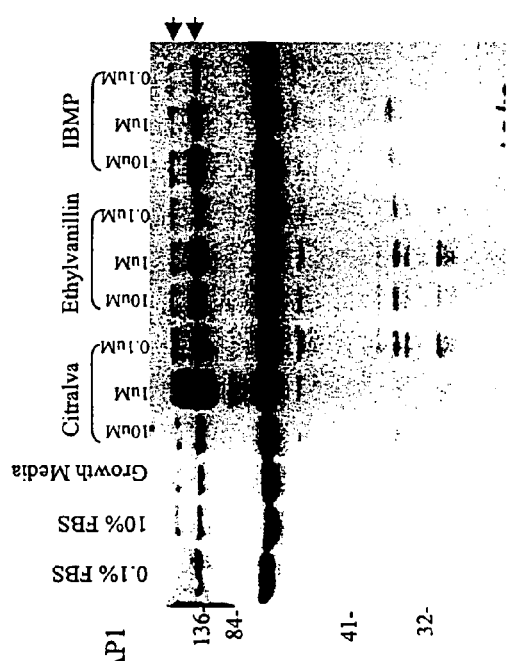
FIG. 29A
PC3-Neo
FIG. 29B
PC3-STEAP1

SERPENTINE TRANSMEMBRANE ANTIGENS EXPRESSED IN HUMAN CANCERS AND USES THEREOF

This application is a continuation of U.S. Ser. No. 10/165,044 filed 6 Jun. 2002, now abandoned, which claims priority under 35. U.S.C. §119(e) to provisional application No. 60/296,656 filed 6 Jun. 2001, and which is a continuation-in-part of U.S. Ser. No. 09/455,486 filed 6 Dec. 1999, now U.S. Pat. No. 6,833,438, which is a continuation-in-part of U.S. Ser. No. 09/323,873 filed 1 Jun. 1999, now U.S. Pat. No. 6,329,503, which claims priority under 35. U.S.C. §119(e) from U.S. Ser. No. 60/091,183 filed 30 Jun. 1998 and U.S. Ser. No. 60/087,520 filed Jun. 1, 1998. The contents of these applications are incorporated herein by reference.

FIELD OF THE INVENTION

The invention described herein relates to a family of novel genes and their encoded proteins and tumor antigens, termed STEAPs, and to diagnostic and therapeutic methods and compositions useful in the management of various cancers, particularly including prostate cancer, colon cancer, bladder cancer, lung cancer, ovarian cancer and pancreatic cancer.

BACKGROUND OF THE INVENTION

Cancer is the second leading cause of human death next to coronary disease. Worldwide, millions of people die from cancer every year. In the United States alone, cancer causes the death of well over a half-million people annually, with some 1.4 million new cases diagnosed per year. While deaths from heart disease have been declining significantly, those resulting from cancer generally are on the rise. In the early part of the next century, cancer is predicted to become the leading cause of death.

Worldwide, several cancers stand out as the leading killers. In particular, carcinomas of the lung, prostate, breast, colon, pancreas, and ovary represent the primary causes of cancer death. These and virtually all other carcinomas share a common lethal feature. With very few exceptions, metastatic disease from a carcinoma is fatal. Moreover, even for those cancer patients who initially survive their primary cancers, common experience has shown that their lives are dramatically altered. Many cancer patients experience strong anxieties driven by the awareness of the potential for recurrence or treatment failure. Many cancer patients experience physical debilitations following treatment. Many cancer patients experience a recurrence.

Worldwide, prostate cancer is the fourth most prevalent cancer in men. In North America and Northern Europe, it is by far the most common male cancer and is the second leading cause of cancer death in men. In the United States alone, well over 40,000 men die annually of this disease—second only to lung cancer. Despite the magnitude of these figures, there is still no effective treatment for metastatic prostate cancer. Surgical prostatectomy, radiation therapy, hormone ablation therapy, and chemotherapy continue to be the main treatment modalities. Unfortunately, these treatments are ineffective for many and are often associated with undesirable consequences.

On the diagnostic front, the lack of a prostate tumor marker that can accurately detect early-stage, localized tumors remains a significant limitation in the management of this disease. Although the serum PSA assay has been a very useful tool, its specificity and general utility is widely regarded as lacking in several important respects.

Progress in identifying additional specific markers for prostate cancer has been improved by the generation of prostate cancer xenografts that can recapitulate different stages of the disease in mice. The LAPC (Los Angeles Prostate Cancer) xenografts are prostate cancer xenografts that have survived passage in severe combined immune deficient (SCID) mice and have exhibited the capacity to mimic disease progression, including the transition from androgen dependence to androgen independence and the development of metastatic lesions (U.S. Pat. No. 6,107,540; Klein et al., 1997, Nat. Med. 3:402). More recently identified prostate cancer markers include PCTA-1 (Su et al., 1996, Proc. Natl. Acad. Sci. USA 93: 7252), prostate stem cell antigen (PSCA) (Reiter et al., 1998, Proc. Natl. Acad. Sci. USA 95: 1735), and STEAP (Hubert et al., 1999, Proc. Natl. Acad. Sci. USA 96: 14523).

While previously identified markers such as PSA, PSM, PCTA and PSCA have facilitated efforts to diagnose and treat prostate cancer, there is need for the identification of additional markers and therapeutic targets for prostate and related cancers in order to further improve diagnosis and therapy.

SUMMARY OF THE INVENTION

The present invention relates to a novel family of cell surface serpentine transmembrane antigens. Two of the proteins in this family are exclusively or predominantly expressed in the prostate, as well as in prostate cancer, and thus members of this family have been termed "STEAP" (Six Transmembrane Epithelial Antigen of the Prostate). Four particular human STEAPs are described and characterized herein. The human STEAPs exhibit a high degree of structural conservation among them but show no significant structural homology to any known human proteins.

The prototype member of the STEAP family, STEAP-1, appears to be a type IIIa membrane protein expressed predominantly in prostate cells in normal human tissues. Structurally, STEAP-1 is a 339 amino acid protein characterized by a molecular topology of six transmembrane domains and intracellular N- and C-termini, suggesting that it folds in a "serpentine" manner into three extracellular and two intracellular loops. STEAP-1 protein expression is maintained at high levels across various stages of prostate cancer. Moreover, STEAP-1 is highly over-expressed in certain other human cancers. In particular, cell surface expression of STEAP-1 has been definitively confirmed in a variety of prostate and prostate cancer cells, lung cancer, bladder cancer cells and colon cancer cells. These characteristics indicate that STEAP-1 is a specific cell-surface tumor antigen expressed at high levels in prostate, bladder, colon, and other cancers.

A second member of the family, STEAP-2, is a 454 amino acid protein with a predicted molecular topology similar to that of STEAP-1. STEAP-2, like STEAP-1, is prostate-specific in normal human tissues and is also expressed in prostate cancer. Alignment of the STEAP-2 and STEAP-1 ORFs shows 54.9% identity over a 237 amino acid residue overlap, and the locations of the six putative transmembrane domains in STEAP-2 coincide with the locations of the transmembrane domains in STEAP-1 (FIG. 11A-B).

STEAP-3 and STEAP-4 are also described herein. These are also structurally related, and show unique expression profiles. In particular, STEAP-3 and STEAP-4 appear to show a different tissue restriction patterns. An amino acid sequence alignment of all four STEAPs is shown in FIG. 11A-B.

The invention provides polynucleotides corresponding or complementary to all or part of the STEAP gene as described herein, mRNAs, and/or coding sequences, preferably in isolated form, including polynucleotides encoding STEAP proteins and fragments thereof, DNA, RNA, DNA/RNA hybrid, and related molecules, polynucleotides or oligonucleotides complementary to the STEAP gene or mRNA sequences or parts thereof, and polynucleotides or oligonucleotides which hybridize to the STEAP gene, mRNAs, or to STEAP-encoding polynucleotides. Also provided are means for isolating cDNAs and the genes encoding STEAP. Recombinant DNA molecules containing STEAP polynucleotides, cells transformed or transduced with such molecules, and host vector systems for the expression of STEAP gene products are also provided.

The invention further provides STEAP proteins and polypeptide fragments thereof. The invention further provides antibodies that bind to STEAP proteins and polypeptide fragments thereof, including polyclonal and monoclonal antibodies, murine and other mammalian antibodies, chimeric antibodies, humanized and fully human antibodies, and antibodies labeled with a detectable market, and antibodies conjugated to radionuclides/radioisotopes, toxins or other therapeutic compositions. The invention further provides methods for detecting the presence of STEAP polynucleotides and proteins in various biological samples, as well as methods for identifying cells that express a STEAP. The invention further provides various therapeutic compositions and strategies for treating prostate and other cancers, including particularly, antibody, vaccine and small molecule therapy.

The invention further provides methods for detecting the presence of STEAP polynucleotides and proteins in various biological samples, as well as methods for identifying cells that express STEAP. The invention further provides various therapeutic compositions and strategies, including particularly, antibody, vaccine and small molecule therapy, for treating cancers of the prostate. The extracellular nature of this protein presents a number of therapeutic approaches using molecules that target STEAP and its function, as well as molecules that target other proteins, factors and ligands that interact with STEAP. These therapeutic approaches include antibody therapy with anti-STEAP antibodies, small molecule therapies, and vaccine therapies. In addition, given its up-regulated expression in prostate cancer, STEAP is useful as a diagnostic, staging and/or prognostic marker for prostate cancer and, similarly, may be a marker for other cancers expressing this protein. In particular, STEAP-1 provides an excellent marker for identifying prostate cancer metastases.

BRIEF DESCRIPTION OF THE FIGURES

FIG. 2. Predominant expression of STEAP-1 in prostate tissue. First strand cDNA was prepared from 16 normal tissues, the LAPC xenografts (4AD, 4AI and 9AD) and HeLa cells. Normalization was performed by PCR using primers to actin and GAPDH. Semi-quantitative PCR, using primers derived from STEAP-1 (8P1D4) cDNA (FIG. 1A-B), shows predominant expression of STEAP-1 in normal prostate and the LAPC xenografts. The following primers were used to amplify STEAP-1:

8P1D4.1 5' ACTTTGTTGATGACCAGGATTGGA 3' (SEQ ID NO: 4)

8P1D4.2 5' CAGAACTTCAGCACACACAGGAAC 3' (SEQ ID NO: 5).

FIG. 2A. Lanes are as follows: 1 brain; 2 prostate; 3 LAPC-4 AD; 4 LAPC-4 AI; 5 LAPC-9 AD; 6 HeLa; 7 murine cDNA; 8 negative control.

FIG. 2B. Lanes are as follows: 1 brain; 2 heart; 3 kidney; 4 liver; 5 lung; 6 pancreas; 7 placenta; 8 skeletal muscle.

FIG. 2C. Lanes are as follows: 1 colon; 2 ovary; 3 leukocytes; 4 prostate; 5 small intestine; 6 spleen; 7 testis; 8 thymus.

FIG. 3. Northern blot analyses of STEAP-1 expression in various normal human tissues and prostate cancer xenografts, showing predominant expression of STEAP-1 in prostate tissue.

Figure 1C:
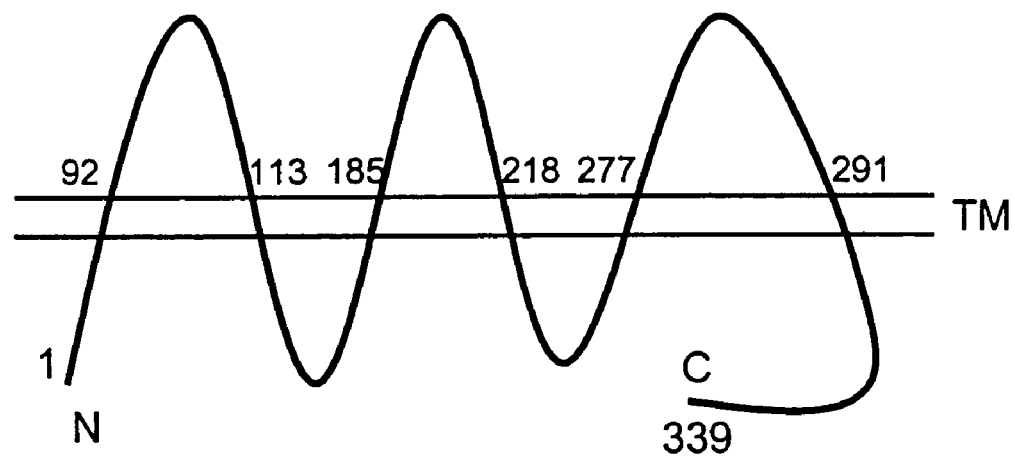
FIG. 1. STEAP-1 structure. 1A-B: Nucleotide and deduced amino acid sequences of STEAP-1 (8P1B4) clone 10 cDNA (SEQ ID NOS. 1 and 2, respectively). The start methionine is indicated in bold at amino acid residue position 1 and six putative transmembrane domains are indicated in bold and are underlined. 1C: Schematic representation of STEAP-1 transmembrane orientation; amino acid residues bordering the predicted extracellular domains are indicated and correspond to the numbering scheme of FIG. 1A-B. 1D: G/C rich 5' non-coding sequence of the STEAP-1 gene (SEQ ID NO: 3) as determined by overlapping sequences of clone 10 and clone 3.
Figure 3A:
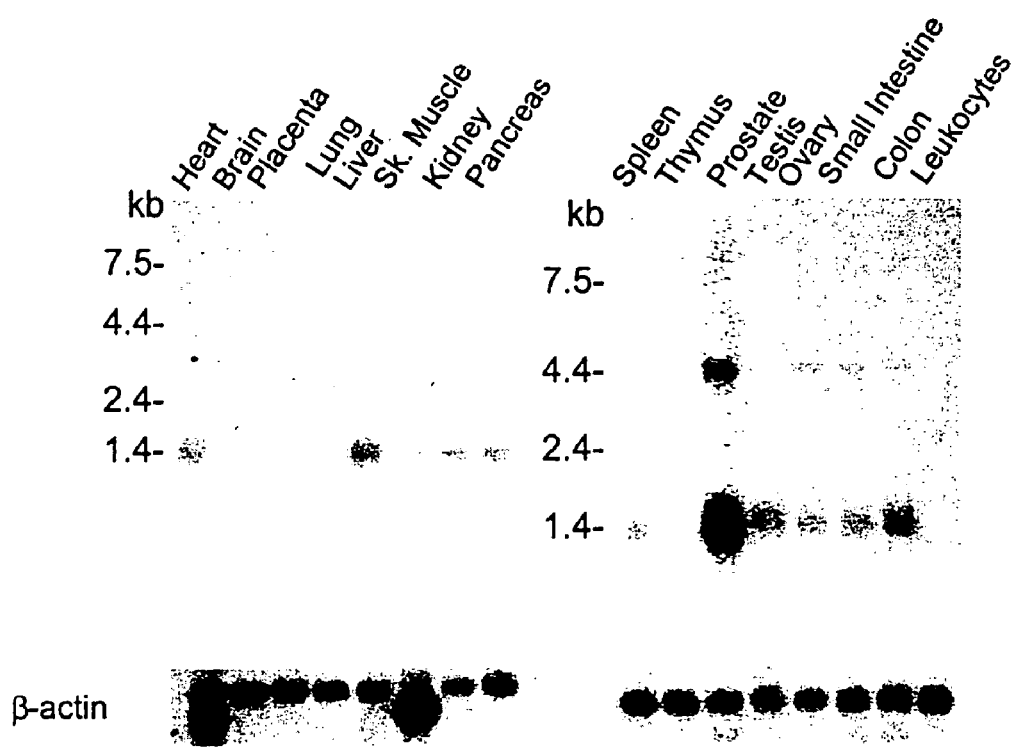

FIG. 3A: Two multiple tissue northern blots (Clontech) were probed with a full length STEAP cDNA clone 10 (FIG. 1A-B). Size standards in kilobases (kb) are indicated on the side. Each lane contains 2 μg of mRNA that was normalized by using a β-actin probe. A1 brain; A2 amygdala; A3 caudate nucleus; A4 cerebellum; A5 cerebral cortex; A6 frontal lobe; A7 hippocampus; A8 medulla oblongata; B1 occipital lobe; B2 putamen; B3 substantia nigra; B4 temporal lobe; B5 thalamus; B6 sub-thalamic nucleus; B7 spinal cord; C1 heart; C2 aorta; C3 skeletal muscle; C4 colon; C5 bladder; C6 uterus; C7 prostate; C8 stomach; D1 testis; D2 ovary; D3 pancreas; D4 pituitary gland; D5 adrenal gland; D6 thyroid gland; D7 salivary gland; D8 mammary gland; E1 kidney; E2 liver; E3 small intestine; E4 spleen; E5 thymus; E6 peripheral leukocytes; E7 lymph node; E8 bone marrow; F1 appendix; F2 lung; F3 trachea; F4 placenta; G1 fetal brain; G2 fetal heart; G3 fetal kidney; G4 fetal liver; G5 fetal spleen; G6 fetal thymus; G7 fetal lung.

Figure 3B:
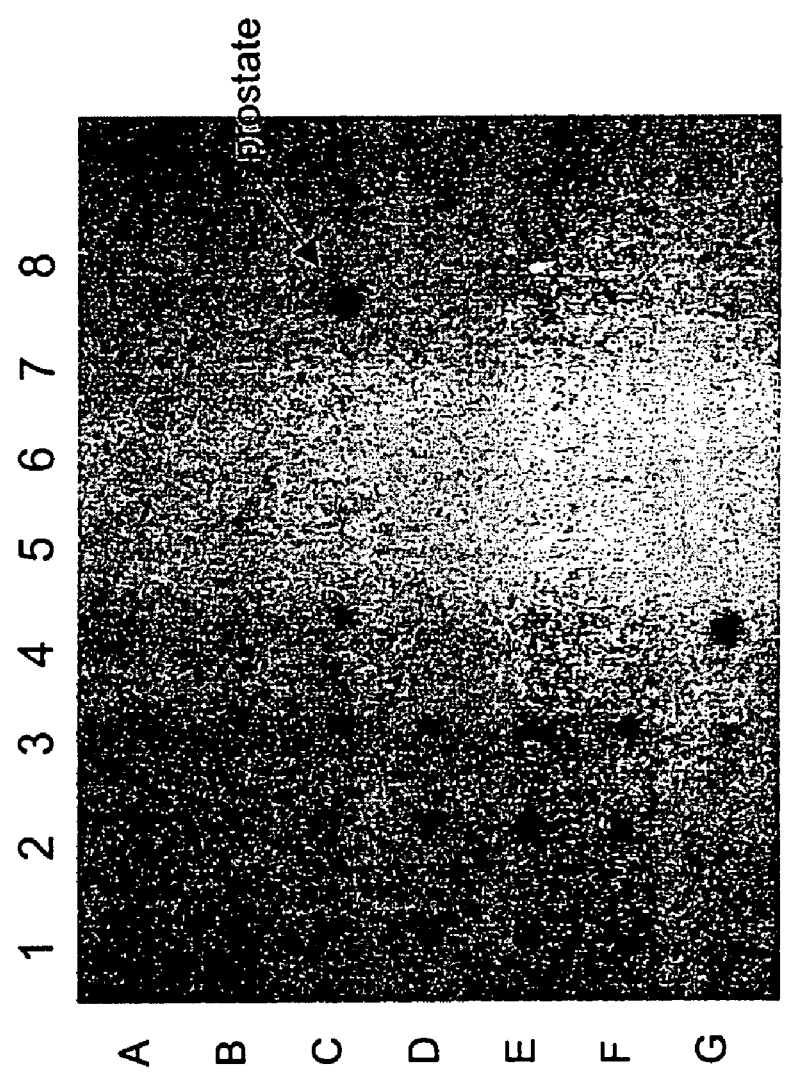

FIG. 3B: Multiple tissue RNA dot blot (Clontech, Human Master Blot cat# 7770-1) probed with STEAP-1 cDNA clone 10 (FIG. 1A-B), showing approximately five-fold greater expression in prostate relative to other tissues with significant detectable expression.

FIG. 4A-B. Nucleotide sequence (SEQ ID NO: 6) of STEAP-1 GTH9 clone corresponding to the 4 kb message on northern blots (FIG. 3A). The sequence contains an intron of 2399 base pairs relative to the STEAP-1 clone 10 sequence of FIG. 1A-B; coding regions are nucleotides 96-857 and 3257-3510 (indicated in bold). The start ATG is in bold and underlined, the STOP codon is in bold and underlined, and the intron-exon boundaries are underlined.

Figure 5A:
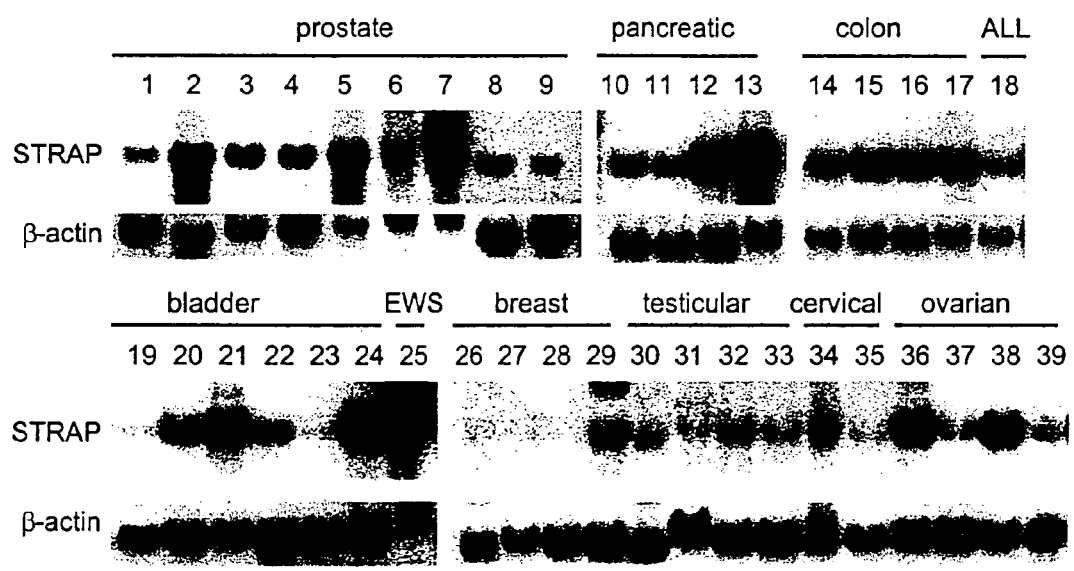
Figure 5B:
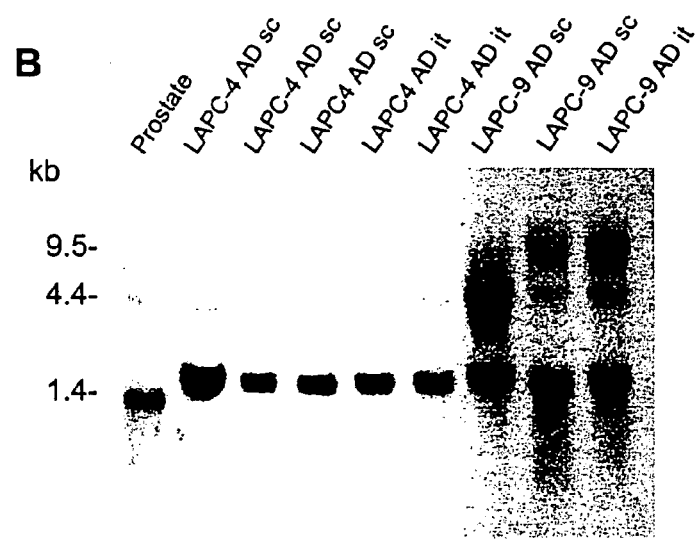

FIG. 5. Expression of STEAP-1 in prostate and multiple cancer cell lines and prostate cancer xenografts. Xenograft and cell line filters were prepared with 10 μg of total RNA per lane. The blots were analyzed using the STEAP-1 clone 10 as probe. All RNA samples were normalized by ethidium bromide staining and subsequent analysis with a β-actin probe. FIG. 5A: Expression in various cancer cell lines and xenografts and prostate. Lanes as follows: (1) PrEC cells, (2) normal prostate tissue, (3) LAPC-4 AD xenograft, (4) LAPC-4 AI xenograft, (5) LAPC-9 AD xenograft, (6) LAPC-9 AI xenograft, (7) LNCaP cells, (8) PC-3 cells, (9) DU145 cells, (10) PANC-1 cells, (11) BxPC-3 cells, (12) HPAC cells, (13) Capan-1 cells, (14) CACO-2 cells, (15) LOVO cells, (16) T84 cells, (17) COLO-205 cells, (18) KCL-22 cells (acute lymphocytic leukemia, ALL), (19) HT1197 cells, (20) SCABER cells, (21) UM-UC-3 cells, (22) TCCSUP cells, (23) J82 cells, (24) 5637 cells, (25) RD-ES cells (Ewing sarcoma, EWS), (26) CAMA-1 cells, (27) DU4475 cells, (28) MCF-7 cells, (29) MDA-MB-435s cells, (30) NTERA-2 cells, (31) NCCIT cells, (32) TERA-1 cells, (33) TERA-2 cells, (34) A431 cells, (35) HeLa cells, (36) OV-1063 cells, (37) PA-1 cells, (38) SW 626 cells, (39) CAOV-3 cells. FIG. 5B: The expression of STEAP-1 in subcutaneously (sc) grown LAPC xenografts compared to the expression in LAPC-4 and LAPC-9 xenografts grown in the tibia (it) of mice.

Figure 6A:
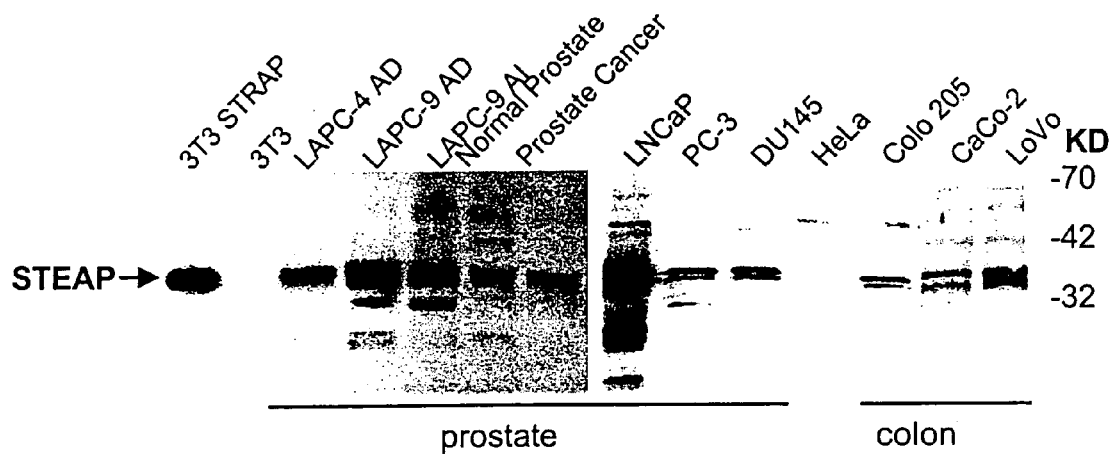
Figure 6B:
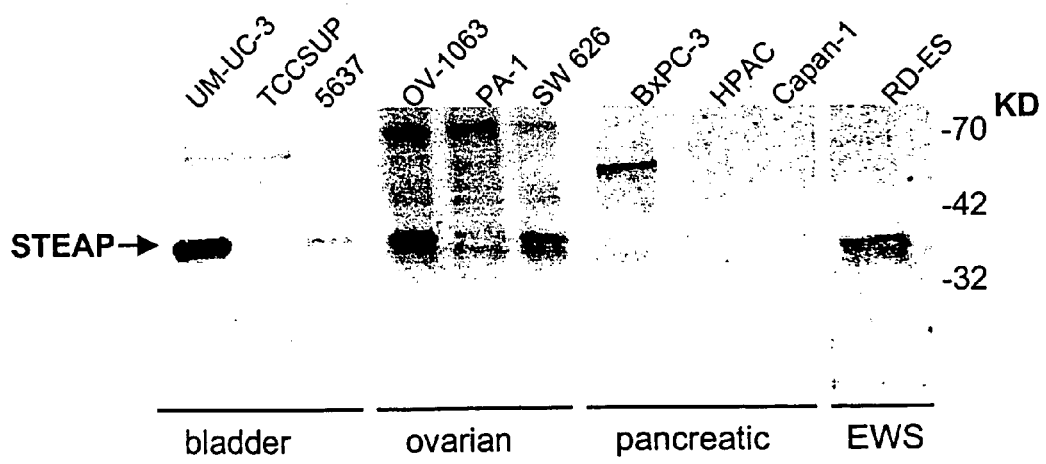

FIG. 6A-B. Western blot analysis of STEAP-1 protein expression in tissues and multiple cell lines. Western blots of cell lysates prepared from prostate cancer xenografts and cell lines were probed with a polyclonal anti-STEAP-1 antibody preparation. The samples contain 20 µg of protein and were normalized with anti-Grb-2 probing of the western blots.

Figure 7A:
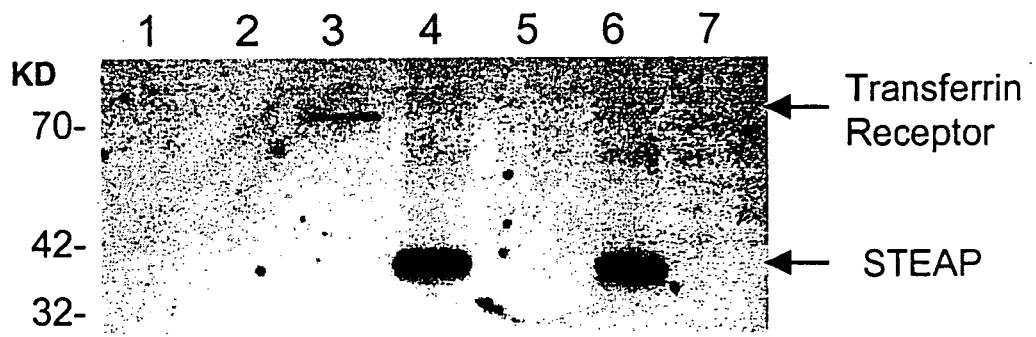
Figure 7B:
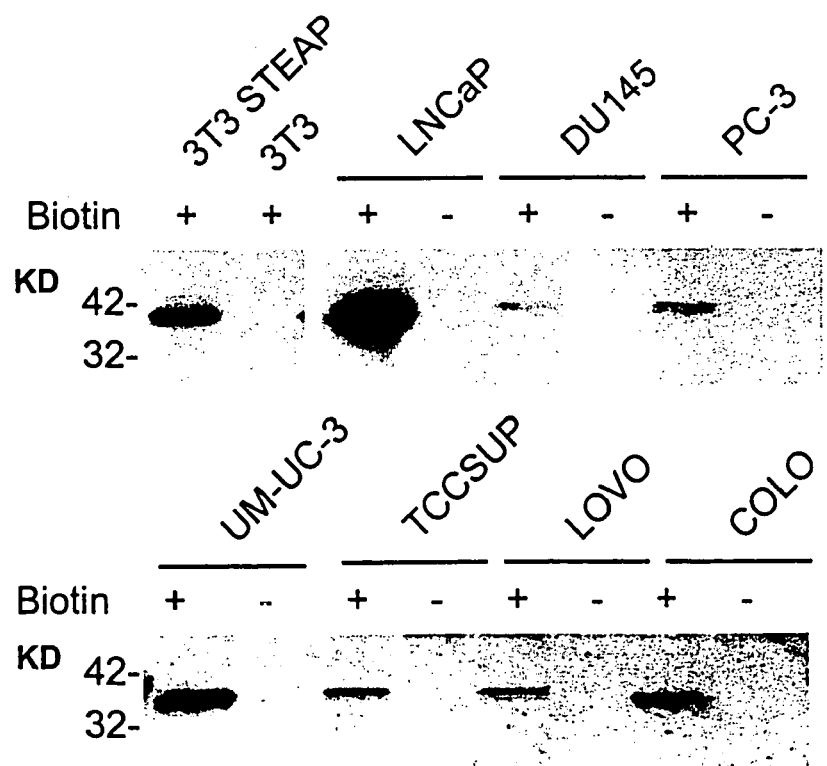

FIG. 7A-B. Cell surface biotinylation of STEAP-1. FIG. 7A: Cell surface biotinylation of 293T cells transfected with vector alone or with vector containing cDNA encoding 6His-tagged STEAP-1. Cell lysates were immunoprecipitated with specific antibodies, transferred to a membrane and probed with horseradish peroxidase-conjugated streptavidin. Lanes 1-4 and 6 correspond to immunoprecipitates from lysates prepared from STEAP-1 expressing 293T cells. Lanes 5 and 7 are immunoprecipitations from vector transfected cells. The immunoprecipitations were performed using the following antibodies: (1) sheep non-immune, (2) anti-Large T antigen, (3) anti-CD71 (transferrin receptor), (4) anti-His, (5) anti-His, (6) anti-STEAP-1, (7) anti-STEAP-1. FIG. 7B: Prostate cancer (LNCaP, PC-3, DU145), bladder cancer (UM-UC-3, TCCSUP) and colon cancer (LOVO, COLO) cell lines were either biotinylated (+) or not (−) prior to lysis. Western blots of streptavidin-gel purified proteins were probed with anti-STEAP-1 antibodies. Molecular weight markers are indicated in kilodaltons (kD).

FIG. 8. Immunohistochemical analysis of STEAP-1 expression using anti-STEAP-1 polyclonal antibody. Tissues were fixed in 10% formalin and embedded in paraffin. Tissue sections were stained using anti-STEAP-1 polyclonal antibodies directed towards the N-terminal peptide. FIG. 8A: LNCaP cells probed in the presence of N-terminal STEAP-1 peptide 1, FIG. 8B: LNCaP plus non specific peptide 2, FIG. 8C: normal prostate tissue, FIG. 8D: grade 3 prostate carcinoma, FIG. 8E: grade 2, Gleason 7 prostate carcinoma, FIG. 8F: LAPC-9 AD xenograft, FIG. 8G: normal bladder, FIG. 8H: normal colon. All images are at 400× magnification.

FIG. 9A-D. Nucleotide (SEQ ID NO: 7) and deduced amino acid (SEQ ID NO: 8) sequences of STEAP-2 (98P4B6) clone GTD3 cDNA. The start methionine and Kozak sequence are indicated in bold, and the putative transmembrane domains are underlined in bold. The 5' UTR exhibits a high GC content of 72%.

FIG. 10A-E. Nucleotide (SEQ ID NO: 9) and deduced amino acid (SEQ ID NO: 10) sequences of STEAP-3. Kozak region is in bold.

FIG. 10F. Nucleotide sequences (SEQ ID NOS: 11-14, respectively) of dbEST database entries corresponding to additional STEAP family members obtained by searching with the protein sequence of STEAP-1.

Figure 11B:
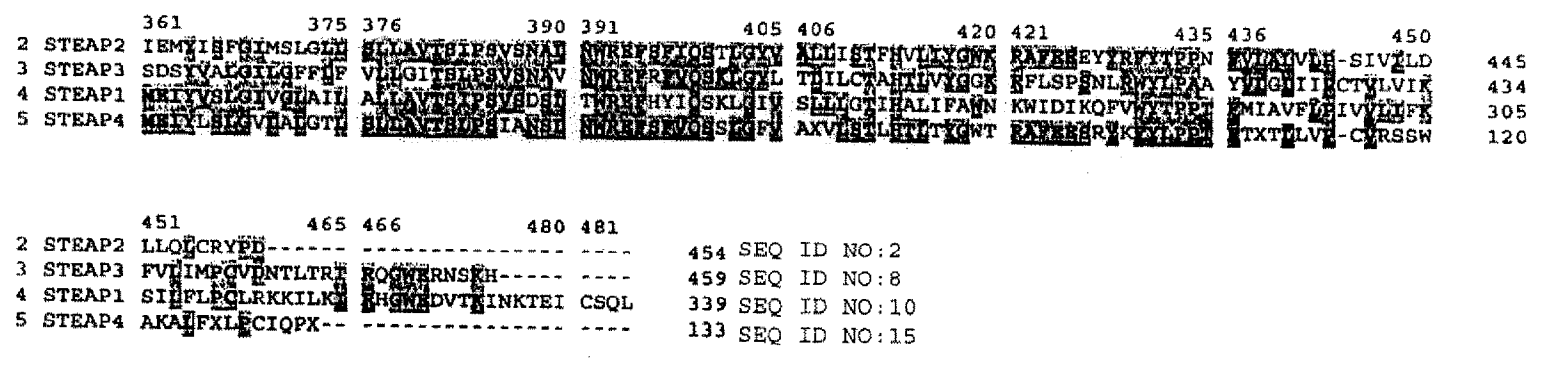

FIG. 11. Primary structural comparisons of STEAP family proteins:

FIGS. 11A-B. Amino acid sequence alignment of STEAPs 1-4 (SEQ ID NOS: 2, 8, 10 and 15, respectively) using the PIMA 1.4 program; transmembrane domains identified by the SOSUI program are in bold. PIMA maximal linkage clustering results shown; identical residues shown in bold.

FIG. 11C. Amino acid sequence alignment of STEAP-1 (8P1D4 clone 10; SEQ ID NO: 2) and STEAP-2 (98P4B6 clone GTD3; SEQ ID NO: 8) sequences. The alignment was performed using the SIM alignment program of the Baylor College of Medicine Search Launcher Web site. Transmembrane domains are indicated in boldface. The results show a 54.9% identity in a 237 residues overlap (Score: 717.0; Gap frequency: 0.0%).

FIG. 11D. Amino acid sequence alignment of STEAP-1 (SEQ ID NO: 2) and STEAP-3 (98P4B6 clone GTD3; SEQ ID NO: 10) sequences. Identical residues indicated with asterisks. SIM results: 40.9% identity in 264 residues overlap; Score: 625.0; Gap frequency: 0.0%.

FIG. 11E. Amino acid sequence alignment of STEAP-2 (SEQ ID NO: 8) and STEAP-3 (98P4B6 clone GTD3; SEQ ID NO: 10) sequences. Identical residues indicated with asterisks. SIM results: 47.8% identity in 416 residues overlap; Score: 1075.0; Gap frequency: 0.2%.

Figure 12A:
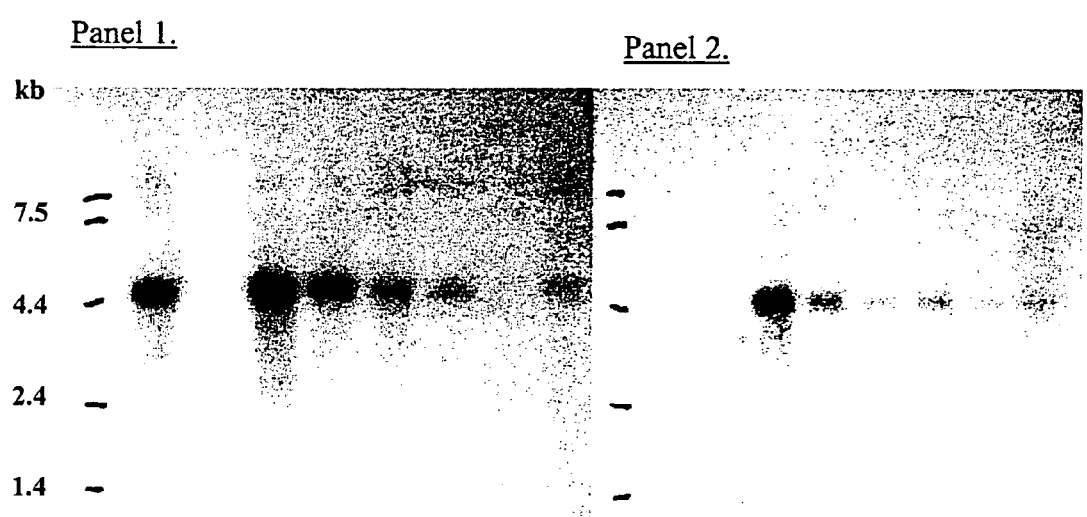

FIG. 12. Expression of STEAP-3 mRNA in normal tissues by northern blot (FIG. 12A-B) and RT-PCR (FIG. 12B). For RT-PCR analysis, first strand cDNA was prepared from 16 normal tissues. Normalization was performed by PCR using primers to actin and GAPDH. Semi-quantitative PCR, using primers to AI139607, shows predominant expression of AI139607 in placenta and prostate after 25 cycles of amplification. The following primers were used to amplify AI139607:

AI139607.1 5' TAGGACAACTTGATCACCAGCA 3' (SEQ ID NO: 16)
AI139607.2 5' TGTCCAGTCCAAACTGGGTTATTT 3' (SEQ ID NO: 17).

FIG. 12A. Lanes are as follows (from left to right): Panel 1: heart, brain, placenta, lung, liver, skeletal muscle, kidney and pancreas; Panel 2: spleen, thymus, prostate, testis, ovary, small intestine, colon and white blood cells.

FIG. 12B. Lanes are as follows: 1 brain; 2 heart; 3 kidney; 4 liver; 5 lung; 6 pancreas; 7 placenta; 8 skeletal muscle.

FIG. 12C. Lanes are as follows: 1 colon; 2 ovary; 3 leukocytes; 4 prostate; 5 small intestine; 6 spleen; 7 testis; 8 thymus.

FIG. 13. Predominant expression of STEAP-4/R80991 in liver. First strand cDNA was prepared from 16 normal tissues. Normalization was performed by PCR using primers to actin and GAPDH. Semi-quantitative PCR, using primers to R80991, shows predominant expression of R80991 in liver after 25 cycles of amplification. The following primers were used to amplify R80991:

R80991.1    5'AGGGAGTTCAGCTTCGTTCAGTC3' (SEQ ID NO:18)
R80991.2    5'GGTAGAACTTGTAGCGGCTCTCCT3' (SEQ ID NO: 19).

Figure 13A:

FIG. 13A. Lanes are as follows: 1 brain; 2 heart; 3 kidney; 4 liver; 5 lung; 6 pancreas; 7 placenta; 8 skeletal muscle.

Figure 13B:
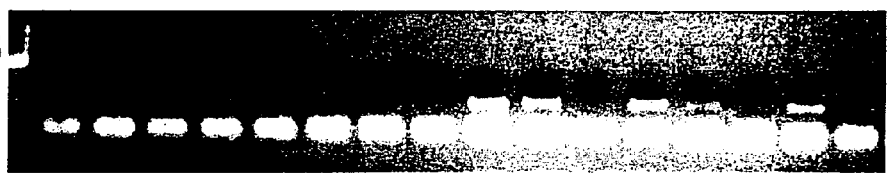

FIG. 13B. Lanes are as follows: 1 colon; 2 ovary; 3 leukocytes; 4 prostate; 5 small intestine; 6 spleen; 7 testis; 8 thymus.

FIG. 14. Predominant expression of STEAP-2 (98P4B6) in prostate tissue. First strand cDNA was prepared from 8 normal tissues, the LAPC xenografts (4AD, 4AI and 9AD) and HeLa cells. Normalization was performed by PCR using primers to actin and GAPDH. Semi-quantitative PCR, using primers to 98P4B6, shows predominant expression of 98P4B6 in normal prostate and the LAPC xenografts. The following primers were used to amplify STEAP II:

98P4B6.1    5'GACTGAGCTGGAACTGGAATTTGT3' (SEQ ID NO: 20)
98P4B6.2    5'TTTGAGGAGACTTCATCTCACTGG3' (SEQ ID NO: 21)

Figure 14A:
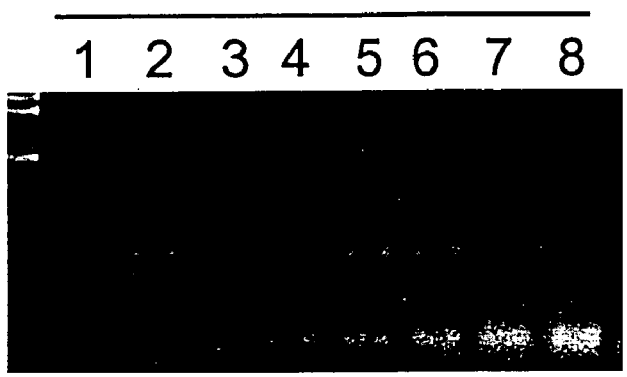

FIG. 14A. Lanes are as follows: 1 brain; 2 prostate; 3 LAPC-4 AD; 4 LAPC-4 AI; 5 LAPC-9 AD; 6 HeLa; 7 murine cDNA; 8 negative control.

Figure 14B:
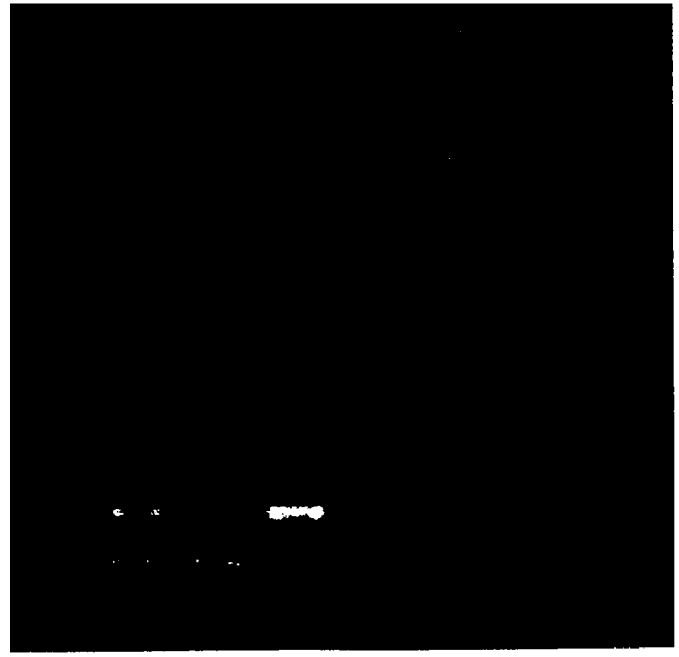

FIG. 14B. Lanes are as follows: 1 colon; 2 ovary; 3 leukocytes; 4 prostate; 5 small intestine; 6 spleen; 7 testis; 8 thymus.

FIG. 15. Expression of the prostate-specific STEAP-2/98P4B6 gene in normal tissues and in prostate cancer xenografts determined by Northern blot analysis. Human normal tissue filters (A and B) were obtained from CLONTECH and contain 2 µg of mRNA per lane. Xenograft filter (C) was prepared with 10 µg of total RNA per lane. The blots were analyzed using the SSH derived 98P4B6 clone as probe. All RNA samples were normalized by ethidium bromide staining.

Figure 15A:
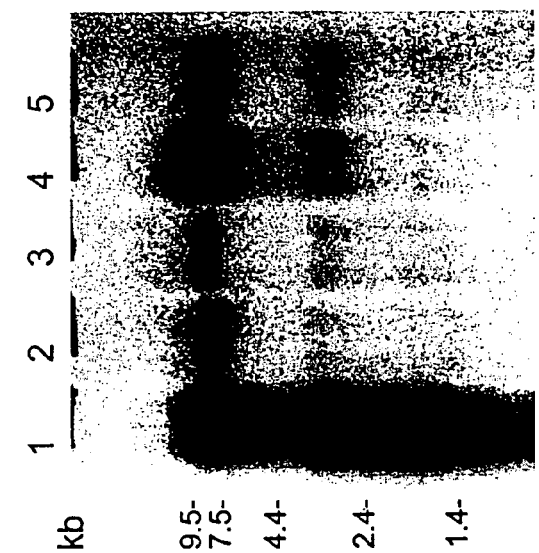

FIG. 15A. Lanes are as follows: 1 heart; 2 brain; 3 placenta; 4 lung; 5 liver; 6 skeletal muscle; 7 kidney; 8 pancreas.

Figure 15B:
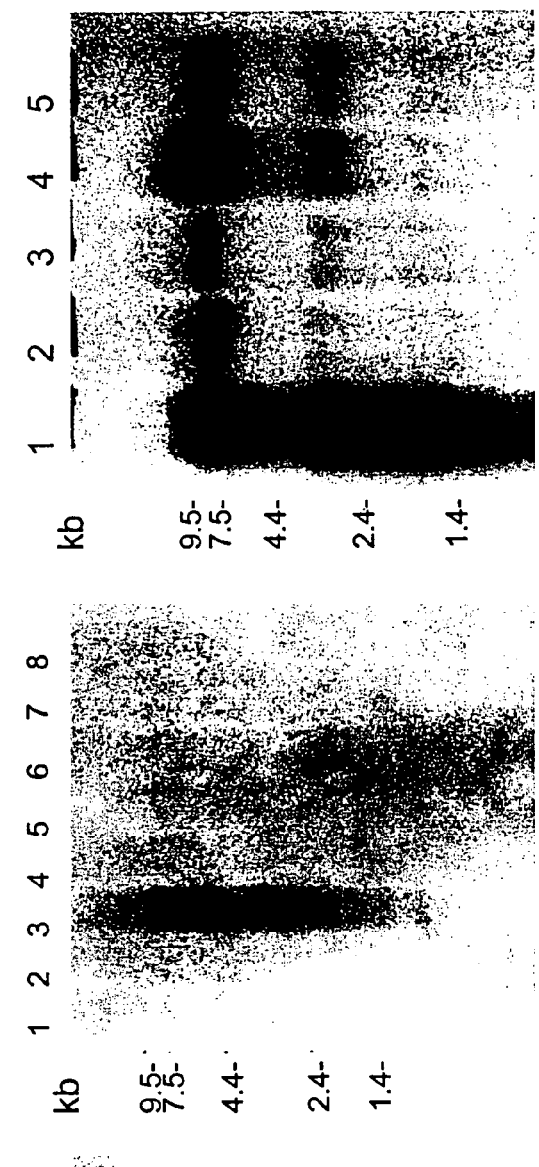

FIG. 15B. Lanes are as follows: 1 spleen; 2 thymus; 3 prostate; 4 testis; 5 ovary; 6 small intestine; 7 colon; 8 leukocytes.

Figure 15C:
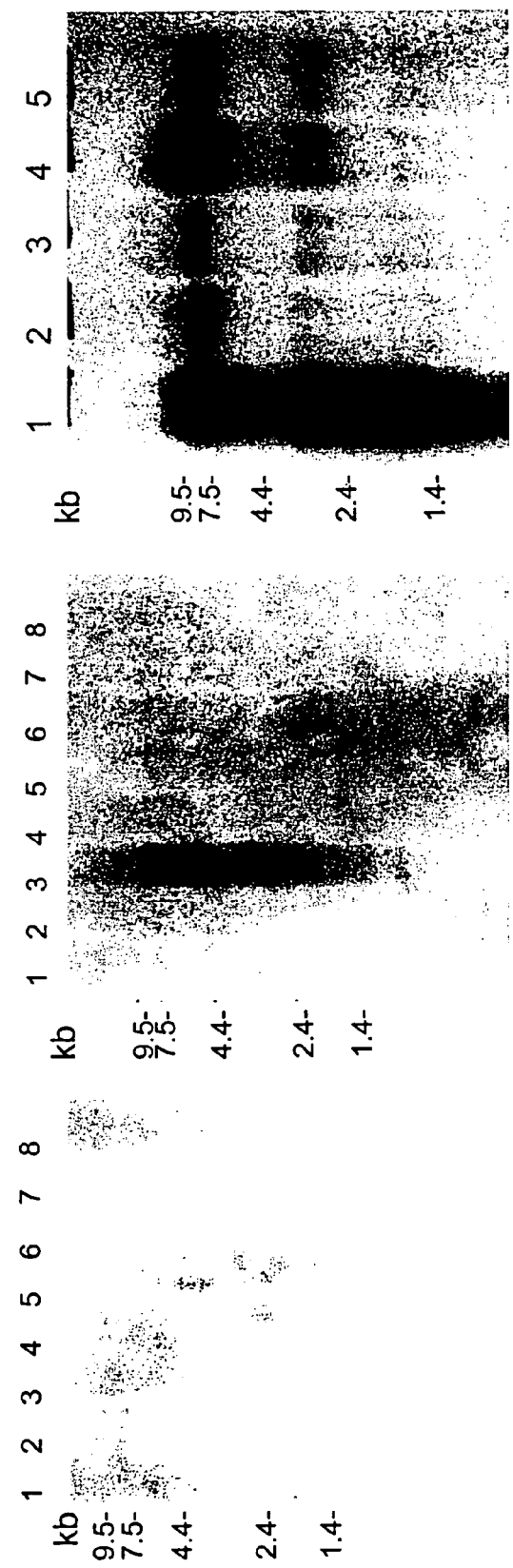

FIG. 15C. Lanes are as follows: 1 prostate; 2 LAPC-4 AD; 3 LAPC-4 AI; 4 LAPC-9 AD; LAPC-9AI.

Figure 16:
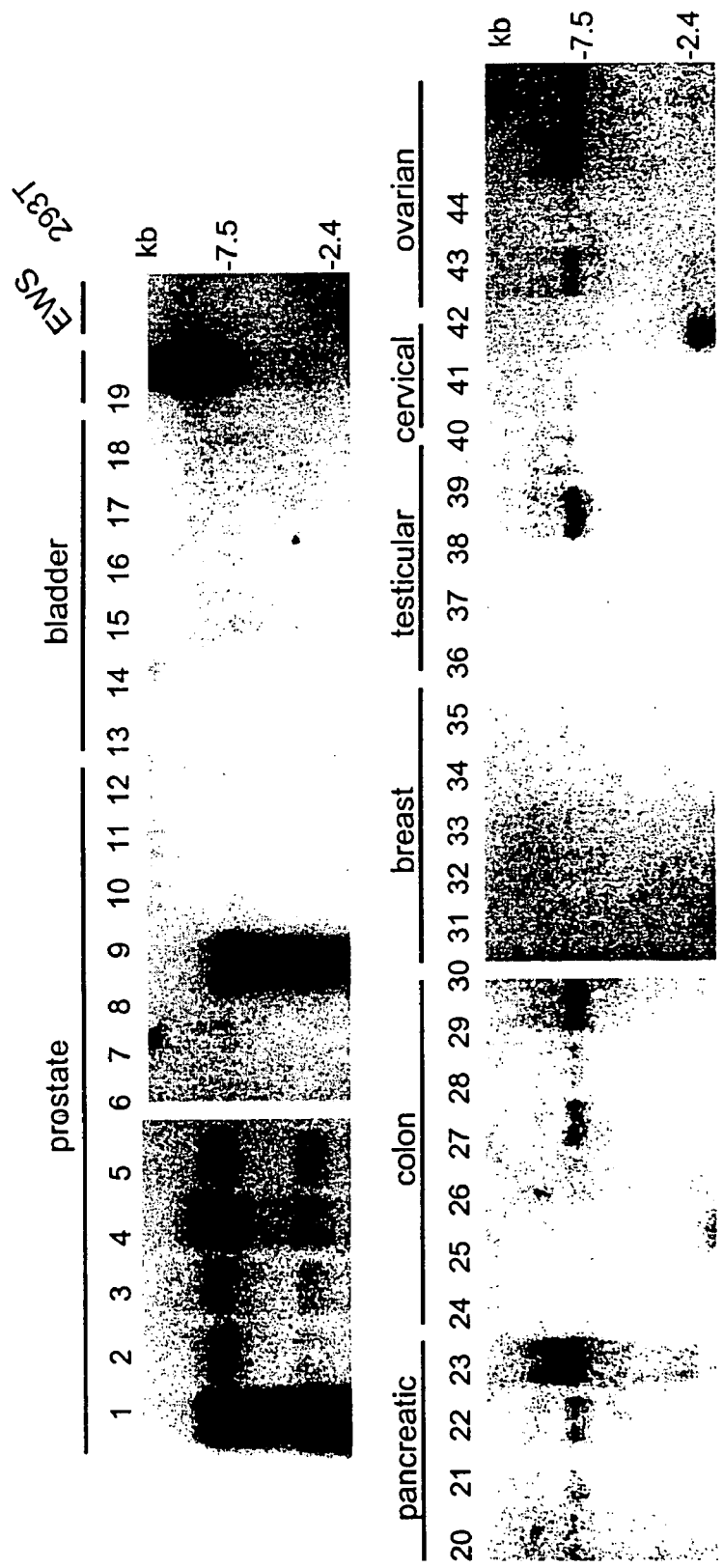

FIG. 16. Expression of STEAP-2 in prostate and select cancer cell lines as determined by Northern blot analysis. Xenograft and cell line filters were prepared with 10 µg total RNA per lane. The blots were analyzed using an SSH derived 98P4B6 clone as probe. All RNA samples were normalized by ethidium bromide staining. Lanes are as follows: 1 prostate; 2 LAPC-4 AD; 3 LAPC-4 AI; 4 LAPC-9 AD; 5 LAPC-9 AI; 6 TsuPr1; 7 DU145; 8 LNCaP; 9 PC-3; 10 LAPC-4 CL; 11 PrEC; 12 HT1197; 13 SCaBER; 14 UM-UC-3; 15 TCCSUP; 16 J82; 17 5637; 18 RD-ES; 19 293T; 20 PANC-1; 21 BxPC-3; 22 HPAC; 23 Capan-1; 24 LS180; 25 SK-CO-1; 26 CaCo-2; 27 LoVo; 28 T84; 29 Colo-205; 30 BT-20; 31 CAMA-1; 32 DU4475; 33 MCF-7; 34 MDA-MB-435s; 35 NTERA-2; 36 NCCIT; 37 TERA-1; 38 TERA-2; 39 A431; 40 HeLa; 41 OV-1063; 42 PA-1; 43 SW626; 44 CAOV-3.

Figure 17:
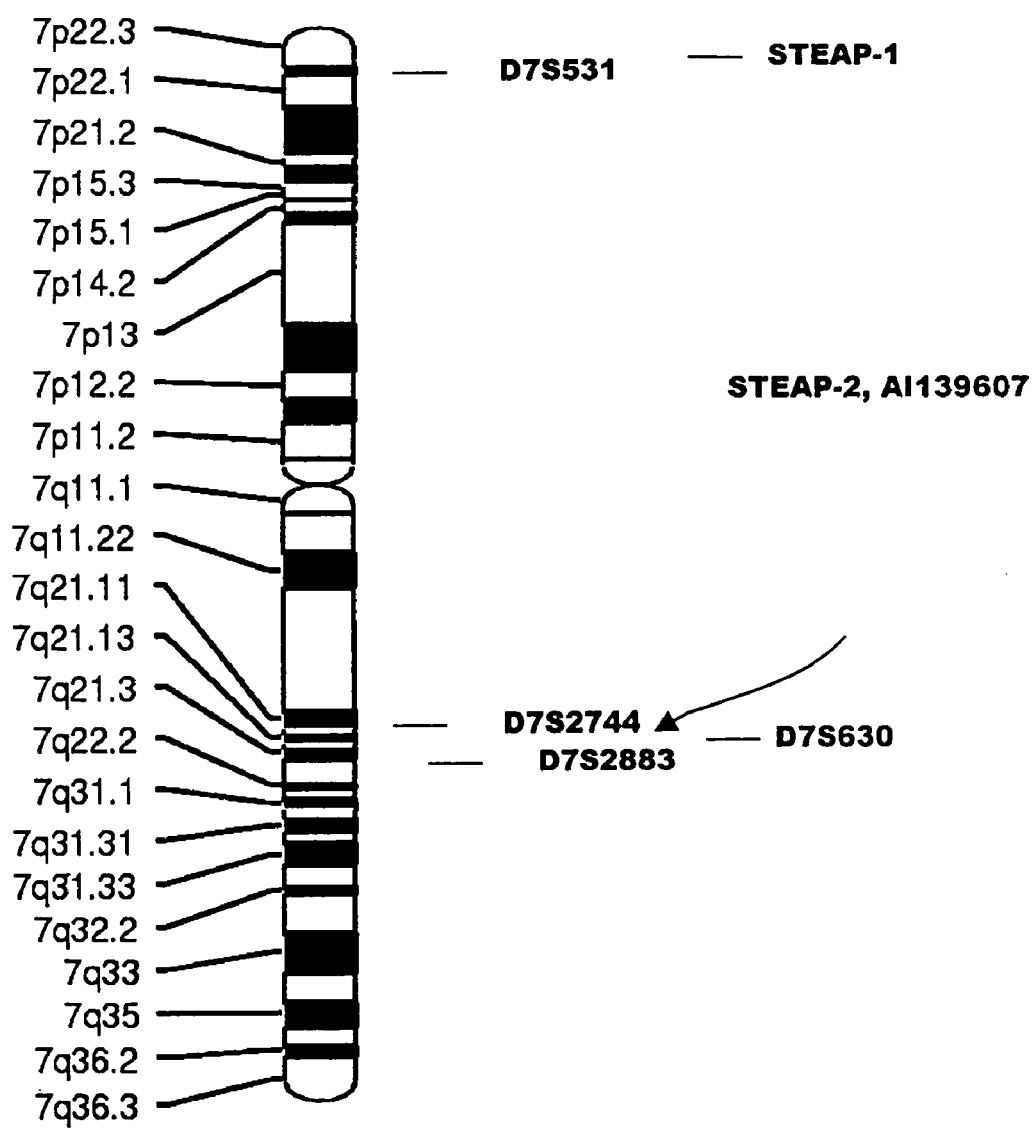

FIG. 17. Chromosomal localization of STEAP family members. The chromosomal localizations of the STEAP genes described herein were determined using the GeneBridge4 radiation hybrid panel (Research Genetics, Huntsville Ala.). The mapping for STEAP-2 and A1139607 was performed using the Stanford G3 radiation hybrid panel (Research Genetics, Huntsville Ala.

Figure 18:

FIG. 18. Schematic representation of Intron-Exon boundaries within the ORF of human STEAP-1 gene. A total of 3 introns (i) and 4 exons (e) were identified.

Figure 19:
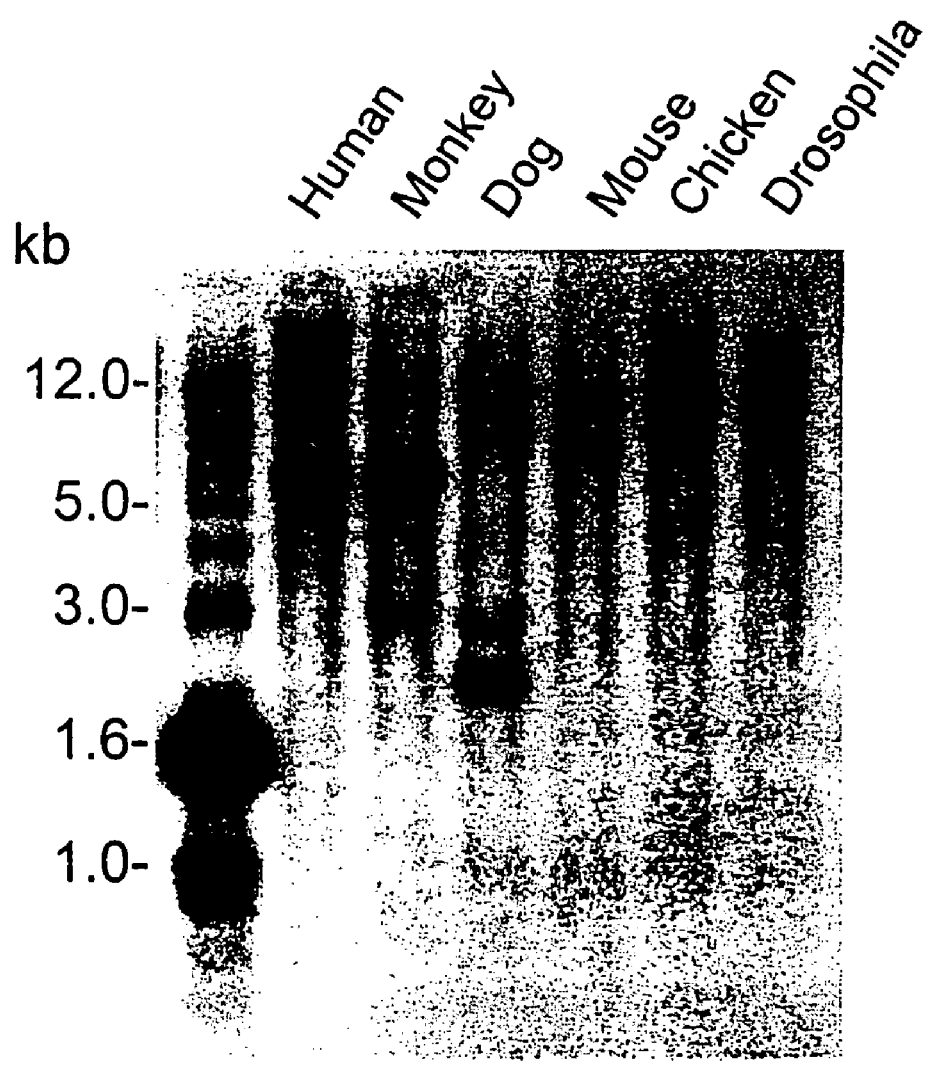

FIG. 19. Zooblot southern analysis of STEAP-1 gene in various species. Genomic DNA was prepared from several different organisms including human, monkey, dog, mouse, chicken and *Drosophila*. Ten micrograms of each DNA sample was digested with EcoRI, blotted onto nitrocellulose and probed with a STEAP-1 probe. Size standards are indicated on the side in kilobases (kb).

Figure 20:
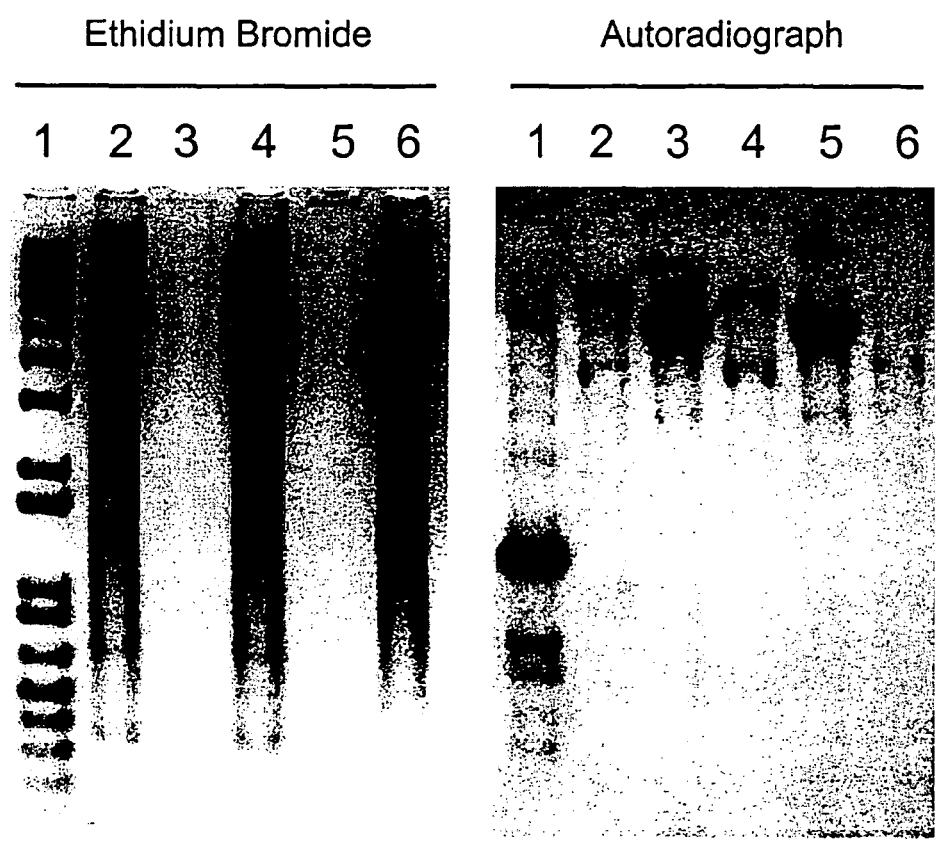

FIG. 20. Southern blot analysis of mouse BAC with a STEAP-1 probe. DNA was prepared from human cells to isolate genomic DNA and from a mouse BAC clone (12P11) that contains the mouse STEAP gene. Each DNA sample was digested with EcoRI, blotted onto nitrocellulose and probed. Eight micrograms of genomic DNA was compared to 250 ng of mouse BAC DNA. Lanes are as follows: (1) 1 kb ladder; (2) human female genomic; (3) 12P11 BAC mus; (4) human female genomic; (5) 12P11 BAC mus; (6) 3T3.

Figure 21A:

FIG. 21A. Immunohistochemical staining using a sheep polyclonal antibody directed against STEAP-1 and showing pericellular staining in a bladder cancer specimen.

Figure 21B:

FIG. 21B. Immunohistochemical staining using a sheep polyclonal antibody directed against STEAP-1 and showing pericellular staining in a second bladder cancer specimen.

Figure 21C:
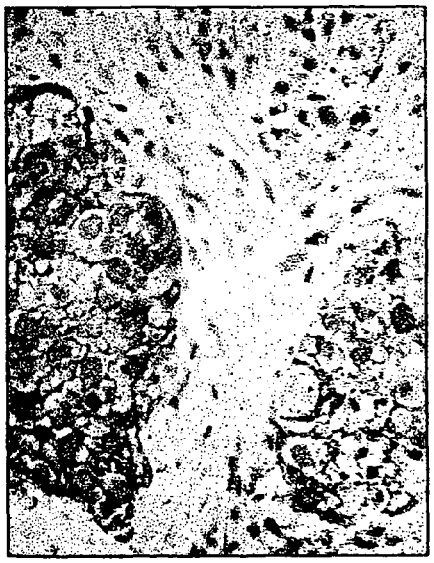

FIG. 21C. Immunohistochemical staining using a sheep polyclonal antibody directed against STEAP-1 and showing pericellular staining in a lung cancer specimen.

Figure 21D:

FIG. 21D. Immunohistochemical staining using a sheep polyclonal antibody directed against STEAP-1 and showing pericellular staining in a second lung cancer specimen.

Figure 22A:

FIG. 22A. STEAP-2 expression in normal prostate shown by RNA in situ hybridization with an antisense probe.

Figure 22B:
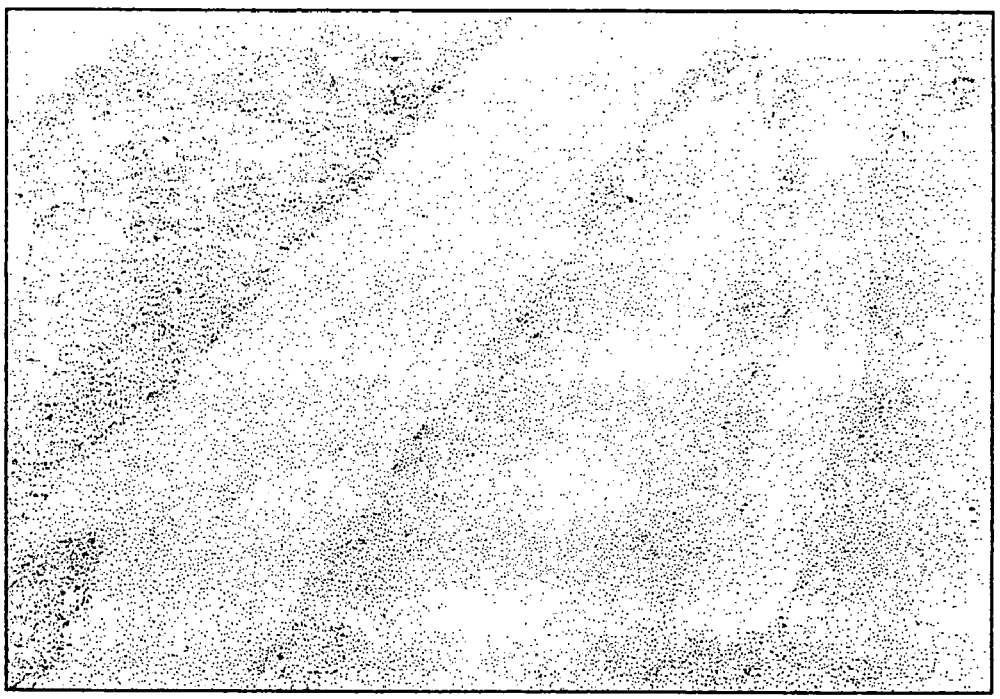

FIG. 22B. STEAP-2 expression in normal prostate by RNA in situ hybridization using a sense probe as control.

Figure 23A:
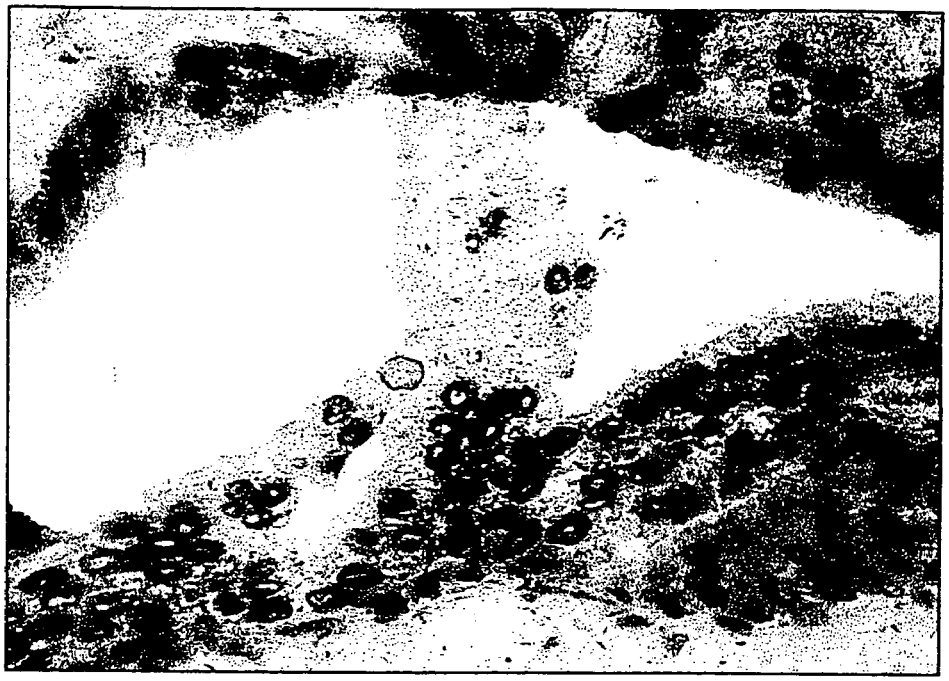

FIG. 23A. STEAP-2 expression in prostate cancer shown by RNA in situ hybridization with an antisense probe.

Figure 23B:
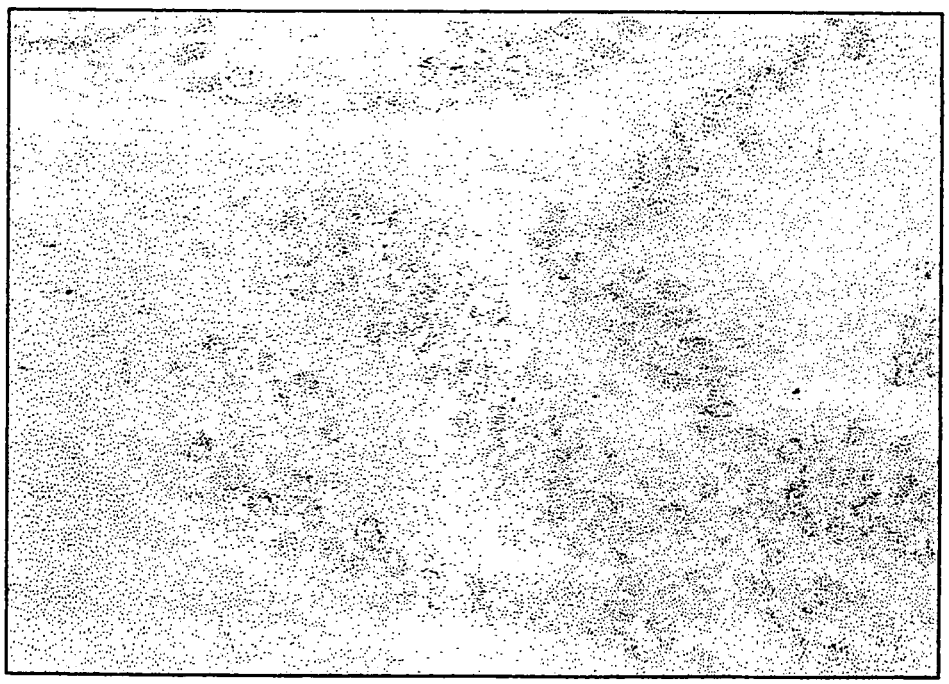

FIG. 23B. STEAP-2 expression in prostate cancer control for RNA in situ hybridization using a sense probe.

Figure 24:

FIG. 24. Expression of STEAP-2 in various cancer tissues as examined using RT-PCR. Lane 1 represents a sample from an LAPC4 AD xenograft; lane 2 is LAPC9 AD xenograft; lane 3 is LAPC9 $AD^2$ xenograft (grown with human bone explant); lane 4 is LAPC9 AD IT (grown intratibially); lane 5 is pooled tissue from colon cancer patients; lane 6 is pooled tissue from lung cancer patients; M represents a marker lane; lane 7 is patient normal prostate tissue; lane 8 is patient prostate cancer tissue; lane 9 is pooled tissue from kidney cancer patients; lane 10 is pooled tissue from bladder cancer patients; lane 11 is HeLa cells; and lane 12 is a water blank.

Figure 25:
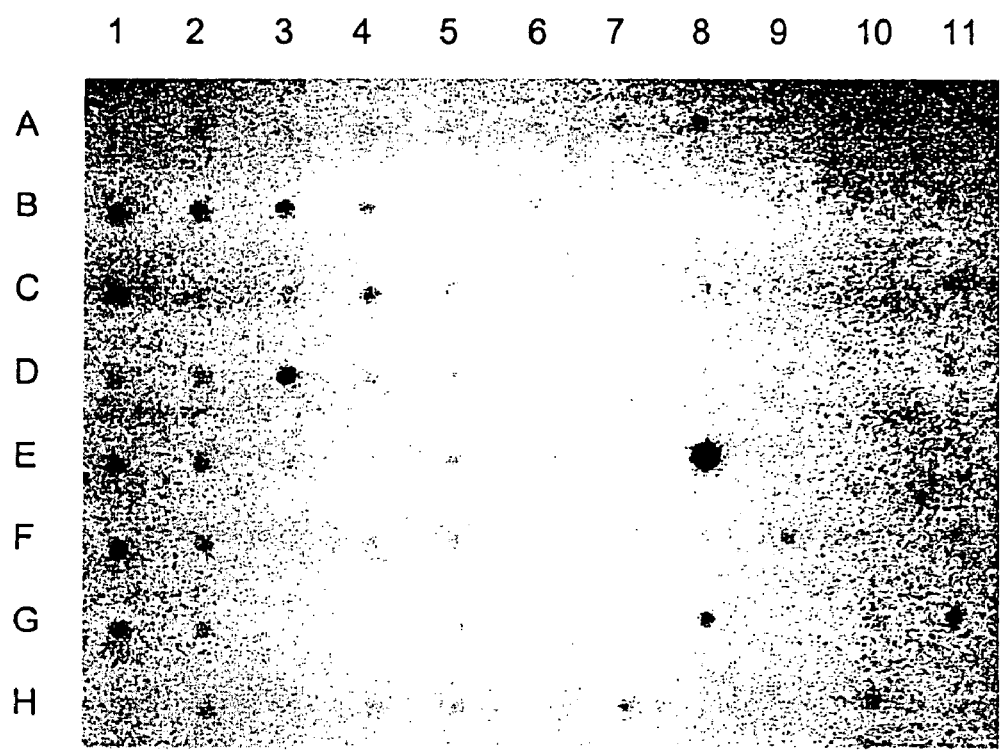

FIG. 25. RNA dot blot analysis of STEAP-2 expression in 76 normal tissues, showing prostate-specific expression. RNA tissue sources: A1 whole brain; A2 cerebellum, left; A3 substantia nigra; A4 heart; A5 esophagus; A6 colon, transverse; A7 kidney; A8 lung; A9 liver; A10 HL60, leukemia; A11 fetal brain; B1 cerebral cortex; B2 cerebellum, right; B3 accumbens nucleus; B4 aorta; B5 stomach; B6 colon, descending; B7 skeletal muscle; B8 placenta; B9 pancreas; B10 HeLa, S3; B11 fetal heart; C1 frontal lobe; C2 corpus callosum; C3 thalamus; C4 atrium, left; C5 duodenum; C6 rectum; C7 spleen; C8 bladder; C9 adrenal gland; C10 K562, leukemia; C11 fetal kidney; D1 parietal lobe; D2 amygdala; D3 pituitary gland; D4 atrium, right; D5 jejunum; D6 blank; D7 thymus; D8 uterus; D9 thyroid gland; D10 MOLT-4, leukemia; D11 fetal liver; E1 occipital lobe; E2 caudate nucleus; E3 spinal cord; E4 ventricle, left; E5 ileum; E6 blank; E7 leukocytes; E8 prostate; E9 salivary gland; E10 RAJI, lymphoma; E11 fetal spleen; F1 temporal lobe; F2 hippocampus; F3 blank; F4 ventricle, right; F5 ileocecum; F6 blank; F7 lymph node; F8 testis; F9 mammary gland; F10 DAUDI, lymphoma; F11 fetal thymus; G1 paracentral gyrus; G2 medulla oblongata; G3 blank; G4 interventricular septum; G5 appendix; G6 blank; G7 bone marrow; G8 ovary; G9 blank; G10 SW480, colon cancer; G11 fetal lung; H1 pons; H2 putamen; H3 blank; H4 apex of the heart; H5 colon, ascending; H6 blank; H7 trachea; H8 blank; H9 blank; H10 A549, lung cancer; H11 blank.

Figure 26:
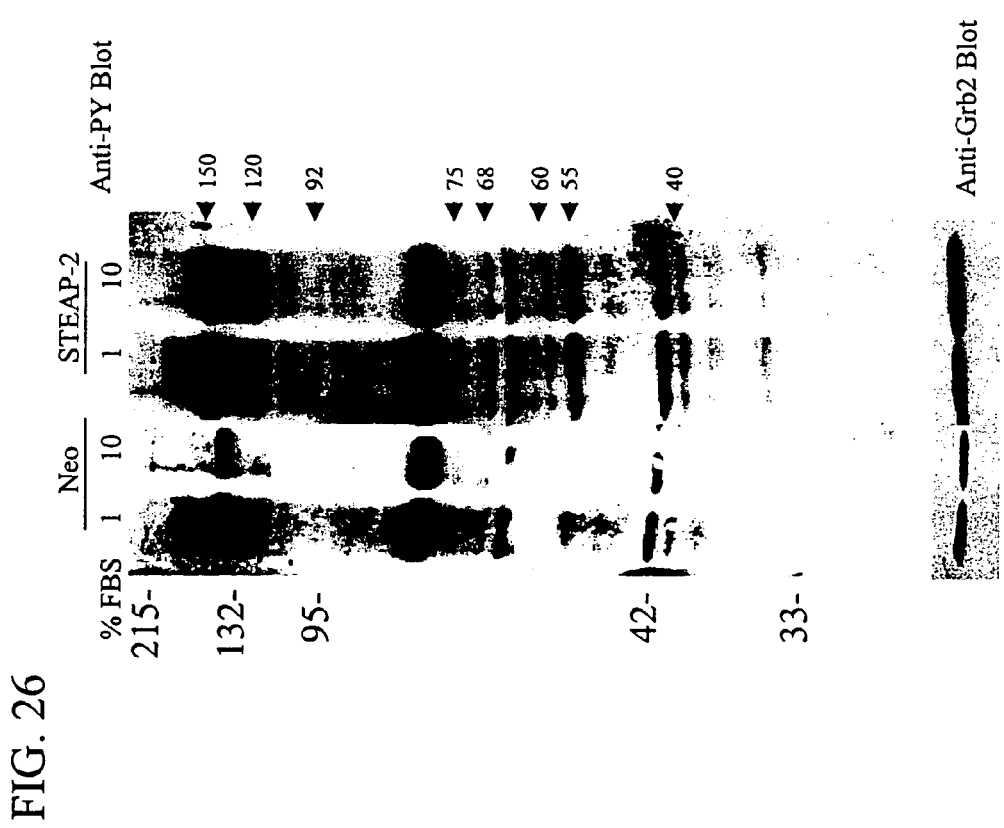

FIG. 26. Western blot with anti-phosphotyrosine (4G10 mAb) showing that expression of STEAP-2 in PC3 cells is sufficient to induce phosphorylation of various proteins on tyrosine residues, including p150, p120 and p75. An overlay using anti-Grb2 Ab shows that the gel was equally loaded.

FIG. 27A. Western blot using anti-phospho-p38 showing that expression of STEAP-1 or STEAP-2 in PC3 cells activates the p38 kinase, as compared to PC3-neo controls. TNF-NaSaI and NaSaI, known p38 activators, served as positive controls.

FIG. 27B. Western blot, as in FIG. 27A, using anti-p38 to demonstrate equal protein loading on the gels.

FIG. 28A. Western blot using anti-phospho-ERK to examine activation of the ERK pathway in 1% FBS. PC3 cells expressing Ras (positive control), STEAP-1, STEAP-2, or neo (negative control), were grown in 1% FBS. The results show that, while expression of the neo control gene has no effect on ERK phosphorylation, expression of STEAP-1 and STEAP-2 induces ERK phosphorylation. An anti-ERK antibody was used to confirm the presence of ERK in all lanes.

FIG. 28B. Western blot using anti-phospho-ERK to examine activation of the ERK pathway in 0.1% and 10% FBS. PC3 cells expressing STEAP-1 or neo (negative control), were grown in either 0.1% or 10% FBS. The results confirm that expression of STEAP-1 is sufficient to induce activation of the ERK signaling cascade.

FIG. 29. Signaling in PC3-STEAP-1 cells mediated by odorants.

FIG. 29A. Anti-phosphotyrosine western blot of PC3 cells, stably expressing neo, were grown overnight in 0.1% FBS to allow for receptor occupancy, and then treated with citralva, ethylvanillin or IBMP. Treatment with 10% FBS was used as a control.

FIG. 29B. Anti-phosphotyrosine western blot of PC3 cells, stably expressing STEAP-1, were treated as described for FIG. 29A. The results show that citralva and ethylvanillin specifically induce the phosphorylation of p136-140 in PC3-STEAP-1 cells. In addition, citralva induces the de novo phosphorylation of a protein at 160-200 kDa.

Figure 30:
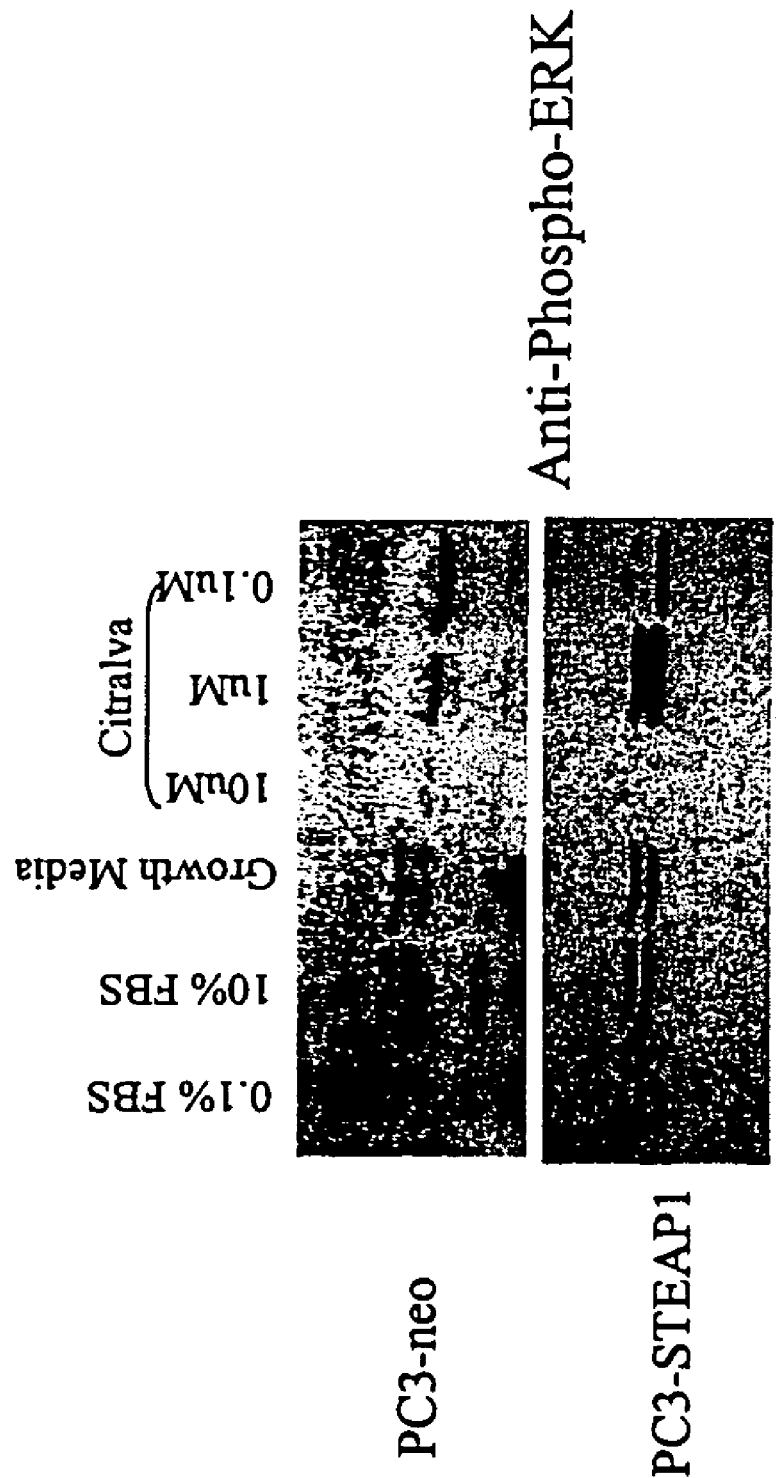

FIG. 30. Activation of the ERK cascade by odorants. Anti-ERK western blot of PC3 cells, stably expressing either neo or STEAP-1, were grown overnight in 0.1% FBS. Cells were then treated with citralva for 5 min. Treatment with 10% FBS was used as a control. Whole cell lysates were analyzed using anti-phospho-ERK. The results show that citralva induces the phosphorylation of ERK, and therefore activation of the ERK pathway, in a STEAP-1 specific manner.

Figure 31A:

FIG. 31A. Anti-STEAP-1 immunohistochemistry analysis on the LAPC-9 orthotopic prostate cancer tumor (magnification 200×). Cells expressing STEAP-1 show perinuclear staining.

Figure 31B:
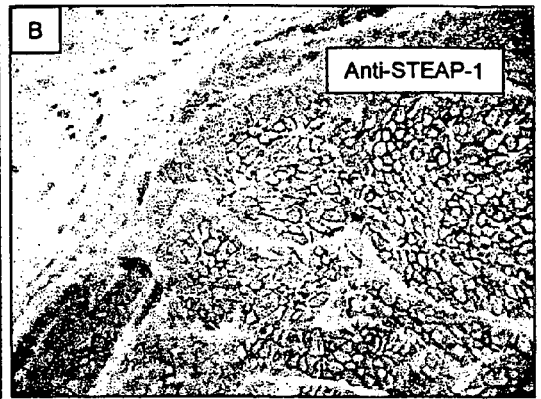

FIG. 31B. Anti-STEAP-1 immunohistochemistry analysis on the LAPC-9 lymph node metastasis (magnification 400×). Cells expressing STEAP-1 show perinuclear staining.

Figure 31C:
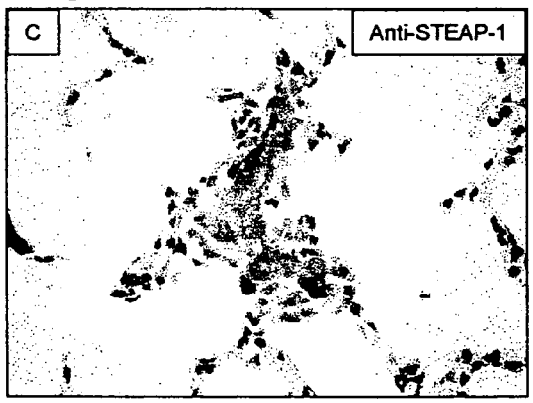
Figure 31D:
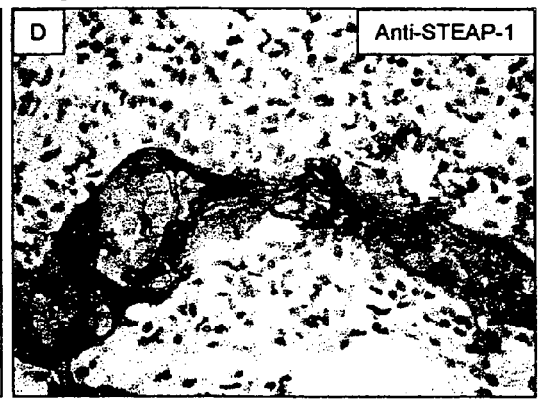

FIG. 31C-D. Anti-STEAP-1 immunohistochemistry analysis on the LAPC-9 lung metastasis (magnification 800×). Cells expressing STEAP-1 show perinuclear staining.

Figure 31E:
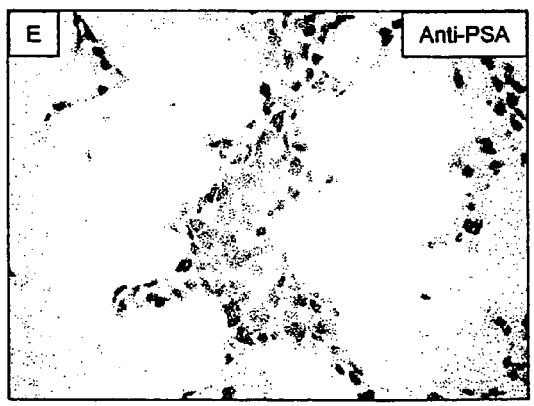
Figure 31F:
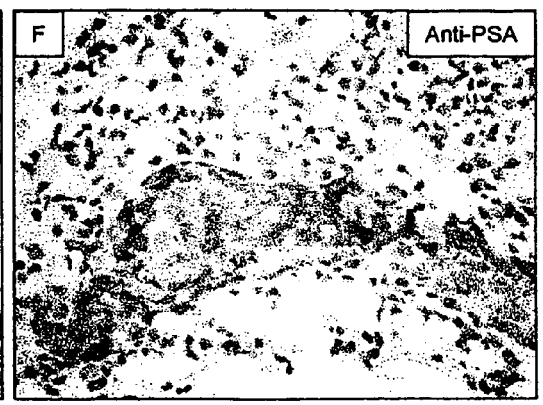

FIG. 31E-F. Anti-PSA immunohistochemistry analysis on a LAPC-9 prostate cancer lung micrometastasis (magnification 800×). Cells expressing PSA show perinuclear staining.

Figure 32A:
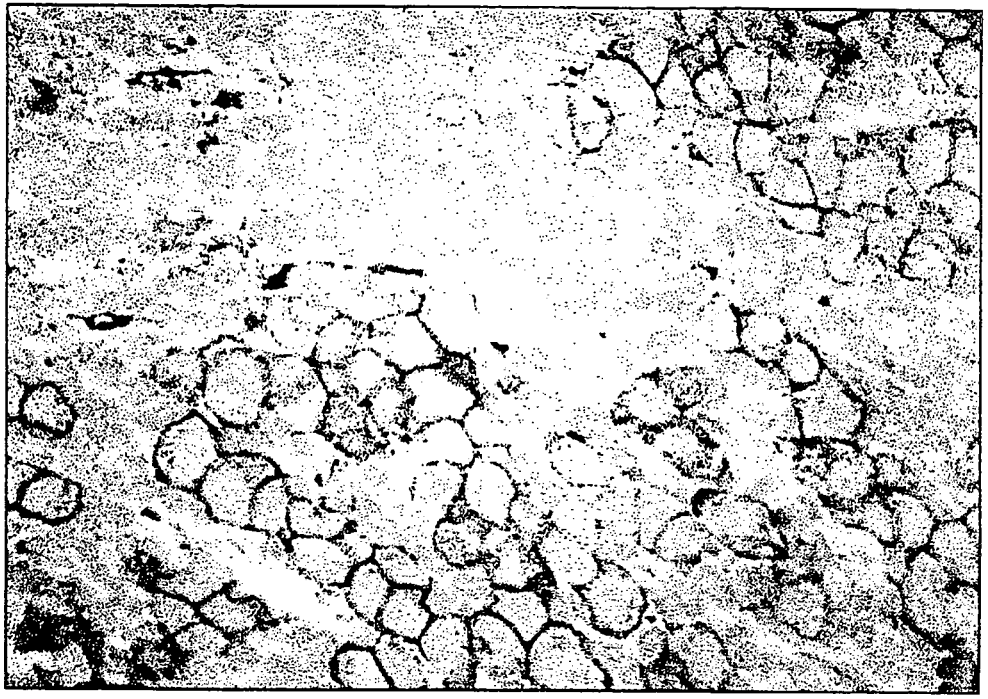

FIG. 32A. Immunohistochemical detection of STEAP-1 showing intense pericellular staining in lymph node metastasis of a human patient.

Figure 32B:

FIG. 32B. Immunohistochemical detection of STEAP-1 showing intense pericellular staining in bone metastasis of a human patient.

Figure 33:
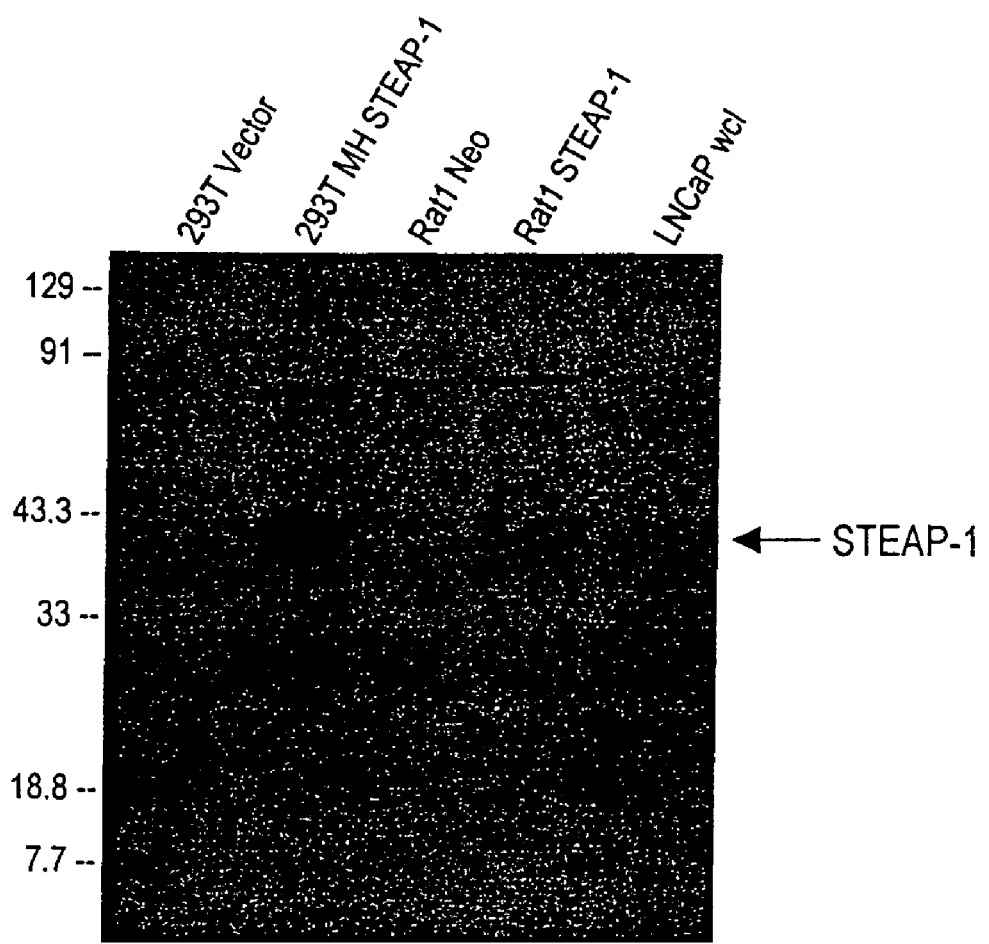

FIG. 33. Western blot showing that anti-STEAP-1 murine pAb recognizes STEAP-1 protein in engineered cell lines and endogenous STEAP-1 protein in LNCaP cells. Lysates of LNCaP cells and 293T cells transfected with either pcDNA 3.1 MYC/HIS tagged STEAP-1 or neo empty vector, and RAT1 cells engineered to express STEAP-1 or a neo control gene, were separated by SDS-PAGE and transferred to nitrocellulose. The blot was then subjected to anti-STEAP western analysis using a 1:1000 dilution of serum from mice immunized with a GST-STEAP-1 fusion protein.

DETAILED DESCRIPTION OF THE INVENTION

The present invention relates to a novel family of cell surface serpentine transmembrane antigens. Two of the proteins in this family are exclusively or predominantly expressed in the prostate, as well as in prostate cancer, and thus members of this family have been termed "STEAP" (Six Transmembrane Epithelial Antigen of the Prostate). Four particular human STEAPs are described and characterized herein. The human STEAPs exhibit a high degree of structural conservation among them but show no significant structural homology to any known human proteins. The present invention relates to methods and compositions for the diagnosis and therapy of prostate and other cancers, which methods utilize isolated polynucleotides corresponding to human STEAP genes, proteins encoded by the STEAP genes and fragments thereof, and antibodies capable of specifically recognizing and binding to STEAP proteins.

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. The techniques and procedures described or referenced herein are generally well understood and commonly employed using conventional methodology by those skilled in the art, such as, for example, the widely utilized molecular cloning methodologies described in Sambrook et al., Molecular Cloning: A Laboratory Manual 2nd. edition (1989) Cold Spring Harbor Laboratory Press, Cold Spring Harbor, N.Y. As appropriate, procedures involving the use of commercially available kits and reagents are generally carried out in accordance with manufacturer defined protocols and/or parameters unless otherwise noted.

As used herein, the terms "advanced prostate cancer", "locally advanced prostate cancer", "advanced disease" and "locally advanced disease" mean prostate cancers that have extended through the prostate capsule, and are meant to include stage C disease under the American Urological Association (AUA) system, stage C1-C2 disease under the Whitmore-Jewett system, and stage T3-T4 and N+ disease under the TNM (tumor, node, metastasis) system. In general, surgery is not recommended for patients with locally advanced disease, and these patients have substantially less favorable outcomes compared to patients having clinically localized (organ-confined) prostate cancer. Locally advanced disease is clinically identified by palpable evidence of induration beyond the lateral border of the prostate, or asymmetry or induration above the prostate base. Locally advanced prostate cancer is presently diagnosed pathologically following radical prostatectomy if the tumor invades or penetrates the prostatic capsule, extends into the surgical margin, or invades the seminal vesicles.

As used herein, the terms "metastatic prostate cancer" and "metastatic disease" mean prostate cancers that have spread to regional lymph nodes or to distant sites, and are meant to include stage D disease under the AUA system and stage TxNxM+ under the INM system. As is the case with locally advanced prostate cancer, surgery is generally not indicated for patients with metastatic disease, and hormonal (androgen ablation) therapy is the preferred treatment modality. Patients with metastatic prostate cancer eventually develop an androgen-refractory state within 12 to 18 months of treatment initiation, and approximately half of these patients die within 6 months thereafter. The most common site for prostate cancer metastasis is bone. Prostate cancer bone metastases are, on balance, characteristically osteoblastic rather than osteolytic (i.e., resulting in net bone formation). Bone metastases are found most frequently in the spine, followed by the femur, pelvis, rib cage, skull and humerus. Other common sites for metastasis include lymph nodes, lung, liver and brain. Metastatic prostate cancer is typically diagnosed by open or laparoscopic pelvic lymphadenectomy, whole body radionuclide scans, skeletal radiography, and/or bone lesion biopsy.

As used herein, the term "polynucleotide" means a polymeric form of nucleotides of at least 10 bases or base pairs in length, either ribonucleotides or deoxynucleotides or a modified form of either type of nucleotide, and is meant to include single and double stranded forms of DNA.

As used herein, the term "polypeptide" means a polymer of at least 10 amino acids. Throughout the specification, standard three letter or single letter designations for amino acids are used.

As used herein, the terms "hybridize", "hybridizing", "hybridizes" and the like, used in the context of polynucleotides, are meant to refer to conventional hybridization conditions, preferably such as hybridization in 50% form amide/ 6×SSC/0.1% SDS/100 μg/ml ssDNA, in which temperatures for hybridization are above 37° C. and temperatures for washing in 0.1×SSC/0.1% SDS are above 55° C., and most preferably to stringent hybridization conditions.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature that can be used. As a result, it follows that higher relative temperatures would tend to make the reaction conditions more stringent, while lower temperatures less so. For additional details and explanation of stringency of hybridization reactions, see Ausubel et al., Current Protocols in Molecular Biology, Wiley Interscience Publishers, (1995).

"Stringent conditions" or "high stringency conditions", as defined herein, may be identified by those that: (1) employ low ionic strength and high temperature for washing, for example 0.015 M sodium chloride/0.0015 M sodium citrate/ 0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC (sodium chloride/sodium. citrate) and 50% formamide at 55° C., followed by a high-stringency wash consisting of 0.1×SSC containing EDTA at 55° C.

"Moderately stringent conditions" may be identified as described by Sambrook et al., Molecular Cloning: A Laboratory Manual, New York: Cold Spring Harbor Press, 1989, and include the use of washing solution and hybridization conditions (e.g., temperature, ionic strength and % SDS) less stringent than those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

In the context of amino acid sequence comparisons, the term "identity" is used to express the percentage of amino acid residues at the same relative positions that are the same. Also in this context, the term "homology" is used to express the percentage of ammo acid residues at the same relative positions that are either identical or are similar, using the conserved amino acid criteria of BLAST analysis, as is generally understood in the art For example, % identity values may be generated by WU-BLAST-2 (Altschul et al., Methods in Enzymology, 266: 460-480 (1996). Further details regarding amino acid substitutions, which are considered conservative under such criteria, are provided below.

Additional definitions are provided throughout the subsections that follow.

STEAP Polynucleotides

One aspect of the invention provides polynucleotides corresponding or complementary to all or part of a STEAP gene, mRNA, and/or coding sequence, preferably in isolated form, including polynucleotides encoding a STEAP protein and fragments thereof, DNA, RNA, DNA/RNA hybrid, and related molecules, polynucleotides or oligonucleotides complementary to a STEAP gene or mRNA sequence or a part thereof, and polynucleotides or oligonucleotides that hybridize to a STEAP gene, mRNA, or to a STEAP encoding polynucleotide (collectively, "STEAP polynucleotides"). As used herein, STEAP genes and proteins are meant to include the STEAP-1, STEAP-2 and STEAP-3 genes and proteins, and the gene and protein corresponding to GenBank Accession number R80991 (STEAP-4), and the genes and proteins corresponding to other STEAP proteins and structurally similar variants of the foregoing. Such other STEAP proteins and variants will generally have coding sequences that are highly homologous to the STEAP coding sequence, and preferably will share at least about 50% amino acid identity and at least about 60% amino acid homology (using BLAST criteria), more preferably sharing 70% or greater homology (using BLAST criteria).

The STEAP family member gene sequences described herein encode STEAP proteins sharing unique highly conserved amino acid sequence domains which distinguish them from other proteins. Proteins which include one or more of these unique highly conserved domains may be related to the STEAP family members or may represent new STEAP proteins. Referring to FIG. 11A-B, which is an amino acid sequence alignment of the full STEAP-1, STEAP-2, and STEAP-3 protein sequences as well as the partial STEAP-4 sequence, it is clear that the STEAPs are closely related at the structural level. Referring to FIG. 11C, which is an amino acid sequence alignment of the fill STEAP-1 and STEAP-2 protein sequences, close structural conservation is apparent, particularly in the predicted transmembrane domains. The STEAP-1 and STEAP-2 sequences share 54.9% identity over a 237 amino acid overlap. Additional amino acid sequence alignments between the STEAPs are shown in FIGS. 11D and 11E. These alignments show that STEAP-1 and STEAP-3 are 40.9% identical over a 264 amino acid region, while STEAP-2 and STEAP-3 are 47.8% identical over a 416 amino acid region.

A STEAP polynucleotide may comprise a polynucleotide having the nucleotide sequence of human STEAP-1 as shown in FIG. 1A-B, the nucleotide sequence of human STEAP-2 as shown in FIG. 9A-D, the nucleotide sequence of human STEAP-3 as shown in FIG. 10A-E, or the nucleotide sequence of STEAP-4 as shown in FIG. 10F, or a sequence complementary thereto, or a polynucleotide fragment of any of the foregoing. Another embodiment comprises a polynucleotide which encodes the human STEAP-1, STEAP-2, STEAP-3 or STEAP-4 protein amino acid sequences, a sequence complementary thereto, or a polynucleotide fragment of any of the foregoing. Another embodiment comprises a polynucleotide which is capable of hybridizing under stringent hybridization conditions to the human STEAP-1 cDNA shown in FIG. 1A-B, the human STEAP-2 cDNA shown in FIG. 9A-D, the human STEAP-3 cDNA shown in FIG. 10A-E, or the STEAP-4 as shown in FIG. 10F, or to a polynucleotide fragment thereof.

Typical embodiments of the invention disclosed herein include STEAP polynucleotides encoding specific portions of a STEAP mRNA sequence such as those that encode the protein and fragments thereof. For example, representative embodiments of the invention disclosed herein include: polynucleotides encoding about amino acid 1 to about amino acid 10 of a STEAP protein shown in FIG. 11A-B, polynucleotides encoding about amino acid 20 to about amino acid 30 of a STEAP protein shown in FIG. 11A-B, polynucleotides encoding about amino acid 30 to about amino acid 40 of a STEAP protein shown in FIG. 11A-B, polynucleotides encoding about amino acid 40 to about amino acid 50 of a STEAP protein shown in FIG. 11A-B, polynucleotides encoding about amino acid 50 to about amino acid 60 of a STEAP protein shown in FIG. 11A-B, polynucleotides encoding about amino acid 60 to about amino acid 70 of a STEAP protein shown in FIG. 11A-B, polynucleotides encoding about amino acid 70 to about amino acid 80 of a STEAP protein shown in FIG. 11A-B, polynucleotides encoding about amino acid 80 to about amino acid 90 of a STEAP protein shown in FIG. 11A-B and polynucleotides encoding about amino acid 90 to about amino acid 100 of a STEAP protein shown in FIG. 11A-B, etc. Following this scheme, polynucleotides (of at least 10 amino acids) encoding further portions of the amino acid sequence of a STEAP protein are typical embodiments of the invention. Such portions of a STEAP protein include amino acids 100-339 of a STEAP-1 protein shown in FIG. 11A-B, or amino acids 100-454 of a STEAP-2 protein shown in FIG. 11A-B, or amino acids 100-459 of a STEAP-3 protein shown in FIG. 11A-B, and amino acids 100-133 of a STEAP-4 protein shown in FIG. 11A-B. Polynucleotides encoding larger portions of the STEAP protein are also contemplated. For example polynucleotides encoding from about amino acid 1 (or 20 or 30 or 40 etc.) to about amino acid 20, (or 30, or 40 or 50 etc.) of a STEAP protein shown in FIG. 11A-B may be generated by a variety of techniques well known in the art.

Additional illustrative embodiments of the invention disclosed herein include STEAP polynucleotide fragments encoding one or more of the biological motifs contained within the STEAP protein sequence. In one embodiment, typical polynucleotide fragments of the invention can encode one or more of the regions of STEAP that exhibit homology to other STEAP family members, such as one or more of the transmembrane domains. In another embodiment of the invention, typical polynucleotide fragments can encode sequences that are unique to one or more STEAP alternative splicing variants. In yet another embodiment, typical polynucleotide fragments can encode an immunogenic portion of a STEAP protein. One example of an immunogenic portion of a STEAP protein is amino acid residues 14 through 28 of the STEAP-1 amino acid sequence as shown in FIG. 1A-B (WK-MKPRRNLEEDDYL; SEQ ID NO: 22).

The polynucleotides of the preceding paragraphs have a number of different specific uses. As STEAPs are differentially expressed in prostate and other cancers, these polynucleotides may be used in methods assessing the status of STEAP gene products in normal versus cancerous tissues. Typically, polynucleotides encoding specific regions of a STEAP protein may be used to assess the presence of perturbations (such as deletions, insertions, point mutations etc.) in specific regions of the STEAP gene products. Exemplary assays include both RT-PCR assays as well as single-strand conformation polymorphism (SSCP) analysis (see e.g. Marrogi et al., J. Cutan. Pathol. 26(8): 369-378 (1999), both of which utilize polynucleotides encoding specific regions of a protein to examine these regions within the protein. Assays and methods for analyzing sequences to detect single nucleotide polymorphisms are also available (Irizarry, et al., 2000, Nature Genetics 26(2):223-236.

Other specifically contemplated embodiments of the invention disclosed herein are genomic DNA, cDNAs, ribozymes, and antisense molecules, including morpholino anti-sense molecules, as well as nucleic acid molecules based on an alternative backbone or including alternative bases, whether derived from natural sources or synthesized. For example, antisense molecules can be RNAs or other molecules, including peptide nucleic acids (PNAs) or non-nucleic acid molecules such as phosphorothioate derivatives, that specifically bind DNA or RNA in a base pair-dependent manner. A skilled artisan can readily obtain these classes of nucleic acid molecules using the STEAP polynucleotides and polynucleotide sequences disclosed herein.

Antisense technology entails the administration of exogenous oligonucleotides that bind to a target polynucleotide located within the cells. The term "antisense" refers to the fact that such oligonucleotides are complementary to their intracellular targets, e.g., STEAP. See for example, Jack Cohen, OLIGODEOXYNUCLEOTIDES, Antisense Inhibitors of Gene Expression, CRC Press, 1989; and Synthesis 1:1-5 (1988). The STEAP antisense oligonucleotides of the present invention include derivatives such as S-oligonucleotides (phosphorothioate derivatives or S-oligos, see, Jack Cohen, supra), which exhibit enhanced cancer cell growth inhibitory action. S-oligos (nucleoside phosphorothioates) are isoelectronic analogs of an oligonucleotide (O-oligo) in which a nonbridging oxygen atom of the phosphate group is replaced by a sulfur atom. The S-oligos of the present invention may be prepared by treatment of the corresponding O-oligos with 3H-1,2-benzodithiol-3-one-1,2-dioxide, which is a sulfur transfer reagent. See Iyer, R. P. et al, J. Org. Chem. 55:4693-4698 (1990); and Iyer, R. P. et al., J. Am. Chem. Soc. 112: 1253-1254 (1990), the disclosures of which are fully incorporated by reference herein. Additional STEAP antisense oligonucleotides of the present invention include morpholino antisense oligonucleotides known in the art (see e.g. Partridge et al., 1996, Antisense & Nucleic Acid Drug Development 6: 169-175).

The STEAP antisense oligonucleotides of the present invention typically may be RNA or DNA that is complementary to and stably hybridizes with the first 100 N-terminal codons or last 100 C-terminal codons, or overlapping with the ATG start site, of the STEAP genome or the corresponding mRNA. While absolute complementarity is not required, high degrees of complementarity are preferred. Use of an oligonucleotide complementary to this region allows for the selective hybridization to STEAP mRNA and not to mRNA specifying other regulatory subunits of protein kinase. Preferably, the STEAP antisense oligonucleotides of the present invention are a 15 to 30-mer fragment of the antisense DNA molecule having a sequence that hybridizes to STEAP mRNA. Optionally, STEAP antisense oligonucleotide is a 30-mer oligonucleotide that is complementary to a region in the first 10 N-terminal codons and last 10 C-terminal codons of STEAP. Alternatively, the antisense molecules are modified to employ ribozymes in the inhibition of STEAP expression. L. A. Couture & D. T. Stinchcomb; *Trends Genet* 12: 510-515 (1996).

Further specific embodiments of this aspect of the invention include primers and primer pairs, which allow the specific amplification of the polynucleotides of the invention or of any specific parts thereof, and probes that selectively or specifically hybridize to nucleic acid molecules of the invention or to any part thereof. Probes may be labeled with a detectable marker, such as, for example, a radioisotope, fluorescent compound, bioluminescent compound, a chemiluminescent compound, metal chelator or enzyme. Such probes and primers can be used to detect the presence of a STEAP polynucleotide in a sample and as a means for detecting a cell expressing a STEAP protein. Examples of such probes include polypeptides comprising all or part of a human STEAP cDNA sequence shown in FIG. 1A-B (SEQ ID NO: 1), FIG. 9A-D (SEQ ID NO: 7) or FIG. 10A-E (SEQ ID NO: 9). Examples of primer pairs capable of specifically amplifying STEAP mRNAs are also described in the Examples that follow. As will be understood by the skilled artisan, a great many different primers and probes may be prepared based on the sequences provided in herein and used effectively to amplify and/or detect a STEAP mRNA.

As used herein, a polynucleotide is said to be "isolated" when it is substantially separated from contaminant polynucleotides that correspond or are complementary to genes other than the STEAP gene or that encode polypeptides other than STEAP gene product or fragments thereof. A skilled artisan can readily employ nucleic acid isolation procedures to obtain an isolated STEAP polynucleotide.

The STEAP polynucleotides of the invention are useful for a variety of purposes, including but not limited to their use as probes and primers for the amplification and/or detection of the STEAP gene(s), mRNA(s), or fragments thereof; as reagents for the diagnosis and/or prognosis of prostate cancer and other cancers; as tools for identifying molecules that inhibit calcium entry specifically into prostate cells; as coding sequences capable of directing the expression of STEAP polypeptides; as tools for modulating or inhibiting the expression of the STEAP gene(s) and/or translation of the STEAP transcript(s); and as therapeutic agents.

Molecular and Biochemical Features of the STEAPs

The invention relates to a novel family of proteins, termed STEAPs. Four STEAPs are specifically described herein by way of structural, molecular and biochemical features. As is further described in the Examples which follow, the STEAPs have been characterized in a variety of ways. For example, analyses of nucleotide coding and amino acid sequences were conducted in order to identify conserved structural elements within the STEAP family. Extensive RT-PCR and Northern blot analyses of STEAP mRNA expression were conducted in order to establish the range of normal and cancerous tissues expressing the various STEAP messages. Western blot, immunohistochemical and flow cytometric analyses of STEAP protein expression were conducted to determine protein expression profiles, cell surface localization and gross molecular topology of STEAP.

The prototype member of the STEAP family, STEAP-1, is a six-transmembrane cell surface protein of 339 amino acids with no identifiable homology to any known human protein. The cDNA nucleotide and deduced amino acid sequences of human STEAP-1 are shown in FIG. 1A-B. A gross topological schematic of the STEAP-1 protein integrated within the cell membrane is shown in FIG. 1B. STEAP-1 expression is predominantly prostate-specific in normal tissues. Specifically, extensive analysis of STEAP-1 mRNA and protein expression in normal human tissues shows that STEAP-1 protein is predominantly expressed in prostate and, to a far smaller degree, in bladder. STEAP-1 mRNA is also relatively prostate specific, with only very low level expression detected in a few other normal tissues. In cancer, STEAP-1 mRNA and protein is consistently expressed at high levels in prostate cancer (including androgen-dependent and androgen-independent tumors) and during all stages of the disease. STEAP-1 is also expressed in other cancers. Specifically, STEAP-1 mRNA is expressed at very high levels in bladder, colon, pancreatic, and ovarian cancer (as well as other cancers). In addition, cell surface expression of STEAP-1 protein has been established in prostate, bladder, lung and colon cancers. Therefore, STEAP-1 has all of the hallmark characteristics of an excellent diagnostic and therapeutic target for the treatment of certain cancers, including particularly prostate, colon and bladder carcinomas.

A second member of the family, STEAP-2, is a 454 amino acid protein encoded by a distinct gene and having a predicted molecular topology similar to that of STEAP-1. The cDNA nucleotide and deduced amino acid sequences of STEAP-2 are shown in FIG. 9A-D. Amino acid alignment of the STEAP-1 and STEAP-2 sequences show a high degree of structural conservation (54.9% identity over a 237 amino acid residue overlap, and the locations of the six putative transmembrane domains in STEAP-1 and STEAP-2 coincide (FIGS. 11A-B, 11C). Structural homology between these STEAP-1 and STEAP-2 is highest in the regions spanned by the first putative extracellular loop to the fifth transmembrane domain. However, some significant structural differences between STEAP-1 and STEAP-2 are apparent. For example, STEAP-2 exhibits a 205 a.a. long intracellular N-terminus (compared to 69 a.a. in STEAP-1) and a short 4 a.a. intracellular C-terminus (compared to 26 a.a. in STEAP-1). In addition, both the STEAP-1 and STEAP-2 genes are located on chromosome 7, but on different arms. These differences could imply significant differences in function and/or interaction with intracellular signaling pathways.

STEAP-2 is expressed only in normal prostate among human tissues tested (FIGS. 14 and 15) and is also expressed in prostate cancer (FIG. 15), and thus shows some similarity in expression profile to STEAP-1. However, STEAP-2 exhibits a different mRNA expression profile relative to STEAP-1 in prostate cancer samples (compare FIGS. 3 and 15) and in other non-prostate cancers tested (compare FIGS. 5 and 16). These differences in the expression profiles of STEAP-1 and STEAP-2 suggest that they are differentially regulated.

STEAP-3 and STEAP-4 appear to be closely related to both STEAP-1 and STEAP-2 on a structural level, and both appear to be transmembrane proteins as well. STEAP-3 is more related to STEAP-2 (47.8% identity) than to STEAP-1 (40.9% identity). STEAP-3 and STEAP-4 show unique expression profiles. STEAP-3, for example, appears to have an expression pattern which is predominantly restricted to placenta and, to a smaller degree, expression is seen in prostate but not in other normal tissues tested. STEAP-4 seems to be expressed predominantly in liver by RT-PCR analysis. Neither STEAP-3 nor STEAP-4 appear to be expressed in prostate cancer xenografts which exhibit high level STEAP-1 and STEAP-2 expression.

The STEAP proteins exhibit characteristics of proteins involved in cell signaling pathways. Specifically, STEAP-1 and STEAP-2, when expressed in PC3 cells, activate phosphorylation of p3[8], a protein involved in the MAPK signaling cascade. In addition, STEAP-2 expression induces tyrosine phosphorylation, and STEAP-1 mediates activation of tyrosine kinase in odorant-treated cells. These findings support the use of STEAP-related molecules and cells modified to express STEAP in high throughput assays to identify molecules capable of altering cellular signaling pathways, leading to the identification of novel therapeutic agents. In one embodiment, the assay identifies molecules capable of inhibiting STEAP function, which molecules are thereby capable of modulating the progression of cancer or other disease associated with dysregulated cell growth.

Three of the four STEAPs described herein map to human chromosome 7 (STEAP-1, -2 and 3). Interestingly, STEAP-1 maps within 7p22 (7p22.3), a large region of allelic gain reported for both primary and recurrent prostate cancers (Visakorpi et al., 1995 Cancer Res. 55: 342, Nupponen et al., 1998 American J. Pathol. 153: 141), suggesting that up-regulation of STEAP-1 in cancer might include genomic mechanisms. In addition, both STEAP-2 and STEAP-3 locate to chromosome 7q21, suggesting that these two genes arose by gene duplication.

Other cell surface molecules that contain six transmembrane domains include ion channels (Dolly and Parcej, 1996J Bioenerg Biomembr 28:231) and water channels or aquaporins (Reizer et al., 1993 Crit Rev Biochem Mol Biol 28:235). Structural studies show that both types of molecules assemble into tetrameric complexes to form functional channels (Christie, 1995, Clin Exp Pharmacol Physiol 22:944, Walz et al., 1997 Nature 387:624, Cheng et al., 1997 Nature 387:627). Immunohistochemical staining of STEAP-1 in the prostate gland seems to be concentrated at the cell-cell boundaries, with less staining detected at the lumenal side. This may suggest a role for STEAP-1 in tight-junctions, gap-junctions, cell communication, adhesion or as a transporter protein.

To test these possibilities, xenopus oocytes (or other cells) expressing STEAP may be analyzed using voltage-clamp and patch-clamp experiments to determine if STEAP functions as an ion-channel Oocyte cell volume may also be measured to determine if STEAP exhibits water channel properties. If STEAPs function as channel or gap junction proteins, they may serve as excellent targets for inhibition using, for example, antibodies, small molecules, and polynucleotides capable of inhibiting expression or function. The restricted expression pattern in normal tissue, and the high levels of expression in cancer tissue suggest that interfering with STEAP function may selectively kill cancer cells.

Since the STEAP gene family is predominantly expressed in epithelial tissue, it seems possible that the STEAP proteins function as ion channels, transport proteins or gap-junction proteins in epithelial cell function. Ion channels have been implicated in proliferation and invasiveness of prostate cancer cells (Lalani et al., 1997, Cancer Metastasis Rev 16:29). Both rat and human prostate cancer cells contain sub-population of cells with higher and lower expression levels of sodium channels. Higher levels of sodium channel expression correlate with more aggressive invasiveness in vitro (Smith et al., 1998, FEBS Lett. 423:19). Similarly, it has been shown that a specific blockade of sodium channels inhibits the invasiveness of PC-3 cells in vitro (Laniado et al., 1997, Am. J. Pathol. 150:1213), while specific inhibition of potassium channels in LNCaP cells inhibited cell proliferation (Skryma et al., 1997, Prostate 33:112). These reports suggest a role for ion channels in prostate cancer and also demonstrate that small molecules that inhibit ion channel function may interfere with prostate cancer proliferation.

Isolation of STEAP-Encoding Nucleic Acid Molecules

The STEAP cDNA sequences described herein enable the isolation of other polynucleotides encoding STEAP gene product(s), as well as the isolation of polynucleotides encoding STEAP gene product homologues, alternatively spliced isoforms, allelic variants, and mutant forms of the STEAP gene product. Various molecular cloning methods that can be employed to isolate full length cDNAs encoding a STEAP gene are well known (See, for example, Sambrook, J. et al. Molecular Cloning: A Laboratory Manual, 2d edition., Cold Spring Harbor Press, New York, 1989; Current Protocols in Molecular Biology. Ausubel et al., Eds., Wiley and Sons, 995). For example, lambda phage cloning methodologies may be conveniently employed, using commercially available cloning systems (e.g., Lambda ZAP Express, Stratagene). Phage clones containing STEAP gene cDNAs may be identified by probing with labeled STEAP cDNA or a fragment thereof. For example, in one embodiment, a STEAP cDNA or a portion thereof can be synthesized and used as a probe to retrieve overlapping and full length cDNAs corresponding to a STEAP gene. The STEAP gene itself may be isolated by screening genomic DNA libraries, bacterial artificial chromosome libraries (BACs), yeast artificial chromosome libraries (YACs), and the like, with STEAP DNA probes or primers.

Recombinant DNA Molecules and Host-Vector Systems

The invention also provides recombinant DNA or RNA molecules containing a STEAP polynucleotide, including but not limited to phages, plasmids, phagemids, cosmids, YACs, BACs, as well as various viral and non-viral vectors well known in the art, and cells transformed or transfected with such recombinant DNA or RNA molecules. As used herein, a recombinant DNA or RNA molecule is a DNA or RNA molecule that has been subjected to molecular manipulation in vitro. Methods for generating such molecules are well known (see, for example, Sambrook et al, 1989, supra).

The invention further provides a host-vector system comprising a recombinant DNA molecule containing a STEAP polynucleotide within a suitable prokaryotic or eukaryotic host cell. Examples of suitable eukaryotic host cells include a yeast cell, a plant cell, or an animal cell, such as a mammalian cell or an insect cell (e.g., a baculovirus-infectible cell such as an Sf9 cell). Examples of suitable mammalian cells include various prostate cancer cell lines such LNCaP, PC-3, DU145, LAPC-4, TsuPr1, other transfectable or transducible prostate cancer cell lines, as well as a number of mammalian cells routinely used for the expression of recombinant proteins (e.g., COS, CHO, 293, 293T cells). More particularly, a polynucleotide comprising the coding sequence of a STEAP may be used to generate STEAP proteins or fragments thereof using any number of host vector systems routinely used and widely known in the art.

A wide range of host vector systems suitable for the expression of STEAP proteins or fragments thereof are available, see for example, Sambrook et al., 1989, supra; Current Protocols in Molecular Biology, 1995, supra). Preferred vectors for mammalian expression include but are not limited to pcDNA 3.1 myc-His-tag (Invitrogen) and the retroviral vector pSRαtkneo (Muller et al., 1991, MCB 11:1785). Using these expression vectors, STEAP may be preferably expressed in several prostate cancer and non-prostate cell lines, including for example 293, 293T, rat-1, 3T3, PC-3, LNCaP and TsuPr1. The host vector systems of the invention are useful for the production of a STEAP protein or fragment thereof. Such host-vector systems may be employed to study the functional properties of STEAP and STEAP mutations.

Proteins encoded by the STEAP genes, or by fragments thereof, will have a variety of uses, including but not limited to generating antibodies and in methods for identifying ligands and other agents and cellular constituents that bind to a STEAP gene product. Antibodies raised against a STEAP protein or fragment thereof may be useful in diagnostic and prognostic assays, imaging methodologies (including, particularly, cancer imaging), and therapeutic methods in the management of human cancers characterized by expression of a STEAP protein, including but not limited to cancer of the prostate. Various immunological assays useful for the detection of STEAP proteins are contemplated, including but not limited to various types of radioimmunoassays, enzyme-linked immunosorbent assays (ELISA), enzyme-linked immunofluorescent assays (ELIFA), immunocytochemical methods, and the like. Such antibodies may be labeled and used as immunological imaging reagents capable of detecting prostate cells (e.g., in radioscintigraphic imaging methods). STEAP proteins may also be particularly useful in generating cancer vaccines, as further described below.

STEAP Proteins

Another aspect of the present invention provides various STEAP proteins and polypeptide fragments thereof. As used herein, a STEAP protein refers to a protein that has or includes the amino acid sequence of human STEAP-1 as provided in FIG. 1A-B, human STEAP-2 as provided in FIG. 9A-D, human STEAP-3 as provided in FIG. 10A-E, the amino acid sequence of other mammalian STEAP homologs (e.g., STEAP-4) and variants, as well as allelic variants and conservative substitution mutants of these proteins that have STEAP biological activity, to the extent that such variants and homologs can be isolated/generated and characterized without undue experimentation following the methods outlined below. Fusion proteins that combine parts of different STEAP proteins or fragments thereof, as well as fusion proteins of a STEAP protein and a heterologous polypeptide, are also included. Such STEAP proteins will be collectively referred to as the STEAP proteins, the proteins of the invention, or STEAP. As used herein, the term "STEAP polypeptide" refers to a polypeptide fragment or a STEAP protein of at least 10 amino acids, preferably at least 15 amino acids.

A specific embodiment of a STEAP protein comprises a polypeptide having the amino acid sequence of human STEAP-1 as shown in FIG. 1A-B. Another embodiment of a STEAP protein comprises a polypeptide containing the STEAP-2 amino acid sequence as shown in FIG. 9A-D. Another embodiment comprises a polypeptide containing the STEAP-3 amino acid sequence of shown in FIG. 10A-E. Yet another embodiment comprises a polypeptide containing the partial STEAP amino acid sequence of shown in FIG. 11A-B.

In general, naturally occurring allelic variants of human STEAP will share a high degree of structural identity and homology (e.g., 90% or more identity). Typically, allelic variants of the STEAP proteins will contain conservative amino acid substitutions within the STEAP sequences described herein or will contain a substitution of an amino acid from a corresponding position in a STEAP homologue. One class of STEAP allelic variants will be proteins that share a high degree of homology with at least a small region of a particular STEAP amino acid sequence, but will further contain a radical departure from the sequence, such as a non-conservative substitution, truncation insertion or frame shift.

Conservative amino acid substitutions can frequently be made in a protein without altering either the conformation or the function of the protein. Such changes include substituting any of isoleucine (I), valine (V), and leucine (L) for any other of these hydrophobic amino acids; aspartic acid (D) for glutamic acid (E) and vice versa; glutamine (Q) for asparagine (N) and vice versa; and serine (S) for threonine (T) and vice versa. Other substitutions can also be considered conservative, depending on the environment of the particular amino acid and its role in the three-dimensional structure of the protein. For example, glycine (G) and alanine (A) can frequently b interchangeable, as can alanine (A) and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pK's of these two amino acid residues are not significant. Still other changes can be considered "conservative" in particular environments.

STEAP proteins, including variants, comprise at least one epitope in common with a STEAP protein having an amino acid sequence shown in FIG. 11A-B, such that an antibody that specifically binds to a STEAP protein or variant will also specifically bind to the STEAP protein having an amino acid sequence shown in FIG. 11A-B. One class of STEAP protein variants shares 90% or more identity with an amino acid sequence of FIG. 11A-B. A more specific class of STEAP protein variants comprises an extracellular protein SCP motif as described above. Preferred STEAP protein variants are capable of exhibiting one or more of the defensin functions described herein, including, for example, the ability to induce tumor death or to chemoattract and/or induce migration of cells.

STEAP proteins may be embodied in many forms, preferably in isolated form. As used herein, a protein is said to be "isolated" when physical, mechanical or chemical methods are employed to remove the STEAP protein from cellular constituents that are normally associated with the protein. A skilled artisan can readily employ standard purification methods to obtain an isolated STEAP protein. A purified STEAP protein molecule will be substantially free of other proteins or molecules that impair the binding of STEAP to antibody or other ligand. The nature and degree of isolation and purification will depend on the intended use. Embodiments of a STEAP protein include a purified STEAP protein and a functional, soluble STEAP protein. In one form, such functional, soluble STEAP proteins or fragments thereof retain the ability to bind antibody or other ligand.

The invention also provides STEAP polypeptides comprising biologically active fragments of the STEAP amino acid sequence, such as a polypeptide corresponding to part of the amino acid sequences for STEAP-1 as shown in FIG. 1A-B, STEAP-2 as shown in FIG. 9A-D, STEAP-3 as shown in FIG. 10A-E, or STEAP-4 as shown in FIG. 11A-B. Such polypeptides of the invention exhibit properties of a STEAP protein, such as the ability to elicit the generation of antibodies which specifically bind an epitope associated with a STEAP protein. Polypeptides comprising amino acid sequences which are unique to a particular STEAP protein (relative to other STEAP proteins) may be used to generate antibodies which will specifically react with that particular STEAP protein. For example, referring to the amino acid alignment of the STEAP structures shown in FIGS. 11A-E, the skilled artisan will readily appreciate that each molecule contains stretches of sequence unique to its structure. These unique stretches can be used to generate antibodies specific to a particular STEAP. Similarly, regions of conserved sequence may be used to generate antibodies that may bind to multiple STEAPs.

Embodiments of the invention disclosed herein include a wide variety of art accepted variants of STEAP proteins such as polypeptides having amino acid insertions, deletions and substitutions. STEAP variants can be made using methods known in the art such as site-directed mutagenesis, alanine scanning, and PCR mutagenesis. Site-directed mutagenesis [Carter et al., *Nucl. Acids Res.*, 13:4331 (1986); Zoller et al., *Nucl. Acids Res.*, 10:6487 (1987)], cassette mutagenesis [Wells et al., *Gene*, 34:315 (1985)], restriction selection mutagenesis [Wells et al., *Philos. Trans. R. Soc. London SerA*, 317:415 (1986)] or other known techniques can be performed on the cloned DNA to produce the STEAP variant DNA. Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant. Alanine is also typically preferred because it is the most common amino acid. Further, it is frequently found in both buried and exposed positions [Creighton, *The Proteins*, (W. H. Freeman & Co., N.Y.); Chothia, J. Mol. Biol., 150:1 (1976)]. If alanine substitution does not yield adequate amounts of variant; an isosteric amino acid can be used.

As discussed above, embodiments of the claimed invention include polypeptides containing less than the full amino acid sequence of a STEAP protein shown in FIG. 11A-B. For example, representative embodiments of the invention disclosed herein include polypeptides consisting of about amino acid 1 to about amino acid 10 of a STEAP protein shown in FIG. 11A-B, polypeptides consisting of about amino acid 20 to about amino acid 30 of a STEAP protein shown in FIG. 11A-B, polypeptides consisting of about amino acid 30 to about amino acid 40 of a STEAP protein shown in FIG. 11A-B, polypeptides consisting of about amino acid 40 to about amino acid 50 of a STEAP protein shown in FIG. 11A-B, polypeptides consisting of about amino acid 50 to about amino acid 60 of a STEAP protein shown in FIG. 11A-B, polypeptides consisting of about amino acid 60 to about amino acid 70 of a STEAP protein shown in FIG. 11A-B, polypeptides consisting of about amino acid 70 to about amino acid 80 of a STEAP protein shown in FIG. 11A-B, polypeptides consisting of about amino acid 80 to about amino acid 90 of a STEAP protein shown in FIG. 11A-B and polypeptides consisting of about amino acid 90 to about amino acid 100 of a STEAP protein shown in FIG. 11A-B, etc. Following this scheme, polypeptides consisting of portions of the amino acid sequence of amino acids 100-339 of a STEAP-1 protein shown in FIG. 11A-B, or amino acids 100-454 of a STEAP-2 protein shown in FIG. 11A-B, or amino acids 100-459 of a STEAP-3 protein shown in FIG. 11A-B, or amino acids 100-133 of a STEAP-4 protein shown in FIG. 11A-B, are typical embodiments of the invention. Polypeptides consisting of larger portions of the STEAP protein are also contemplated. For example polypeptides consisting of about amino acid 1 (or 20 or 30 or 40 etc.) to about amino acid 20, (or 30, or 40 or 50 etc.) of a STEAP protein shown in FIG. 11A-B may be generated by a variety of techniques well known in the art.

Additional illustrative embodiments of the invention disclosed herein include STEAP polypeptides containing the amino acid residues of one or more of the biological motifs contained within a STEAP polypeptide sequence as shown in FIG. 11A-B. STEAP polypeptides containing one or more of these motifs or other select regions of interest described herein will typically include an additional 5 to 25 or more amino acid residues of adjacent STEAP protein sequence on one or both sides of the selected motif(s). In one embodiment, typical polypeptides of the invention can contain one or more of the regions of STEAP that exhibit homology to one or more other STEAP proteins. In another embodiment, typical polypeptides of the invention can contain one or more immunogenic portions of a STEAP protein. One example of an immunogenic portion of a STEAP protein is amino acid residues 14 through 28 of the STEAP-1 amino acid sequence as shown in FIG. 1A-B (WKMKPRRNLEEDDYL; SEQ ID NO: 22). In another embodiment, typical polypeptides of the invention can contain one or more predicted HLA-A2 binding peptides such as amino acids 165-173 of STEAP-1, amino acids 86-94 of STEAP-1, amino acids 262-270 of STEAP-1, amino acids 302-310 of STEAP-1, amino acids 158-166 of STEAP-1, amino acids 227-235 of STEAP-2, amino acids 402-410 of STEAP-2, amino acids 307-315 of STEAP-2, amino acids 306-314 of STEAP-2, and amino acids 100-108 of STEAP-2. In another embodiment, typical polypeptides of the invention consist of all or part of a fragment of STEAP-2, such as amino acids 1-245, 2-204, 121-454, 153-165, 182-454, 183-387, 276-453, 345-358, or 419-454 of the STEAP-2 protein shown in FIG. 8. Related embodiments of these inventions include polypeptides containing combinations of the different motifs discussed above with preferable embodiments being those that contain no insertions, deletions or substitutions either within the motifs or the intervening sequences of these polypeptides.

STEAP polypeptides can be generated using standard peptide synthesis technology or using chemical cleavage methods well known in the art based on the amino acid sequences of the human STEAP proteins disclosed herein. Alternatively, recombinant methods can be used to generate nucleic acid molecules that encode a polypeptide fragment of a STEAP protein. In this regard, the STEAP-encoding nucleic acid molecules described herein provide means for generating defined fragments of STEAP proteins. STEAP polypeptides are particularly useful in generating and characterizing domain specific antibodies (e.g., antibodies recognizing an extracellular or intracellular epitope of a STEAP protein), in identifying agents or cellular factors that bind to STEAP or a particular structural domain thereof, and in various therapeutic contexts, including but not limited to cancer vaccines. STEAP polypeptides containing particularly interesting structures can be predicted and/or identified using various analytical techniques well known in the art, including, for example, the methods of Chou-Fasman, Garnier-Robson, Kyte-Doolittle, Eisenberg, Karplus-Schultz or Jameson-Wolf analysis, or on the basis of immunogenicity. Fragments containing such structures are particularly useful in generating subunit specific anti-STEAP antibodies or in identifying cellular factors that bind to STEAP.

In a specific embodiment described in the examples that follow, a secreted form of STEAP may be conveniently expressed in 293T cells transfected with a CMV-driven expression vector encoding STEAP with a C-terminal 6×His and MYC tag (pcDNA3.1/mycHIS, Invitrogen). The secreted HIS-tagged STEAP in the culture media may be purified using a nickel column and standard techniques. Alternatively, an AP-tag system may be used. Various constructs for expression of STEAP are described in the examples below.

Modifications of STEAP such as covalent modifications are included within the scope of this invention. One type of covalent modification includes reacting targeted amino acid residues of an STEAP polypeptide with an organic derivatizing agent that is capable of reacting with selected side chains or the N- or C-terminal residues of the STEAP. Another type of covalent modification of the STEAP polypeptide included within the scope of this invention comprises altering the native glycosylation pattern of the polypeptide. "Altering the native glycosylation pattern" is intended for purposes herein to mean deleting one or more carbohydrate moieties found in native sequence STEAP (either by removing the underlying glycosylation site or by deleting the glycosylation by chemical and/or enzymatic means), and/or adding one or more glycosylation sites that are not present in the native sequence STEAP. In addition, the phrase includes qualitative changes in the glycosylation of the native proteins, involving a change in the nature and proportions of the various carbohydrate moieties present. Another type of covalent modification of STEAP comprises linking the STEAP polypeptide to one of a variety of nonproteinaceous polymers, e.g., polyethylene glycol (PEG), polypropylene glycol, or polyoxyalkylenes, in the manner set forth in U.S. Pat. Nos. 4,640,835; 4,496,689; 4,301,144; 4,670,417; 4,791,192 or 4,179,337.

The STEAP of the present invention may also be modified in a way to form a chimeric molecule comprising STEAP fused to another, heterologous polypeptide or amino acid sequence. In one embodiment, such a chimeric molecule comprises a fusion of the STEAP with a polyhistidine epitope tag, which provides an epitope to which immobilized nickel can selectively bind. The epitope tag is generally placed at the amino- or carboxyl-terminus of the STEAP. In an alternative embodiment, the chimeric molecule may comprise a fusion of the STEAP with an immunoglobulin or a particular region of an immunoglobulin. For a bivalent form of the chimeric molecule (also referred to as an "immunoadhesin"), such a fusion could be to the Fc region of an IgG molecule. The Ig fusions preferably include the substitution of a soluble (transmembrane domain deleted or inactivated) form of an STEAP polypeptide in place of at least one variable region within an Ig molecule. In a particularly preferred embodiment, the immunoglobulin fusion includes the hinge, CH2 and CH3, or the hinge, CH1, CH2 and CH3 regions of an IgG1 molecule. For the production of immunoglobulin fusions see also U.S. Pat. No. 5,428,130 issued Jun. 27, 1995.

STEAP Antibodies

Another aspect of the invention provides antibodies that bind to STEAP proteins and polypeptides. The most preferred antibodies will selectively bind to a STEAP protein and will not bind (or will bind weakly) to non-STEAP proteins and polypeptides. Anti-STEAP antibodies that are particularly contemplated include monoclonal and polyclonal antibodies as well as fragments containing the antigen-binding domain and/or one or more complementarity determining regions of these antibodies. As used herein, an antibody fragment is defined as at least a portion of the variable region of the immunoglobulin molecule that binds to its target, i.e., the antigen binding region.

For some applications, it may be desirable to generate antibodies which specifically react with a particular STEAP protein and/or an epitope within a particular structural domain. For example, preferred antibodies useful for cancer therapy and diagnostic imaging purposes are those which react with an epitope in an extracellular region of the STEAP protein as expressed in cancer cells. Such antibodies may be generated by using the STEAP proteins described herein, or using peptides derived from predicted extracellular domains thereof, as an immunogen. In this regard, with reference to the STEAP-1 protein topological schematic shown in FIG. 1B, regions in the extracellular loops between the indicated transmembrane domains may be selected as used to design appropriate immunogens for raising extracellular-specific antibodies.

STEAP antibodies of the invention may be particularly useful in prostate cancer therapeutic strategies, diagnostic and prognostic assays, and imaging methodologies. Similarly, such antibodies may be useful in the treatment, diagnosis, and/or prognosis of other cancers, to the extent STEAP is also expressed or overexpressed in other types of cancer. The invention provides various immunological assays useful for the detection and quantification of STEAP and mutant STEAP proteins and polypeptides. Such assays generally comprise one or more STEAP antibodies capable of recognizing and binding a STEAP or mutant STEAP protein, as appropriate, and may be performed within various immunological assay formats well known in the art, including but not limited to various types of radioimmunoassays, enzyme-linked immunosorbent assays (ELISA), enzyme-linked immunofluorescent assays (ELIFA), and the like. In addition, immunological imaging methods capable of detecting prostate cancer are also provided by the invention, including but limited to radioscintigraphic imaging methods using labeled STEAP antibodies. Such assays may be used clinically in the detection, monitoring, and prognosis of prostate cancer, particularly advanced prostate cancer.

STEAP antibodies may also be used in methods for purifying STEAP and mutant STEAP proteins and polypeptides and for isolating STEAP homologues and related molecules. For example, in one embodiment, the method of purifying a STEAP protein comprises incubating a STEAP antibody, which has been coupled to a solid matrix, with a lysate or other solution containing STEAP under conditions which permit the STEAP antibody to bind to STEAP; washing the solid matrix tQ eliminate impurities; and eluting the STEAP from the coupled antibody. Other uses of the STEAP antibodies of the invention include generating anti-idiotypic antibodies that mimic the STEAP protein.

STEAP antibodies may also be used therapeutically by, for example, modulating or inhibiting the biological activity of a STEAP protein or targeting and destroying cancer cells expressing a STEAP protein. Antibody therapy of prostate and other cancers is more specifically described in a separate subsection below.

Various methods for the preparation of antibodies are well known in the art. For example, antibodies may be prepared by immunizing a suitable mammalian host using a STEAP protein, peptide, or fragment, in isolated or immunoconjugated form (Antibodies: A Laboratory Manual, CSH Press, Eds., Harlow, and Lane (1988); Harlow, Antibodies, Cold Spring Harbor Press, NY (1989)). Examples of protein immunogens include recombinant STEAP (expressed in a baculovirus system, mammalian system, etc.), STEAP extracellular domain or extracellular loops of STEAP protein conjugated to one or more antibody constant regions, AP-tagged STEAP, etc. In addition, fusion proteins of STEAP may also be used, such as a fusion of STEAP with GST, maltose-binding protein (MBP), green fluorescent protein (GFP), HisMax-TOPO or MycHis (see Examples below).

In a particular embodiment, a GST fusion protein comprising all or most of an open reading frame amino acid sequence as shown in FIG. 11A-B may be produced and used as an immunogen to generate appropriate antibodies. Cells expressing or overexpressing STEAP may also be used for immunizations. Similarly, any cell engineered to express STEAP may be used. Such strategies may result in the production of monoclonal antibodies with enhanced capacities for recognizing endogenous STEAP. Another useful immunogen comprises STEAP peptides linked to the plasma membrane of sheep red blood cells.

The amino acid sequences of STEAP proteins as shown in FIG. 11A-B may be used to select specific regions of a STEAP protein for generating antibodies. For example, hydrophobicity and hydrophilicity analyses of the STEAP amino acid sequence may be used to identify hydrophilic regions in the STEAP structure. Regions of the STEAP protein that show immunogenic structure, as well as other regions and domains, can readily be identified using various other methods known in the art, such as Chou-Fasman, Garnier Robson, Kyte-Doolittle, Eisenberg, Karplus-Schultz or Jameson-Wolf analysis. Peptides of STEAP predicted to bind HLA-A2 may be selected for the generation of antibodies or used to generate a CTL response. Such predicted HLA-A2 binding peptides include, but are not limited to, amino acids 165-173 of STEAP-1, amino acids 86-94 of STEAP-1, amino acids 262-270 of STEAP-1, amino acids 302-310 of STEAP-1, amino acids 158-166 of STEAP-1, amino acids 227-235 of STEAP-2, amino acids 402-410 of STEAP-2, amino acids 307-315 of STEAP-2, amino acids 306-314 of STEAP-2, and amino acids 100-108 of STEAP-2. As discussed in the examples below, immunogenicity has been demonstrated with STEAP, which was used to generate polyclonal and monoclonal antibodies using rabbits and mice, respectively. This B cell response (antibody production) is the result of an initial T cell response elicited by the immunogenic portions of STEAP.

Methods for preparing a protein or polypeptide for use as an immunogen and for preparing immunogenic conjugates of a protein with a carrier such as BSA, KLH, or other carrier proteins are well known in the art. In some circumstances, direct conjugation using, for example, carbodiimide reagents may be used; in other instances linking reagents such as those supplied by Pierce Chemical Co., Rockford, Ill., may be effective. Administration of a STEAP immunogen is conducted generally by injection over a suitable period and with use of a suitable adjuvant, as is generally understood in the art. During the immunization schedule, titers of antibodies can be taken to determine adequacy of antibody formation.

STEAP monoclonal antibodies are preferred and may be produced by various means well known in the art. For example, immortalized cell lines which secrete a desired monoclonal antibody may be prepared using the standard hybridoma technology of Kohler and Milstein or modifications which immortalize producing B cells, a is generally known. The immortalized cell lines secreting the desired antibodies are screened by immunoassay in which the antigen is the STEAP protein or STEAP fragment. When the appropriate immortalized cell culture secreting the desired antibody is identified, the cells may be expanded and antibodies produced either from in vitro cultures or from ascites fluid.

The antibodies or fragments may also be produced, using current technology, by recombinant means. Regions that bind specifically to the desired regions of the STEAP protein can also be produced in the context of chimeric or CDR grafted antibodies of multiple species origin. Humanized or human STEAP antibodies may also be produced and are preferred for use in therapeutic contexts. Methods for humanizing murine and other non-human antibodies by substituting one or more of the non-human antibody CDRs for corresponding human antibody sequences are well known (see for example, Jones et al., 1986, Nature 321: 522-525; Riechmann et al., 1988, Nature 332: 323-327; Verhoeyen et al., 1988, Science 239:1534-1536). See also, Carter et al., 1993, Proc. Nat'l Acad. Sci. USA 89: 4285 and Sims et al., 1993, J. Immunol. 151: 2296. Methods for producing fully human monoclonal antibodies include phage display and transgenic animal technologies (for review, see Vaughan et al., 1998, Nature Biotechnology 16: 535-539).

Fully human STEAP monoclonal antibodies may be generated using cloning technologies employing large human Ig gene combinatorial libraries (i.e., phage display) (Griffiths and Hoogenboom, Building an in vitro immune system: human antibodies from phage display libraries. In: Protein Engineering of Antibody Molecules for Prophylactic and Therapeutic Applications in Man. Clark, M. (Ed.), Nottingham Academic, pp 45-64 (1993); Burton and Barbas, Human Antibodies from combinatorial libraries. Id., pp 65-82). Fully human STEAP monoclonal antibodies may also be produced using transgenic mice engineered to contain human immunoglobulin gene loci as described in U.S. Pat. No. 6,150,584 and in PCT Patent Application WO98/24893, published Dec. 3, 1997 (see also, Jakobovits, 1998, Exp. Opin. Invest. Drugs 7(4): 607-614). This method avoids the in vitro manipulation required with phage display technology and efficiently produces high affinity authentic human antibodies.

Reactivity of STEAP antibodies with a STEAP protein may be established by a number of well known means, including western blot, immunoprecipitation, ELISA, and FACS analyses using, as appropriate, STEAP proteins, peptides, STEAP expressing cells or extracts thereof.

A STEAP antibody or fragment thereof of the invention may be labeled with a detectable marker or conjugated to a second molecule, such as a cytotoxin or other therapeutic agent, and used for targeting the second molecule to a STEAP positive cell (Vitetta, E. S. et al., 1993, Immunotoxin therapy, in DeVita, Jr., V. T. et al., eds., Cancer: Principles and Practice of Oncology, 4th ed., J. B. Lippincott Co., Philadelphia, 2624-2636). Examples of cytotoxic agents include, but are not limited to ricin, ricin A-chain, doxorubicin, maytansinoids, daunorubicin, taxol, ethidium bromide, mitomycin, etoposide, tenoposide, vincristine, vinblastine, colchicine, dihydroxy anthracin dione, actinomycin, diphtheria toxin, Pseudomonas exotoxin (PE) A, PE40, abrin, abrin A chain, modeccin A chain, alpha-sarcin, gelonin, mitogellin, retstrictocin, phenomycin, enomycin, curicin, crotin, calicheamicin, sapaonaria officinalis inhibitor, and glucocorticoid and other chemotherapeutic agents, as well as radioisotopes such as $^{212}$Bi, $^{131}$I, $^{131}$In, $^{90}$Y, and $^{186}$Re. Suitable detectable markers include, but are not limited to, a radioisotope, a fluorescent compound, a bioluminescent compound, chemiluminescent compound, a metal chelator or an enzyme. Antibodies may also be conjugated to an anti-cancer pro-drug activating enzyme capable of converting the pro-drug to its active form. See, for example, U.S. Pat. No. 4,975,287.

Further, bi-specific antibodies specific for two or more STEAP epitopes may be generated using methods generally known in the art. Further, antibody effector functions may be modified to enhance the therapeutic effect of STEAP antibodies on cancer cells. For example, cysteine residues may be engineered into the Fc region, permitting the formation of interchain disulfide bonds and the generation of homodimers which may have enhanced capacities for internalization, ADCC and/or complement mediated cell killing (see, for example, Caron et al., 1992, J. Exp. Med. 176: 1191-1195; Shopes, 1992, J. Immunol. 148: 2918-2922). Homodimeric antibodies may also be generated by cross-linking techniques known in the art (e.g., Wolff et al., Cancer Res. 53: 2560-2565).

STEAP Transgenic Animals

Nucleic acids that encode STEAP or its modified forms can also be used to generate either transgenic animals or "knock out" animals which, in turn, are useful in the development and screening of therapeutically useful reagents. A transgenic animal (e.g., a mouse or rat) is an animal having cells that contain a transgene, which transgene was introduced into the animal or an ancestor of the animal at a prenatal, e.g., an embryonic stage. A transgene is a DNA that is integrated into the genome of a cell from which a transgenic animal develops. In one embodiment, cDNA encoding STEAP can be used to clone genomic DNA encoding STEAP in accordance with established techniques and the genomic sequences used to generate transgenic animals that contain cells that express DNA encoding STEAP.

Methods for generating transgenic animals, particularly animals such as mice or rats, have become conventional in the art and are described, for example, in U.S. Pat. Nos. 4,736,866 and 4,870,009. Typically, particular cells would be targeted for STEAP transgene incorporation with tissue-specific enhancers. Transgenic animals that include a copy of a transgene encoding STEAP introduced into the germ line of the animal at an embryonic stage can be used to examine the effect of increased expression of DNA encoding STEAP. Such animals can be used as tester animals for reagents thought to confer protection from, for example, pathological conditions associated with its overexpression. In accordance with this facet of the invention, an animal is treated with the reagent and a reduced incidence of the pathological condition, compared to untreated animals bearing the transgene, would indicate a potential therapeutic intervention for the pathological condition.

Alternatively, non-human homologues of STEAP can be used to construct a STEAP "knock out" animal that has a defective or altered gene encoding STEAP as a result of homologous recombination between the endogenous gene encoding STEAP and altered genomic DNA encoding STEAP introduced into an embryonic cell of the animal. For example, cDNA encoding STEAP can be used to clone genomic DNA encoding STEAP in accordance with established techniques. A portion of the genomic DNA encoding STEAP can be deleted or replaced with another gene, such as a gene encoding a selectable marker that can be used to monitor integration.

Typically, several kilobases of unaltered flanking DNA (both at the 5' and 3' ends) are included in the vector (see e.g., Thomas and Capecchi, 1987, Cell 51:503 for a description of homologous recombination vectors). The vector is introduced into an embryonic stem cell line (e.g., by electroporation) and cells in which the introduced DNA has homologously recombined with the endogenous DNA are selected (see e.g., Li et al., 1992, Cell 69:915). The selected cells are then injected into a blastocyst of an animal (e.g., a mouse or rat) to form aggregation chimeras (see e.g., Bradley, in *Teratocarcinomas and Embryonic Stem Cells: A Practical Approach*, E. J. Robertson, ed., IRL, Oxford, 1987, pp. 113-152).

A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knockout animals can be characterized for instance, for their ability to defend against certain pathological conditions and for their development of pathological conditions due to absence of the STEAP polypeptide.

Monitoring the Status of STEAP and its Products

Assays that evaluate the status of a STEAP gene and STEAP gene products in an individual may provide information on the growth or oncogenic potential of a biological sample from this individual. For example, because STEAP mRNA is so highly expressed in prostate, and not in most normal tissue, and because its expression is associated with certain cancers, assays that evaluate the relative levels of STEAP mRNA transcripts or proteins in a biological sample may be used to diagnose a disease associated with STEAP dysregulation, such as cancer or benign prostatic hyperplasia (BPH), and may provide prognostic information useful in defining appropriate therapeutic options. Similarly, assays that evaluate the integrity STEAP nucleotide and amino acid sequences in a biological sample, may also be used in this context.

The finding that STEAP mRNA is expressed in prostate and other cancers, and not in most normal tissue, provides evidence that this gene is associated with dysregulated cell growth and therefore identifies this gene and its products as targets that the skilled artisan can use to evaluate biological samples from individuals suspected of having a disease associated with STEAP dysregulation. In another example, because the expression of STEAP is normally restricted to prostate, one can also evaluate biological samples taken from other tissues to detect STEAP expression as an indication of metastasis. For example, as shown in FIG. 31A-F, antibodies directed to STEAP-1 provide a superior marker for detection of metastases, as compared to the conventional prostate cancer marker, PSA. Such a marker can be useful both in evaluation tissue biopsies and as part of in vivo imaging strategies. In this context, the evaluation of the expression status of STEAP gene and its products can be used to gain information on the disease potential of a tissue sample. The terms "expression status" in this context is used to broadly refer to the variety of factors involved in the expression, function and regulation of a gene and its products such as the level of mRNA expression, the integrity of the expressed gene products (such as the nucleic and amino acid sequences) and transcriptional and translational modifications to these molecules.

The expression status of STEAP may provide information useful for predicting susceptibility to particular disease stages, progression, and/or tumor aggressiveness. The invention provides methods and assays for determining STEAP expression status and diagnosing cancers that express STEAP, such as cancers of the prostate. STEAP expression status in patient samples may be analyzed by a number of means well known in the art, including without limitation, immunohistochemical analysis, in situ hybridization, RT-PCR analysis on laser capture micro-dissected samples, western blot analysis of clinical samples and cell lines, and tissue array analysis. Typical protocols for evaluating the expression status of the STEAP gene and gene products can be found, for example in *Current Protocols In Molecular Biology*, Units 2 [Northern Blotting], 4 [Southern Blotting], 15 [Immunoblotting] and 18 [PCR Analysis], Frederick M. Ausubul et al. eds., 1995.

In one aspect, the invention provides methods for monitoring STEAP gene products by determining the status of STEAP gene products expressed by cells in a test tissue sample from an individual suspected of having a disease associated with dysregulated cell growth (such as hyperplasia or cancer) and then comparing the status so determined to the status of STEAP gene products in a corresponding normal sample, the presence of aberrant or altered status of STEAP gene products in the test sample relative to the normal sample providing an indication of the presence of dysregulated cell growth within the cells of the individual.

The invention additionally provides methods of examining a biological sample for evidence of dysregulated cellular growth. In one embodiment, the method comprises comparing the status of STEAP in the biological sample to the status of STEAP in a corresponding normal sample, wherein alterations in the status of STEAP in the biological sample are associated with dysregulated cellular growth. The status of STEAP in the biological sample can be evaluated by, for example, examining levels of STEAP mRNA expression or levels of STEAP protein expression. In one embodiment, an alteration in the status of STEAP is identified by the presence of STEAP expressing cells in a biological sample from a tissue in which STEAP expressing cells are normally absent.

In another aspect, the invention provides assays useful in determining the presence of cancer in an individual, comprising detecting a significant increase in STEAP mRNA or protein expression in a test cell or tissue sample relative to expression levels in the corresponding normal cell or tissue. The presence of STEAP mRNA may, for example, be evaluated in tissue samples including but not limited to colon, lung, prostate, pancreas, bladder, breast, ovary, cervix, testis, head and neck, brain, stomach, bone, etc. The presence of significant STEAP expression in any of these tissues may be useful to indicate the emergence, presence and/or severity of these cancers or a metastasis of cancer originating in another tissue, since the corresponding normal tissues do not express STEAP mRNA or express it at lower levels.

In a related embodiment, STEAP expression status may be determined at the protein level rather than at the nucleic acid level. For example, such a method or assay would comprise determining the level of STEAP protein expressed by cells in a test tissue sample and comparing the level so determined to the level of STEAP expressed in a corresponding normal sample. In one embodiment, the presence of STEAP protein is evaluated, for example, using immunohistochemical methods. STEAP antibodies or binding partners capable of detecting STEAP protein expression may be used in a variety of assay formats well known in the art for this purpose. As shown in the accompanying examples, STEAP immunoreactivity is associated with prostate, bladder and lung cancer, as well as BPH and prostate cancer metastases.

In other related embodiments, one can evaluate the integrity STEAP nucleotide and amino acid sequences in a biological sample in order to identify perturbations in the structure of these molecules such as insertions, deletions, substitutions and the like. Such embodiments are useful because perturbations in the nucleotide and amino acid sequences are observed in a large number of proteins associated with a growth dysregulated phenotype (see e.g. Marrogi et al., J. Cutan. Pathol. 26(8): 369-378 (1999)). In this context, a wide variety of assays for observing perturbations in nucleotide and amino acid sequences are well known in the art. For example, the size and structure of nucleic acid or amino acid sequences of STEAP gene products may be observed by the northern, Southern, western, PCR and DNA sequencing protocols discussed herein. In addition, other methods for observing perturbations in nucleotide and amino acid sequences such as single strand conformation polymorphism analysis are well known in the art (see e.g. U.S. Pat. Nos. 5,382,510 and 5,952,170).

In another embodiment, one can examine the methylation status of the STEAP gene in a biological sample. Aberrant demethylation and/or hypermethylation of CpG islands in gene 5' regulatory regions frequently occurs in immortalized and transformed cells and can result in altered expression of various genes. For example, promoter hypermethylation of the pi-class glutathione S-transferase (a protein expressed in normal prostate but not expressed in >90% of prostate carcinomas) appears to permanently silence transcription of this gene and is the most frequently detected genomic alteration in prostate carcinomas (De Marzo et al., 1999, Am. J. Pathol. 155(6): 1985-1992). In addition, this alteration is present in at least 70% of cases of high-grade prostatic intraepithelial neoplasia (PIN) (Brooks et al., 1998, Cancer Epidemiol. Biomarkers Prev., 7:531-536).

In another example, expression of the LAGE-I tumor specific gene (which is not expressed in normal prostate but is expressed in 25-50% of prostate cancers) is induced by deoxy-azacytidine in lymphoblastoid cells, suggesting that tumoral expression is due to demethylation (Lethe et al., 1998, Int. J. Cancer 76(6): 903-908). In this context, a variety of assays for examining methylation status of a gene are well known in the art. For example, one can utilize in Southern hybridization approaches methylation-sensitive restriction enzymes which can not cleave sequences that contain methylated CpG sites in order to assess the overall methylation status of CpG islands.

In addition, MSP (methylation specific PCR) can rapidly profile the methylation status of all the CpG sites present in a CpG island of a given gene. This procedure involves initial modification of DNA by sodium bisulfite (which will convert all unmethylated cytosines to uracil) followed by amplification using primers specific for methylated versus unmethylated DNA. Protocols involving methylation interference can also be found for example in *Current Protocols In Molecular Biology*, Units 12, Frederick M. Ausubel et al. eds., 1995.

In another related embodiment, the invention provides assays useful in determining the presence of cancer in an individual, comprising detecting a significant change in the STEAP alternative splice variants expressed in a test cell or tissue sample relative to expression levels in the corresponding normal cell or tissue. The monitoring of alternative splice variants of STEAP is useful because changes in the alternative splicing of proteins is suggested as one of the steps in a series of events that lead to the progression of cancers (see e.g. Carstens et al., Oncogene 15(250: 3059-3065 (1997)).

Gene amplification provides an additional method of assessing the status of STEAP. Gene amplification may be measured in a sample directly, for example, by conventional Southern blotting, northern blotting to quantitate the transcription of mRNA [Thomas, *Proc. Natl. Acad. Sci. USA*, 77:5201-5205 (1980)], dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

In addition to the tissues discussed above, peripheral blood may be conveniently assayed for the presence of cancer cells, including but not limited to prostate cancers, using RT-PCR to detect STEAP expression. The presence of RT-PCR amplifiable STEAP mRNA provides an indication of the presence of the cancer. RT-PCR detection assays for tumor cells in peripheral blood are currently being evaluated for use in the diagnosis and management of a number of human solid tumors. In the prostate cancer field, these include RT-PCR assays for the detection of cells expressing PSA and PSM (Verkaik et al., 1997, Urol. Res. 25: 373-384; Ghossein et al., 1995, J. Clin. Oncol. 13: 1195-2000; Heston et al., 1995, Clin. Chem. 41: 1687-1688). RT-PCR assays are well known in the art.

A related aspect of the invention is directed to predicting susceptibility to developing cancer in an individual. In one embodiment, a method for predicting susceptibility to cancer comprises detecting STEAP mRNA or STEAP protein in a tissue sample, its presence indicating susceptibility to cancer, wherein the degree of STEAP mRNA expression present is proportional to the degree of susceptibility. In a specific embodiment, the presence of STEAP in prostate tissue is examined, with the presence of STEAP in the sample providing an indication of prostate cancer susceptibility (or the emergence or existence of a prostate tumor). In a closely related embodiment, one can evaluate the integrity STEAP nucleotide and amino acid sequences in a biological sample in order to identify perturbations in the structure of these molecules such as insertions, deletions, substitutions and the like, with the presence of one or more perturbations in STEAP gene products in the sample providing an indication of cancer susceptibility (or the emergence or existence of a tumor).

Yet another related aspect of the invention is directed to methods for gauging tumor aggressiveness. In one embodiment, a method for gauging aggressiveness of a tumor comprises determining the level of STEAP mRNA or STEAP protein expressed by cells in a sample of the tumor, comparing the level so determined to the level of STEAP mRNA or STEAP protein expressed in a corresponding normal tissue taken from the same individual or a normal tissue reference sample, wherein the degree of STEAP mRNA or STEAP protein expression in the tumor sample relative to the normal sample indicates the degree of aggressiveness. In a specific embodiment, aggressiveness of prostate tumors is evaluated by determining the extent to which STEAP is expressed in the tumor cells, with higher expression levels indicating more aggressive tumors. In a closely related embodiment, one can evaluate the integrity STEAP nucleotide and amino acid sequences in a biological sample in order to identify perturbations in the structure of these molecules such as insertions, deletions, substitutions and the like, with the presence of one or more perturbations indicating more aggressive tumors.

Yet another related aspect of the invention is directed to methods for observing the progression of a malignancy in an individual over time. In one embodiment, methods for observing the progression of a malignancy in an individual over time comprise determining the level of STEAP mRNA or STEAP protein expressed by cells in a sample of the tumor, comparing the level so determined to the level of STEAP mRNA or STEAP protein expressed in an equivalent tissue sample taken from the same individual at a different time, wherein the degree of STEAP mRNA or STEAP protein expression in the tumor sample over time provides information on the progression of the cancer. In a specific embodiment, the progression of a cancer is evaluated by determining the extent to which STEAP expression in the tumor cells alters over time, with higher expression levels indicating a progression of the cancer. In a closely related embodiment, one can evaluate the integrity STEAP nucleotide and amino acid sequences in a biological sample in order to identify perturbations in the structure of these molecules such as insertions, deletions, substitutions and the like, with the presence of one or more perturbations indicating a progression of the cancer.

The above diagnostic approaches may be combined with any one of a wide variety of prognostic and diagnostic protocols known in the art. For example, another embodiment of the invention disclosed herein is directed to methods for observing a coincidence between the expression of STEAP gene and STEAP gene products (or perturbations in STEAP gene and STEAP gene products) and a factor that is associated with malignancy as a means of diagnosing and prognosticating the status of a tissue sample. In this context, a wide variety of factors associated with malignancy may be utilized such as the expression of genes otherwise associated with malignancy (including PSA, PSCA and PSM expression) as well as gross cytological observations (see e.g. Bocking et al., 1984, Anal. Quant. Cytol. 6(2):74-88; Epstein, 1995, Hum. Pathol. 1995 February; 26(2):223-9; Thorson et al., 1998, Mod. Pathol. 11(6):543-51; Baisden et al., 1999, Am. J. Surg. Pathol. 23(8):918-24). Methods for observing a coincidence between the expression of STEAP gene and STEAP gene products (or perturbations in STEAP gene and STEAP gene products) and an additional factor that is associated with malignancy are useful, for example, because the presence of a set or constellation of specific factors that coincide provides information crucial for diagnosing and prognosticating the status of a tissue sample.

In a typical embodiment, methods for observing a coincidence between the expression of STEAP gene and STEAP gene products (or perturbations in STEAP gene and STEAP gene products) and a factor that is associated with malignancy entails detecting the overexpression of STEAP mRNA or protein in a tissue sample, detecting the overexpression of PSA mRNA or protein in a tissue sample, and observing a coincidence of STEAP mRNA or protein and PSA mRNA or protein overexpression. In a specific embodiment, the expression of STEAP and PSA mRNA in prostate tissue is examined. In a preferred embodiment, the coincidence of STEAP and PSA mRNA overexpression in the sample provides an indication of prostate cancer, prostate cancer susceptibility or the emergence or existence of a prostate tumor.

Methods for detecting and quantifying the expression of STEAP mRNA or protein are described herein and use standard nucleic acid and protein detection and quantification technologies well known in the art. Standard methods for the detection and quantification of STEAP mRNA include in situ hybridization using labeled STEAP riboprobes, northern blot and related techniques using STEAP polynucleotide probes, RT-PCR analysis using primers specific for STEAP, and other amplification type detection methods, such as, for example, branched DNA, SISBA, TMA and the like. In a specific embodiment, semi-quantitative RT-PCR may be used to detect and quantify STEAP mRNA expression as described in the Examples that follow. Any number of primers capable of amplifying STEAP may be used for this purpose, including but not limited to the various primer sets specifically described herein. Standard methods for the detection and quantification of protein may be used for this purpose. In a specific embodiment, polyclonal or monoclonal antibodies specifically reactive with the wild-type STEAP protein may be used in an immunohistochemical assay of biopsied tissue. Antibodies directed against STEAP protein can also be used to detect STEAP in a patient specimen (e.g., blood, urine, semen or other sample) using conventional techniques such as fluorescence-activated cell sorting (FACS) and/or ELISA.

Identifying Molecules that Interact with STEAP

The STEAP protein sequences disclosed herein allow the skilled artisan to identify proteins, small molecules and other agents that interact with STEAP and pathways activated by STEAP via any one of a variety of art accepted protocols. For example one can utilize one of the variety of so-called interaction trap systems (also referred to as the "two-hybrid assay"). In such systems, molecules that interact reconstitute a transcription factor and direct expression of a reporter gene, the expression of which is then assayed. Typical systems identify protein-protein interactions in vivo through reconstitution of a eukaryotic transcriptional activator and are disclosed for example in U.S. Pat. Nos. 5,955,280, 5,925,523, 5,846,722 and 6,004,746.

Alternatively one can identify molecules that interact with STEAP protein sequences by screening peptide libraries. In such methods, peptides that bind to selected receptor molecules such as STEAP are identified by screening libraries that encode a random or controlled collection of amino acids. Peptides encoded by the libraries are expressed as fusion proteins of bacteriophage coat proteins, and bacteriophage particles are then screened against the receptors of interest. Peptides having a wide variety of uses, such as therapeutic or diagnostic reagents, may thus be identified without any prior information on the structure of the expected ligand or receptor molecule. Typical peptide libraries and screening methods that can be used to identify molecules that interact with STEAP protein sequences are disclosed for example in U.S. Pat. Nos. 5,723,286 and 5,733,731.

Alternatively, cell lines expressing STEAP can be used to identify protein-protein interactions mediated by STEAP. This possibility can be examined using immunoprecipitation techniques as shown by others (Hamilton B J, et al. Biochem. Biophys. Res. Commun. 1999, 261:646-51). Typically STEAP protein can be immunoprecipitated from STEAP expressing prostate cancer cell lines using anti-STEAP antibodies. Alternatively, antibodies against His-tag can be used in a cell line engineered to express STEAP (vectors mentioned above). The immunoprecipitated complex can be examined for protein association by procedures such as western blotting, $^{35}$S-methionine labeling of proteins, protein microsequencing, silver staining and two dimensional gel electrophoresis.

Small molecules that interact with STEAP can be identified through related embodiments of such screening assays. For example, small molecules can be identified that interfere with STEAP function, including molecules that interfere with STEAP's ability to bind to cells and/or to modulate tumor formation, progression, migration and/or apoptosis. Typical methods are discussed for example in U.S. Pat. No. 5,928,868 and include methods for forming hybrid ligands in which at least one ligand is a small molecule. In an illustrative embodiment, the hybrid ligand is introduced into cells that in turn contain a first and a second expression vector. Each expression vector includes DNA for expressing a hybrid protein that encodes a target protein linked to a coding sequence for a transcriptional module. The cells further contains a reporter gene, the expression of which is conditioned on the proximity of the first and second hybrid proteins to each other, an event that occurs only if the hybrid ligand binds to target sites on both hybrid proteins. Those cells that express the reporter gene are selected and the unknown small molecule or the unknown hybrid protein is identified.

A typical embodiment of this invention consists of a method of screening for a molecule that interacts with a STEAP amino acid sequence shown in FIG. 11A-B, comprising the steps of contacting a population of molecules with the STEAP amino acid sequence, allowing the population of molecules and the STEAP amino acid sequence to interact under conditions that facilitate an interaction, determining the presence of a molecule that interacts with the STEAP amino acid sequence and then separating molecules that do not interact with the STEAP amino acid sequence from molecules that do interact with the STEAP amino acid sequence. In a specific embodiment, the method further includes purifying a molecule that interacts with the STEAP amino acid sequence. In a preferred embodiment, the STEAP amino acid sequence is contacted with a library of peptides. Additional assays for identifying molecules that modulate STEAP function are described in the Examples that follow.

The invention additionally provides a method of screening for a molecule that modulates the activity of STEAP or a STEAP-related pathway. The method comprises contacting a molecule with a cell that expresses a STEAP protein and determining the activity of STEAP or a STEAP-related pathway. The determining can be via use of one of the phosphorylation assays described in the examples that follow, such as western blotting with an antibody directed to a phosphorylated signaling molecule. Alterations in the phosphorylation of the signaling molecule indicate a candidate molecule that modulates the activity of STEAP or a STEAP-related pathway.

Therapeutic Methods and Compositions

The identification of STEAP as a prostate cancer protein opens a number of therapeutic approaches to the treatment of prostate and other STEAP-associated cancers. As discussed above, STEAP is a transmembrane protein, and its interaction with other cells and molecules likely plays a role in the regulation of the prostate environment and the initiation, development and/or progression of cancer. STEAP can be targeted for therapy via approaches aimed at inhibiting activity of the STEAP protein, inhibiting the binding or association of STEAP protein with other cells and molecules, inhibiting transcription or translation of STEAP, and/or via the use of cancer vaccines based on STEAP. The therapeutic strategy can thus be designed to inhibit a function of the molecule or to target the STEAP molecule itself.

The expression profile of STEAP is reminiscent of the MAGEs, PSA and PMSA, which are tissue-specific genes that are up-regulated in melanomas and other cancers (Van den Eynde and Boon, Int J Clin Lab Res. 27:81-86, 1997). Due to their tissue-specific expression and high expression levels in cancer, these molecules are currently being investigated as targets for cancer vaccines (Durrant, Anticancer Drugs 8:727-733, 1997; Reynolds et al., Int J Cancer 72:972-976, 1997). The expression pattern of STEAP provides evidence that it is likewise an ideal target for a cancer vaccine approach to prostate cancer, as its expression is not detected in most normal tissues.

Accordingly, therapeutic approaches targeting particular motifs of STEAP, or aimed at inhibiting the activity of the STEAP protein, are expected to be useful for patients suffering from prostate cancer and other cancers expressing STEAP. The therapeutic approaches aimed at inhibiting the activity of the STEAP protein generally fall into two classes. One class comprises various methods for inhibiting the binding or association of the STEAP protein with its binding partner or with other proteins. Another class comprises a variety of methods for inhibiting the transcription of the STEAP gene or translation of STEAP mRNA.

STEAP as a Target for Antibody-Based Therapy

The cell surface nature and expression profiles of the STEAPs in cancers including prostate cancer indicate that they are promising targets for antibody therapy of prostate and other cancers expressing STEAPs. The experimental results described in the Examples herein provide compelling evidence that STEAP-1 and STEAP-2 are strongly expressed uniformly over the surface of glandular epithelial cells within prostate and prostate cancer cells. In particular, immunohistochemical analysis results show that the surface of human prostate epithelial cells (normal and cancer) appear to be uniformly coated with STEAP-1. Biochemical analysis confirms the cell surface localization of STEAP-1 initially suggested by its putative 6-transmembrane primary structural elements and by the pericellular staining plainly evident by immunohistochemical staining.

STEAP-1 and STEAP-2 are uniformly expressed at high levels over the surface of prostate glandular epithelia, an ideal situation for immunotherapeutic intervention strategies that target extracellular STEAP epitopes. Systemic administration of STEAP-immunoreactive compositions would be expected to result in extensive contact of the composition with prostate epithelial cells via binding to STEAP extracellular epitopes. Moreover, given the near absence of STEAP-1 protein expression in normal human tissues, there is ample reason to expect exquisite sensitivity without toxic, non-specific and/or non-target effects caused by the binding of the immunotherapeutic composition to STEAP-1 on non-target organs and tissues.

In addition to the high level expression of STEAP-1 in prostate and prostate cancer cells, STEAP-1 appears to be substantially over-expressed in a variety of other human cancers, including bladder, lung, colon, pancreatic and ovarian cancers. In particular, high level STEAP-1 mRNA expression is detected in all tested prostate cancer tissues and cell lines, and in most of the pancreatic, colon, and bladder cancer cell lines tested. High level expression of STEAP-1 is also observed in some ovarian cancer cell lines. Lower level expression is observed in some breast, testicular, and cervical cancer cell lines. Very high level expression is also detected in a Ewing sarcoma cell line. Applicants have shown that cell surface STEAP-1 protein is expressed in bladder, lung and colon cancers, while there is no detectable cell surface (or intracellular) STEAP-1 protein in normal colon and low expression in normal bladder. Antibodies specifically reactive with extracellular domains of STEAP-1 may be useful to treat these cancers systemically, either as toxin or therapeutic agent conjugates or as naked antibodies capable of inhibiting cell proliferation or function.

STEAP-2 protein is also expressed in prostate cancer, and in other cancers as well, including colon and lung cancers. STEAP-2 mRNA analysis by RT-PCR and northern blot show that expression is restricted to prostate in normal tissues, is also expressed in some prostate, pancreatic, colon, testicular, ovarian and other cancers. Therefore, antibodies reactive with STEAP-2 may be useful in the treatment of prostate and other cancers. Similarly, the expression of STEAP-3 and STEAP-4 (as well as other STEAPs) may be associated with some cancers. Thus antibodies reactive with these STEAP family member proteins may also be useful therapeutically.

STEAP antibodies may be introduced into a patient such that the antibody binds to STEAP on the cancer cells and mediates the destruction of the cells and the tumor, inhibits the growth of the cells or the tumor, and/or eliminates STEAP function in the primary tumor, in circulating micrometastases, and/or in established metastases. The degree of tumor vascularization may provide guidance on which delivery approach is recommended. Similarly, the grade and/or stage of disease would be expected to provide useful information in this regard. For example, a higher grade, more advanced tumor may be more likely to seed metastases, suggesting systemic administration in order to treat or prevent the emergence of metastases. Mechanisms by which such antibodies exert a therapeutic effect may include complement-mediated cytolysis, antibody-dependent cellular cytotoxicity, modulating the physiologic function of STEAP, inhibiting ligand binding or signal transduction pathways, modulating tumor cell differentiation, altering tumor angiogenesis factor profiles, and/or by inducing apoptosis. STEAP antibodies conjugated to toxic or therapeutic agents may also be used therapeutically to deliver the toxic or therapeutic agent directly to STEAP-bearing tumor cells.

Cancer immunotherapy using anti-STEAP antibodies may follow the teachings generated from various approaches that have been successfully employed in the treatment of other types of cancer, including but not limited to colon cancer (Arlen et al., 1998, Crit. Rev. Immunol. 18:133-138), multiple myeloma (Ozaki et al., 1997, Blood 90:3179-3186; Tsunenari et al., 1997, Blood 90:2437-2444), gastric cancer (Kasprzyk et al., 1992, Cancer Res. 52:2771-2776), B-cell lymphoma (Funakoshi et al., 1996, J. Immunother. Emphasis Tumor Immunol. 19:93-101), leukemia (Zhong et al., 1996, Leuk. Res. 20:581-589), colorectal cancer (Moun et al., 1994, Cancer Res. 54:6160-6166); Velders et al., 1995, Cancer Res. 55:4398-4403), and breast cancer (Shepard et al., 1991, J. Clin. Immunol. 11:117-127). Some therapeutic approaches involve conjugation of naked antibody to a toxin, such as the conjugation of $^{131}$I to anti-CD20 antibodies (e.g., Bexxar, Coulter Pharmaceutical), while others involve co-administration of antibodies and other therapeutic agents, such as Herceptin™ (trastuzumab) with paclitaxel (Genentech, Inc.). For treatment of prostate cancer, for example, STEAP antibodies can be administered in conjunction with radiation, chemotherapy or hormone ablation.

Although STEAP antibody therapy may be useful for all stages of cancer, antibody therapy may be particularly appropriate in advanced or metastatic cancers. Treatment with the antibody therapy of the invention may be indicated for patients who have received previously one or more chemotherapy, while combining the antibody therapy of the invention with a chemotherapeutic or radiation regimen may be preferred for patients who have not received chemotherapeutic treatment. Additionally, antibody therapy may enable the use of reduced dosages of concomitant chemotherapy, particularly for patients who do not tolerate the toxicity of the chemotherapeutic agent very well.

It may be desirable for some cancer patients to be evaluated for the presence and level of STEAP expression, preferably using immunohistochemical assessments of tumor tissue, quantitative STEAP imaging, or other techniques capable of reliably indicating the presence and degree of STEAP expression. Immunohistochemical analysis of tumor biopsies or surgical specimens may be preferred for this purpose. Methods for immunohistochemical analysis of tumor tissues are well known in the art.

Anti-STEAP monoclonal antibodies useful in treating prostate and other cancers include those that are capable of initiating a potent immune response against the tumor and those that are capable of direct cytotoxicity. In this regard, anti-STEAP monoclonal antibodies (mAbs) may elicit tumor cell lysis by either complement-mediated or antibody-dependent cell cytotoxicity (ADCC) mechanisms, both of which require an intact Fc portion of the immunoglobulin molecule for interaction with effector cell Fc receptor sites or complement proteins. In addition, anti-STEAP mAbs that exert a direct biological effect on tumor growth are useful in the practice of the invention. Potential mechanisms by which such directly cytotoxic mAbs may act include inhibition of cell growth, modulation of cellular differentiation, modulation of tumor angiogenesis factor profiles, and the induction of apoptosis. The mechanism by which a particular anti-STEAP mAb exerts an anti-tumor effect may be evaluated using any number of in vitro assays designed to determine ADCC, ADMMC, complement-mediated cell lysis, and so forth, as is generally known in the art.

The anti-tumor activity of a particular anti-STEAP mAb, or combination of anti-STEAP mAbs, may be evaluated in vivo using a suitable animal model. For example, xenogenic prostate cancer models wherein human prostate cancer explants or passaged xenograft tissues are introduced into immune compromised animals, such as nude or SCID mice, are appropriate in relation to prostate cancer and have been described (U.S. Pat. No. 6,107,540; Klein et al., 1997, Nature Medicine 3: 402-408). For Example, PCT Patent Application WO98/16628, Sawyers et al., published Apr. 23, 1998, describes various xenograft models of human prostate cancer capable recapitulating the development of primary tumors, micrometastasis, and the formation of osteoblastic metastases characteristic of late stage disease. Efficacy may be predicted using assays which measure inhibition of tumor formation, tumor regression or metastasis, and the like.

The use of murine or other non-human monoclonal antibodies, or human/mouse chimeric mAbs may induce moderate to strong immune responses in some patients. In some cases, this will result in clearance of the antibody from circulation and reduced efficacy. In the most severe cases, such an immune response may lead to the extensive formation of immune complexes that, potentially, can cause renal failure. Accordingly, preferred monoclonal antibodies used in the practice of the therapeutic methods of the invention are those that are either fully human or humanized and that bind specifically to the target STEAP antigen with high affinity but exhibit low or no antigenicity in the patient.

Therapeutic methods of the invention contemplate the administration of single anti-STEAP mAbs as well as combinations, or cocktails, of different mAbs. Such mAb cocktails may have certain advantages inasmuch as they contain mAbs that target different epitopes, exploit different effector mechanisms or combine directly cytotoxic mAbs with mAbs that rely on immune effector functionality. Such mAbs in combination may exhibit synergistic therapeutic effects. In addition, the administration of anti-STEAP mAbs may be combined with other therapeutic agents, including but not limited to various chemotherapeutic agents, androgen-blockers, and immune modulators (e.g., IL-2, GM-CSF). The anti-STEAP mAbs may be administered in their "naked" or unconjugated form, or may have therapeutic agents conjugated to them.

The anti-STEAP monoclonal antibodies used in the practice of the method of the invention may be formulated into pharmaceutical compositions comprising a carrier suitable for the desired delivery method. Suitable carriers include any material which when combined with the anti-STEAP mAbs retains the anti-tumor function of the antibody and is non-reactive with the subject's immune systems. Examples include, but are not limited to, any of a number of standard pharmaceutical carriers such as sterile phosphate buffered saline solutions, bacteriostatic water, and the like.

The anti-STEAP antibody formulations may be administered via any route capable of delivering the antibodies to the tumor site. Potentially effective routes of administration include, but are not limited to, intravenous, intraperitoneal, intramuscular, intratumor, intradermal, and the like. The preferred route of administration is by intravenous injection. A preferred formulation for intravenous injection comprises the anti-STEAP mAbs in a solution of preserved bacteriostatic water, sterile unpreserved water, and/or diluted in polyvinylchloride or polyethylene bags containing 0.9% sterile Sodium Chloride for Injection, USP. The anti-STEAP mAb preparation may be lyophilized and stored as a sterile powder, preferably under vacuum, and then reconstituted in bacteriostatic water containing, for example, benzyl alcohol preservative, or in sterile water prior to injection.

Treatment will generally involve the repeated administration of the anti-STEAP antibody preparation via an acceptable route of administration such as intravenous injection (IV), typically at a dose in the range of about 0.1 to about 10 mg/kg body weight. Doses in the range of 10-500 mg mAb per week may be effective and well tolerated. Based on clinical experience with the Herceptin mAb in the treatment of metastatic breast cancer, an initial loading dose of approximately 4 mg/kg patient body weight IV followed by weekly doses of about 2 mg/kg IV of the anti-STEAP mAb preparation may represent an acceptable dosing regimen. Preferably, the initial loading dose is administered as a 90 minute or longer infusion. The periodic maintenance dose may be administered as a 30 minute or longer infusion, provided the initial dose was well tolerated. However, as one of skill in the art will understand, various factors will influence the ideal dose regimen in a particular case. Such factors may include, for example, the binding affinity and half life of the mAb or mAbs used, the degree of STEAP overexpression in the patient, the extent of circulating shed STEAP antigen, the desired steady-state antibody concentration level, frequency of treatment, and the influence of chemotherapeutic agents used in combination with the treatment method of the invention.

Optimally, patients should be evaluated for the level of circulating shed STEAP antigen in serum in order to assist in the determination of the most effective dosing regimen and related factors. Such evaluations may also be used for monitoring purposes throughout therapy, and may be useful to gauge therapeutic success in combination with evaluating other parameters (such as serum PSA levels in prostate cancer therapy).

Inhibition of STEAP Protein Function

The invention includes various methods and compositions for inhibiting the binding of STEAP to its binding partner or ligand, or its association with other protein(s) as well as methods for inhibiting STEAP function.

Inhibition of STEAP With Recombinant Proteins

In one approach, recombinant molecules that are capable of binding to STEAP thereby preventing STEAP from accessing/binding to its binding partner(s) or associating with other protein(s) are used to inhibit STEAP function. Such recombinant molecules may, for example, contain the reactive part(s) of a STEAP specific antibody molecule. In a particular embodiment, the STEAP binding domain of a STEAP binding partner may be engineered into a dimeric fusion protein comprising two STEAP ligand binding domains linked to the Fc portion of a human IgG, such as human IgG1. Such IgG portion may contain, for example, the CH2 and CH3 domains and the hinge region, but not the CH1 domain. Such dimeric fusion proteins may be administered in soluble form to patients suffering from a cancer associated with the expression of STEAP, including but not limited to prostate cancer, where the dimeric fusion protein specifically binds to STEAP thereby blocking STEAP interaction with a binding partner and/or modulating STEAP function. Such dimeric fusion proteins may be further combined into multimeric proteins using known antibody linking technologies.

Inhibition of STEAP With Intracellular Antibodies

In another approach, recombinant vectors encoding single chain antibodies that specifically bind to STEAP may be introduced into STEAP expressing cells via gene transfer technologies, wherein the encoded single chain anti-STEAP antibody is expressed intracellularly, binds to STEAP protein, and thereby inhibits its function. Methods for engineering such intracellular single chain antibodies are well known. Such intracellular antibodies, also known as "intrabodies", may be specifically targeted to a particular compartment within the cell, providing control over where the inhibitory activity of the treatment will be focused. This technology has been successfully applied in the art (for review, see Richardson and Marasco, 1995, TIBTECH vol. 13). Intrabodies have been shown to virtually eliminate the expression of otherwise abundant cell surface receptors. See, for example, Richardson et al., 1995, Proc. Natl. Acad. Sci. USA 92: 3137-3141; Beerli et al., 1994, J. Biol. Chem. 289: 23931-23936; Deshane et al., 1994, Gene Ther. 1: 332-337.

Single chain antibodies comprise the variable domains of the heavy and light chain joined by a flexible linker polypeptide, and are expressed as a single polypeptide. Optionally, single chain antibodies may be expressed as a single chain variable region fragment joined to the light chain constant region. Well known intracellular trafficking signals may be engineered into recombinant polynucleotide vectors encoding such single chain antibodies in order to precisely target the expressed intrabody to the desired intracellular compartment. For example, intrabodies targeted to the endoplasmic reticulum (ER) may be engineered to incorporate a leader peptide and, optionally, a C-terminal ER retention signal, such as the KDEL amino acid motif. Intrabodies intended to exert activity in the nucleus may be engineered to include a nuclear localization signal. Lipid moieties may be joined to intrabodies in order to tether the intrabody to the cytosolic side of the plasma membrane. Intrabodies may also be targeted to exert function in the cytosol. For example, cytosolic intrabodies may be used to sequester factors within the cytosol, thereby preventing them from being transported to their natural cellular destination.

In one embodiment, STEAP intrabodies are designed to bind specifically to a particular STEAP domain. For example, cytosolic intrabodies that specifically bind to the STEAP protein may be used to prevent STEAP related molecules from gaining access to the nucleus, thereby preventing it from exerting any biological activity within the nucleus.

In order to direct the expression of such intrabodies specifically to particular tumor cells, the transcription of the intrabody may be placed under the regulatory control of an appropriate tumor-specific promoter and/or enhancer. In order to target intrabody expression specifically to prostate, for example, the PSA promoter and/or promoter/enhancer may be utilized (See, for example, U.S. Pat. No. 5,919,652).

Inhibition of STEAP Transcription or Translation

Within another class of therapeutic approaches, the invention provides various methods and compositions for inhibiting the transcription of the STEAP gene. Similarly, the invention also provides methods and compositions for inhibiting the translation of STEAP mRNA into protein.

In one approach, a method of inhibiting the transcription of the STEAP gene comprises contacting the STEAP gene with a STEAP antisense polynucleotide. In another approach, a method of inhibiting STEAP mRNA translation comprises contacting the STEAP mRNA with an antisense polynucleotide. In another approach, a STEAP specific ribozyme may be used to cleave the STEAP message, thereby inhibiting translation. Such antisense and ribozyme based methods may also be directed to the regulatory regions of the STEAP gene, such as the STEAP promoter and/or enhancer elements. Similarly, proteins capable of inhibiting a STEAP gene transcription factor may be used to inhibit STEAP mRNA transcription. The various polynucleotides and compositions useful in the aforementioned methods have been described above. The use of antisense and ribozyme molecules to inhibit transcription and translation is well known in the art.

Other factors that inhibit the transcription of STEAP through interfering with STEAP transcriptional activation may also be useful for the treatment of cancers expressing STEAP. Similarly, factors that are capable of interfering with STEAP processing may be useful for the treatment of cancers expressing STEAP. Cancer treatment methods utilizing such factors are also within the scope of the invention.

General Considerations for Therapeutic Strategies

Gene transfer and gene therapy technologies may be used for delivering therapeutic polynucleotide molecules to tumor cells synthesizing STEAP (i.e., antisense, ribozyme, polynucleotides encoding intrabodies and other STEAP inhibitory molecules). A number of gene therapy approaches are known in the art. Recombinant vectors encoding STEAP antisense polynucleotides, ribozymes, factors capable of interfering with STEAP transcription, and so forth, may be delivered to target tumor cells using such gene therapy approaches.

The above therapeutic approaches may be combined with any one of a wide variety of chemotherapy or radiation therapy regimens. These therapeutic approaches may also enable the use of reduced dosages of chemotherapy and/or less frequent administration, particularly in patients that do not tolerate the toxicity of the chemotherapeutic agent well.

The anti-tumor activity of a particular composition (e.g., antisense, ribozyme, intrabody), or a combination of such compositions, may be evaluated using various in vitro and in vivo assay systems. In vitro assays for evaluating therapeutic potential include cell growth assays, soft agar assays and other assays indicative of tumor promoting activity, binding assays capable of determining the extent to which a therapeutic composition will inhibit the binding of STEAP to a binding partner, etc.

In vivo, the effect of a STEAP therapeutic composition may be evaluated in a suitable animal model. For example, xenogeneic prostate cancer models wherein human prostate cancer explants or passaged xenograft tissues are introduced into immune compromised animals, such as nude or SCID mice, are appropriate in relation to prostate cancer and have been described (Klein et al., 1997, Nature Medicine 3: 402-408). For example, PCT Patent Application WO98/16628, Sawyers et al., published Apr. 23, 1998, describes various xenograft models of human prostate cancer capable of recapitulating the development of primary tumors, micrometastasis, and the formation of osteoblastic metastases characteristic of late stage disease. Efficacy may be predicted using assays that measure inhibition of tumor formation, tumor regression or metastasis, and the like. See, also, the Examples below.

In vivo assays that qualify the promotion of apoptosis may also be useful in evaluating potential therapeutic compositions. In one embodiment, xenografts from bearing mice treated with the therapeutic composition may be examined for the presence of apoptotic foci and compared to untreated control xenograft-bearing mice. The extent to which apoptotic foci are found in the tumors of the treated mice provides an indication of the therapeutic efficacy of the composition.

The therapeutic compositions used in the practice of the foregoing methods may be formulated into pharmaceutical compositions, including vaccine compositions, comprising a carrier suitable for the desired delivery method. Suitable carriers include any material that when combined with the therapeutic composition retains the anti-tumor function of the therapeutic composition and is non-reactive with the patient's immune system. Examples include, but are not limited to, any of a number of standard pharmaceutical carriers such as sterile phosphate buffered saline solutions, bacteriostatic water, and the like (see, generally, Remington's Pharmaceutical Sciences 16th Edition, A. Osal., Ed., 1980).

Therapeutic formulations may be solubilized and administered via any route capable of delivering the therapeutic composition to the tumor site. Potentially effective routes of administration include, but are not limited to, intravenous, parenteral, intraperitoneal, intramuscular, intratumor, intradermal, intraorgan, orthotopic, and the like. A preferred formulation for intravenous injection comprises the therapeutic composition in a solution of preserved bacteriostatic water, sterile unpreserved water, and/or diluted in polyvinylchloride or polyethylene bags containing 0.9% sterile Sodium Chloride for Injection, USP. Therapeutic protein preparations may be lyophilized and stored as sterile powders, preferably under vacuum, and then reconstituted in bacteriostatic water containing, for example, benzyl alcohol preservative, or in sterile water prior to injection.

Dosages and administration protocols for the treatment of cancers using the foregoing methods will vary with the method and the target cancer and will generally depend on a number of other factors appreciated in the art.

Cancer Vaccines

The invention further provides cancer vaccines comprising a STEAP protein or fragment thereof, as well as DNA based vaccines. In view of the prostate- and tumor-restricted expression of STEAP, STEAP cancer vaccines are expected to be effective at specifically preventing and/or treating STEAP expressing cancers without creating non-specific effects on non-target tissues. The use of a tumor antigen in a vaccine for generating humoral and cell-mediated immunity for use in anti-cancer therapy is well known in the art and has been employed in prostate cancer using human PSMA and rodent PAP immunogens (Hodge et al., 1995, Int. J. Cancer 63: 231-237; Fong et al., 1997, J. Immunol. 159: 3113-3117). Such methods can be readily practiced by employing a STEAP protein, or fragment thereof, or a STEAP-encoding nucleic acid molecule and recombinant vectors capable of expressing and appropriately presenting the STEAP immunogen.

For example, viral gene delivery systems may be used to deliver a STEAP-encoding nucleic acid molecule. Various viral gene delivery systems that can be used in the practice of this aspect of the invention include, but are not limited to, vaccinia, fowlpox, canarypox, adenovirus, influenza, poliovirus, adeno-associated virus, lentivirus, and sindbus virus (Restifo, 1996, Curr. Opin. Immunol. 8: 658-663). Non-viral delivery systems may also be employed by using naked DNA encoding a STEAP protein or fragment thereof introduced into the patient (e.g., intramuscularly) to induce an anti-tumor response. In one embodiment, the full-length human STEAP cDNA may be employed.

In one embodiment, a STEAP cancer vaccine is based on the identification of immunogenic peptides within a STEAP amino acid sequence shown in FIG. 11A-B. As discussed further in the examples below, STEAPs have been shown to induce T and B cell responses. STEAP-1 and STEAP-2 polypeptides have been used to generate an immune response in mice and rabbits for the production of monoclonal and polyclonal antibodies. Thus, specific portions of STEAP, and polynucleotides encoding these portions, may be selected for the production of a cancer vaccine. One example of such a portion of a STEAP protein is amino acid residues 14 through 28 of the STEAP-1 amino acid sequence as shown in FIG. 1A-B (WKMKPRRNLEEDDYL; SEQ ID NO: 22).

In another embodiment, STEAP nucleic acid molecules encoding specific cytotoxic T lymphocyte (CTL) epitopes may be employed. CTL epitopes can be determined using specific algorithms (e.g., Epimer, Brown University) to identify peptides within a STEAP protein that are capable of optimally binding to specified HLA alleles. One suitable algorithm is the HLA Peptide Motif Search algorithm available at the Bioinformatics and Molecular Analysis Section (BIMAS) web site. This algorithm is based on binding of specific peptide sequences in the groove of HLA Class I molecules and specifically HLA-A2 (Falk et al., 1991, Nature 351:290-6; Hunt et al., 1992, Science 255:1261-3; Parker et al., 1992, J. Immunol. 149:3580-7; Parker et al., 1994, J. Immunol. 152:163-75). The HLA Peptide Motif Search algorithm allows location and ranking of 8-mer, 9-mer, and 10-mer peptides from a complete protein sequence for predicted binding to HLA-A2 as well as other Class I molecules. Most HLA-A2 binding peptides are 9-mers, favorably containing a leucine at position 2 and a valine or leucine at position 9 (Parker et al., 1992, J. Immunol. 149:3580-7). Actual binding of peptides to HLA-A2 can be evaluated by stabilization of HLA-A2 expression on the antigen processing defective cell line T2 (Xue et al., 1997, Prostate 30:73-8; Peshwa et al., 1998, Prostate 36:129-38). Immunogenicity of specific peptides can be evaluated in vitro by stimulation of CD8+ CTL in the presence of dendritic cells (Xue et al.; Peshwa et al., supra).

Specific STEAP peptides predicted to bind HLA-A2 and preferred for use in cancer vaccines include peptides corresponding to amino acids 165-173 of STEAP-1, amino acids 86-94 of STEAP-1, amino acids 262-270 of STEAP-1, amino acids 302-310 of STEAP-1, amino acids 158-166 of STEAP-1, amino acids 227-235 of STEAP-2, amino acids 402-410 of STEAP-2, amino acids 307-315 of STEAP-2, amino acids 306-314 of STEAP-2, and amino acids 100-108 of STEAP-2.

Various ex vivo strategies may also be employed. One approach involves the use of dendritic cells to present STEAP antigen to a patient's immune system. Dendritic cells express MHC class I and II, B7 co-stimulator, and IL-12, and are thus highly specialized antigen presenting cells. In prostate cancer, autologous dendritic cells pulsed with peptides of the prostate-specific membrane antigen (PSMA) are being used in a Phase I clinical trial to stimulate prostate cancer patients' immune systems (Tjoa et al., 1996, Prostate 28: 65-69; Murphy et al., 1996, Prostate 29: 371-380). Dendritic cells can be used to present STEAP peptides to T cells in the context of MHC class I and II molecules. In one embodiment, autologous dendritic cells are pulsed with STEAP peptides capable of binding to MHC molecules. In another embodiment, dendritic cells are pulsed with the complete STEAP protein. Yet another embodiment involves engineering the overexpression of the STEAP gene in dendritic cells using various implementing vectors known in the art, such as adenovirus (Arthur et al., 1997, Cancer Gene Ther. 4: 17-25), retrovirus (Henderson et al., 1996, Cancer Res. 56: 3763-3770), lentivirus, adeno-associated virus, DNA transfection (Ribas et al., 1997, Cancer Res. 57: 2865-2869), and tumor-derived RNA transfection (Ashley et al., 1997, J. Exp. Med. 186: 1177-1182). Cells expressing STEAP may also be engineered to express immune modulators, such as GM-CSF, and used as immunizing agents.

Anti-idiotypic anti-STEAP antibodies can also be used in anti-cancer therapy as a vaccine for inducing an immune response to cells expressing a STEAP protein. Specifically, the generation of anti-idiotypic antibodies is well known in the art and can readily be adapted to generate anti-idiotypic anti-STEAP antibodies that mimic an epitope on a STEAP protein (see, for example, Wagner et al., 1997, Hybridoma 16: 33-40; Foon et al., 1995, J Clin Invest 96: 334-342; Herlyn et al., 1996, Cancer Immunol Immunother 43: 65-76). Such an anti-idiotypic antibody can be used in cancer vaccine strategies.

Genetic immunization methods may be employed to generate prophylactic or therapeutic humoral and cellular immune responses directed against cancer cells expressing STEAP. Constructs comprising DNA encoding a STEAP protein/immunogen and appropriate regulatory sequences may be injected directly into muscle or skin of an individual, such that the cells of the muscle or skin take up the construct and express the encoded STEAP protein/immunogen. Expression of the STEAP protein immunogen results in the generation of prophylactic or therapeutic humoral and cellular immunity against prostate and other STEAP-expressing cancers. Various prophylactic and therapeutic genetic immunization techniques known in the art may be used (for review, see information and references published at Internet address www.genweb.com).

Diagnostic Compositions and Kits

For use in the diagnostic and therapeutic applications described or suggested above, kits are also provided by the invention. Such kits may comprise a carrier means being compartmentalized to receive in close confinement one or more container means such as vials, tubes, and the like, each of the container means comprising one of the separate elements to be used in the method. For example, one of the container means may comprise a probe that is or can be detectably labeled. Such probe may be an antibody or polynucleotide specific for a STEAP protein or a STEAP gene or message, respectively. Where the kit utilizes nucleic acid hybridization to detect the target nucleic acid, the kit may also have containers containing nucleotide(s) for amplification of the target nucleic acid sequence and/or a container comprising a reporter-means, such as a biotin-binding protein, such as avidin or streptavidin, bound to a reporter molecule, such as an enzymatic, florescent, or radioisotope label.

The kit of the invention will typically comprise the container described above and one or more other containers comprising materials desirable from a commercial and user standpoint, including buffers, diluents, filters, needles, syringes, and package inserts with instructions for use. A label may be present on the on the container to indicate that the composition is used for a specific therapy or non-therapeutic application, and may also indicate directions for either in vivo or in vitro use, such as those described above.

Accordingly, the invention also provides diagnostic compositions comprising STEAP-related molecules. Such molecules include the various STEAP polynucleotides, primers, probes, proteins, fragments, antibodies described herein. The molecules included in the diagnostic composition may optionally be labeled with a detectable marker. STEAP diagnostic compositions may further comprise appropriate buffers, diluents, and other ingredients as desired.

EXAMPLES

Various aspects of the invention are further described and illustrated by way of the several examples that follow, none of which are intended to limit the scope of the invention.

Example 1

SSH-Generated Isolation of cDNA Fragment of the STEAP Gene

Materials and Methods
LAPC Xenografts:

LAPC xenografts were obtained from Dr. Charles Sawyers (UCLA) and generated as described (Klein et al 1997, Nature Med. 3: 402-408; Craft et al., 1999, Cancer Res. 59: 5030-5036). Androgen dependent and independent LAPC-4 xenografts (LAPC-4 AD and AI, respectively) and LAPC-9 xenografts (LAPC-9 AD and AI, respectively) were grown in intact male SCID mice or in castrated males, respectively, and were passaged as small tissue chunks in recipient males. LAPC-4 AI xenografts were derived from LAPC-4 AD tumors and LAPC-9 AI xenografts were derived from LAPC-9 AD tumors. To generate the AI xenografts, male mice bearing LAPC AD tumors were castrated and maintained for 2-3 months. After the LAPC tumors re-grew, the tumors were harvested and passaged in castrated males or in female SCID mice.

LAPC-4 AD xenografts were grown intratibially as follows. LAPC-4 AD xenograft tumor tissue grown subcutaneously was minced into 1-2 $mm^3$ sections while the tissue was bathed in 1× Iscoves medium, minced tissue was then centrifuged at 1.3K rpm for 4 minutes, the supernatant was resuspended in 10 ml ice cold 1× Iscoves medium and centrifuged at 1.3K rpm for 4 minutes. The pellet was then resuspended in 1× Iscoves with 1% pronase E and incubated for 20 minutes at room temperature with mild rocking agitation followed by incubation on ice for 2-4 minutes. Filtrate was centrifuged at 1.3K rmp for 4 minutes, and the pronase was removed from the aspirated pellet by resuspending in 10 ml Iscoves and re-centrifuging. Clumps of cells were then plated in PrEGM medium and grown overnight. The cells were then harvested, filtered, washed 2×RPMI, and counted. Approximately 50,000 cells were mixed with and equal volume of ice-cold Matrigel on ice, and surgically injected into the proximal tibial metaphyses of SCID mice via a 27 gauge needle. After 10-12 weeks, LAPC-4 tumors growing in bone marrow were recovered.

Cell Lines and Tissues:

Human cell lines (e.g., HeLa) were obtained from the ATCC and were maintained in DMEM with 5% fetal calf serum. Human tissues for RNA and protein analyses were obtained from the Human Tissue Resource Center (HTRC) at the UCLA (Los Angeles, Calif.) and from QualTek, Inc. (Santa Barbara, Calif.).

RNA Isolation:

Tumor tissue and cell lines were homogenized in Trizol reagent (Life Technologies, Gibco BRL) using 10 ml/g tissue or 10 ml/$10^8$ cells to isolate total RNA. Poly A RNA was purified from total RNA using Qiagen's Oligotex mRNA Mini and Midi kits. Total and mRNA were quantified by spectrophotometric analysis (O.D. 260/280 nm) and analyzed by gel electrophoresis.

Oligonucleotides:

The following HPLC purified oligonucleotides were used.

DPNCDN (cDNA synthesis primer):
5'TTTTGATCAAGCTT$_{30}$3' (SEQ ID NO: 23)

Adaptor 1:
5'CTAATACGACTCACTATAGGGCTCGAGCGGCCGCCCGGGCAG3'
       3'GGCCCGTCCTAG5' (SEQ ID NO: 24, 25)

Adaptor 2:
5'GTAATACGACTCACTATAGGGCAGCGTGGTCGCGGCCGAG3'
        3'CGGCTCCTAG5' (SEQ ID NO: 26,27)

PCR primer 1:
5'CTAATACGACTCACTATAGGGC3' (SEQ ID NO: 28)

Nested primer (NP)1:
5'TCGAGCGGCCGCCCGGGCAGGA3' (SEQ ID NO: 29)

Nested primer (NP)2:
5'AGCGTGGTCGCGGCCGAGGA3' (SEQ ID NO: 30)

Suppression Subtractive Hybridization:

Suppression Subtractive Hybridization (SSH) was used to identify cDNAs corresponding to genes which may be up-regulated in androgen dependent prostate cancer compared to benign prostatic hyperplasia (BPH).

Double stranded cDNAs corresponding to the LAPC-4 AD xenograft (tester) and the BPH tissue (driver) were synthesized from 2 μg of poly(A)+ RNA isolated from xenograft and BPH tissue, as described above, using CLONTECH's PCR-Select cDNA Subtraction Kit and 1 ng of oligonucleotide RSACDN as primer. First- and second-strand synthesis were carried out as described in the Kit's user manual protocol (CLONTECH Protocol No. PT1117-1, Catalog No. K11804-1). The resulting cDNA was digested with Rsa I for 3 hrs. at 37° C. Digested cDNA was extracted with phenol/chloroform (1:1) and ethanol precipitated.

Driver cDNA (BPH) was generated by combining in a 4 to 1 ratio Rsa I digested BPH cDNA with digested cDNA from mouse liver, in order to ensure that murine genes were subtracted from the tester cDNA (LAPC-4 AD).

Tester cDNA (LAPC-4 AD) was generated by diluting 1 μl of Rsa I digested LAPC-4 AD cDNA (400 ng) in 5 μl of water. The diluted cDNA (2 μl, 160 ng) was then ligated to 2 μl of adaptor 1 and adaptor 2 (10 μM), in separate ligation reactions, in a total volume of 10 μl at 16° C. overnight, using 400 u of T4 DNA ligase (CLONTECH). Ligation was terminated with 1 μl of 0.2 M EDTA and heating at 72° C. for 5 min.

The first hybridization was performed by adding 1.5 μl (600 ng) of driver cDNA to each of two tubes containing 1.5 μl (20 ng) adaptor 1- and adaptor 2-ligated tester cDNA. In a final volume of 4 μL the samples were overlayed with mineral oil, denatured in an MJ Research thermal cycler at 98° C. for 1.5 minutes, and then were allowed to hybridize for 8 hrs at 68° C. The two hybridizations were then mixed together with an additional 1 μl of fresh denatured driver cDNA and were allowed to hybridize overnight at 68° C. The second hybridization was then diluted in 200 μl of 20 mM Hepes, pH 8.3, 50 mM NaCl, 0.2 mM EDTA, heated at 70° C. for 7 min. and stored at −20° C.

PCR Amplification, Cloning and Sequencing of Gene Fragments Generated from SSH:

To amplify gene fragments resulting from SSH reactions, two PCR amplifications were performed. In the primary PCR reaction 1 μl of the diluted final hybridization mix was added to 1 μl of PCR primer 1 (10 μM), 0.5 μl dNTP mix (10 μM), 2.5 μl 10× reaction buffer (CLONTECH) and 0.5 μl 50× Advantage cDNA polymerase Mix (CLONTECH) in a final volume of 25 μl. PCR 1 was conducted using the following conditions: 75° C. for 5 min., 94° C. for 25 sec., then 27 cycles of 94° C. for 10 sec, 66° C. for 30 sec, 72° C. for 1.5 min. Five separate primary PCR reactions were performed for each experiment. The products were pooled and diluted 1:10 with water. For the secondary PCR reaction, 1 μl from the pooled and diluted primary PCR reaction was added to the same reaction mix as used for PCR 1, except that primers NP1 and NP2 (10 μM) were used instead of PCR primer 1. PCR 2 was performed using 10-12 cycles of 94° C. for 10 sec, 68° C. for 30 sec, 72° C. for 1.5 minutes. The PCR products were analyzed using 2% agarose gel electrophoresis.

The PCR products were inserted into pCR2.1 using the T/A vector cloning kit (Invitrogen). Transformed E. coli were subjected to blue/white and ampicillin selection. White colonies were picked and arrayed into 96 well plates and were grown in liquid culture overnight. To identify inserts, PCR amplification was performed on 1 ml of bacterial culture using the conditions of PCR1 and NP1 and NP2 as primers. PCR products were analyzed using 2% agarose gel electrophoresis.

Bacterial clones were stored in 20% glycerol in a 96 well format. Plasmid DNA was prepared, sequenced, and subjected to nucleic acid homology searches of the GenBank, dbEST, and NCI-CGAP databases.

RT-PCR Expression Analysis:

First strand cDNAs were generated from 1 μg of mRNA with oligo (dT)12-18 priming using the Gibco-BRL Superscript Preamplification system. The manufacturers protocol was used and included an incubation for 50 min at 42° C. with reverse transcriptase followed by RNase H treatment at 37° C. for 20 min. After completing the reaction, the volume was increased to 200 μl with water prior to normalization. First strand cDNAs from 16 different normal human tissues were obtained from Clontech.

Normalization of the first strand cDNAs from multiple tissues was performed by using the primers 5'atatcgc-cgcgctcgtcgtcgacaa3' (SEQ ID NO: 31) and 5'agccacacg-cagctcattgtagaagg 3' (SEQ ID NO: 32) to amplify β-actin. First strand cDNA (5 μl) was amplified in a total volume of 50 μl containing 0.4 μM primers, 0.2 μM each dNTPs, 1×PCR buffer (Clontech, 10 mM Tris-HCL, 1.5 mM MgCl$_2$, 50 mM KCl pH8.3) and 1× Klentaq DNA polymerase (Clontech). Five μl of the PCR reaction was removed at 18, 20, and 22 cycles and used for agarose gel electrophoresis. PCR was performed using an MJ Research thermal cycler under the following conditions: initial denaturation was at 94° C. for 15 sec, followed by a 18, 20, and 22 cycles of 94° C. for 15, 65° C. for 2 min, 72° C. for 5 sec. A final extension at 72° C. was carried out for 2 min. After agarose gel electrophoresis, the band intensities of the 283 bp β-actin bands from multiple tissues were compared by visual inspection. Dilution factors for the first strand cDNAs were calculated to result in equal β-actin band intensities in all tissues after 22 cycles of PCR. Three rounds of normalization were required to achieve equal band intensities in all tissues after 22 cycles of PCR.

To determine expression levels of the 8P1D4 gene, 5 μl of normalized first strand cDNA was analyzed by PCR using 25, 30, and 35 cycles of amplification using the following primer pairs:

5' ACT TTG TTG ATG ACC AGG ATT GGA 3' (SEQ ID NO: 4)

5' CAG AAC TTC AGC ACA CAC AGG AAC 3' (SEQ ID NO: 5)

Semi quantitative expression analysis was achieved by comparing the PCR products at cycle numbers that give light band intensities.

Results

Several SSH experiments were conduced as described in the Materials and Methods, supra, and led to the isolation of numerous candidate gene fragment clones. All candidate clones were sequenced and subjected to homology analysis against all sequences in the major public gene and EST databases in order to provide information on the identity of the corresponding gene and to help guide the decision to analyze a particular gene for differential expression. In general, gene fragments which had no homology to any known sequence in any of the searched databases, and thus considered to represent novel genes, as well as gene fragments showing homology to previously sequenced expressed sequence tags (ESTs), were subjected to differential expression analysis by RT-PCR and/or Northern analysis.

One of the cDNA clones, designated 8P1D4, was 436 bp in length and showed homology to an EST sequence in the NCI-CGAP tumor gene database. The full length cDNA encoding the 8P1D4 gene was subsequently isolated using this cDNA and re-named STEAP-1. The 8P1D4 cDNA nucleotide sequence corresponds to nucleotide residues 150 through 585 in the STEAP-1 cDNA sequence as shown in FIG. 1A-B. Another clone, designated 28P3E1, 561 bp in length showed homology to a number of EST sequences in the NCI-CGAP tumor gene database or in other databases. Part of the 28P3E1 sequence (356 bp) is identical to an EST derived from human fetal tissue. After the full length STEAP-1 cDNA was obtained and sequenced, it became apparent that this clone also corresponds to STEAP-1 (more specifically, to residues 622 through the 3' end of the STEAP-1 nucleotide sequence as shown in FIG. 1A-B).

Differential expression analysis by RT-PCR using primers derived from the 8P1D4 cDNA clone showed that the 8P1D4 (STEAP-1) gene is expressed at approximately equal levels in normal prostate and the LAPC-4 and LAPC-9 xenografts (FIG. 2, panel A). Further RT-PCR expression analysis of first strand cDNAs from 16 normal tissues showed greatest levels of 8P1D4 expression in prostate. Substantially lower level expression in several other normal tissues (i.e., colon, ovary, small intestine, spleen and testis) was detectable only at 30 cycles of amplification in brain, pancreas, colon and small intestine (FIG. 2, panels B and C).

Example 2

Isolation of Full Length STEAP-1 Encoding cDNA

The 436 bp 8P1D4 gene fragment (Example 1) was used to isolate additional cDNAs encoding the 8P1D4/STEAP-1 gene. Briefly, a normal human prostate cDNA library (Clontech) was screened with a labeled probe generated from the 436 bp 8P1D4 cDNA. One of the positive clones, clone 10, is 1195 bp in length and encodes a 339 amino acid protein having nucleotide and encoded amino acid sequences bearing no significant homology to any known human genes or proteins (homology to a rat Kidney Injury Protein recently described in International Application WO98/53071). The encoded protein contains at least 6 predicted transmembrane motifs implying a cell surface orientation (see FIG. 1A-B, predicted transmembrane motifs underlined). These structural features led to the designation "STEAP", for "Six Transmembrane Epithelial Antigen of the Prostate".

Subsequent identification of additional STEAP proteins led to the re-designation of the 8P1D4 gene product as "STEAP-1". The STEAP-1 cDNA and encoded amino acid sequences are shown in FIG. 1A-B and correspond to SEQ ID NOS: 1 and 2, respectively. STEAP-1 cDNA clone 10 was deposited with the American Type Culture Collection ("ATCC") (10801 University Blvd., Manassas, Va. 20110-2209 USA) as plasmid 8P1D4 clone 10.1 on Aug. 26, 1998 as ATCC Accession Number 98849. The STEAP-1 cDNA clone can be excised therefrom using EcoRI/XbaI double digest (EcoRI at the 5'end, XbaI at the 3'end).

Example 3

STEAP-1 Gene and Protein Expression Analysis

In order to begin to characterize the biological characteristics of STEAP-1, an extensive evaluation of STEAP-1 mRNA and STEAP-1 protein expression across a variety of human tissue specimens was undertaken. This evaluation included Northern blot, Western blot and immunohistochemical analysis of STEAP-1 expression in a large number of normal human tissues, human prostate cancer xenografts and cell lines, and various other human cancer cell lines.

Example 3A

Northern Blot Analysis of STEAP-1 mRNA Expression in Normal Human Tissues

Initial analysis of STEAP-1 mRNA expression in normal human tissues was conducted by northern blotting two multiple tissue blots obtained from Clontech (Palo Alto, Calif.), comprising a total of 16 different normal human tissues, using labeled STEAP-1 clone 10 as a probe. RNA samples were quantitatively normalized with a β-actin probe. The results are shown in FIG. 3A. The highest expression level was detected in normal prostate, with an approximately 5-10 fold lower level of expression detected in colon and liver. These northern blots showed two transcripts of approximately 1.4 kb and 4.0 kb, the former of which corresponds to the full length STEAP-1 clone 10 cDNA, which encodes the entire STEAP-1 open reading frame. The larger transcript was separately cloned as a 3627 bp cDNA from a normal prostate library, the sequence of which contains a 2399 bp intron (FIG. 4).

This initial analysis was extended by using the STEAP-1 clone 10 probe to analyze an RNA dot blot matrix of 37 normal human tissues (Clontech, Palo Alto, Calif.; Human Master Blot™). The results are shown in FIG. 3B and show strong STEAP-1 expression only in prostate. Very low level STEAP-1 RNA expression was detected in liver, lung, trachea and fetal liver tissue, at perhaps a 5-fold lower level compared to prostate. No expression was detected in any of the remaining tissues. Based on these analyses, significant STEAP-1 expression appears to be prostate specific in normal tissues.

Example 3B

Northern Blot Analysis of STEAP-1 mRNA Expression in Prostate Cancer Xenografts and Cell Lines To analyze STEAP-1 expression in human cancer tissues and cell lines, RNAs derived from human prostate cancer xenografts and an extensive panel of prostate and non-prostate cancer cell lines were analyzed by Northern blot using STEAP-1 cDNA clone 10 as probe. All RNA samples were quantitatively normalized by ethidium bromide staining and subsequent analysis with a labeled β-actin probe.

The results, presented in FIG. 5, show high level STEAP-1 expression in all the LAPC xenografts and all of the prostate cancer cell lines. Expression in the LAPC-9 xenografts was higher compared to the LAPC-4 xenografts, with no significant difference observed between androgen-dependent and androgen-independent sublines (FIG. 5A). Expression in the LAPC-4 xenografts was comparable to expression in normal prostate. Lower levels of expression were detected in PrEC cells (Clonetics), which represent the basal cell compartment of the prostate. Analysis of prostate cancer cell lines showed highest expression levels in LNCaP, an androgen dependent prostate carcinoma cell line. Significant expression was also detected in the androgen-independent cell lines PC-3 and DU145. High levels of STEAP expression were also detected in LAPC-4 and LAPC-9 tumors that were grown within the tibia of mice as a model of prostate cancer bone metastasis (FIG. 5B).

Significantly, very strong STEAP-1 expression was also detected in many of the non-prostate human cancer cell lines analyzed (FIG. 5A). Particularly high level expression was observed in RD-ES cells, an Ewing sarcoma (EWS) derived cell line. Additionally, very high level expression was also detected in several of the colon cancer cell lines (e.g., CaCo-2, LoVo, T84 and Colo-205), bladder carcinoma cell lines (e.g., SCABER, UM-UC-3, TCCSUP and 5637), ovarian cancer cell lines (e.g., OV-1063 and SW 626) and pancreatic cancer cell lines (e.g., HPAC, Capan-1, PANC-1 and BxPC-3). These results, combined with the absence of strong expression in the corresponding normal tissues (FIG. 3), indicate that STEAP-1 may be generally up-regulated in these types (as well as other types) of human cancers.

Example 3C

Western Blot Analysis of STEAP-1 Protein Expression in Prostate and Other Cancers A 15 mer peptide corresponding to amino acid residues 14 through 28 of the STEAP-1 amino acid sequence as shown in FIG. 1A-B (WKMKPRRNLEEDDYL; SEQ ID NO: 22) was synthesized and used to immunize sheep for the generation of sheep polyclonal antibodies towards the amino-terminus of the protein (anti-STEAP-1) as follows. The peptide was conjugated to KLH keyhole limpet hemocyanin). The sheep was initially immunized with 400 μg of peptide in complete Freund's adjuvant. The animal was subsequently boosted every two weeks with 200 μg of peptide in incomplete Freund's adjuvant. Anti-STEAP antibody was affinity-purified from sheep serum using STEAP peptide coupled to affigel 10 (Bio Rad). Purified antibody is stored in phosphate-buffered saline with 0.1% sodium azide.

To test antibody specificity, the cDNA of STEAP-1 was cloned into a retroviral expression vector (pSRatkneo, Muller et al., 1991, MCB 11:1785). NIH 3T3 cells were infected with retroviruses encoding STEAP-1 and were selected in G418 for 2 weeks. Western blot analysis of protein extracts of infected and uninfected NIH 3T3 cells showed expression of a protein with an apparent molecular weight of 36 kD only in the infected cells (FIG. 6, lanes marked "3T3 STEAP" AND "3T3").

The anti-STEAP-1 polyclonal antibody was used to probe western blots of cell lysates prepared from a variety of prostate cancer xenograft tissues, prostate cancer cell lines and other non-prostate cancer cell lines. Protein samples (20 μg each) were quantitatively normalized by probing the blots with an anti-Grb-2 antibody.

The results are shown in FIG. 6. STEAP-1 protein was detected in all of the LAPC prostate cancer xenografts, all of the prostate cancer cell lines, a primary prostate cancer specimen and its matched normal prostate control. Highest STEAP-1 protein expression was detected in the LAPC-9 xenograft and in LINCaP cells, in agreement with the northern blot analysis described immediately above. High level expression was also observed in the bladder carcinoma cell line UM-UC-3. Expression in other cancer cell lines was also detectable (FIG. 6).

Example 3D

Immunohistochemical Analysis of STEAP-1 Protein Expression in Prostate Tumor Biopsy and Surgical Specimens To determine the extent of STEAP-1 protein expression in clinical materials, tissue sections were prepared from a variety of prostate cancer biopsies and surgical samples for immunohistochemical analysis. Tissues were fixed in 10% formalin, embedded in paraffin, and sectioned according to standard protocol. Formalin-fixed, paraffin-embedded sections of LNCaP cells were used as a positive control. Sections were stained with a sheep anti-STEAP-1 polyclonal antibody directed against a STEAP-1 N-terminal epitope (as described immediately above). LNCaP sections were stained in the presence of an excess amount of the STEAP-1 N-terminal peptide immunogen used to generate the polyclonal antibody (peptide 1) or a non-specific peptide derived from a distinct region of the STEAP-1 protein (peptide 2; YQQVQQNKEDAWIEH; SEQ ID NO: 33).

The results are shown in FIG. 8. LNCaP cells showed uniformly strong pericellular staining in all cells (FIG. 8B). Excess STEAP N-terminal peptide (peptide 1) was able to competitively inhibit antibody staining (FIG. 8A), while peptide 2 had no effect (FIG. 8B). Similarly, uniformly strong pericellular staining was seen in the LAPC-9 (FIG. 8F) and LAPC-4 prostate cancer xenografts. These results are clear and suggest that the staining is STEAP specific. Moreover, these results show localization of STEAP to the plasma membrane, corroborating the biochemical findings presented in Example 4 below.

Figure 8A:
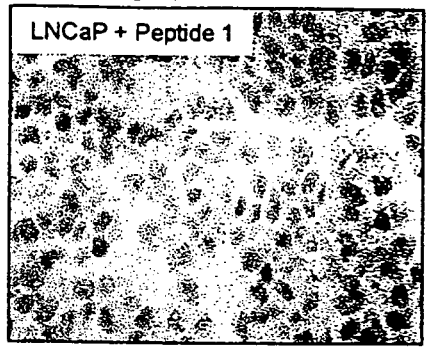
Figure 8B:
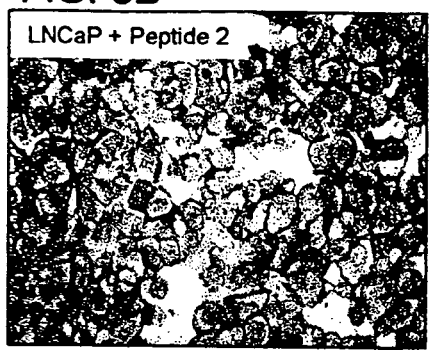
Figure 8C:
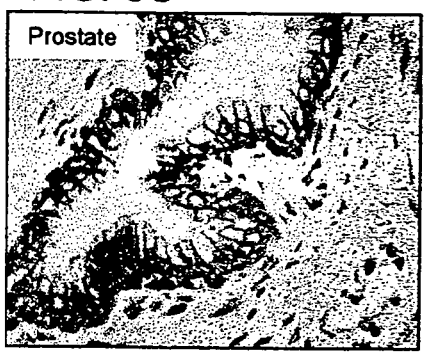
Figure 8D:
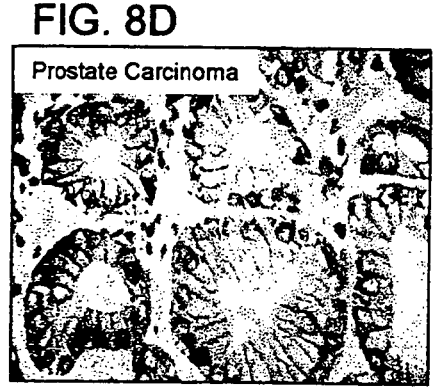
Figure 8E:
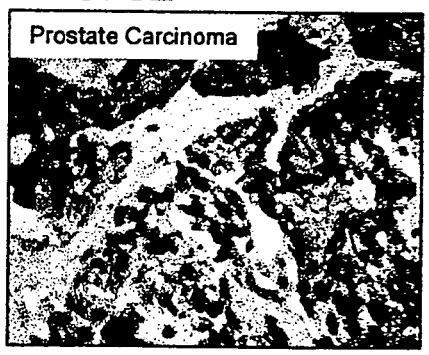
Figure 8F:
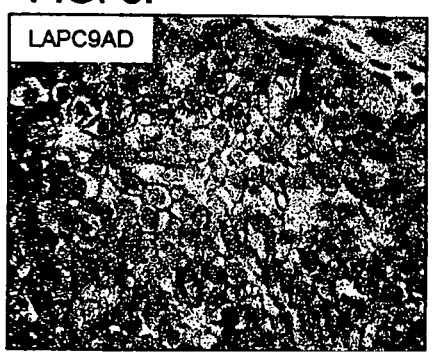

The results obtained with the various clinical specimens are show in FIG. 8C (normal prostate tissue), FIG. 8D (grade 3 prostatic carcinoma), and FIG. 8E (grade 4 prostatic carcinoma), and are also included in the summarized results shown in Table 1. Light to strong staining was observed in the glandular epithelia of all prostate cancer samples tested as well as in all samples derived from normal prostate or benign disease (e.g., BPH). The signal appears to be strongest at the cell membrane of the epithelial cells, especially at the cell-cell junctions (FIG. 8C-E) and is also inhibited with excess STEAP N-terminal peptide 1. Some basal cell staining is also seen in normal prostate (FIG. 8C), which is more apparent when examining atrophic glands. STEAP-1 seems to be expressed at all stages of prostate cancer since lower grades (FIG. 8D), higher grades (FIG. 8E) and metastatic prostate cancer (represented by LAPC-9; FIG. 8F; See also human patient metastases shown in FIG. 32A-B) all exhibit strong staining.

Figure 8G:
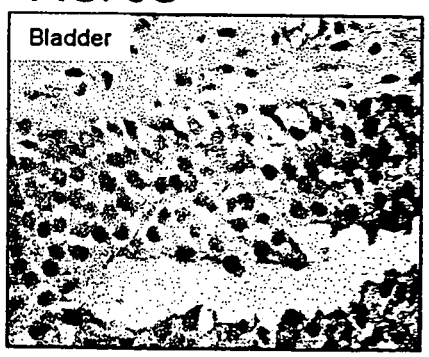
Figure 8H:
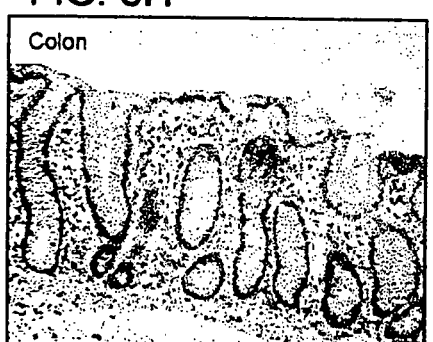

Immunohistochemical staining of a large panel of normal non-prostate tissues showed no detectable STEAP-1 expression in most of these normal tissues (Table 1). Normal bladder exhibited low levels of cell surface staining in the transitional epithelium (FIG. 8G). Pancreas, stomach, uterus, fallopian tubes and pituitary showed low levels of cytoplasmic staining (Table 1). It is unclear whether the observed cytoplasmic staining is specific or is due to non-specific binding of the antibody, since northern blotting showed little to no STEAP-1 expression in pancreas (FIG. 3). These results indicate that cell surface expression of STEAP-1 in normal tissues appears to be restricted to prostate and bladder.

TABLE 1

Immunohistochemical Staining of Human Tissues With Anti-STEAP-1 Sheep Polyclonal Antibody

| Staining Intensity | Tissues* |
| --- | --- |
| None | Cerebellum, cerebral cortex, spinal cord, heart, skeletal muscle (2), artery, thymus, spleen (4), bone marrow, lymph node (3), lung (8), liver (4), ileum, kidney (2), testis (2), ovary, placenta, breast, adrenal gland (2), thyroid gland (2), skin (2) |

TABLE 1-continued

Immunohistochemical Staining of Human Tissues With Anti-STEAP-1 Sheep Polyclonal Antibody

| Staining Intensity | Tissues* |
|---|---|
| Light Cytoplasmic | Ureter, bladder cancer (2/5), colon (4/7), colon cancer (4/7), fallopian tubes (2), pituitary gland, pancreas, stomach (1/2), uterus (1/2) |
| Light Membrane | Prostate cancer bone marrow metastasis (1/6), prostate cancer lymph node metastasis (1/5), lung cancer (1/6) |
| Moderate to Strong Membrane | Prostate (7/7), BPH (5/5), prostate cancer (20/20)**, prostate cancer lymph node metastasis (4/5), prostate cancer bone marrow metastasis (5/6), bladder (2/5), bladder cancer (3/5), lung cancer (3/6) |

*In cases where more than one sample was analyzed per tissue, the number in parenthesis indicates how many samples showed positive staining/total analyzed.
**Prostate cancer grades varied from 3 to 5 and Gleason scores of 7 to 10.

Example 3E

Immunohistochemical Analysis of STEAP-1 Protein Expression in Bladder and Lung Cancer To determine the extent of STEAP-1 protein expression in other cancers, tissue from bladder and lung cancer clinical specimens were subjected to immunohistochemical analysis using the polyclonal antibody and methods as described in Example 3D. The results, shown in FIGS. 21A-D, reveal a pericellular staining pattern similar to that observed with prostate cancer tissue.

Example 4

Biochemical Characterization of STEAP-1 Protein

To initially characterize the STEAP-1 protein, cDNA clone 10 was cloned into the pcDNA 3.1 Myc-His plasmid (Invitrogen), which encodes a 6His tag at the carboxyl-terminus, transfected into 293T cells, and analyzed by flow cytometry using anti-His monoclonal antibody (His-probe, Santa Cruz) as well as the anti-STEAP-1 polyclonal antibody described above. Staining of cells was performed on intact cells as well as permeabilized cells. The results indicated that only permeabilized cells stained with both antibodies, suggesting that both termini of the STEAP-1 protein are localized intracellularly. It is therefore possible that one or more of the STEAP-1 protein termini are associated with intracellular organelles rather than the plasma membrane.

To determine whether STEAP-1 protein is expressed at the cell surface, intact STEAP-1-transfected 293T cells were labeled with a biotinylation reagent that does not enter live cells. STEAP-1 was then immunoprecipitated from cell extracts using the anti-His and anti-STEAP antibodies. SV40 large T antigen, an intracellular protein that is expressed at high levels in 293T cells, and the endogenous cell surface transferrin receptor were immunoprecipitated as negative and positive controls, respectively. After immunoprecipitation, the proteins were transferred to a membrane and visualized with horseradish peroxidase-conjugated streptavidin. The results of this analysis are shown in FIG. 7; Only the transferrin receptor (positive control) and STEAP-1 were labeled with biotin, while the SV40 large T antigen (negative control) was not detectably labeled (FIG. 7A). Since only cell surface proteins are labeled with this technique, it is clear from these results that STEAP-1 is a cell surface protein. Combined with the results obtained from the flow cytometric analysis, it is clear that STEAP-1 is a cell surface protein with intracellular amino- and carboxyl-termini.

Furthermore, the above results together with the STEAP-1 secondary structural predictions, shows that STEAP-1 is a type IIIa membrane protein with a molecular topology of six potential transmembrane domains, 3 extracellular loops, 2 intracellular loops and two intracellular termini. A schematic representation of STEAP-1 protein topology relative to the cell membrane is shown in FIG. 1B.

In addition, prostate, bladder and colon cancer cells were directly analyzed for cell surface expression of STEAP-1 by biotinylation studies. Briefly, biotinylated cell surface proteins were affinity purified with streptavidin-gel and probed with the anti-STEAP-1 polyclonal antibody described above. Western blotting of the streptavidin purified proteins clearly show cell surface biotinylation of endogenous STEAP-1 in all prostate (LNCaP, PC-3, DU145), bladder (UM-UC-3, TCCSUP) and colon cancer (LoVo, Colo) cells tested, as well as in NIH 3T3 cells infected with a STEAP-1 encoding retrovirus, but not in non-expressing NIH 3T3 cells used as a negative control (FIG. 7B). In a further negative control STEAP-1 protein was not detected in streptavidin precipitates from non-biotinylated STEAP expressing cells (FIG. 7B).

Example 5

Constructs for Recombinant Expression of STEAP-1 pGEX Constructs

To express STEAP-1 in bacterial cells, portions of STEAP-1 were fused to the Glutathione S-transferase (GST) gene by cloning into pGEX-6P-1 (Amersham Pharmacia Biotech, NJ). All constructs were made to generate recombinant STEAP-1 protein sequences with GST fused at the N-terminus and a six histidine epitope at the C-terminus. The six histidine epitope tag was generated by adding the histidine codons to the cloning primer at the 3' end of the ORF. A PreScission™ recognition site permits cleavage of the GST tag from STEAP-1. The ampicillin resistance gene and pBR322 origin permits selection and maintenance of the plasmid in E. coli. The following fragments of STEAP-1 were cloned into pGEX-6P-1:

Amino acids 148 to 251; amino acids 144 to 339; amino acids 39 to 253; amino acids 70 to 136; amino acids 254 to 313.

And into pGEX-4T: Amino acids 2 to 247; amino acids 135-318; and amino acids 144-339.

Exemplary additional constructs that can be made in pGEX-6P-1 spanning the following regions of the STEAP-1 protein include:

Amino acids 1 to 339; amino acids 1 to 144.

pcDNA3.1/MycHis Construct

To express STEAP-1 in mammalian cells, the 1,017 bp STEAP-1 ORF (with translational start Kozak consensus) was cloned into pcDNA3.1/MycHis Version B (Invitrogen, Carlsbad, Calif.). Protein expression is driven from the cytomegalovirus (CMV) promoter. The recombinant protein has the myc and six histidines fused to the C-terminus. The pcDNA3.1/MycHis vector also contains the bovine growth hormone (BGH) polyadenylation signal and transcription termination sequence to enhance mRNA stability along with the SV40 origin for episomal replication and simple vector rescue in cell lines expressing the large T antigen. The Neomycin resistance gene allows for selection of mammalian cells expressing the protein and the ampicillin resistance gene and ColE1 origin permits selection and maintenance of the plasmid in E. coli.

pSRa Constructs

To generate mammalian cell lines expressing STEAP-1 constitutively, the 1,017 bp ORF (with translational start Kozak consensus) was cloned into pSRa constructs. Amphotropic and ecotropic retroviruses are generated by transfection of pSRa constructs into the 293T-10A1 packaging line or co-transfection of pSRa and a helper plasmid (φ-) in 293 cells, respectively. The retrovirus can be used to infect a variety of mammalian cell lines, resulting in the integration of the cloned gene, STEAP-1, into the host cell lines. Protein expression is driven from a long terminal repeat (LTR). The Neomycin resistance gene allows for selection of mammalian cells expressing the protein and the ampicillin resistance gene and ColE1 origin permits selection and maintenance of the plasmid in E. coli. Additional pSRa constructs were made that fused the FLAG tag to the C and N-terminus to allow detection using anti-FLAG antibodies. The FLAG sequence 5' gat tac aag gat gac gac gat aag 3' (SEQ ID NO: 34) were added to cloning primer at the 3' end of the ORF. Another pSRa construct was made that contained amino acids 182 to 454. This truncated form of the STEAP-1 protein will help determine the function of the long extracellular N-Terminal region.

An Additional pSRa construct is being made to produce a myc/6 HIS fusion protein of the full length STEAP-1 protein.

Example 6

Identification and Structural Analysis of Other Human STEAPs

STEAP-1 has no homology to any known human genes. In an attempt to identify additional genes that are homologous to STEAP-1, the protein sequence of STEAP-1 was used as an electronic probe to identify family members in the public EST (expression sequence tag) database (dbEST). Using the "tblastn" function in NCBI (National Center for Biotechnology Information), the dbEST database was queried with the STEAP-1 protein sequence. This analysis revealed additional putative STEAP-1 homologues or STEAP family members, as further described below.

In addition, SSH cloning experiments also identified a STEAP-1 related cDNA fragment, clone 98P4B6. This clone was isolated from SSH cloning using normal prostate cDNA as tester and LAPC-4 AD cDNA as driver. A larger partial sequence of the 98P4B6 clone was subsequently isolated from a normal prostate library; this clone encodes an ORF of 173 amino acids with close homology to the primary structure of STEAP-1, and thus was designated STEAP-2. A full length STEAP-2 cDNA of 2454 bp was isolated from a prostate library. The STEAP-2 nucleotide and encoded ORF amino acid sequences are shown in FIG. 9A-D. An amino acid alignment of the STEAP-1 and partial STEAP-2 primary structures is shown in FIGS. 11A-B and 11C. STEAP-1 and -2 share 61% identity over their 171 amino acid residue overlap (FIG. 11C). The STEAP-2 cDNA has been deposited with the American Type Culture Collection ("ATCC"; 10801 University Blvd., Manassas, Va. 20110-2209 USA) as plasmid 98P4B6-GTD3 on Jul. 2, 1999 as ATCC Accession Number PTA-311.

This deposit was made under the provisions of the Budapest Treaty on the International Recognition of the Deposit of Microorganisms for the Purpose of Patent Procedure and the Regulations thereunder (Budapest Treaty). This assures maintenance of a viable culture of the deposit for 30 years from the date of deposit and for at least five (5) years after the most recent request for the furnishing of a sample of the deposit received by the depository. The deposits will be made available by ATCC under the terms of the Budapest Treaty, and subject to an agreement between Genentech, Inc. and ATCC, which assures that all restrictions imposed by the depositor on the availability to the public of the deposited material will be irrevocably removed upon the granting of the pertinent U.S. patent, assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 U.S.C. §122 and the Commissioner's rules pursuant thereto (including 37 C.F.R. §1.14 with particular reference to 8860G 638).

The STEAP-2 cDNA (98P4B6-GTD3) contains a 355 bp 5'UTR (untranslated region) that is 72% GC rich, suggesting that it contains translational regulatory elements. The cDNA encodes an open reading frame (ORF) of 454 amino acids (a.a.) with six potential transmembrane domains. This is in contrast to STEAP-1, which is 339 a.a. in length. Alignment with STEAP-1 demonstrates 54.9% identity over a 237 amino acid overlap. Interestingly, the locations of the six putative transmembrane domains in STEAP-2 coincide with the locations of the transmembrane domains in STEAP-1 (see alignment). The homology of STEAP-2 with STEAP-1 is highest in the regions spanned by the first putative extracellular loop to the fifth transmembrane domain. This analysis and the sequence of STEAP-2 suggest some significant differences between STEAP-1 and STEAP-2: STEAP-2 exhibits a 205 a.a. long intracellular N-terminus (compared to 69 a.a. in STEAP-1) and a short 4 a.a. intracellular C-terminus (compared to 26 a.a. in STEAP-1). These differences could imply significant differences in function and/or interaction with intracellular signaling pathways. To identify a unique mouse EST corresponding to STEAP-2, the unique N-terminus of STEAP-2 was used to query the dbEST database. One mouse EST was isolated (AI747886, mouse kidney) that may be used in the identification of mouse STEAP-2 and in expression analysis of STEAP-2 in mouse.

Two ESTs encoding ORFs bearing close homology to the STEAP-1 and STEAP-2 sequences were also identified by electronic probing with the STEAP-1 protein sequence. These ESTs (AI139607 and R80991) were provisionally designated STEAP-3 and STEAP-4. A full length cDNA encoding STEAP-3 was subsequently cloned, and its nucleotide and deduced amino acid sequences are shown in FIG. 10A-E. The STEAP-3 cDNA has been deposited with the American Type Culture Collection ("ATCC"; 10801 University Blvd., Manassas, Va. 20110-2209 USA) on Dec. 8, 1999 as plasmid pSTEAP-3 EBB4 as ATCC Accession Number PTA-1033. The nucleotide sequences of the ESTs corresponding to the STEAPs are reproduced in FIG. 10F.

An amino acid alignment of the structures of STEAP-1, STEAP-2, STEAP-3 and the partial sequence of the putative STEAP-4 is shown in FIG. 11A-B. This alignment shows a close structural similarity between all four STEAP family proteins, particularly in the predicted transmembrane domains. As indicated above, STEAP-1 and STEAP-2 demonstrate 54.9% identity over a 237 amino acid overlap. STEAP-1 and STEAP-3 are 40.9% identical over a 264 amino acid region, while STEAP-2 and STEAP-3 are 47.8% identical over a 416 amino acid region.

Example 7

Constructs for Recombinant Expression of STEAP-2 pGEX Constructs

To express STEAP-2 in bacterial cells, portions of STEAP-2 were fused to the Glutathione S-transferase (GST) gene by cloning into pGEX-6P-1 (Amersham Pharmacia Biotech, NJ). All constructs were made to generate recombinant STEAP-2 protein sequences with GST fused at the N-terminus and a six histidine epitope at the C-terminus. The six histidine epitope tag was generated by adding the histidine codons to the cloning primer at the 3' end of the ORF. A PreScission™ recognition site permits cleavage of the GST tag from STEAP-2. The ampicillin resistance gene and pBR322 origin permits selection and maintenance of the plasmid in *E. coli*. The following fragments of STEAP-2 were cloned into pGEX-6P-1:

Amino acids 287 to 390; amino acids 285 to 454; amino acids 193 to 454.

Additional exemplary constructs that can be made in pGEX-6P-1 spanning the following regions of the STEAP-2 protein include:

Amino acids 1 to 193; amino acids 1 to 454.

And in pGEX-4T: Amino acids 2-204; 183-387; and 276-453.

pCRII Construct

To generate sense and anti-sense riboprobes for RNA in situ investigations, a pCRII construct was generated using bp 367 to 877 of the GTD3 STEAP-2 cDNA. The pCRII vector has Sp6 and T7 promoters flanking the insert to drive the production of STEAP-2 RNA riboprobes which were used in RNA in situ hybridization experiments.

pcDNA4/HisMax-TOPO Construct

To express STEAP-2 in mammalian cells, the 1,362 bp STEAP-2 ORF was cloned into pcDNA4/HisMax-TOPO Version A (cat# K864-20, Invitrogen, Carlsbad, Calif.). Protein expression is driven from the cytomegalovirus (CMV) promoter and the SP163 translational enhancer. The recombinant protein has Xpress™ and six histidine epitopes fused to the N-terminus. In addition to this construct containing only the 1,362 bp ORF an additional construct was made with the C-terminus of the recombinant protein containing a 28 amino acid fusion resulting from vector sequences prior to the termination codon. The pcDNA4/HisMax-TOPO vector also contains the bovine growth hormone (BGH) polyadenylation signal and transcription termination sequence to enhance mRNA stability along with the SV40 origin for episomal replication and simple vector rescue in cell lines expressing the large T antigen. The Zeocin resistance gene allows for selection of mammalian cells expressing the protein and the ampicillin resistance gene and ColE1 origin permits selection and maintenance of the plasmid in *E. coli*.

pcDNA3.1/MycHis Construct

To express STEAP-2 in mammalian cells, the 1,362 bp STEAP-2 ORF (with start Kozak consensus) was cloned into pcDNA3.1/MycHis Version A (Invitrogen, Carlsbad, Calif.). Protein expression is driven from the cytomegalovirus (CMV) promoter. The recombinant protein has the myc and six histidines fused to the C-terminus. The pcDNA3.1/MycHis vector also contains the bovine growth hormone (BGH) polyadenylation signal and transcription termination sequence to enhance mRNA stability along with the SV40 origin for episomal replication and simple vector rescue in cell lines expressing the large T antigen. The neomycin resistance gene allows for selection of mammalian cells expressing the protein and the ampicillin resistance gene and ColE1 origin permits selection and maintenance of the plasmid in *E. coli*. Additional pcDNA3.1/MycHis constructs were generated using STEAP-2 amino acids 6 to 454, 121-454 and 182-454.

pBlueBacHIS2a

To express STEAP-1 in SF9 insect cells, the STEAP-1 ORF was cloned into pBlueBacHIS2A (Invitrogen, California). Protein expression is driven under the polyhedrin promoter. N-terminus poly HIS and Xpress tags allow for detection and purification of the recombinant STEAP-1 protein. A C-terminus enterokinase recognition site allows for cleavage of these tags. The ampicillin resistance gene and ColE1 origin permits selection and maintenance of the plasmid in *E. coli*. Following cotransfection with AcMNPV DNA, a homologous recombination event occurs between these sequences resulting in a recombinant virus carrying the gene of interest and the polyhedrin. A variety of restriction enzyme sites for simplified subcloning are present. In addition, a reporter gene (b-galactosidase) conveniently identifies recombinant plaques, to eliminate tedious plaque screening.

pcDNA3.1CT-GFP-TOPO Construct

To express STEAP-2 in mammalian cells and to allow detection of the recombinant protein using fluorescence, the 1,362 bp ORF (with start Kozak consensus) was cloned into pcDNA3.1CT-GFP-TOPO (Invitrogen, CA). Protein expression is driven from the cytomegalovirus (CMV) promoter. The recombinant protein has the Green Fluorescent Protein (GFP) fused to the C-terminus facilitating non-invasive, in vivo detection and cell biology studies. The pcDNA3.1/MycHis vector also contains the bovine growth hormone (BGH) polyadenylation signal and transcription termination sequence to enhance mRNA stability along with the SV40 origin for episomal replication and simple vector rescue in cell lines expressing the large T antigen. The neomycin resistance gene allows for selection of mammalian cells expressing the protein and the ampicillin resistance gene and ColE1 origin permits selection and maintenance of the plasmid in *E. coli*.

An additional construct with a N-terminal GFP fusion is being made in pcDNA3.1NT-GFP-TOPO spanning the entire length of the STEAP-2 protein.

pSRa Constructs

To generate mammalian cell lines expressing STEAP-2 constitutively, the 1362 bp ORF was cloned into pSRa constructs. Amphotropic and ecotropic retroviruses are generated by transfection of pSRa constructs into the 293T-10A1 packaging line or co-transfection of pSRa and a helper plasmid (φ−) in 293 cells, respectively. The retrovirus can be used to infect a variety of mammalian cell lines, resulting in the integration of the cloned gene, STEAP-2, into the host cell-lines. Protein expression is driven from a long terminal repeat (LTR). The neomycin resistance gene allows for selection of mammalian cells expressing the protein and the ampicillin resistance gene and ColE1 origin permits selection and maintenance of the plasmid in *E. coli*. Additional pSRa constructs were made that fused the FLAG tag to the C and N-terminus to allow detection using anti-FLAG antibodies. The FLAG sequence 5' gat tac aag gat gac gac gat aag 3' (SEQ ID NO: 34) was added to cloning primer at the 3' end of the ORF. Another pSRa construct was made that contained amino acids 182 to 454. This truncated form of the STEAP-2 protein will help determine the function of the long extracellular N-Terminal region.

In addition, a pSRa construct can be made to produce a myc/6 HIS fusion protein of the fill length STEAP protein.

Example 8

Expression Analysis of STEAP-2 and Other Human STEAP Family Members

Example 8A

Tissue Specific Expression of STEAP Family Members in Normal Human Tissues RT-PCR analysis of STEAP-2 shows expression in all the LAPC prostate cancer xenografts and in normal prostate (FIG. 14, panel A). Analysis of 8 normal human tissues shows prostate-specific expression after 25 cycles of amplification (FIG. 14, panel B). Lower level expression in other tissues was detected only after 30 cycles of amplification. Northern blotting for STEAP-2 shows a pattern of 2 transcripts (approximately 3 and 8 kb in size) expressed only in prostate (and at significantly lower levels in the LAPC xenografts), with no detectable expression in any of the 15 other normal human tissues analyzed (FIG. 15, panel C). Thus, STEAP-2 expression in normal human tissues appears to be highly prostate-specific.

Expression analysis of STEAP family members in normal tissues was performed by Northern blot and/or RT-PCR. All STEAP family members appeared to exhibit tissue restricted expression patterns. STEAP-3/AI139607 expression is shown in FIG. 12A (Northern) and FIG. 12B (RT-PCR). STEAP-4/R80991 expression is shown in FIG. 13.

Example 8B

Expression of STEAP-2 in Various Cancer Cell Lines

The RT-PCR results above suggested that the different STEAP family members exhibit different tissue expression patterns. Interestingly, STEAP-2, which appears very prostate-specific, seems to be expressed at lower levels in the LAPC xenografts. This is in contrast to STEAP-1, which is highly expressed in both normal and malignant prostate tissue.

To better characterize this suggested difference in the STEAP-2 prostate cancer expression profile (relative to STEAP-1), Northern blotting was performed on RNA derived from the LAPC xenografts, as well as several prostate and other cancer cell lines, using a STEAP-2 specific probe labeled cDNA clone 98P4B6). The results are shown in FIG. 16 and can be summarized as follows. STEAP-2 is highly expressed in normal prostate and in some of the prostate cancer xenografts and cell lines. More particularly, very strong expression was observed in the LAPC-9 AD xenograft and the LNCaP cells. Significantly attenuated or no expression was observed in the other prostate cancer xenografts and cell lines. Very strong expression was also evident in the Ewing Sarcoma cell line RD-ES. Unlike STEAP-1, which is highly expressed in cancer cell lines derived from bladder, colon, pancreatic and ovarian tumors, STEAP-2 showed low to non-detectable expression in these same cell lines (compare with FIG. 5). Interestingly, STEAP-2 was also non-detectable in PrEC cells, which are representative of the normal basal cell compartment of the prostate. These results suggests that expression of STEAP-1 and STEAP-2 are differentially regulated. While STEAP-1 may be a gene that is generally up-regulated in cancer, STEAP-2 may be a gene that is more restricted to normal prostate and prostate cancer.

Example 8C

Analysis of in Situ Expression of STEAP-2 RNA in Normal Prostate and Prostate Cancer The expression of STEAP-2 RNA was evaluated using in situ hybridization with a labeled antisense probe and using a labeled sense probe as control. All four of four normal prostate tissue specimens examined were positive for STEAP (FIGS. 22A-B). Likewise, five of five prostate cancer tissue specimens were positive using STEAP RNA in situ hybridization (FIGS. 23A-B). A PIN specimen and a sample of LNCaP cells that were examined were positive as well.

Example 8D

Analysis of STEAP-2 Expression in Cancer Tissues

The expression of STEAP-2 in various cancer tissues was examined using RT-PCR. The results are shown in FIG. 24, in which lane 1 represents a sample from an LAPC4 AD xenograft; lane 2 is LAPC9 AD xenograft; lane 3 is LAPC9 $AD^2$ xenograft (grown with human bone explant); lane 4 is LAPC9 AD IT (grown intratribially); lane 5 is pooled tissue from colon cancer patients; lane 6 is pooled tissue from lung cancer patients; M represents a marker lane; lane 7 is patient normal prostate tissue; lane 8 is patient prostate cancer tissue; lane 9 is pooled tissue from kidney cancer patients; lane 10 is pooled tissue from bladder cancer patients; lane 11 is HeLa cells; and lane 12 is a water blank. The highest expression is found in the three LAPC9 AD xenografts. High expression is observed in the LAPC4 AD xenograft as well, and in normal prostate and lung cancer. Significant expression was detected also in colon and bladder cancer. Lower expression was detected in prostate and kidney cancer patient samples.

Example 8E

Analysis of STEAP-2 Expression in Normal Tissues

The expression of STEAP-2 in 76 normal human tissues was examined using a dot blot analysis of RNA samples. As shown in FIG. 25, STEAP-2 is expressed at very high levels only in normal prostate.

Example 9

Chromosomal Localization of STEAP Genes

The chromosomal localization of STEAP-1 was determined using the GeneBridge 4 Human/Hamster radiation hybrid (RH) panel (Walter et al., 1994, Nat. Genetics 7:22) (Research Genetics, Huntsville Ala.), while STEAP-2 and the STEAP homologues were mapped using the Stanford G3 radiation hybrid panel (Stewart et al., 1997, Genome Res. 7:422).

The following PCR primers were used for STEAP-1:
8P1D4.1    5'ACTTTGTTGATGACCAGGATTGGA3' (SEQ ID NO: 4)
8P1D4.2    5'CAGAACTTCAGCACACACAGGAAC3' (SEQ ID NO: 5)

The resulting STEAP-1 mapping vector for the 93 radiation hybrid panel DNAs (2100000201101010001000000101110101221000110011

1011010 100010001 000101001-0 2100000111 100101 00 0 0), and the mapping program RHMapper available at the Broad Institute website, localized the STEAP-1 gene to chromosome 7p22.3, telomeric to D7S531.

The following PCR primers were used for 98P4B6/STEAP-2:
98P4B6.1 5'GACTGAGCTGGAACTGGAATTTGT3' (SEQ ID NO: 20)
98P4B6.2 5'TTTGAGGAGACTTCATCTCACTGG3' (SEQ ID NO: 21)
The resulting vector (000001001000000000000000000000000100100000000001 00 0100000000000001000010101010010011), and the mapping program RHServer available at the website for the Stanford Human Genome Center maps the 98P4B6 (STEAP-2) gene to chromosome 7q21.

The following PCR primers were used for AI139607:
AI139607.1 5'TTAGGACAACTTGATCACCAGCA3' (SEQ ID NO: 16)
AI139607.2 5'TGTCCAGTCCAAACTGGGTTATTT3' (SEQ ID NO: 17)
The resulting vector (00000000010000000000000000001000100000200000001 00 010000000100000100000100001010010010), and the mapping program RHServer available at the website for the Stanford Human Genome Center maps AI139607 to chromosome 7q21.

The following PCR primers were used for R80991:
R80991.3 5'ACAAGAGCCACCTCTGGGTGAA3' (SEQ ID NO: 35)
R80991.4 5'AGTTGAGCGAGTTTGCAATGGAC3' (SEQ ID NO: 36)
The resulting vector (0000000000020000102000000001000000000000000000 0010000000001000011100000001001000001), and the mapping program RHServer available at the website for the Stanford Human Genome Center maps R80991 to chromosome 2q14-q21, near D2S2591.

In summary, the above results show that three of the putative human STEAP family members localize to chromosome 7, as is schematically depicted in FIG. 17. In particular, the STEAP-1 gene localizes to the far telomeric region of the short arm of chromosome 7, at 7p22.3, while STEAP-2 and AI139607 localize to the long arm of chromosome 7, at 7q21 (FIG. 17). R80991 maps to chromosome 2q14-q21.

Example 10

Identification of Intron-Exon Boundaries of STEAP-1

Genomic clones for STEAP-1 were identified by searching GenBank for BAC clones containing STEAP-1 sequences, resulting in the identification of accession numbers AC004969 (PAC DJ1121E10) and AC005053 (BAC RG041D11). Using the sequences derived from the PAC and BAC clones for STEAP the intron-exon boundaries were defined (FIG. 18). A total of 4 exons and 3 introns were identified within the coding region of the STEAP gene. Knowledge of the exact exon-intron structure of the STEAP-1 gene may be used for designing primers within intronic sequences which in turn may be used for genomic amplification of exons. Such amplification permits single-stranded conformational polymorphism (SSCP) analysis to search for polymorphisms associated with cancer. Mutant or polymorphic exons may be sequenced and compared to wild type STEAP. Such analysis may be useful to identify patients who are more susceptible to aggressive prostate cancer, as well as other types of cancer, particularly colon, bladder, pancreatic, ovarian, cervical and testicular cancers.

Southern blot analysis shows that the STEAP-1 gene exists in several species including mouse (FIG. 19). Therefore, a mouse BAC library (Mouse ES 129-V release I, Genome Systems, FRAC-4431) was screened with the human cDNA for STEAP-1 (clone 10, Example 2). One positive clone, 12P11, was identified and confirmed by southern blotting (FIG. 20). The intron-exon boundary information for human STEAP may be used to identify the mouse STEAP-1 coding sequences.

The mouse STEAP-1 genomic clone may be used to study the biological role of STEAP-1 during development and tumorigenesis. Specifically, the mouse genomic STEAP-1 clone may be inserted into a gene knock-out (K/O) vector for targeted disruption of the gene in mice, using methods generally known in the art. In addition, the role of STEAP in metabolic processes and epithelial cell function may be elucidated. Such K/O mice may be crossed with other prostate cancer mouse models, such as the TRAMP model (Greenberg et al., 1995, PNAS 92:3439), to determine whether STEAP influences the development and progression of more or less aggressive and metastatic prostate cancers.

Example 11

Predicted HLA-A2 Binding Peptides of STEAP-1 and STEAP-2

The complete amino acid sequences of the STEAP-1 and STEAP-2 proteins were entered into the HLA Peptide Motif Search algorithm found in the Bioinformatics and Molecular Analysis Section (BIMAS) Web site. The HLA Peptide Motif Search algorithm was developed by Dr. Ken Parker based on binding of specific peptide sequences in the groove of HLA Class I molecules and specifically HLA-A2 (Falk et al., 1991, Nature 351: 290-6; Hunt et al., 1992, Science 255:1261-3; Parker et al., 1992, J. Immunol. 149:3580-7; Parker et al., 1994, J. Immunol. 152:163-75). This algorithm allows location and ranking of 8-mer, 9-mer, and 10-mer peptides from a complete protein sequence for predicted binding to HLA-A2 as well as other HLA Class I molecules. Most HLA-A2 binding peptides are 9-mers favorably containing a leucine (L) at position 2 and a valine (V) or leucine (L) at position 9.

The results of STEAP-1 and STEAP-2 predicted binding peptides are shown in Table 2 below. For both proteins the top 5 ranking candidates are shown along with their location, the amino acid sequence of each specific peptide, and an estimated binding score. The binding score corresponds to the estimated half-time of dissociation of complexes containing the peptide at 37° C. at pH 6.5. Peptides with the highest binding score (i.e. 10776.470 for STEAP-1 peptide 165; 1789.612 for STEAP-2 peptide 227) are predicted to be the most tightly bound to HLA Class I on the cell surface and thus represent the best immunogenic targets for T-cell recognition. Actual binding of peptides to HLA-A2 can be evaluated by stabilization of HLA-A2 expression on the antigen-processing defective cell line T2 (Refs. 5,6). Immunogenicity of specific peptides can be evaluated in vitro by stimulation of CD8+ cytotoxic T lymphocytes (CTL) in the presence of dendritic cells (Xue et al., 1997, Prostate 30:73-8; Peshwa et al., 1998, Prostate 36:129-38).

TABLE 2

Predicted Binding of STEAP-1 and STEAP-2 Peptide
Sequences With Highest Affinity for HLA-A2

| Rank | Start Position | Subsequence Residue Listing | Score (Estimate of Half Time of Disassociation) |
|---|---|---|---|
| STEAP-1 | | | |
| 1 | 165 | GLLSFFFAV (SEQ ID NO: 47) | 10776.470 |
| 2 | 86 | FLYTLLREV (SEQ ID NO: 48) | 470.951 |
| 3 | 262 | LLLGTIHAL (SEQ ID NO: 49) | 309.050 |
| 4 | 302 | LIFKSILFL (SEQ ID NO: 50) | 233.719 |
| 5 | 158 | MLTRKQFGL (SEQ ID NO: 51) | 210.633 |
| STEAP-2 | | | |
| 1 | 227 | FLYSFVRDV (SEQ ID NO: 52) | 1789.612 |
| 2 | 402 | ALLISTFHV (SEQ ID NO: 53) | 1492.586 |
| 3 | 307 | LLSFFFAMV (SEQ ID NO: 54) | 853.681 |
| 4 | 306 | GLLSFFFAM (SEQ ID NO: 55) | 769.748 |
| 5 | 100 | SLWDLRHLL (SEQ ID NO: 56) | 726.962 |

Example 12

STEAP-2 Induction of Tyrosine Phosphorylation of Cellular Proteins

Multi-transmembrane proteins have the ability to transmit signal from the membrane and initiate signaling cascades that regulate a variety of downstream events, including gene expression, cellular differentiation, migration and proliferation (Biochim. Biophys. Acta 1997; 1348:56-62, J. Virol. 1995; 69:675-83). In order to determine the involvement of STEAP-1 and STEAP-2 in downstream signaling events, the effect of STEAP-1 and STEAP-2 on tyrosine phosphorylation of PC3 cells was investigated (FIG. 26). PC3 cells, stably expressing neo, STEAP-1, or STEAP-2 were grown overnight in 1% fetal bovine serum (FBS) to reduce receptor occupancy and background activity. The cells were then incubated for 5 minutes in the presence of either 1% or 10% FBS, lysed and analyzed by western blotting with anti-phosphotyrosine (4G10 mAb). An overlay using anti-Grb2 Ab was used to show that the gel was equally loaded.

The results (FIG. 26) show that expression of STEAP-2 in PC3 cells induces the phosphorylation of several proteins on tyrosine residues, including p150, p120 and p75. In contrast, expression of STEAP-1 induced the de-phosphorylation of p150. Several of the phosphorylated proteins correspond to known signaling proteins, indicating that STEAP-1 and STEAP-2 may be controlling the activation of specific signaling cascades.

Example 13

STEAP-1- and STEAP-2-Mediated Activation of MAPK Cascades

Several multi-transmembrane proteins induce specific biological responses by activating protein kinase cascades, including the MAPK pathways (Curr. Med. Chem. 2000; 7:911-43, Life Sci. 2000; 67:335-6, Biol. Chem. 2000; 275: 4660-9). In order to determine whether expression of STEAP-1 and STEAP-2 is sufficient to regulate specific signaling pathways not otherwise active in resting PC3 cells, the effect of these genes on the activation of the p38 MAPK cascade was investigated in the prostate cancer cell line PC3 (FIG. 27A-B). Activation of the p38 kinase is dependent on its phosphorylation on tyrosine and serine residues. Phosphorylated p38 can be distinguished from the non-phosphorylated state by a Phospho-p38 mAb. This phospho-specific Ab was used to study the phosphorylation state of p38 in engineered PC3 cell lines.

PC3 cells stably expressing STEAP-1, STEAP-2 or neo were grown overnight in either 1% or 10% FBS. Whole cell lysates were analyzed by western blotting. PC3 cells treated with the known p38 activators, NaSal or TNF, were used as a positive control. The results show that while expression of the control neo gene has no effect on p38 phosphorylation, expression of STEAP-1 and STEAP-2 in PC3 cells is sufficient to induce the activation of the p38 pathway (FIG. 27A). The results were verified using western blotting with an anti-p38 Ab, which shows equal protein loading on the gels (FIG. 27B).

In another set of experiments, the sufficiency of expression of STEAP-1 or STEAP-2 in the prostate cancer cell line PC3 to activate the mitogenic MAPK pathway, namely the ERK cascade, was examined (FIG. 28A-B). Activation of ERK is dependent on its phosphorylation on tyrosine and serine residues. Phosphorylated ERK can be distinguished from the non-phosphorylated state by a Phospho-ERK mAb. This phospho-specific Ab was used to study the phosphorylation state of ERK in engineered PC3 cell lines. PC3 cells, expressing an activated form of Ras, were used as a positive control.

The results show that while expression of the control neo gene has no effect on ERK phosphorylation, expression of STEAP-2 in PC3 cells is sufficient to induce at least a 3-fold increase in ERK phosphorylation (FIG. 28A). Expression of STEAP-1 also induced some ERK phosphorylation in PC3 cells grown in 1% FBS. These results were verified using anti-ERK western blotting (FIG. 28A) and confirm the activation of the ERK pathway by STEAP-1 and STEAP-2.

Since FBS contains several components that may contribute to receptor-mediated ERK activation, we examined the effect of STEAP-1 in low and optimal levels of FBS. PC3 cells expressing neo or STEAP-1 were grown in either 0.1% or 10% FBS overnight The cells were analyzed by anti-Phospho-ERK western blotting. This experiment shows that STEAP-1 induces the phosphorylation of ERK in 0.1% FBS, and confirms that expression of STEAP-1 is sufficient to induce activation of the ERK signaling cascade in the absence of additional stimuli.

Example 14

Ligand-Mediated Activation of STEAP-1

Several factors have been shown to activate multi-transmembrane proteins and mediate downstream signaling events, including ions, leukotrienes, lipophosphatidic acid, etc. (Cell Biochem. Biophys. 1999; 30:213-42). One group of compounds known to activate multi-transmembrane proteins are odorants (Neuron 2000; 25:503-4). In this example, 3 classes of odorants were screened for their ability to induce the activation of tyrosine kinase-mediated signaling in PC3 cells (FIG. 29).

PC3 cells, stably expressing neo or STEAP-1 were grown overnight in 0.1% FBS to allow for receptor occupancy. The cells were then treated for 5 min with the indicated concentrations (0.1-10 µM) of citralva, ethylvanillin or IBMP. Treatment with 10% FBS was used as a control. Whole cell lysates (20 µg) generated from the different treatment conditions were separated by SDS-PAGE and analyzed by anti-phosphotyrosine western blotting.

This experiment shows that, while all 3 classes of odorant induce some tyrosine phosphorylation in PC3-STEAP-1 cells, only IBMP had a measurable effect on the phosphorylation of PC3-neo cells that do not express the STEAP-1 gene. Moreover both citralva and ethylvanillin induced an increase in the phosphorylation of p136-140 and p200-210 in PC3-STEAP-1 cells in a STEAP-1 specific manner. In addition, citralva induced the de novo phosphorylation of a protein at 160-200 kDa. The results demonstrate that STEAP-1 is mediating the activation of tyrosine kinase pathways in odorant treated cells.

The finding that citralva induced the tyrosine phosphorylation of proteins in a STEAP-1 mediated manner suggests that STEAP-1 may initiate the activation of one or more signaling cascades. In order to identify potential signaling cascade associated with odorant activation of STEAP-1, the effect of odorants on the activation of the MAPK cascade was studied in PC3 cells (FIG. 30). PC3 cells, stably expressing either neo or STEAP-1, were grown overnight in 0.1% FBS. Cells were then treated with citralva for 5 min. Treatment with 10% FBS was used as a control. As observed using phospho-specific mAb (anti-phospho-ERK), citralva activated the ERK pathway in a STEAP-2 specific manner. These results also confirm the findings described in FIGS. 27-28, that expression of STEAP-1 alone is sufficient to induce the activation of the ERK pathway.

Example 15

Identification of Potential Signal Transduction Pathways

To confirm that STEAP directly or indirectly activates known signal transduction pathways in cells and to delineate STEAP-mediated downstream events, luciferase (luc) based transcriptional reporter assays are carried out in cells expressing STEAP. These transcriptional reporters contain consensus binding sites for known transcription factors which lie downstream of well characterized signal transduction pathways. The reporters and examples of their associated transcription factors, signal transduction pathways, and activation stimuli are listed below.
1. NFkB-luc, NFkB/Rel; Ik-kinase/SAPK; growth/apoptosis/stress
2. SRE-luc, SRF/TCF/ELK1; MAPK/SAPK; growth/differentiation
3. AP-1-luc, FOS/JUN; MAPK/SAPK/PKC; growth/apoptosis/stress
4. ARE-luc, androgen receptor; steroids/MAPK; growth/differentiation/apoptosis
5. p53-luc, p53; SAPK; growth/differentiation/apoptosis
6. CRE-luc, CREB/ATF2; PKA/p38; growth/apoptosis/stress STEAP-mediated effects may be assayed in cells showing mRNA expression. Luciferase reporter plasmids may be introduced by lipid mediated transfection (TFX-50, Promega). Luciferase activity, an indicator of relative transcriptional activity, is measured by incubation of cells extracts with luciferin substrate and luminescence of the reaction is monitored in a luminometer.

Example 16

In Vitro Assays of STEAP Function

The expression profile of STEAP in prostate cancer suggests a functional role in tumor initiation, progression and/or maintenance. STEAP function can be assessed in mammalian cells using in vitro approaches. For mammalian expression, STEAP can be cloned into a number of appropriate vectors, including pcDNA 3.1 myc-His-tag and the retroviral vector pSRatkneo (Muller et al., 1991, MCB 11:1785). Using such expression vectors, STEAP can be expressed in several cancer cell lines, including for example PC-3, NIH 3T3, LNCaP and 293T. Expression of STEAP can be monitored using anti-STEAP antibodies.

Mammalian cell lines expressing STEAP can be tested in several in vitro and in vivo assays, including cell proliferation in tissue culture, activation of apoptotic signals, primary and metastatic tumor formation in SCID mice, and in vitro invasion using a membrane invasion culture system (MICS) (Welch et al., Int. J. Cancer 43: 449-457). STEAP cell phenotype is compared to the phenotype of cells that lack expression of STEAP. In addition, cells treated with and without exogenously added STEAP protein may be analyzed for altered growth parameters.

Cell lines expressing STEAP can also be assayed for alteration of invasive and migratory properties by measuring passage of cells through a matrigel coated porous membrane chamber (Becton Dickinson). Passage of cells through the membrane to the opposite side is monitored using a fluorescent assay (Becton Dickinson Technical Bulletin #428) using calcein-Am (Molecular Probes) loaded indicator cells. Cell lines analyzed include parental and STEAP overexpressing PC3, 3T3 and LNCaP cells. To assay whether STEAP has chemoattractant properties, parental indicator cells are monitored for passage through the porous membrane toward a gradient of STEAP conditioned media compared to control media. This assay may also be used to qualify and quantify specific neutralization of the STEAP induced effect by candidate cancer therapeutic compositions.

In order to establish whether STEAP binds to cellular proteins expressed in prostate cancer cells and other cancer cells or normal cells, two approaches may be taken. In the first approach, in vitro assay for recombinant HIS-tagged STEAP binding to various cell lines are used. In another approach, a recombinant alkaline phosphatase-STEAP fusion protein is generated using the AP-TAG system from GenHunter Corporation (Nashville, Tenn., cat# Q202), and the AP-TAG fusion used to test STEAP binding to a variety of prostate cancer cell lines as described (Cheng and Flanagan, 1994, Cell 79:157-168). After washing the cells and adding the AP substrate BCIP, which forms an insoluble blue precipitate upon dephosphorylation, STEAP binding is determined by identifying cells staining blue under the light microscope.

Various cancer cell lines can be examined, including without limitation, various prostate cancer cell lines (e.g., LNCaP, PC-3, DU145, TSUPR, LAPC4). Other cell lines such as PREC prostate cell line, 293T, PIN cells, and NIH 3T3, etc. may also be examined. Additionally, the LAPC and other prostate cancer xenografts may be tested. Equilibrium dissociation rate constants may be calculated to evaluate the strength of the binding interaction. In addition, the number of cell surface receptors per cell can be determined. Cell lines or tissues with the highest binding capacity for STEAP would be preferred for cloning a STEAP binding partner.

In another functional assay, NIH-3T3 cells stably expressing STEAP can be analyzed for their ability to form colonies in soft agar. In these experiments, cells used in such procedures (e.g. NIH-3T3 cells), can be transfected to stably express STEAP or neo or activated-Ras (as the test gene, the negative and the positive controls, respectively) in order to assess the transforming capabilities of STEAP. Typically experiments are performed in duplicate and the assays are evaluated approximately 4 weeks after cell plating. Where experimental observations demonstrate that STEAP induces an increase in colony formation relative to a negative control (e.g. neo) such results indicate that STEAP has significant transforming capabilities.

Example 17

In Vivo Assay for STEAP Tumor Growth Promotion

The effect of the STEAP protein on tumor cell growth may be evaluated in vivo by gene overexpression in tumor-beating mice. For example, SCID mice can be injected subcutaneously on each flank with 1×10⁶ of a prostate cell line containing tkneo empty vector or STEAP. At least two strategies may be used: (1) Constitutive STEAP expression under regulation of an LTR promoter, and (2) Regulated expression under control of an inducible vector system, such as ecdysone, tet, etc. Tumor volume is then monitored at the appearance of palpable tumors and followed over time to determine if STEAP expressing cells grow at a faster rate. Additionally, mice may be implanted with 1×10⁵ of the same cells orthotopically to determine if STEAP has an effect on local growth in the target tissue (i.e., prostate) or on the ability of the cells to metastasize, specifically to lungs, lymph nodes, liver, bone marrow, etc. The effect of STEAP on bone tumor formation and growth may be assessed by injecting prostate tumor cells intratibially, as described in Example 1.

These assays are also useful to determine the STEAP inhibitory effect of candidate therapeutic compositions, such as for example, STEAP antibodies, STEAP antisense molecules and ribozymes.

Example 18

Detection of Prostate Cancer Metastases in Mice and Humans Using Anti-STEAP-1 Polyclonal Antibodies Mice STEAP-1 immunohistochemical analysis was performed on 4 µm formalin-fixed tissues derived from mice beating orthotopic LAPC-9 prostate cancer tumors and their derived lung and lymph node metastases. Serial lung sections were tested using anti-STEAP-1 sheep polyclonal antibody and anti-PSA rabbit polyclonal antibody (pAb). Microscopic examination of stained tissue was used to detect LAPC-9 prostate cancer cells, and the results are shown in FIGS. 31A-F.

The anti-STEAP-1 sheep pAb readily detected human prostate cancer cells in the mouse prostate (FIG. 31A), as well as in metastases to lymph nodes (FIG. 31B) and lung (FIG. 31C-D). Both small (FIG. 31C) and large (FIG. 31D) micrometastases to the lung were readily detected using the anti-STEAP-1 pAb. To confirm that the lung metastases were of prostate cancer origin, immunohistochemistry on serial lung sections was performed using the anti-PSA pAb (FIG. 31E-F). The strong cell surface staining observed with the anti-STEAP-1 pAb allows for easier detection of micrometastases as compared to the use of the anti-PSA polyclonal antibody.

Humans

The STEAP-1 polyclonal Ab was used in a similar immunohistochemical assay of metastatic prostate cancer specimens from human patients. High expression of STEAP-1 was detected in both the lymph node and bone metastases studied. As shown in FIG. 32A (lymph node metastasis) and 32B (bone metastasis), intense pericellular staining is observed in these human patient samples, confirming that STEAP-1 is an excellent marker for the detection of metastatic prostate cancer.

Example 19

STEAP-1, STEAP-2 and STEAP-3 Extracellular Loop-Fc Fusion Constructs

To express and secrete the extracellular loops of STEAP-1, STEAP-2, and STEAP-3 into conditioned media of mammalian cell lines, fragments of these genes can be cloned into the pFc vector to generate C-terminal fusions of the human IgG1 Fc region. The pFc vector was generated by cloning human immunoglobulin G1, Fc (bases 74-768 of GenBank accession X70421) proceeded by the IgA protease cleavage site (Roche, Cat 1461265) coded by 5' cctcgacctccaacaccgggg 3' (SEQ ID NO: 47) into pTag-5 (GenHunter Corp. Nashville, Tenn.) using XhoI and ApaI. This construct generates an IgG1 Fc fusion at the C-terminus of STEAP-1, STEAP-2 and STEAP-3 extracellular regions while fusing the IgGK signal sequence to N-terminus.

The resulting recombinant proteins are optimized for secretion into the media of transfected mammalian cells and can be used to identify proteins such as ligands or receptors that interact with the STEAP-1, STEAP-2, and STEAP-3 protein. These protein fusions can also be used as immunogen to generate antibodies. Protein expression is driven from the CMV promoter. The Zeosin resistance gene allows for selection of mammalian cells expressing the protein and the ampicillin resistance gene permits selection of the plasmid in *E. coli*.

The following extracellular loops of the STEAP-1, STEAP-2, and STEAP-3 proteins are suitable for cloning into pFc:

```
STEAP-1    revihplatshqqyfykipilv (SEQ ID NO: 37)
           rrsyrykllnwayqqvqqnkedawiehdvwrmei
           (SEQ ID NO: 38)
           widikqfvwytpptf (SEQ ID NO: 39)

STEAP-2    ysfvrdvihpyarnqqsdfykipiei
           (SEQ ID NO: 40)
           rrserylflnmayqqvhanienswneeevwrie
           (SEQ ID NO: 41)
           krafeeeyyrfy (SEQ ID NO: 42)

STEAP-3    ypyvyekkdntfrmaisipnrifp (SEQ ID NO: 43)
           yyvrwrlgnltvtqailkkenpfstssawlsdsy
           (SEQ ID NO: 44)
```

Example 20

Generation of Polyclonal Antibodies to STEAP-2

Three immunogens were used to generate antibodies specific to STEAP-2. Two immunogens were peptides encoding amino acids 153-165 (ALQLGPKDASRQV; SEQ ID NO:

45) and amino acids 345-358 (IENSWNEEEVWRIE; SEQ ID NO: 46) of the STEAP-2 protein sequence. The first peptide resides in the N-terminus of STEAP-2, which is intracellular using the membrane topology prediction program SOSUI. The latter peptide resides in the region between transmembrane domains 3 and 4, and this region is predicted to encode the second of 3 extracellular loops. A third immunogen was a glutathione-S-transferase (GST) fusion protein encompassing amino acids 2-204 of the STEAP-2 protein sequence. The recombinant GST-STEAP-2 fusion protein was purified from induced bacteria by glutathione-sepharose affinity chromatography.

In addition to the above antigens, peptides encoding other regions of the STEAP-2 protein, or bacterial and baculovirus virus produced proteins encoding either full length or partial sequences of the STEAP-2 protein, are use to generate a variety of STEAP-2 specific antibodies. These antibodies are directed to regions that may modulate STEAP-2 function.
Generation of Polyclonal Antibodies (pAbs)

To generate pAbs to STEAP-2, the purified GST-fusion protein and the peptides coupled to Keyhole limpet hemacyanin (KLH) were used to immunize individual rabbits as follows. The rabbits were immunized with 200 μg of fusion protein or KLH-peptide antigen mixed in complete Freund's adjuvant. The rabbits were then injected every two weeks with 200 μg of immunogen in incomplete Freund's adjuvant. Test bleeds were taken approximately 7-10 days following each immunization. The titer of peptide 153-165 antiserum was at least 25,000 and of peptide 345-358 antiserum at least 10,000 as determined by ELISA to the respective immunogens. The titer of the GST-fusion serum was at least 300,000. Peptide antiserum is affinity purified by passage of the serum over an affinity column composed of the respective peptide covalently coupled to Affigel matrix (BioRad). Serum raised to the GST-fusion is semi-purified first by removal of GST-reactive antibodies by passage over a GST affinity column. STEAP-2 specific antibody is then isolated by passage over a GST-STEAP-2 affinity column. Alternatively, STEAP-2 specific antisera is isolated by affinity chromatography using a maltose binding protein (MBP)-STEAP-2 fusion protein encoding the same amino acids

Example 21

Generation of Monoclonal Antibodies to STEAP Proteins

To generate mAbs to STEAP-1, STEAP-2, STEAP-3, or STEAP-4 proteins, Balb C mice are immunized intraperitoneally with 20-50 μg of KLH-coupled peptide or with bacterial recombinant polypeptides, such as GST-fusion proteins, encoding regions of the respective STEAP member protein sequence mixed in complete Freund's adjuvant Mice are then subsequently immunized every 2-4 weeks with 20-50 μg of immunogen mixed in Freund's incomplete adjuvant. Alternatively, Ribi adjuvant is used for initial immunizations. Test bleeds are taken 7-10 days following immunization to monitor titer and specificity of the immune response.

Serum from mice immunized with a GST-fusion protein encompassing amino acids 148-251 of STEAP-1 attained a titer of at least $8 \times 10^6$ as determined by ELISA and specifically recognized STEAP-1 protein by western blot (FIG. 33). Once appropriate reactivity and specificity are obtained as determined by ELISA, western blotting, and flow cytometry analyses, fusion and hybridoma generation is then carried out using established procedures well known in the art (Harlow and Lane, 1988).

FIG. 33 is a western blot showing that anti-STEAP-1 murine pAb recognizes STEAP-1 protein in engineered cell lines and endogenous STEAP-1 protein in LNCaP cells. Lysates of LNCaP cells and 293T cells transfected with either pcDNA 3.1 MYC/HIS tagged STEAP-1 or neo empty vector, and RAT1 cells engineered to express STEAP-1 or a neo control gene, were separated by SDS-PAGE and transferred to nitrocellulose. The blot was then subjected to anti-STEAP western analysis using a 1:1000 dilution of serum from mice immunized with a GST-STEAP-1 fusion protein.

Alternative antigens and immunization strategies are also used to generate mAbs with specific reactivity and specificity to various regions of the STEAP proteins. Such antigens may include baculovirus produced recombinant proteins or mammalian expressed and secreted human IgG FC-fusion proteins encoding various regions of each STEAP family member protein sequence, such as predicted extracellular domains. A cell based immunization strategy is also used in which the cDNA of a STEAP family member is overexpressed in cells such as NIH3T3 mouse fibroblasts or 300.19 murine pre-B cells and whole cells or membrane preparations from these cells are used as immunogen. In addition, a DNA-based immunization protocol in which a mammalian expression vector encoding the STEAP-1 or STEAP-2 cDNA such as pcDNA 3.1 is used to immunize mice by direct injection of the plasmid DNA. This protocol is used either alone or in combination with protein and/or cell-based immunization strategies.

Throughout this application, various publications are referenced. The disclosures of these publications are hereby incorporated by reference herein in their entireties.

The present invention is not to be limited in scope by the embodiments disclosed herein, which are intended as single illustrations of individual aspects of the invention, and any that are functionally equivalent are within the scope of the invention. Various modifications to the models and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

The invention claimed is:

1. An assay for detecting the presence of a STEAP-2 protein having the amino acid sequence of SEQ ID NO: 8 in a biological sample comprising contacting the sample with a monoclonal antibody or antibody fragment which specifically binds to an epitope within amino acids 1-205 or 229-254 of said STEAP-2 protein having the amino acid sequence of SEQ ID NO: 8, and to said STEAP-2 protein having the amino acid sequence of SEQ ID NO: 8, and detecting the binding of said STEAP-2 protein in the sample thereto.

2. An assay for detecting the presence of a STEAP-2 protein having the amino acid sequence of SEQ ID NO: 8 in a biological sample comprising contacting the sample with recombinant protein comprising the antigen binding region of a monoclonal antibody or antibody fragment which specifically binds to an epitope within amino acids 1-205 or 229-254 of said STEAP-2 protein having the amino acid sequence of SEQ ID NO: 8, and to the STEAP-2 protein having the amino acid sequence of SEQ ID NO: 8.

3. The assay of claim 1 wherein the antibody or antibody fragment is labeled with a detectable marker.

4. The assay of claim 3 wherein the detectable marker comprises a radioisotope, metal chelator, enzyme or fluorescent, bioluminescent or chemiluminescent compound.

5. The assay of claim 1 wherein the antibody or antibody fragment is a human antibody.

6. The assay of claim 1, wherein the antibody or antibody fragment comprises murine antigen binding region residues and human antibody residues.

7. The assay of claim 1, wherein the sample is from prostate, lung, colon or bladder.

8. The assay of claim 1, wherein the sample is a biopsied tissue.

9. The assay of claim 8 wherein the binding of the antibody or antibody fragment to said STEAP-2 protein in the sample is detected using a radioscintigraphic imaging apparatus.

10. The assay of claim 1, wherein the sample is blood, urine, or semen.

11. The assay of claim 10, wherein the binding of the antibody or antibody fragment to said STEAP-2 protein in the sample is detected using fluorescence-activated cell sorting (FACS) or ELISA.

* * * * *

SEQUENCE LISTING

```
<160> NUMBER OF SEQ ID NOS: 57

<210> SEQ ID NO 1
<211> LENGTH: 1193
<212> TYPE: DNA
<213> ORGANISM: Homo sapiens
<220> FEATURE:
```

<221> NAME/KEY: CDS
<222> LOCATION: (64)...(1191)

<400> SEQUENCE: 1

| | | | | | | | | | | | | | | | | |
|---|---|---|---|---|---|---|---|---|---|---|---|---|---|---|---|---|
| gagactcacg | gtcaagctaa | ggcgaagagt | gggtggctga | agccatacta | ttttatagaa | | | | | | | | | | | 60 |

```
tta atg gaa agc aga aaa gac atc aca aac caa gaa gaa ctt tgg aaa        108
    Met Glu Ser Arg Lys Asp Ile Thr Asn Gln Glu Glu Leu Trp Lys
    1               5                  10                  15 atg aag cct agg aga aat tta gaa gaa gac gat tat ttg cat aag gac        156
Met Lys Pro Arg Arg Asn Leu Glu Glu Asp Asp Tyr Leu His Lys Asp
                20                  25                  30 acg gga gag acc agc atg cta aaa aga cct gtg ctt ttg cat ttg cac        204
Thr Gly Glu Thr Ser Met Leu Lys Arg Pro Val Leu Leu His Leu His
                35                  40                  45 caa aca gcc cat gct gat gaa ttt gac tgc cct tca gaa ctt cag cac        252
Gln Thr Ala His Ala Asp Glu Phe Asp Cys Pro Ser Glu Leu Gln His
            50                  55                  60 aca cag gaa ctc ttt cca cag tgg cac ttg cca att aaa ata gct gct        300
Thr Gln Glu Leu Phe Pro Gln Trp His Leu Pro Ile Lys Ile Ala Ala
        65                  70                  75 att ata gca tct ctg act ttt ctt tac act ctt ctg agg gaa gta att        348
Ile Ile Ala Ser Leu Thr Phe Leu Tyr Thr Leu Leu Arg Glu Val Ile
80                  85                  90                  95 cac cct tta gca act tcc cat caa caa tat ttt tat aaa att cca atc        396
His Pro Leu Ala Thr Ser His Gln Gln Tyr Phe Tyr Lys Ile Pro Ile
                100                 105                 110 ctg gtc atc aac aaa gtc ttg cca atg gtt tcc atc act ctc ttg gca        444
Leu Val Ile Asn Lys Val Leu Pro Met Val Ser Ile Thr Leu Leu Ala
                115                 120                 125 ttg gtt tac ctg cca ggt gtg ata gca gca att gtc caa ctt cat aat        492
Leu Val Tyr Leu Pro Gly Val Ile Ala Ala Ile Val Gln Leu His Asn
            130                 135                 140 gga acc aag tat aag aag ttt cca cat tgg ttg gat aag tgg atg tta        540
Gly Thr Lys Tyr Lys Lys Phe Pro His Trp Leu Asp Lys Trp Met Leu
        145                 150                 155 aca aga aag cag ttt ggg ctt ctc agt ttc ttt ttt gct gta ctg cat        588
Thr Arg Lys Gln Phe Gly Leu Leu Ser Phe Phe Phe Ala Val Leu His
160                 165                 170                 175 gca att tat agt ctg tct tac cca atg agg cga tcc tac aga tac aag        636
Ala Ile Tyr Ser Leu Ser Tyr Pro Met Arg Arg Ser Tyr Arg Tyr Lys
                180                 185                 190 ttg cta aac tgg gca tat caa cag gtc caa caa aat aaa gaa gat gcc        684
Leu Leu Asn Trp Ala Tyr Gln Gln Val Gln Gln Asn Lys Glu Asp Ala
                195                 200                 205 tgg att gag cat gat gtt tgg aga atg gag att tat gtg tct ctg gga        732
Trp Ile Glu His Asp Val Trp Arg Met Glu Ile Tyr Val Ser Leu Gly
            210                 215                 220 att gtg gga ttg gca ata ctg gct ctg ttg gct gtg aca tct att cca        780
Ile Val Gly Leu Ala Ile Leu Ala Leu Leu Ala Val Thr Ser Ile Pro
        225                 230                 235 tct gtg agt gac tct ttg aca tgg aga gaa ttt cac tat att cag agc        828
Ser Val Ser Asp Ser Leu Thr Trp Arg Glu Phe His Tyr Ile Gln Ser
240                 245                 250                 255 aag cta gga att gtt tcc ctt cta ctg ggc aca ata cac gca ttg att        876
Lys Leu Gly Ile Val Ser Leu Leu Leu Gly Thr Ile His Ala Leu Ile
                260                 265                 270 ttt gcc tgg aat aag tgg ata gat ata aaa caa ttt gta tgg tat aca        924
Phe Ala Trp Asn Lys Trp Ile Asp Ile Lys Gln Phe Val Trp Tyr Thr
                275                 280                 285 cct cca act ttt atg ata gct gtt ttc ctt cca att gtt gtc ctg ata        972
```

```
                Pro Pro Thr Phe Met Ile Ala Val Phe Leu Pro Ile Val Val Leu Ile
                            290                 295                 300 ttt aaa agc ata cta ttc ctg cca tgc ttg agg aag aag ata ctg aag              1020
Phe Lys Ser Ile Leu Phe Leu Pro Cys Leu Arg Lys Lys Ile Leu Lys
            305                 310                 315 att aga cat ggt tgg gaa gac gtc acc aaa att aac aaa act gag ata              1068
Ile Arg His Gly Trp Glu Asp Val Thr Lys Ile Asn Lys Thr Glu Ile
320             325                 330                 335 tgt tcc cag ttg tag aat tac tgt tta cac aca ttt tgt tca aat att              1116
Cys Ser Gln Leu  *  Asn Tyr Cys Leu His Thr Phe Leu Phe Asn Ile
                340                 345                 350 gat ata ttt tat cac caa cat ttc aag ttt gta ttt gtt aat aaa atg              1164
Asp Ile Phe Tyr His Gln His Phe Lys Phe Val Phe Val Asn Lys Met
                355                 360                 365 att att caa gga aaa aaa aaa aaa aa                                           1193
Ile Ile Gln Gly Lys Lys Lys Lys
                370                 375

<210> SEQ ID NO 2
<211> LENGTH: 375
<212> TYPE: PRT
<213> ORGANISM: Homo sapiens

<400> SEQUENCE: 2

Met Glu Ser Arg Lys Asp Ile Thr Asn Gln Glu Glu Leu Trp Lys Met
 1               5                  10                  15

Lys Pro Arg Arg Asn Leu Glu Glu Asp Asp Tyr Leu His Lys Asp Thr
                20                  25                  30

Gly Glu Thr Ser Met Leu Lys Arg Pro Val Leu Leu His Leu His Gln
            35                  40                  45

Thr Ala His Ala Asp Glu Phe Asp Cys Pro Ser Glu Leu Gln His Thr
        50                  55                  60

Gln Glu Leu Phe Pro Gln Trp His Leu Pro Ile Lys Ile Ala Ala Ile
65                  70                  75                  80

Ile Ala Ser Leu Thr Phe Leu Tyr Thr Leu Arg Glu Val Ile His
                    85                  90                  95

Pro Leu Ala Thr Ser His Gln Gln Tyr Phe Lys Ile Pro Ile Leu
                100                 105                 110

Val Ile Asn Lys Val Leu Pro Met Val Ser Ile Thr Leu Leu Ala Leu
                115                 120                 125

Val Tyr Leu Pro Gly Val Ile Ala Ala Ile Val Gln Leu His Asn Gly
            130                 135                 140

Thr Lys Tyr Lys Lys Phe Pro His Trp Leu Asp Lys Trp Met Leu Thr
145                 150                 155                 160

Arg Lys Gln Phe Gly Leu Leu Ser Phe Phe Ala Val Leu His Ala
                    165                 170                 175

Ile Tyr Ser Leu Ser Tyr Pro Met Arg Arg Ser Tyr Arg Tyr Lys Leu
                180                 185                 190

Leu Asn Trp Ala Tyr Gln Gln Val Gln Gln Asn Lys Glu Asp Ala Trp
            195                 200                 205

Ile Glu His Asp Val Trp Arg Met Glu Ile Tyr Val Ser Leu Gly Ile
        210                 215                 220

Val Gly Leu Ala Ile Leu Ala Leu Leu Ala Val Thr Ser Ile Pro Ser
225                 230                 235                 240

Val Ser Asp Ser Leu Thr Trp Arg Glu Phe His Tyr Ile Gln Ser Lys
                    245                 250                 255

Leu Gly Ile Val Ser Leu Leu Leu Gly Thr Ile His Ala Leu Ile Phe
```

```
        260             265             270
Ala Trp Asn Lys Trp Ile Asp Ile Lys Gln Phe Val Trp Tyr Thr Pro
        275             280             285

Pro Thr Phe Met Ile Ala Val Phe Leu Pro Ile Val Val Leu Ile Phe
        290             295             300

Lys Ser Ile Leu Phe Leu Pro Cys Leu Arg Lys Lys Ile Leu Lys Ile
305             310             315             320

Arg His Gly Trp Glu Asp Val Thr Lys Ile Asn Lys Thr Glu Ile Cys
                325             330             335

Ser Gln Leu Asn Tyr Cys Leu His Thr Phe Leu Phe Asn Ile Asp Ile
        340             345             350

Phe Tyr His Gln His Phe Lys Phe Val Phe Val Asn Lys Met Ile Ile
        355             360             365

Gln Gly Lys Lys Lys Lys Lys
        370             375

<210> SEQ ID NO 3
<211> LENGTH: 111
<212> TYPE: DNA
<213> ORGANISM: Homo sapiens

<400> SEQUENCE: 3
ggcggaggcg aggcggagg gcgaggggcg gggagcgccg cctggagcgc ggcaggtcat     60
attgaacatt ccagatacct atcattactc gatgctgttg ataacagcaa g            111

<210> SEQ ID NO 4
<211> LENGTH: 24
<212> TYPE: DNA
<213> ORGANISM: Artificial Sequence
<220> FEATURE:
<223> OTHER INFORMATION: Primer

<400> SEQUENCE: 4
actttgttga tgaccaggat tgga                                           24

<210> SEQ ID NO 5
<211> LENGTH: 24
<212> TYPE: DNA
<213> ORGANISM: Artificial Sequence
<220> FEATURE:
<223> OTHER INFORMATION: Primer

<400> SEQUENCE: 5
cagaacttca gcacacacag gaac                                           24

<210> SEQ ID NO 6
<211> LENGTH: 3627
<212> TYPE: DNA
<213> ORGANISM: Homo sapiens

<400> SEQUENCE: 6
ggggcccgca cctctgggca gcagcggcag ccgagactca cggtcaagct aaggcgaaga     60
gtgggtggct gaagccatac tattttatag aattaatgga aagcagaaaa gacatcacaa    120
accaagaaga actttggaaa atgaagccta ggagaaattt agaagaagac gattatttgc    180
ataaggacac gggagagacc agcatgctaa aaagacctgt gcttttgcat ttgcaccaaa    240
cagcccatgc tgatgaattt gactgcccctt cagaacttca gcacacacag gaactctttc    300
cacagtggca cttgccaatt aaaatagctg ctattatagc atctctgact tttcttaca     360 ctcttctgag ggaagtaatt cacccccttag caacttccca tcaacaatat ttttataaaa    420
```

```
ttccaatcct ggtcatcaac aaagtcttgc caatggtttc catcactctc ttggcattgg    480
tttacctgcc aggtgtgata gcagcaattg tccaacttca taatggaacc aagtataaga    540
agtttccaca ttggttggat aagtggatgt taacaagaaa gcagtttggg cttctcagtt    600
tcttttttgc tgtactgcat gcaatttata gtctgtctta cccaatgagg cgatcctaca    660
gatacaagtt gctaaactgg gcatatcaac aggtccaaca aaataaagaa gatgcctgga    720
ttgagcatga tgtttggaga atggagattt atgtgtctct gggaattgtg ggattggcaa    780
tactggctct gttggctgtg acatctattc catctgtgag tgactctttg acatggagag    840
aatttcacta tattcaggta aataatatat aaaataaccc taagaggtaa atcttctttt    900
tgtgtttatg atatagaata tgttgacttt accccataaa aaataacaaa tgttttttcaa   960 cagcaaagat cttatacttg ttccaattaa taatgtgctc tcctgttgtt ttccctattg    1020
cttctaatta ggacaagtgt ttcctagaca taaataaaag gcattaaaat attctttgtt    1080 ttttttttt tgtttgtttg tttttttgttt gtttgtttgt tttttgaga tgaagtctcg     1140 ctctgttgcc catgctggag tacagtggca cgatctcggc tcactgcaac ctgcgcctcc    1200
tgggttcagg cgattctctt gcctcagcct cctgagtagc tgggattaca ggcacccatc    1260
accatgtcca gctaattttt gtatttttag tagagacagg ttttcccat gttggccagg     1320 ctggtctcga tctcctgacc tcaaatgatc cgcccacctc ggcctcccaa agtgctggga    1380
tgacagttgt gagccaccac actcagcctg ctctttctaa tatttgaaac ttgttagaca    1440
atttgctacc catctaatgt gatattttag gaatccaata tgcatggttt attatttctt    1500
aaaaaaaata ttcttttacc tgtcacctga atttagtaat gcctttatg ttacacaact     1560 tagcactttc cagaaacaaa aactctctcc ttgaaataat agagttttta tctaccaaag    1620
atatgctagt gtctcatttc aaaggctgct ttttccagct tacattttat atacttactc    1680
acttgaagtt tctaaatatt cttgtaattt taaaactatc tcagatttac tgaggtttat    1740
cttctggtgg tagattatcc ataagaagag tgatgtgcca gaatcactct gggatccttg    1800
tctgacaaga ttcaaaggac taaatttaat tcagtcatga acactgccaa ttaccgttta    1860
tgggtagaca tctttggaaa tttccacaag gtcagacatt cgcaactatc ccttctacat    1920
gtccacacgt atactccaac actttattag gcatctgatt agtttggaaa gtatgcctcc    1980
atctgaatta gtccagtgtg gcttagagtt ggtacaacat tctcacagaa tttcctaatt    2040
ttgtaggttc agcctgataa ccactggagt tctttggtcc tcattaaata gctttcttca    2100
cacattgctc tgcctgttac acatatgatg aacactgctt tttagacttc attaggaatt    2160
taggactgca tcttgacaac tgagcctatt ctactatatg tacaatacct agcccataat    2220
aggtatacaa tacacatttg gtaaaactaa ttttcaacca atgacatgta tttttcaact    2280
agtaacctag aaatgtttca cttaaaatct gagaactggt tacactacaa gttaccttgg    2340
agattcatat atgaaaacgc aaacttagct atttgattgt attcactggg acttaagaat    2400
gcgcctgaat aattgtgagt tcgatttgtt ctggcaggct aatgaccatt tccagtaaag    2460
tgaatagagg tcagaagtcg tataaaagag gtgttgtcag aacaccgttg agattacata    2520
ggtgaacaac tattttttaag caactttatt tgtgtagtga caaagcatcc caatgcaggc    2580
tgaaatgttt catcacatct ctggatctct ctattttgtg cagacattga aaaaattgtt    2640
catattattt ccatgttatc agaatatttg attttttaaa aacataggcc aagttcattc    2700
acttcattat tcatttatca aaatcagagt gaatcacatt agtcgccttc acaactgata    2760
aagatcactg aagtcaaatt gattttttgct ataatcttca atctacctat atttaattga    2820
```

-continued

```
gaatctaaaa tgtacaaatc attgtgttga ttctgcagtg atcctgctat aagtaagact    2880
cagtccctga ttttaggtat cctgtgaaaa gcagaattaa gacaaataca caagagacaa    2940
agcacaaaaa ataaatatca taaggggatg aacaaaatgg tggagaaaga gtagacaaag    3000
tttttgatca cctgccttca aagaaaggct gtgaattttg ttcacttaga cagcttggag    3060
acaagaaatt acccaaaagt aaggtgagga ggataggcaa aaagagcaga agatgtgaa     3120 tggacattgt tgagaaatgt gataggaaaa caatcataga taaggatttt ccaagcaaca    3180
gagcatatcc agatgaggta ggatgggata aactcttatt gaaccaatct tcaccaattt    3240
tgtttttctt ttgcagagca agctaggaat tgtttcccct ctactgggca aatacacgc     3300 attgattttt gcctggaata agtggataga tataaaacaa tttgtatggt atacacctcc    3360 aactttatg atagctgttt tccttccaat tgttgtcctg atatttaaaa gcatactatt      3420
cctgccatgc ttgaggaaga agatactgaa gattagacat ggttgggaag acgtcaccaa    3480
aattaacaaa actgagatat gttcccagtt gtagaattac tgtttacaca catttttgtt   3540
caatattgat atattttatc accaacattt caagtttgta tttgttaata aatgattat     3600 tcaaggaaaa aaaaaaaaaa aaaaaaa                                        3627

<210> SEQ ID NO 7
<211> LENGTH: 2453
<212> TYPE: DNA
<213> ORGANISM: Homo sapiens
<220> FEATURE:
<221> NAME/KEY: CDS
<222> LOCATION: (355)...(1719)

<400> SEQUENCE: 7
ggacgcgtgg gcggacgcgt gggttcctcg ggccctcggc gccacaagct gtccgggcac      60
gcagccccta gcggcgcgtc gctgccaagc cggcctccgc gcgcctccct ccttccttct    120
cccctggctg ttcgcgatcc agcttgggta ggcggggaag cagctggagt gcgaccgcca    180
cggcagccac cctgcaaccg ccagtcggag gtgcagtccg taggccctgg ccccgggtg     240 ggcccttggg gagtcggcgc cgctcccgag gagctgcaag gctcgcccct gcccggcgtg    300
gagggcgcgg ggggcgcgga ggatattctt ggtgatcttg gaagtgtccg tatc atg      357
                                                              Met
                                                               1 gaa tca atc tct atg atg gga agc cct aag agc ctt agt gaa act tgt       405
Glu Ser Ile Ser Met Met Gly Ser Pro Lys Ser Leu Ser Glu Thr Cys
          5                  10                  15 tta cct aat ggc ata aat ggt atc aaa gat gca agg aag gtc act gta      453
Leu Pro Asn Gly Ile Asn Gly Ile Lys Asp Ala Arg Lys Val Thr Val
         20                  25                  30 ggt gtg att gga agt gga gat ttt gcc aaa tcc ttg acc att cga ctt      501
Gly Val Ile Gly Ser Gly Asp Phe Ala Lys Ser Leu Thr Ile Arg Leu
     35                  40                  45 att aga tgc ggc tat cat gtg gtc ata gga agt aga aat cct aag ttt      549
Ile Arg Cys Gly Tyr His Val Val Ile Gly Ser Arg Asn Pro Lys Phe
 50                  55                  60                  65 gct tct gaa ttt ttt cct cat gtg gta gat gtc act cat cat gaa gat      597
Ala Ser Glu Phe Phe Pro His Val Val Asp Val Thr His His Glu Asp
                 70                  75                  80 gct ctc aca aaa aca aat ata ata ttt gtt gct ata cac aga gaa cat      645
Ala Leu Thr Lys Thr Asn Ile Ile Phe Val Ala Ile His Arg Glu His
             85                  90                  95 tat acc tcc ctg tgg gac ctg aga cat ctg ctt gtg ggt aaa atc ctg      693
Tyr Thr Ser Leu Trp Asp Leu Arg His Leu Leu Val Gly Lys Ile Leu
```

```
                    -continued
          100              105              110
att gat gtg agc aat aac atg agg ata aac cag tac cca gaa tcc aat      741
Ile Asp Val Ser Asn Asn Met Arg Ile Asn Gln Tyr Pro Glu Ser Asn
            115              120              125 gct gaa tat ttg gct tca tta ttc cca gat tct ttg att gtc aaa gga      789
Ala Glu Tyr Leu Ala Ser Leu Phe Pro Asp Ser Leu Ile Val Lys Gly
130              135              140              145 ttt aat gtt gtc tca gct tgg gca ctt cag tta gga cct aag gat gcc      837
Phe Asn Val Val Ser Ala Trp Ala Leu Gln Leu Gly Pro Lys Asp Ala
                 150              155              160 agc cgg cag gtt tat ata tgc agc aac aat att caa gcg cga caa cag      885
Ser Arg Gln Val Tyr Ile Cys Ser Asn Asn Ile Gln Ala Arg Gln Gln
             165              170              175 gtt att gaa ctt gcc cgc cag ttg aat ttc att ccc att gac ttg gga      933
Val Ile Glu Leu Ala Arg Gln Leu Asn Phe Ile Pro Ile Asp Leu Gly
180              185              190 tcc tta tca tca gcc aga gag att gaa aat tta ccc cta cga ctc ttt      981
Ser Leu Ser Ser Ala Arg Glu Ile Glu Asn Leu Pro Leu Arg Leu Phe
195              200              205 act ctc tgg aga ggg cca gtg gtg gta gct ata agc ttg gcc aca ttt     1029
Thr Leu Trp Arg Gly Pro Val Val Val Ala Ile Ser Leu Ala Thr Phe
210              215              220              225 ttt ttc ctt tat tcc ttt gtc aga gat gtg att cat cca tat gct aga     1077
Phe Phe Leu Tyr Ser Phe Val Arg Asp Val Ile His Pro Tyr Ala Arg
                 230              235              240 aac caa cag agt gac ttt tac aaa att cct ata gag att gtg aat aaa     1125
Asn Gln Gln Ser Asp Phe Tyr Lys Ile Pro Ile Glu Ile Val Asn Lys
             245              250              255 acc tta cct ata gtt gcc att act ttg ctc tcc cta gta tac ctt gca     1173
Thr Leu Pro Ile Val Ala Ile Thr Leu Leu Ser Leu Val Tyr Leu Ala
260              265              270 ggt ctt ctg gca gct gct tat caa ctt tat tac ggc acc aag tat agg     1221
Gly Leu Leu Ala Ala Ala Tyr Gln Leu Tyr Tyr Gly Thr Lys Tyr Arg
275              280              285 aga ttt cca cct tgg ttg gaa acc tgg tta cag tgt aga aaa cag ctt     1269
Arg Phe Pro Pro Trp Leu Glu Thr Trp Leu Gln Cys Arg Lys Gln Leu
290              295              300              305 gga tta cta agt ttt ttc ttc gct atg gtc cat gtt gcc tac agc ctc     1317
Gly Leu Leu Ser Phe Phe Phe Ala Met Val His Val Ala Tyr Ser Leu
                 310              315              320 tgc tta ccg atg aga agg tca gag aga tat ttg ttt ctc aac atg gct     1365
Cys Leu Pro Met Arg Arg Ser Glu Arg Tyr Leu Phe Leu Asn Met Ala
             325              330              335 tat cag cag gtt cat gca aat att gaa aac tct tgg aat gag gaa gaa     1413
Tyr Gln Gln Val His Ala Asn Ile Glu Asn Ser Trp Asn Glu Glu Glu
340              345              350 gtt tgg aga att gaa atg tat atc tcc ttt ggc ata atg agc ctt ggc     1461
Val Trp Arg Ile Glu Met Tyr Ile Ser Phe Gly Ile Met Ser Leu Gly
355              360              365 tta ctt tcc ctc ctg gca gtc act tct atc cct tca gtg agc aat gct     1509
Leu Leu Ser Leu Leu Ala Val Thr Ser Ile Pro Ser Val Ser Asn Ala
370              375              380              385 tta aac tgg aga gaa ttc agt ttt att cag tct aca ctt gga tat gtc     1557
Leu Asn Trp Arg Glu Phe Ser Phe Ile Gln Ser Thr Leu Gly Tyr Val
                 390              395              400 gct ctg ctc ata agt act ttc cat gtt tta att tat gga tgg aaa cga     1605
Ala Leu Leu Ile Ser Thr Phe His Val Leu Ile Tyr Gly Trp Lys Arg
             405              410              415 gct ttt gag gaa gag tac tac aga ttt tat aca cca cca aac ttt gtt     1653
Ala Phe Glu Glu Glu Tyr Tyr Arg Phe Tyr Thr Pro Pro Asn Phe Val
```

```
                420             425             430
ctt gct ctt gtt ttg ccc tca att gta att ctg gat ctt ttg cag ctt    1701
Leu Ala Leu Val Leu Pro Ser Ile Val Ile Leu Asp Leu Leu Gln Leu
        435                 440                 445 tgc aga tac cca gac tga gctggaactg gaatttgtct tcctattgac           1749
Cys Arg Tyr Pro Asp  *
450 tctacttctt taaaagcggc tgcccattac attcctcagc tgtccttgca gttaggtgta  1809
catgtgactg agtgttggcc agtgagatga agtctcctca aaggaaggca gcatgtgtcc  1869
tttttcatcc cttcatcttg ctgctgggat tgtggatata acaggagccc tggcagctgt  1929
ctccagagga tcaaagccac acccaaagag taaggcagat tagagaccag aaagaccttg  1989
actacttccc tacttccact gcttttcctg catttaagcc attgtaaatc tgggtgtgtt  2049
acatgaagtg aaaattaatt ctttctgccc ttcagttctt tatcctgata ccatttaaca  2109
ctgtctgaat taactagact gcaataattc tttcttttga aagcttttaa aggataatgt  2169
gcaattcaca ttaaaattga ttttccattg tcaattagtt atactcattt tcctgccttg  2229
atctttcatt agatattttg tatctgcttg gaatatatta tcttctttt aactgtgtaa   2289
ttggtaatta ctaaaactct gtaatctcca aaatattgct atcaaattac acaccatgtt  2349
ttctatcatt ctcatagatc tgccttataa acatttaaat aaaagtact atttaatgat   2409
ttaaaaaaaa aaaaaaaaa aaaaaaaaa aaaaaaaaa aaaa                      2453

<210> SEQ ID NO 8
<211> LENGTH: 454
<212> TYPE: PRT
<213> ORGANISM: Homo sapiens

<400> SEQUENCE: 8

Met Glu Ser Ile Ser Met Met Gly Ser Pro Lys Ser Leu Ser Glu Thr
 1               5                   10                  15

Cys Leu Pro Asn Gly Ile Asn Gly Ile Lys Asp Ala Arg Lys Val Thr
            20                  25                  30

Val Gly Val Ile Gly Ser Gly Asp Phe Ala Lys Ser Leu Thr Ile Arg
        35                  40                  45

Leu Ile Arg Cys Gly Tyr His Val Val Ile Gly Ser Arg Asn Pro Lys
    50                  55                  60

Phe Ala Ser Glu Phe Phe Pro His Val Val Asp Val Thr His His Glu
65                  70                  75                  80

Asp Ala Leu Thr Lys Thr Asn Ile Ile Phe Val Ala Ile His Arg Glu
                85                  90                  95

His Tyr Thr Ser Leu Trp Asp Leu Arg His Leu Leu Val Gly Lys Ile
            100                 105                 110

Leu Ile Asp Val Ser Asn Asn Met Arg Ile Asn Gln Tyr Pro Glu Ser
        115                 120                 125

Asn Ala Glu Tyr Leu Ala Ser Leu Phe Pro Asp Ser Leu Ile Val Lys
    130                 135                 140

Gly Phe Asn Val Val Ser Ala Trp Ala Leu Gln Leu Gly Pro Lys Asp
145                 150                 155                 160

Ala Ser Arg Gln Val Tyr Ile Cys Ser Asn Asn Ile Gln Ala Arg Gln
                165                 170                 175

Gln Val Ile Glu Leu Ala Arg Gln Leu Asn Phe Ile Pro Ile Asp Leu
            180                 185                 190

Gly Ser Leu Ser Ser Ala Arg Glu Ile Glu Asn Leu Pro Leu Arg Leu
        195                 200                 205
```

```
Phe Thr Leu Trp Arg Gly Pro Val Val Ala Ile Ser Leu Ala Thr
    210                 215                 220

Phe Phe Phe Leu Tyr Ser Phe Val Arg Asp Val Ile His Pro Tyr Ala
225                 230                 235                 240

Arg Asn Gln Gln Ser Asp Phe Tyr Lys Ile Pro Ile Glu Ile Val Asn
                245                 250                 255

Lys Thr Leu Pro Ile Val Ala Ile Thr Leu Leu Ser Leu Val Tyr Leu
                260                 265                 270

Ala Gly Leu Leu Ala Ala Ala Tyr Gln Leu Tyr Tyr Gly Thr Lys Tyr
                275                 280                 285

Arg Arg Phe Pro Pro Trp Leu Glu Thr Trp Leu Gln Cys Arg Lys Gln
    290                 295                 300

Leu Gly Leu Leu Ser Phe Phe Ala Met Val His Val Ala Tyr Ser
305                 310                 315                 320

Leu Cys Leu Pro Met Arg Arg Ser Glu Arg Tyr Leu Phe Leu Asn Met
                325                 330                 335

Ala Tyr Gln Gln Val His Ala Asn Ile Glu Asn Ser Trp Asn Glu Glu
                340                 345                 350

Glu Val Trp Arg Ile Glu Met Tyr Ile Ser Phe Gly Ile Met Ser Leu
    355                 360                 365

Gly Leu Leu Ser Leu Leu Ala Val Thr Ser Ile Pro Ser Val Ser Asn
370                 375                 380

Ala Leu Asn Trp Arg Glu Phe Ser Phe Ile Gln Ser Thr Leu Gly Tyr
385                 390                 395                 400

Val Ala Leu Leu Ile Ser Thr Phe His Val Leu Ile Tyr Gly Trp Lys
                405                 410                 415

Arg Ala Phe Glu Glu Tyr Tyr Arg Phe Tyr Thr Pro Pro Asn Phe
    420                 425                 430

Val Leu Ala Leu Val Leu Pro Ser Ile Val Ile Leu Asp Leu Leu Gln
                435                 440                 445

Leu Cys Arg Tyr Pro Asp
    450

<210> SEQ ID NO 9
<211> LENGTH: 4429
<212> TYPE: DNA
<213> ORGANISM: Homo sapiens
<220> FEATURE:
<221> NAME/KEY: CDS
<222> LOCATION: (85)...(1461)

<400> SEQUENCE: 9
cgaaacttcc ctctacccgc ccggcccgcg gcgcgcaccg ttggcgctgg acgcttcctc      60
cttggaagcg cctctcccte agtt atg gag aaa act tgt ata gat gca ctt      111
                          Met Glu Lys Thr Cys Ile Asp Ala Leu
                           1               5 cct ctt act atg aat tct tca gaa aag caa gag act gta tgt att ttt      159
Pro Leu Thr Met Asn Ser Ser Glu Lys Gln Glu Thr Val Cys Ile Phe
 10                  15                  20                  25 gga act ggt gat ttt gga aga tca ctg gga ttg aaa atg ctc cag tgt      207
Gly Thr Gly Asp Phe Gly Arg Ser Leu Gly Leu Lys Met Leu Gln Cys
                 30                  35                  40 ggt tat tct gtt gtt ttt gga agt cga aac ccc cag aag acc acc cta      255
Gly Tyr Ser Val Val Phe Gly Ser Arg Asn Pro Gln Lys Thr Thr Leu
             45                  50                  55 ctg ccc agt ggt gca gaa gtc ttg agc tat tca gaa gca gcc aag aag      303
Leu Pro Ser Gly Ala Glu Val Leu Ser Tyr Ser Glu Ala Ala Lys Lys
```

|     |     |
| --- | --- |
| tct ggc atc ata atc ata gca atc cac aga gag cat tat gat ttt ctc<br>Ser Gly Ile Ile Ile Ile Ala Ile His Arg Glu His Tyr Asp Phe Leu<br>    75                          80                      85 | 351 |
| aca gaa tta act gag gtt ctc aat gga aaa ata ttg gta gac atc agc<br>Thr Glu Leu Thr Glu Val Leu Asn Gly Lys Ile Leu Val Asp Ile Ser<br>90                      95                     100                  105 | 399 |
| aac aac ctc aaa atc aat caa tat cca gaa tct aat gca gag tac ctt<br>Asn Asn Leu Lys Ile Asn Gln Tyr Pro Glu Ser Asn Ala Glu Tyr Leu<br>           110                    115                  120 | 447 |
| gct cat ttg gtg cca gga gcc cac gtg gta aaa gca ttt aac acc atc<br>Ala His Leu Val Pro Gly Ala His Val Val Lys Ala Phe Asn Thr Ile<br>        125                    130                  135 | 495 |
| tca gcc tgg gct ctc cag tca gga gca ctg gat gca agt cgg cag gtg<br>Ser Ala Trp Ala Leu Gln Ser Gly Ala Leu Asp Ala Ser Arg Gln Val<br>        140                    145                  150 | 543 |
| ttt gtg tgt gga aat gac agc aaa gcc aag caa aga gtg atg gat att<br>Phe Val Cys Gly Asn Asp Ser Lys Ala Lys Gln Arg Val Met Asp Ile<br>    155                    160                  165 | 591 |
| gtt cgt aat ctt gga ctt act cca atg gat caa gga tca ctc atg gca<br>Val Arg Asn Leu Gly Leu Thr Pro Met Asp Gln Gly Ser Leu Met Ala<br>170                    175                  180                  185 | 639 |
| gcc aaa gaa att gaa aag tac ccc ctg cag cta ttt cca atg tgg agg<br>Ala Lys Glu Ile Glu Lys Tyr Pro Leu Gln Leu Phe Pro Met Trp Arg<br>           190                    195                  200 | 687 |
| ttc ccc ttc tat ttg tct gct gtg ctg tgt gtc ttc ttg ttt ttc tat<br>Phe Pro Phe Tyr Leu Ser Ala Val Leu Cys Val Phe Leu Phe Phe Tyr<br>        205                    210                  215 | 735 |
| tgt gtt ata aga gac gta atc tac cct tat gtt tat gaa aag aaa gat<br>Cys Val Ile Arg Asp Val Ile Tyr Pro Tyr Val Tyr Glu Lys Lys Asp<br>           220                    225                  230 | 783 |
| aat aca ttt cgt atg gct att tcc att cca aat cgt atc ttt cca ata<br>Asn Thr Phe Arg Met Ala Ile Ser Ile Pro Asn Arg Ile Phe Pro Ile<br>    235                    240                  245 | 831 |
| aca gca ctt aca ctg ctt gct ttg gtt tac ctc cct ggt gtt att gct<br>Thr Ala Leu Thr Leu Leu Ala Leu Val Tyr Leu Pro Gly Val Ile Ala<br>250                    255                  260                  265 | 879 |
| gcc att cta caa ctg tac cga ggc aca aaa tac cgt cga ttc cca gac<br>Ala Ile Leu Gln Leu Tyr Arg Gly Thr Lys Tyr Arg Arg Phe Pro Asp<br>           270                    275                  280 | 927 |
| tgg ctt gac cac tgg atg ctt tgc cga aag cag ctt ggc ttg gta gct<br>Trp Leu Asp His Trp Met Leu Cys Arg Lys Gln Leu Gly Leu Val Ala<br>        285                    290                  295 | 975 |
| ctg gga ttt gcc ttc ctt cat gtc ctc tac aca ctt gtg att cct att<br>Leu Gly Phe Ala Phe Leu His Val Leu Tyr Thr Leu Val Ile Pro Ile<br>        300                    305                  310 | 1023 |
| cga tat tat gta cga tgg aga ttg gga aac tta acc gtt acc cag gca<br>Arg Tyr Tyr Val Arg Trp Arg Leu Gly Asn Leu Thr Val Thr Gln Ala<br>        315                    320                  325 | 1071 |
| ata ctc aag aag gag aat cca ttt agc acc tcc tca gcc tgg ctc agt<br>Ile Leu Lys Lys Glu Asn Pro Phe Ser Thr Ser Ser Ala Trp Leu Ser<br>330                    335                  340                  345 | 1119 |
| gat tca tat gtg gct ttg gga ata ctt ggg ttt ttc ctg ttt gta ctc<br>Asp Ser Tyr Val Ala Leu Gly Ile Leu Gly Phe Phe Leu Phe Val Leu<br>           350                    355                  360 | 1167 |
| ttg gga atc act tct ttg cca tct gtt agc aat gca gtc aac tgg aga<br>Leu Gly Ile Thr Ser Leu Pro Ser Val Ser Asn Ala Val Asn Trp Arg<br>        365                    370                  375 | 1215 |
| gag ttc cga ttt gtc cag tcc aaa ctg ggt tat ttg acc ctg atc ttg<br>Glu Phe Arg Phe Val Gln Ser Lys Leu Gly Tyr Leu Thr Leu Ile Leu | 1263 |

-continued

```
                380             385             390
tgt aca gcc cac acc ctg gtg tac ggt ggg aag aga ttc ctc agc cct   1311
Cys Thr Ala His Thr Leu Val Tyr Gly Gly Lys Arg Phe Leu Ser Pro
    395             400             405 tca aat ctc aga tgg tat ctt cct gca gcc tac gtg tta ggg ctt atc   1359
Ser Asn Leu Arg Trp Tyr Leu Pro Ala Ala Tyr Val Leu Gly Leu Ile
410             415             420                         425 att cct tgc act gtg ctg gtg atc aag ttt gtc cta atc atg cca tgt   1407
Ile Pro Cys Thr Val Leu Val Ile Lys Phe Val Leu Ile Met Pro Cys
                430             435             440 gta gac aac acc ctt aca agg atc cgc cag ggc tgg gaa agg aac tca   1455
Val Asp Asn Thr Leu Thr Arg Ile Arg Gln Gly Trp Glu Arg Asn Ser
            445             450             455 aaa cac tagaaaaagc attgaatgga aaatcaatat ttaaaacaaa gttcaattta   1511
Lys His gctggatttc tgaactatgg ttttgaatgt ttaaagaaga atgatgggta cagttaggaa   1571
agttttttc ttacaccgtg actgagggaa acattgcttg tctttgagaa attgactgac    1631
atactggaag agaacaccat tttatctcag gttagtgaag aatcagtgca ggtccctgac   1691
tcttatttc ccagaggcca tggagctgag attgagacta gccttgtggt ttcacactaa   1751
agagtttcct tgttatgggc aacatgcatg acctaatgtc ttgcaaaatc aatagaagt    1811
attgcagctt ccttctctgg ctcaagggct gagttaagtg aaaggaaaaa cagcacaatg   1871
gtgaccactg ataaaggctt tattaggtat atctgaggaa gtgggtcaca tgaaatgtaa   1931
aaagggaatg aggttttgt tgtttttgg agtaaaggc aaacataaat attaccatga     1991
tgaattctag tgaaatgacc ccttgacttt gcttttctta atacagatat ttactgagag   2051
gaactatttt tataacacaa gaaaaattta caattgatta aaagtatcca tgtcttggat   2111
acatacgtat ctatagagct ggcatgtaat tcttcctcta taaagaatag gtataggaaa   2171
gactgaataa aaatggaggg atatccctt ggatttcact tgcattgtgc aataagcaaa    2231
gaagggttga taaaagttct tgatcaaaaa gttcaaagaa accagaattt tagacagcaa   2291
gctaaataaa tattgtaaaa ttgcactata ttaggttaag tattatttag gtattataat   2351
atgctttgta aatttttatat tccaaatatt gctcaatatt tttcatctat taaattaatt   2411
tctagtgtaa ataagtagct tctatatctg tcttagtcta ttataattgt aaggagtaaa   2471
attaaatgaa tagtctgcag gtataaattt gaacaatgca tagatgatcg aaaattacgg   2531
aaaatcatag ggcagagagg tgtgaagatt catcattatg tgaaatttgg atctttctca   2591
aatccttgct gaaatttagg atggttctca ctgtttttct gtgctgatag tacccttcc    2651
aaggtgacct tcaggggat taaccttcct agctcaagca atgagctaaa aggagcctta    2711
tgcatgatct tcccacatat caaaataact aaaaggcact gagtttggca ttttctgcc    2771
tgctctgcta agacctttt tttttttta ctttcattat aacatattat acatgacatt     2831
atacaaaaat gattaaaata tattaaaaca acatcaacaa tccaggatat ttttctataa   2891
aacttttta aaataattgt atctatatat tcaatttac atccttttc aaaggctttg     2951
tttttctaaa ggctttgttt tccttttat tattttttc tttttatt ttttgagaca       3011
gtcttgctct gtcgctcagg ctggagtgca gtggcacgat ctcagctcac tgcaacctcc   3071
tcctcccagg ttcaagtgat tcttgttcat cagcctcccg agtagctggg actacaggca   3131
tgtgccacta tgcccagcta attttttgtac ttttagtaga cagggtttt caccacattg   3191
gtcaggctgg tcttgaaatg ctggcgtcaa gtgatctgcc tgcctccgcc ttacgtaata   3251
tattttctta atggctgcat aatatcacat caaataggca ttttcaaac ctctttcctt   3311
```

-continued

```
attaaacatg tagactatat ccatttttta ctaaaataaa taacatttca gataatatct    3371
ttgcactgat aatgttgcca agccattcct aaagtgacct tatcaattta attaccattg    3431
gatgagggtg ttgctttcat cgcaccattg tagattgtct tttttatttc aatttgcgtt    3491
tatttataac tggttgcaaa ggtacacaga acacacgctc cttcaactta tctttgataa    3551
acccaagcaa ggatacaaaa agttggacga cattgagtag agtcatggta tacggtgctg    3611
accctacagt atcagtggaa aagataagga aaatgtcact actcacctat gttatgcaaa    3671
acagttaggt gtgctggggc tggatactgc tcttttactt gagcattggt tgattaaagt    3731
ttaggtacca tccaggctgg tctagagaag tctttggagt taaccatgct cttttttgtta    3791 aagaagagag taatgtgttt atcctggctc atagtccgtc accgaaaata gaaaatgcca    3851
tccataggta aaatgctgac ctatagaaaa aaatgaactc tacttttata gcctagtaaa    3911
aatgctctac ctgagtagtt aaaagcaatt catgaagcct gaagctaaag agcactctga    3971
tggttttggc ataatagctg catttccaga cctgaccttt ggccccaacc acaagtgctc    4031
caagccccac cagctgacca agaaagccc aagttctcct tctgtccttc ccacaacctc    4091
cctgctccca aaactatgaa attaatttga ccatattaac acagctgact cctccagttt    4151
acttaaggta gaaagaatga gtttacaaca gatgaaaata agtgctttgg gcgaactgta    4211
ttccttttaa cagatccaaa ctattttaca tttaaaaaaa aagttaaact aaacttcttt    4271
actgctgata tgtttcctgt attctagaaa aattttttaca ctttcacatt attttttgtac    4331 actttcccca tgttaaggga tgatggcttt tataaatgtg tattcattaa atgttacttt    4391
aaaaataaaa aaaaaaaaaa aaaaaaaaa aaaaaaaa                              4429
```

<210> SEQ ID NO 10
<211> LENGTH: 459
<212> TYPE: PRT
<213> ORGANISM: Homo sapiens

<400> SEQUENCE: 10

```
Met Glu Lys Thr Cys Ile Asp Ala Leu Pro Leu Thr Met Asn Ser Ser
 1               5                  10                  15

Glu Lys Gln Glu Thr Val Cys Ile Phe Gly Thr Gly Asp Phe Gly Arg
            20                  25                  30

Ser Leu Gly Leu Lys Met Leu Gln Cys Gly Tyr Ser Val Phe Gly
        35                  40                  45

Ser Arg Asn Pro Gln Lys Thr Thr Leu Leu Pro Ser Gly Ala Glu Val
    50                  55                  60

Leu Ser Tyr Ser Glu Ala Ala Lys Lys Ser Gly Ile Ile Ile Ala
65                  70                  75                  80

Ile His Arg Glu His Tyr Asp Phe Leu Thr Glu Leu Thr Glu Val Leu
                85                  90                  95

Asn Gly Lys Ile Leu Val Asp Ile Ser Asn Asn Leu Lys Ile Asn Gln
            100                 105                 110

Tyr Pro Glu Ser Asn Ala Glu Tyr Leu Ala His Leu Val Pro Gly Ala
        115                 120                 125

His Val Val Lys Ala Phe Asn Thr Ile Ser Ala Trp Ala Leu Gln Ser
    130                 135                 140

Gly Ala Leu Asp Ala Ser Arg Gln Val Phe Val Cys Gly Asn Asp Ser
145                 150                 155                 160

Lys Ala Lys Gln Arg Val Met Asp Ile Val Arg Asn Leu Gly Leu Thr
                165                 170                 175
```

```
Pro Met Asp Gln Gly Ser Leu Met Ala Ala Lys Glu Ile Glu Lys Tyr
            180                 185                 190
Pro Leu Gln Leu Phe Pro Met Trp Arg Phe Pro Phe Tyr Leu Ser Ala
        195                 200                 205
Val Leu Cys Val Phe Leu Phe Phe Tyr Cys Val Ile Arg Asp Val Ile
210                 215                 220
Tyr Pro Tyr Val Tyr Glu Lys Lys Asp Asn Thr Phe Arg Met Ala Ile
225                 230                 235                 240
Ser Ile Pro Asn Arg Ile Phe Pro Ile Thr Ala Leu Thr Leu Leu Ala
            245                 250                 255
Leu Val Tyr Leu Pro Gly Val Ile Ala Ala Ile Leu Gln Leu Tyr Arg
                260                 265                 270
Gly Thr Lys Tyr Arg Arg Phe Pro Asp Trp Leu Asp His Trp Met Leu
        275                 280                 285
Cys Arg Lys Gln Leu Gly Leu Val Ala Leu Gly Phe Ala Phe Leu His
    290                 295                 300
Val Leu Tyr Thr Leu Val Ile Pro Ile Arg Tyr Tyr Val Arg Trp Arg
305                 310                 315                 320
Leu Gly Asn Leu Thr Val Thr Gln Ala Ile Leu Lys Lys Glu Asn Pro
            325                 330                 335
Phe Ser Thr Ser Ser Ala Trp Leu Ser Asp Ser Tyr Val Ala Leu Gly
                340                 345                 350
Ile Leu Gly Phe Phe Leu Phe Val Leu Leu Gly Ile Thr Ser Leu Pro
        355                 360                 365
Ser Val Ser Asn Ala Val Asn Trp Arg Glu Phe Arg Phe Val Gln Ser
    370                 375                 380
Lys Leu Gly Tyr Leu Thr Leu Ile Leu Cys Thr Ala His Thr Leu Val
385                 390                 395                 400
Tyr Gly Gly Lys Arg Phe Leu Ser Pro Ser Asn Leu Arg Trp Tyr Leu
            405                 410                 415
Pro Ala Ala Tyr Val Leu Gly Leu Ile Ile Pro Cys Thr Val Leu Val
                420                 425                 430
Ile Lys Phe Val Leu Ile Met Pro Cys Val Asp Asn Thr Leu Thr Arg
        435                 440                 445
Ile Arg Gln Gly Trp Glu Arg Asn Ser Lys His
    450                 455

<210> SEQ ID NO 11
<211> LENGTH: 322
<212> TYPE: DNA
<213> ORGANISM: Homo sapiens

<400> SEQUENCE: 11
ggtcgacttt tcctttattc ctttgtcaga gatctgattc atccatatgc tagaaaccaa    60
cagagtgact tttacaaaat tcctatagag attgtaataa aaaccttacc tatagttgcc   120
attactttgc tctccctagt ataccttgca ggtcttctgg cagctgctta tcaactttat   180
tacggcacca agtataggag atttccacct tggttggaaa cctggttaca gtgtagaaaa   240
cagcttggat tactaagttg tttcttcgct atggtccatg ttgcctacag cctctgctta   300
ccgatgagaa ggtcagagag at                                            322

<210> SEQ ID NO 12
<211> LENGTH: 183
<212> TYPE: DNA
<213> ORGANISM: Homo sapiens
```

-continued

<400> SEQUENCE: 12

```
tttgcagctt tgcagatacc cagactgagc tggaactgga atttgtcttc ctattgactc    60
tacttcttta aaagcggctg cccattacat tcctcagctg tccttgcagt taggtgtaca   120
tgtgactgag tgttggccag tgagatgaag tctcctcaaa ggaaggcagc atgtgtcctt   180
ttt                                                                 183
```

<210> SEQ ID NO 13
<211> LENGTH: 448
<212> TYPE: DNA
<213> ORGANISM: Homo sapiens

<400> SEQUENCE: 13

```
aagaaggaga atccatttag cacctcctca gcctggctca gtgattcata tgtggctttg    60
ggaatacttg ggttttttct gtttgtactc ttgggaatca cttctttgcc atctgttagc   120
aatgcagtca actggagaga gttccgattt gtccagtcca aactgggtta tttgaccctg   180
atcttgtgta cagcccacac cctggtgtac ggtgggaaga gattcctcag cccttcaaat   240
ctcagatggt atcttcctgc agcctacgtg ttagggctta tcattccttg cactgtgctg   300
gtgatcaagt ttgtcctaat catgccatgt gtagacaaca cccttacaag gatccgccag   360
ggctgggaaa ggaactcaaa acactagaaa aagcattgaa tggaaaatca atatttaaaa   420
caaagttcaa tttagctgga aaaaaaaa                                      448
```

<210> SEQ ID NO 14
<211> LENGTH: 401
<212> TYPE: DNA
<213> ORGANISM: Homo sapiens
<220> FEATURE:
<221> NAME/KEY: misc_feature
<222> LOCATION: 11, 56, 233, 250, 310, 326, 377, 398
<223> OTHER INFORMATION: n = A,T,C or G

<400> SEQUENCE: 14

```
ggccgcggca nccgctacga cctggtcaac ctggcagtca agcaggtctt ggccanacaa    60
gagccacctc tgggtgaagg aggaggtctg gcggatggag atctacctct ccctgggagt   120
gctggccctc ggcacgttgt ccctgctggc cgtgacctca ctgccgtcca ttgcaaactc   180
gctcaactgg agggagttca gcttcgttca gtcctcactg gctttgtgg ccntcgtgct   240
gagcacactn cacacgctca cctacggctg gacccgcgcc ttcgaggaga gccgctacaa   300
gttctacctn cctcccacct tcacgntcac gctgctggtg ccctgcgttc gttcatcctg   360
ggccaaagcc ctgtttntac tgccttgcat tcagccgnag a                       401
```

<210> SEQ ID NO 15
<211> LENGTH: 133
<212> TYPE: PRT
<213> ORGANISM: Homo sapiens
<220> FEATURE:
<221> NAME/KEY: VARIANT
<222> LOCATION: 4, 19, 78, 109, 126, 133
<223> OTHER INFORMATION: Xaa = Any Amino Acid

<400> SEQUENCE: 15

```
Ala Ala Ala Xaa Ala Thr Thr Trp Ser Thr Trp Gln Ser Ser Arg Ser
 1               5                  10                  15

Trp Pro Xaa Lys Ser His Leu Trp Val Lys Glu Glu Val Trp Arg Met
             20                  25                  30

Glu Ile Tyr Leu Ser Leu Gly Val Leu Ala Leu Gly Thr Leu Ser Leu
         35                  40                  45
```

```
Leu Ala Val Thr Ser Leu Pro Ser Ile Ala Asn Ser Leu Asn Trp Arg
     50                  55                  60

Glu Phe Ser Phe Val Gln Ser Leu Gly Phe Val Ala Xaa Val Leu
 65                  70                  75                  80

Ser Thr Leu His Thr Leu Thr Tyr Gly Trp Thr Arg Ala Phe Glu Glu
                 85                  90                  95

Ser Arg Tyr Lys Phe Tyr Leu Pro Pro Thr Phe Thr Xaa Thr Leu Leu
                100                 105                 110

Val Pro Cys Val Arg Ser Ser Trp Ala Lys Ala Leu Phe Xaa Leu Pro
            115                 120                 125

Cys Ile Gln Pro Xaa
        130
```

<210> SEQ ID NO 16
<211> LENGTH: 23
<212> TYPE: DNA
<213> ORGANISM: Artificial Sequence
<220> FEATURE:
<223> OTHER INFORMATION: Primer

<400> SEQUENCE: 16
ttaggacaac ttgatcacca gca         23

<210> SEQ ID NO 17
<211> LENGTH: 24
<212> TYPE: DNA
<213> ORGANISM: Artificial Sequence
<220> FEATURE:
<223> OTHER INFORMATION: Primer

<400> SEQUENCE: 17
tgtccagtcc aaactgggtt attt         24

<210> SEQ ID NO 18
<211> LENGTH: 23
<212> TYPE: DNA
<213> ORGANISM: Artificial Sequence
<220> FEATURE:
<223> OTHER INFORMATION: Primer

<400> SEQUENCE: 18
agggagttca gcttcgttca gtc         23

<210> SEQ ID NO 19
<211> LENGTH: 24
<212> TYPE: DNA
<213> ORGANISM: Artificial Sequence
<220> FEATURE:
<223> OTHER INFORMATION: Primer

<400> SEQUENCE: 19
ggtagaactt gtagcggctc tcct         24

<210> SEQ ID NO 20
<211> LENGTH: 24
<212> TYPE: DNA
<213> ORGANISM: Artificial Sequence
<220> FEATURE:
<223> OTHER INFORMATION: Primer

<400> SEQUENCE: 20
gactgagctg gaactggaat ttgt         24

```
<210> SEQ ID NO 21
<211> LENGTH: 24
<212> TYPE: DNA
<213> ORGANISM: Artificial Sequence
<220> FEATURE:
<223> OTHER INFORMATION: Primer

<400> SEQUENCE: 21
tttgaggaga cttcatctca ctgg                                            24

<210> SEQ ID NO 22
<211> LENGTH: 15
<212> TYPE: PRT
<213> ORGANISM: Homo sapiens

<400> SEQUENCE: 22

Trp Lys Met Lys Pro Arg Arg Asn Leu Glu Glu Asp Asp Tyr Leu
 1               5                  10                  15

<210> SEQ ID NO 23
<211> LENGTH: 14
<212> TYPE: DNA
<213> ORGANISM: Artificial Sequence
<220> FEATURE:
<223> OTHER INFORMATION: cDNA synthesis primer

<400> SEQUENCE: 23
ttttgatcaa gctt                                                       14

<210> SEQ ID NO 24
<211> LENGTH: 42
<212> TYPE: DNA
<213> ORGANISM: Artificial Sequence
<220> FEATURE:
<223> OTHER INFORMATION: primer

<400> SEQUENCE: 24
ctaatacgac tcactatagg gctcgagcgg ccgcccgggc ag                        42

<210> SEQ ID NO 25
<211> LENGTH: 12
<212> TYPE: DNA
<213> ORGANISM: Artificial Sequence
<220> FEATURE:
<223> OTHER INFORMATION: primer

<400> SEQUENCE: 25
gatcctgccc gg                                                         12

<210> SEQ ID NO 26
<211> LENGTH: 40
<212> TYPE: DNA
<213> ORGANISM: Artificial Sequence
<220> FEATURE:
<223> OTHER INFORMATION: primer

<400> SEQUENCE: 26
gtaatacgac tcactatagg gcagcgtggt cgcggccgag                           40

<210> SEQ ID NO 27
<211> LENGTH: 10
<212> TYPE: DNA
<213> ORGANISM: Artificial Sequence
<220> FEATURE:
<223> OTHER INFORMATION: primer

<400> SEQUENCE: 27
```
gatcctcggc                                                                                          10

<210> SEQ ID NO 28
<211> LENGTH: 22
<212> TYPE: DNA
<213> ORGANISM: Artificial Sequence
<220> FEATURE:
<223> OTHER INFORMATION: PCR primer

<400> SEQUENCE: 28
ctaatacgac tcactatagg gc                                                                            22

<210> SEQ ID NO 29
<211> LENGTH: 22
<212> TYPE: DNA
<213> ORGANISM: Artificial Sequence
<220> FEATURE:
<223> OTHER INFORMATION: Nested primer

<400> SEQUENCE: 29
tcgagcggcc gcccgggcag ga                                                                            22

<210> SEQ ID NO 30
<211> LENGTH: 20
<212> TYPE: DNA
<213> ORGANISM: Artificial Sequence
<220> FEATURE:
<223> OTHER INFORMATION: Nested primer

<400> SEQUENCE: 30
agcgtggtcg cggccgagga                                                                               20

<210> SEQ ID NO 31
<211> LENGTH: 25
<212> TYPE: DNA
<213> ORGANISM: Artificial Sequence
<220> FEATURE:
<223> OTHER INFORMATION: Primer

<400> SEQUENCE: 31
atatcgccgc gctcgtcgtc gacaa                                                                         25

<210> SEQ ID NO 32
<211> LENGTH: 26
<212> TYPE: DNA
<213> ORGANISM: Artificial Sequence
<220> FEATURE:
<223> OTHER INFORMATION: Primer

<400> SEQUENCE: 32
agccacacgc agctcattgt agaagg                                                                        26

<210> SEQ ID NO 33
<211> LENGTH: 15
<212> TYPE: PRT
<213> ORGANISM: Homo sapiens

<400> SEQUENCE: 33

Tyr Gln Gln Val Gln Gln Asn Lys Glu Asp Ala Trp Ile Glu His
 1               5                  10                  15

<210> SEQ ID NO 34
<211> LENGTH: 24
<212> TYPE: DNA
<213> ORGANISM: Artificial Sequence
<220> FEATURE:
<223> OTHER INFORMATION: FLAG tag -continued

<400> SEQUENCE: 34
gattacaagg atgacgacga taag                                    24

<210> SEQ ID NO 35
<211> LENGTH: 22
<212> TYPE: DNA
<213> ORGANISM: Artificial Sequence
<220> FEATURE:
<223> OTHER INFORMATION: PCR primer

<400> SEQUENCE: 35
acaagagcca cctctgggtg aa                                      22

<210> SEQ ID NO 36
<211> LENGTH: 23
<212> TYPE: DNA
<213> ORGANISM: Artificial Sequence
<220> FEATURE:
<223> OTHER INFORMATION: PCR primer

<400> SEQUENCE: 36
agttgagcga gtttgcaatg gac                                     23

<210> SEQ ID NO 37
<211> LENGTH: 22
<212> TYPE: PRT
<213> ORGANISM: Homo sapiens

<400> SEQUENCE: 37

Arg Glu Val Ile His Pro Leu Ala Thr Ser His Gln Gln Tyr Phe Tyr
 1               5                  10                  15

Lys Ile Pro Ile Leu Val
            20

<210> SEQ ID NO 38
<211> LENGTH: 34
<212> TYPE: PRT
<213> ORGANISM: Homo sapiens

<400> SEQUENCE: 38

Arg Arg Ser Tyr Arg Tyr Lys Leu Leu Asn Trp Ala Tyr Gln Gln Val
 1               5                  10                  15

Gln Gln Asn Lys Glu Asp Ala Trp Ile Glu His Asp Val Trp Arg Met
            20                  25                  30

Glu Ile

<210> SEQ ID NO 39
<211> LENGTH: 15
<212> TYPE: PRT
<213> ORGANISM: Homo sapiens

<400> SEQUENCE: 39

Trp Ile Asp Ile Lys Gln Phe Val Trp Tyr Thr Pro Pro Thr Phe
 1               5                  10                  15

<210> SEQ ID NO 40
<211> LENGTH: 26
<212> TYPE: PRT
<213> ORGANISM: Homo sapiens

<400> SEQUENCE: 40

Tyr Ser Phe Val Arg Asp Val Ile His Pro Tyr Ala Arg Asn Gln Gln
 1               5                  10                  15

```
Ser Asp Phe Tyr Lys Ile Pro Ile Glu Ile
            20                  25

<210> SEQ ID NO 41
<211> LENGTH: 33
<212> TYPE: PRT
<213> ORGANISM: Homo sapiens

<400> SEQUENCE: 41

Arg Arg Ser Glu Arg Tyr Leu Phe Leu Asn Met Ala Tyr Gln Gln Val
1               5                   10                  15

His Ala Asn Ile Glu Asn Ser Trp Asn Glu Glu Val Trp Arg Ile
            20                  25                  30

Glu

<210> SEQ ID NO 42
<211> LENGTH: 12
<212> TYPE: PRT
<213> ORGANISM: Homo sapiens

<400> SEQUENCE: 42

Lys Arg Ala Phe Glu Glu Glu Tyr Tyr Arg Phe Tyr
1               5                   10

<210> SEQ ID NO 43
<211> LENGTH: 24
<212> TYPE: PRT
<213> ORGANISM: Homo sapiens

<400> SEQUENCE: 43

Tyr Pro Tyr Val Tyr Glu Lys Lys Asp Asn Thr Phe Arg Met Ala Ile
1               5                   10                  15

Ser Ile Pro Asn Arg Ile Phe Pro
            20

<210> SEQ ID NO 44
<211> LENGTH: 34
<212> TYPE: PRT
<213> ORGANISM: Homo sapiens

<400> SEQUENCE: 44

Tyr Tyr Val Arg Trp Arg Leu Gly Asn Leu Thr Val Thr Gln Ala Ile
1               5                   10                  15

Leu Lys Lys Glu Asn Pro Phe Ser Thr Ser Ser Ala Trp Leu Ser Asp
            20                  25                  30

Ser Tyr

<210> SEQ ID NO 45
<211> LENGTH: 13
<212> TYPE: PRT
<213> ORGANISM: Homo sapiens

<400> SEQUENCE: 45

Ala Leu Gln Leu Gly Pro Lys Asp Ala Ser Arg Gln Val
1               5                   10

<210> SEQ ID NO 46
<211> LENGTH: 14
<212> TYPE: PRT
<213> ORGANISM: Homo sapiens

<400> SEQUENCE: 46
```

Ile Glu Asn Ser Trp Asn Glu Glu Glu Val Trp Arg Ile Glu
1               5                   10

<210> SEQ ID NO 47
<211> LENGTH: 9
<212> TYPE: PRT
<213> ORGANISM: Homo sapiens

<400> SEQUENCE: 47

Gly Leu Leu Ser Phe Phe Phe Ala Val
1               5

<210> SEQ ID NO 48
<211> LENGTH: 9
<212> TYPE: PRT
<213> ORGANISM: Homo sapiens

<400> SEQUENCE: 48

Phe Leu Tyr Thr Leu Leu Arg Glu Val
1               5

<210> SEQ ID NO 49
<211> LENGTH: 9
<212> TYPE: PRT
<213> ORGANISM: Homo sapiens

<400> SEQUENCE: 49

Leu Leu Leu Gly Thr Ile His Ala Leu
1               5

<210> SEQ ID NO 50
<211> LENGTH: 9
<212> TYPE: PRT
<213> ORGANISM: Homo sapiens

<400> SEQUENCE: 50

Leu Ile Phe Lys Ser Ile Leu Phe Leu
1               5

<210> SEQ ID NO 51
<211> LENGTH: 9
<212> TYPE: PRT
<213> ORGANISM: Homo sapiens

<400> SEQUENCE: 51

Met Leu Thr Arg Lys Gln Phe Gly Leu
1               5

<210> SEQ ID NO 52
<211> LENGTH: 9
<212> TYPE: PRT
<213> ORGANISM: Homo sapiens

<400> SEQUENCE: 52

Phe Leu Tyr Ser Phe Val Arg Asp Val
1               5

<210> SEQ ID NO 53
<211> LENGTH: 9
<212> TYPE: PRT
<213> ORGANISM: Homo sapiens

<400> SEQUENCE: 53

Ala Leu Leu Ile Ser Thr Phe His Val
1               5

```
<210> SEQ ID NO 54
<211> LENGTH: 9
<212> TYPE: PRT
<213> ORGANISM: Homo sapiens

<400> SEQUENCE: 54

Leu Leu Ser Phe Phe Phe Ala Met Val
1               5

<210> SEQ ID NO 55
<211> LENGTH: 9
<212> TYPE: PRT
<213> ORGANISM: Homo sapiens

<400> SEQUENCE: 55

Gly Leu Leu Ser Phe Phe Phe Ala Met
1               5

<210> SEQ ID NO 56
<211> LENGTH: 9
<212> TYPE: PRT
<213> ORGANISM: Homo sapiens

<400> SEQUENCE: 56

Ser Leu Trp Asp Leu Arg His Leu Leu
1               5

<210> SEQ ID NO 57
<211> LENGTH: 21
<212> TYPE: DNA
<213> ORGANISM: Artificial Sequence
<220> FEATURE:
<223> OTHER INFORMATION: IgA Protease Cleavage site

<400> SEQUENCE: 57
cctcgacctc aacaccggg g                                            21
```